US012194039B2

(12) United States Patent
Honarpour et al.

(10) Patent No.: US 12,194,039 B2
(45) Date of Patent: Jan. 14, 2025

(54) METHODS OF TREATING HEART FAILURE BY ADMINISTERING OMECAMTIV MECARBIL

(71) Applicants: Cytokinetics, Inc., South San Francisco, CA (US); Amgen Inc., Thousand Oaks, CA (US)

(72) Inventors: Narimon Honarpour, Thousand Oaks, CA (US); Fady Malik, Burlingame, CA (US)

(73) Assignees: AMGEN INC, Thousand Oaks, CA (US); CYTOKINETICS, INC., South San Francisco, CA (US)

( * ) Notice: Subject to any disclaimer, the term of this patent is extended or adjusted under 35 U.S.C. 154(b) by 450 days.

(21) Appl. No.: 17/454,592

(22) Filed: Nov. 11, 2021

(65) Prior Publication Data
US 2022/0184068 A1 Jun. 16, 2022

Related U.S. Application Data

(60) Provisional application No. 63/203,436, filed on Jul. 22, 2021, provisional application No. 63/202,873, filed on Jun. 28, 2021, provisional application No. 63/187,084, filed on May 11, 2021, provisional application No. 63/154,077, filed on Feb. 26, 2021, provisional application No. 63/112,995, filed on Nov. 12, 2020.

(51) Int. Cl.
*A61K 31/497* (2006.01)
*A61N 1/39* (2006.01)

(52) U.S. Cl.
CPC .......... *A61K 31/497* (2013.01); *A61N 1/3956* (2013.01)

(58) Field of Classification Search
None
See application file for complete search history.

(56) References Cited

U.S. PATENT DOCUMENTS

| 4,450,150 | A | 5/1984 | Sidman et al. |
| 6,303,144 | B1 | 10/2001 | Omura et al. |
| 7,507,735 | B2 | 3/2009 | Morgan et al. |
| 8,101,617 | B2 | 1/2012 | Morgan et al. |
| 8,110,595 | B2 | 2/2012 | Morgan et al. |
| 8,445,495 | B2 | 5/2013 | Morgan et al. |
| 8,513,257 | B2 | 8/2013 | Morgan et al. |
| 8,871,768 | B2 | 10/2014 | Morgan et al. |
| 8,871,769 | B2 | 10/2014 | Morgan et al. |
| 9,150,564 | B2 | 10/2015 | Morgan et al. |
| 9,643,925 | B2 | 5/2017 | Morgan et al. |
| 9,895,308 | B2 | 2/2018 | Caldwell et al. |
| 9,951,015 | B2 | 4/2018 | Bi et al. |
| 9,988,354 | B2 | 6/2018 | Cui et al. |
| 10,035,770 | B2 | 7/2018 | Morgan et al. |
| 10,385,023 | B2 | 8/2019 | Morgan et al. |
| 10,421,726 | B2 | 9/2019 | Bi et al. |
| 10,543,215 | B2 | 1/2020 | Scott et al. |
| 10,975,034 | B2 | 4/2021 | Morgan et al. |
| 11,040,956 | B2 | 6/2021 | Caille et al. |
| 11,384,053 | B2 | 7/2022 | Bi et al. |
| 11,465,969 | B2 | 10/2022 | Morrison et al. |
| 11,472,773 | B2 | 10/2022 | Cui et al. |
| 11,576,910 | B2 | 2/2023 | Honarpour et al. |
| 11,702,380 | B2 | 7/2023 | Caille et al. |
| 11,753,394 | B2 | 9/2023 | Caille et al. |
| 11,931,358 | B2 | 3/2024 | Honarpour et al. |
| 11,958,809 | B2 | 4/2024 | Cui et al. |
| 11,986,474 | B1 | 5/2024 | Malik |
| 2006/0014761 | A1 | 1/2006 | Morgan et al. |
| 2007/0161617 | A1 | 7/2007 | Morgan et al. |
| 2009/0036447 | A1 | 2/2009 | Morgan et al. |
| 2009/0099198 | A1 | 4/2009 | Morgan et al. |
| 2010/0029680 | A1 | 2/2010 | Morgan et al. |
| 2012/0172372 | A1 | 7/2012 | Morgan et al. |
| 2013/0324549 | A1 | 12/2013 | Morgan et al. |
| 2014/0038983 | A1 | 2/2014 | Morgan et al. |
| 2014/0309235 | A1 | 10/2014 | Bi et al. |
| 2015/0005296 | A1 | 1/2015 | Morgan et al. |
| 2016/0015628 | A1 | 1/2016 | Caldwell et al. |
| 2016/0016906 | A1 | 1/2016 | Cui et al. |
| 2016/0115133 | A1 | 4/2016 | Morgan et al. |
| 2017/0267638 | A1 | 9/2017 | Morgan et al. |
| 2018/0140611 | A1 | 5/2018 | Scott et al. |
| 2018/0273479 | A1 | 9/2018 | Bi et al. |
| 2018/0305316 | A1 | 10/2018 | Morgan et al. |
| 2018/0312469 | A1 | 11/2018 | Cui et al. |
| 2019/0352267 | A1 | 11/2019 | Morgan et al. |

(Continued)

FOREIGN PATENT DOCUMENTS

| JP | 2020526483 A | 8/2020 |
| MX | 2020000190 A | 7/2020 |

(Continued)

OTHER PUBLICATIONS

International Search Report and Written Opinion mailed on Feb. 4, 2022, for PCT Application No. PCT/US2021/058988, filed on Nov. 11, 2021, 17 pages.

Liu, C.Y. et al. (Nov. 20, 2015, e-pub. Dec. 19, 2015). "Omecamtiv Mecarbil: A New Cardiac Myosin Activator for the Treatment of Heart Failure," Expert Opinion on Investigational Drugs 25(1):117-127.

Teerlink, J.R. et al. (Jul. 13, 2021, e-pub. May 17, 2021). "Effect of Ejection Fraction on Clinical Outcomes in Patients Treated With Omecamtiv Mecarbil in GALACTIC-HF," Journal of the American College of Cardiology 78(2):97-108.

(Continued)

*Primary Examiner* — Zinna Northington Davis
(74) *Attorney, Agent, or Firm* — MORRISON & FOERSTER LLP

(57) ABSTRACT

Provided herein are methods of treating heart failure in patients exhibiting one or more additional features, comprising administering to the patient a therapeutically effective amount of omecamtiv mecarbil, or a hydrate, salt, or salt of a hydrate thereof.

30 Claims, 63 Drawing Sheets

(56) References Cited

U.S. PATENT DOCUMENTS

| | | |
|---|---|---|
| 2020/0079736 A1 | 3/2020 | Cui et al. |
| 2020/0108076 A1 | 4/2020 | Scott et al. |
| 2020/0155547 A1 | 5/2020 | Honarpour et al. |
| 2020/0277261 A1 | 9/2020 | Bi et al. |
| 2020/0308143 A1 | 10/2020 | Caille et al. |
| 2020/0331859 A1 | 10/2020 | Cui et al. |
| 2020/0399221 A1 | 12/2020 | Cui et al. |
| 2021/0198203 A1 | 7/2021 | Morgan et al. |
| 2021/0221772 A1 | 7/2021 | Man et al. |
| 2021/0292271 A1 | 9/2021 | Brasola et al. |
| 2021/0371397 A1 | 12/2021 | Caille et al. |
| 2022/0042055 A1 | 2/2022 | Bisagni et al. |
| 2022/0153700 A1 | 5/2022 | Cui et al. |
| 2022/0185779 A1 | 6/2022 | Morgan et al. |
| 2022/0298099 A1 | 9/2022 | Caille et al. |
| 2022/0298114 A1 | 9/2022 | Bi et al. |
| 2022/0324808 A1 | 10/2022 | Chen et al. |
| 2023/0044617 A1 | 2/2023 | Cui et al. |
| 2023/0090391 A1 | 3/2023 | Bi et al. |
| 2023/0108971 A1 | 4/2023 | Morrison et al. |
| 2023/0149394 A1 | 5/2023 | Honarpour et al. |
| 2023/0355615 A1 | 11/2023 | Honarpour et al. |
| 2023/0373955 A1 | 11/2023 | Caille et al. |
| 2024/0101517 A1 | 3/2024 | Cui et al. |
| 2024/0199550 A1 | 6/2024 | Morrison |
| 2024/0217933 A1 | 7/2024 | Bi |

FOREIGN PATENT DOCUMENTS

| | | |
|---|---|---|
| WO | 199940942 A1 | 8/1999 |
| WO | 0032218 A1 | 6/2000 |
| WO | 2004033036 A2 | 4/2004 |
| WO | 2007133747 A2 | 11/2007 |
| WO | 2007141411 A1 | 12/2007 |
| WO | 2008130158 A1 | 10/2008 |
| WO | 2014152236 A1 | 9/2014 |
| WO | 2014152270 A1 | 9/2014 |
| WO | 2016210240 A1 | 12/2016 |
| WO | 2018144968 A1 | 9/2018 |
| WO | 2019006235 A1 | 1/2019 |
| WO | 2020011626 A1 | 1/2020 |
| WO | 2020014406 A1 | 1/2020 |
| WO | 2020020728 A1 | 1/2020 |
| WO | 2020180356 A1 | 10/2020 |
| WO | 2021053175 A1 | 3/2021 |
| WO | 2021053189 A1 | 3/2021 |
| WO | 2021070123 A1 | 4/2021 |
| WO | 2021070124 A1 | 4/2021 |
| WO | 2021092598 A1 | 5/2021 |
| WO | 2021123119 A1 | 6/2021 |
| WO | 2021136477 A1 | 7/2021 |
| WO | 2022103966 A1 | 5/2022 |
| WO | 2023205291 A2 | 10/2023 |
| WO | 2024081611 A1 | 4/2024 |

OTHER PUBLICATIONS

Ahmad, T. et al. (2019, e-pub. Aug. 13, 2019). "Why Has Positive Inotropy Failed in Chronic Heart Failure? Lessons From Prior Inotrope Trials," Eur J Heart Fail 21:1064-1078.
Allen, L.A. et al. (Apr. 2012). "Decision Making in Advanced Heart Failure: A Scientific Statement From the American Heart Association," Circulation 125(5):1928-1952.
Allen, L.A. et al. (Mar. 2014). "Hospital Variation in Intravenous Inotrope Use for Patients Hospitalized With Heart Failure: Insights From Get With the Guidelines," Circ Heart Fail. 7(2):251-260.
Ammar, K.A. et al. (Mar. 27, 2007)."Prevalence and Prognostic Significance of Heart Failure Stages," Circulation 115(12):1563-1570.
Benjamini, Y. et al. (1995). "Controlling the False Discovery Rate: A Practical and Powerful Approach to Multiple Testing," Journal of the Royal Statistical Society. Series B Methodological 57(1):289-300.
Biering-Sorensen, T. et al. (Dec. 2020). "Cardiac Myosin Activator Omecamtiv Mecarbil Improves Left Ventricular Myocardial Deformation in Chronic Heart Failure: The COSMIC-HF Trial," Circ Heart Fail 13(12):e008007, 5 pages.
Burnett, J.C. Jr. (Dec. 2019). "Atrial Natriuretic Peptide, Heart Failure and the Heart as an Endocrine Organ," Clin Chem. 65(12):1602-1603.
Butler, J. et al. (2020, e-pub. Apr. 2, 2020). "Minimal Clinically Important Difference in Quality of Life Scores for Patients With Heart Failure and Reduced Ejection Fraction," Eur J Heart Fail 22:999-1005.
Cleland, J.G.F. et al. (2018, e-pub. Oct. 10, 2017). "Beta-Blockers for Heart Failure With Reduced, Mid-Range, and Preserved Ejection Fraction: an Individual Patient-Level Analysis of Double-Blind Randomized Trials," Eur Heart J 39:26-35.
Cleland, J.G.F. et al. (Aug. 20, 2011). "The Effects of the Cardiac Myosin Activator, Omecamtivmecarbil, on Cardiac Function in Systolic Heart Failure: A Double-Blind, Placebo Controlled, Crossover, Dose-Ranging Phase 2 Trial," Lancet 378:676-683.
Cleland, J.G.F. et al. (Mar. 29, 2016). "Acute Treatment With Omecamtiv Mecarbil to Increase Contractility in Acute Heart Failure: The ATOMIC-AHF Study," J Am Coll Cardiol. 67(12):1444-1455.
Comin-Colet, J. et al. (Jul. 2018). "Efficacy and Safety of Intermittent Intravenous Outpatient Administration of Levosimendan in Patients With Advanced Heart Failure: The Lion-Heart Multicentre Randomised Trial," Eur J Heart Fail. 20(7):1128-1136.
Crespo-Leiro M.G. et al. (2018, e-pub. Jul. 17, 2018). "Advanced Heart Failure: A Position Statement of the Heart Failure Association of the European Society of Cardiology," European Journal of Heart Failure 20:1505-1535.
Cui, D. et al. (Jan. 2021). "Levosimendan Can Improve the Level of B-Type Natriuretic Peptide and the Left Ventricular Ejection Fraction of Patients With Advanced Heart Failure: A Meta-Analysis of Randomized Controlled Trials," Am J Cardiovasc Drugs 21(1):73-81.
Dewan, P. et al. (2020, e-pub. Jun. 15, 2020). Efficacy and Safety of Sodium-Glucose Co-Transporter 2 Inhibition According to Left Ventricular Ejection Fraction in DAPA-HF. Eur J Heart Fail 22:1247-1258.
Ezekowitz, J.A. et al. (Nov. 2020). "N-Terminal Pro-B-Type Natriuretic Peptide and Clinical Outcomes: Vericiguat Heart Failure With Reduced Ejection Fraction Study," JACC Heart Fail 8(11):931-939.
Fang, J.C. et al. (Jun. 2015, e-pub. May 4, 2015). "Advanced (Stage D) Heart Failure: A Statement From the Heart Failure Society of America Guidelines Committee," Journal of Cardiac Failure 21(6):519-534.
Grodin, J.L. et al. (Sep. 2019). Prognostic Implications of Changes in Amino-Terminal Pro-B-Type Natriuretic Peptide in Acute Decompensated Heart Failure: Insights From ASCEND-HF. J Card Fail. 25(9):703-711. (Accepted Manuscript).
Hardy, R.J. et al. (Mar. 30, 1996). "A Likelihood Approach to Meta-Analysis With Random Effects," Stat Med 15(6):619-629.
Haybittle, J.L. (Oct. 1971). "Repeated Assessment of Results in Clinical Trials of Cancer Treatment," Br J Radiol 44(526):793-797.
Hicks, K.A. et al. (Mar. 6, 2018). "2017 Cardiovascular and Stroke Endpoint Definitions for Clinical Trials," J Am Coll Cardiol 71(9):1021-1034.
Ibrahim, N.E. (May 2020). "Natriuretic Peptides as Inclusion Criteria in Clinical Trials: A JACC: Heart Failure Position Paper," JACC Heart Fail. 8(5):347-358.
Kotecha, D. et al. (Dec. 20, 2014). "Efficacy of B Blockers in Patients With Heart Failure Plus Atrial Fibrillation: An Individual-Patient Data Meta-Analysis," The Lancet 384(9961):2235-2243, 44 pages.
Kramer, D.G. et al. (Jul. 27, 2010). "Quantitative Evaluation of Drug or Device Effects on Ventricular Remodeling as Predictors of Therapeutic Effects on Mortality in Patients With Heart Failure and Reduced Ejection Fraction: A Meta-Analytic Approach," J Am Coll Cardiol 56(5):392-406.
Kristensen, S.L. et al. (Mar. 2019). "N-Terminal Pro-B-Type Natriuretic Peptide Levels for Risk Prediction in Patients With Heart Failure

(56) References Cited

OTHER PUBLICATIONS and Preserved Ejection Fraction According to Atrial Fibrillation Status," Circ Heart Fail. 12(3):e005766, 10pgs.

Kristensen, S.L. et al. (Oct. 2017). "Prognostic Value of N-Terminal Pro-B-Type Natriuretic Peptide Levels in Heart Failure Patients With and Without Atrial Fibrillation," Circ Heart Fail. 10(10):e004409, 9 pages.

Lee, D.S. et al. (Sep. 14, 2005). "Risk Treatment Mismatch in the Pharmacotherapy of Heart Failure," JAMA 294(10):1240-1247.

Loungani, R.S. (Jul. 2020). "Biomarkers in Advanced Heart Failure: Implications for Managing Patients With Mechanical Circulatory Support and Cardiac Transplantation," Circ Heart Fail. 13(7):e006840, 10 pages.

Malik, F.I. et al. (Mar. 18, 2011). "Cardiac Myosin Activation: A Potential Therapeutic Approach for Systolic Heart Failure," Science 331(6023):1439-1443.

Mann, D.L. et al. (Oct. 2020). "Sacubitril/Valsartan in Advanced Heart Failure With Reduced Ejection Fraction," JACC: Heart Failure 8(10):789-799.

McMurray, J.J.V. et al. (Nov. 21, 2019, e-pub. Sep. 19, 2019). "Dapagliflozin in Patients with Heart Failure and Reduced Ejection Fraction," N Engl J Med 381(21):1995-2008.

Merck Sharp & Dohme Corp. (Jan. 19, 2021). Verquvo Tablets. Center for Drug Evaluation and Research, Food and Drug Administration. Integrated Review, Application No. 2143770rig1s000, NDA 214377 Vericiguat, 10 pages.

Metra, M. et al. (2007). "Advanced Chronic Heart Failure: A Position Statement From the Study Group on Advanced Heart Failure of the Heart Failure Association of the European Society of Cardiology," European Journal of Heart Failure 9(2007):684-694.

Metra, M. et al. (2009). "Effects of Low-Dose Oral Enoximone Administration on Mortality, Morbidity, and Exercise Capacity in Patients With Advanced Heart Failure: The Randomized, Double-Blind, Placebo-Controlled, Parallel Group Essential Trials," Eur Heart J. 30:3015-3026.

Mueller, C. et al. (Jun. 2019). "Heart Failure Association of the European Society of Cardiology Practical Guidance on the Use of Natriuretic Peptide Concentrations," Eur J Heart Fail. 21(6):715-731.

Najjar, E. et al. (Jun. 2018, e-pub. Feb. 22, 2018). "Haemodynamic Effects of Levosimendan in Advanced But Stable Chronic Heart Failure," ESC Heart Fail. 5(3):302-308.

Nizamic, T. et al. (Sep. 2018). "Ambulatory Inotrope Infusions in Advanced Heart Failure: A Systematic Review and Meta-Analysis. JACC Heart failure," 6(9):757-767.

Packer, M. (Oct. 8, 2020, e-pub. Aug. 28, 2020). "Cardiovascular and Renal Outcomes with Empagliflozin in Heart Failure," N Engl J Med 383(15):1413-1424.

Packer, M. et al. (May 23, 1996). "The Effect of Carvedilol on Morbidity and Mortality in Patients with Chronic Heart Failure," N Engl J Med. 334(21):1349-1355.

Peto, R. et al. (1976). "Design and Analysis of Randomized Clinical Trials Requiring Prolonged Observation of Each Patient. I. Introduction and Design," Br J Cancer 34:585-612.

Pitt, B. et al. (Sep. 2, 1999). "The Effect of Spironolactone on Morbidity and Mortality in Patients With Severe Heart Failure. Randomized Aldactone Evaluation Study Investigators," N Engl J Med. 341(10):709-717.

Planelles-Herrero, V.J. et al. (2017). "Mechanistic and Structural Basis for Activation of Cardiac Myosin Force Production by Omecamtiv Mecarbil," Nat Commun 8(190):1-10.

Psotka, M.A. et al. (2017). "Direct Myosin Activation by Omecamtiv Mecarbil for Heart Failure with Reduced Ejection Fraction," Handb Exp Pharmacol 243:465-490, 35 pages.

Psotka, M.A. et al. (May 14, 2019). "Cardiac Calcitropes, Myotropes, and Mitotropes," J Am Coll Cardiol 73(18):2345-2353.

Rorth, R. et al. (Feb. 2020). "Comparison of BNP and NT-proBNP in Patients With Heart Failure and Reduced Ejection Fraction," Circ Heart Fail. 13(2):e006541, 10 pages.

Shen, Y.T. et al. (Jul. 2010). "Improvement of Cardiac Function by a Cardiac Myosin Activator in Conscious Dogs With Systolic Heart Failure," Circ Heart Fail 3(4):522-527.

Solomon, S.D. et al. (Dec. 13, 2005). "Influence of Ejection Fraction on Cardiovascular Outcomes in a Broad Spectrum of Heart Failure Patients," Circulation 112(24):3738-3744, 11 pages.

Solomon, S.D. et al. (Feb. 4, 2020). "Sacubitril/Valsartan Across the Spectrum of Ejection Fraction in Heart Failure," Circulation 141:352-361.

Solomon, S.D. et al. (Mar. 2016). "Influence of Ejection Fraction on Outcomes and Efficacy of Sacubitril/Valsartan (LCZ696) in Heart Failure with Reduced Ejection Fraction: The Prospective Comparison of ARNI with ACEI to Determine Impact on Global Mortality and Morbidity in Heart Failure (PARADIGM-HF) Trial," Circ Heart Fail 9(3):e002744, 10 pages.

Stewart, G.C. et al. (Nov. 9, 2016). "INTERMACS (Interagency Registry for Mechanically Assisted Circulatory Support) Profiling Identifies Ambulatory Patients at High Risk on Medical Therapy After Hospitalizations for Heart Failure," Circ Heart Fail. 9(11):1-16, 16 pages.

Tahhan, A.S. et al. (2018, e-pub. Aug. 22, 2018). "Enrollment of Older Patients, Women, and Racial and Ethnic Minorities in Contemporary Heart Failure Clinical Trials: A Systematic Review," JAMA Cardiol 3(10):1011-1019.

Teerlink, J.R. et al. (Apr. 2020). "Omecamtiv Mecarbil in Chronic Heart Failure With Reduced Ejection Fraction: Rationale and Design of GALACTIC-HF," JACC Heart Fail 8(4):329-340.

Teerlink, J.R. et al. (Aug. 20, 2011). "Dose-Dependent Augmentation of Cardiac Systolic Function With the Selective Cardiac Myosin Activator, Omecamtiv Mecarbil: A First-In-Man Study," Lancet 378(9792):667-675.

Teerlink, J.R. et al. (Dec. 10, 2016). "Chronic Oral Study of Myosin Activation to Increase Contractility in Heart Failure (COSMIC-HF): A Phase 2, Pharmacokinetic, Randomised, Placebo-Controlled Trial," Lancet 388(10062):2895-2903. (Final Accepted Version, 38 pages).

Teerlink, J.R. et al. (Jan. 14, 2021, e-pub. Nov. 13, 2020). "Cardiac Myosin Activation with Omecamtiv Mecarbil in Systolic Heart Failure," N Engl J Med. 384(2):105-116.

Teerlink, J.R. et al. (Mar. 29, 2016). "Acute Treatment With Omecamtiv Mecarbil to Increase Contractility in Acute Heart Failure: The ATOMIC-AHF Study," J Am Coll Cardiol 67(12):1444-1455.

Teerlink, J.R. et al. (Nov. 2020, e-pub. Oct. 27, 2020). "Omecamtiv Mecarbil in Chronic Heart Failure With Reduced Ejection Fraction: GALACTIC-HF Baseline Characteristics and Comparison With Contemporary Clinical Trials," Eur J Heart Fail. 22(11):2160-2171.

Troughton, R.W. et al. (Jun. 14, 2014, e-pub. Mar. 6, 2014). "Effect of B-type Natriuretic Peptide-Guided Treatment of Chronic Heart Failure on Total Mortality and Hospitalization: An Individual Patient Meta-Analysis," Eur Heart J. 35(23):1559-1567.

Unroe, K.T. et al. (2011, e-pub. Oct. 11, 2010). "Resource Use in the Last 6 Months of Life Among Medicare Beneficiaries With Heart Failure, 2000-2007," Archives of Internal Medicine 171(3):196-203.

Vaduganathan, M. et al. (Jul. 2018). "Natriuretic Peptides as Biomarkers of Treatment Response in Clinical Trials of Heart Failure," JACC Heart Fail. 6(7):564-569.

Wessler, B.S. et al. (2019, e-pub. Mar. 27, 2019). "Relation Between Therapy-Induced Changes in Natriuretic Peptide Levels and Long-Term Therapeutic Effects on Mortality in Patients With Heart Failure and Reduced Ejection Fraction," Eur J Heart Fail. 21(5):613-620.

Yancy, C.W. et al. (Oct. 15, 2013). "2013 ACCF/AHA Guideline for the Management of Heart Failure: A Report of the American College of Cardiology Foundation/American Heart Association Task Force on Practice Guidelines," JACC 62(16):e147-239, 93 pages.

Zile, M.R. et al. (Dec. 6, 2016). "Prognostic Implications of Changes in N-Terminal Pro-B-Type Natriuretic Peptide in Patients With Heart Failure," J Am Coll Cardiol. 68(22):2425-2436.

Adjei, A. et al. (Jun. 7, 1990). "Pulmonary Delivery of Peptide Drugs: Effect of Particle Size on Bioavailability of Leuprolide Acetate in Healthy Male Volunteers," Pharm Res. 7(6):565-569.

(56) References Cited

OTHER PUBLICATIONS

Ambrosy, A. P. et al. (Apr. 1, 2014, e-pub. Feb. 5, 2014). "The Global Health and Economic Burden of Hospitalizations for Heart Failure: Lessons Learned From Hospitalized Heart Failure Registries," J Am Coll Cardiol. 63(12):1123-1133.

Anonymous (Apr. 4, 2016). "Cytokinetics Announces Start of Phase 2 Clinical Trial of Omecamtiv Mecarbil in Japanese Subjects With Heart Failure," Globe Newswire, 5 pages.

Anonymous (Dec. 1, 2016). "Cytokinetics Announces Start of GALACTIC-HF, A Phase 3 Clinical Trial of Omecamtiv Mecarbil," Globe Newswire, 6 pages.

Anonymous (Mar. 13, 2015). "Cytokinetics Announces Completion of Enrollment in Cosmic-HF," Cytokinetics, Inc., 7 pages.

Anonymous (May 1, 2017). "Cytokinetics Announces Results From Dose Escalation Phase of Cosmic-HF Presented at Heart Failure 2017," Globe Newswire, 6 pages.

Anonymous (Nov. 30, 2016). "The Lancet Publishes Results From Cosmic-HF Trial Showing Omecamtiv Mecarbil Significantly Improved Cardiac Function in Patients With Chronic Heart Failure," Globe Newswire, 13 pages.

Anonymous (Oct. 27, 2015). "Amgen and Cytokinetics Announce Positive Top-Line Results From Cosmic-HF, A Phase 2 Trial of Omecamtiv Mecarbil in Patients With Chronic Heart Failure," Globe Newswire, 11 pages.

Anonymous (Sep. 1, 2016). "Cytokinetics and Amgen to Advance Omecamtiv Mecarbil to Phase 3 Clinical Development," Globe Newswire, 6 pages.

American Heart Association Editorial Staff (Last Reviewed Jun. 7, 2023). "Classes and Stages of Heart Failure," American Heart Association, Retrieved from Internet: https://www.heart.org/en/health-topics/heart-failure/what-is-heart-failure/classes-of-heart-failure, 3 pages.

Apple, F. S. et al. (Jul. 2009, e-pub. May 28, 2009). "A New Season for Cardiac Troponin Assays: It's Time to Keep a Scorecard," Clin Chem. 55(7):1303-1306.

Berge, S. et al. (Jan. 1977). "Pharmaceutical Salts," Journal of Pharmaceutical Sciences 66(1):1-19.

Bhatia, R. S. et al. (Jul. 20, 2006). "Outcome of Heart Failure With Preserved Ejection Fraction in a Population-Based Study," N Engl J Med. 355(3):260-269.

Biering-Sorensen, T. et al. (Aug. 2015). "Systolic Ejection Time is an Independent Predictor of Incident Heart Failure in a Community Based Cohort Free of Heart Failure," Journal of Cardiac Failure 21(8 Supplement):S84, 1 page.

Braunwald, E. et al. (Nov. 9, 1967). "Mechanisms of Contraction of the Normal and Failing Heart," N Engl J Med 277(19):1012-1022.

Bretz, F. et al. (Feb. 15, 2009, e-pub. Dec. 2, 2008). "A Graphical Approach to Sequentially Rejective Multiple Test Procedures," Stat Med. 28(4):586-604.

Chen, P-W. et al. (Apr. 1, 2022). "Population Pharmacokinetic Properties of Omecamtiv Mecarbil in Healthy Subjects and Patients With Heart Failure With Reduced Ejection Fraction," J Cardiovasc Pharmacol. 79(4):539-548.

Cleland, J. et al. (Aug. 5, 2008). "Predicting the Long-Term Effects of Cardiac Resynchronization Therapy on Mortality From Baseline Variables and the Early Response a Report From the CARE-HF (Cardiac Resynchronization in Heart Failure) Trial," J Am Coll Cardiol. 52(6):438-445.

Cleland, J. G. F. et al. (Nov. 10, 2009). "Plasma Concentration of Amino-Terminal Pro-Brain Natriuretic Peptide in Chronic Heart Failure: Prediction of Cardiovascular Events and Interaction With the Effects of Rosuvastatin: A Report From CORONA (Controlled Rosuvastatin Multinational Trial in Heart Failure)," J Am Coll Cardiol. 54(20):1850-1859.

clincialtrials.gov (Jun. 21, 2017). "History of Changes for Study: NCT02929329: Registrational Study With Omecamtiv Mecarbil/ AMG 423 to Treat Chronic Heart Failure With Reduced Ejection Fraction (GALACTIC-HF)," 30 pages.

clincialtrials.gov (May 15, 2017). "History of Changes for Study: NCT02695420: Safety, PK, and Efficacy of Omecamtiv Mecarbil in Japanese Subjects with Heart Failure With Reduced Ejection Fraction," 6 pages.

clinicaltrials.gov (May 5, 2016 copy attached; downloaded from the web Nov. 19, 2021). "NCT01786512—COSMIC-HF—Chronic Oral Study of Myosin Activation to Increase Contractility in Heart Failure," 10 pages.

Cytokinetics. (2022). "Empowering Muscle Empowering Lives. Sarcomere Directed Therapies," Cytokinetics 2022, 58 pages.

Dasgupta, A. et al. (2008). "Analytical Techniques for Measuring Concentrations of Therapeutic Drugs in Biological Fluids," Chapter 3 in Handbook of Drug Monitoring Methods, Humana Press, pp. 67-86.

Deluca, P. P. et al. (1982). "Parenteral Drug-Delivery Systems," Chapter 8 in Pharmaceutics and Pharmacy Practice, J. B. Lippincott Company, pp. 238-250, 16 pages.

Dickstein, K. et al. (Oct. 2008, e-pub. Sep. 17, 2008). "ESC Guidelines for the Diagnosis and Treatment of Acute and Chronic Heart Failure 2008: The Task Force for the Diagnosis and Treatment of Acute and Chronic Heart Failure 2008 of the European Society of Cardiology. Developed in Collaboration With the Heart Failure Association of the ESC (HFA) and Endorsed by the European Society of Intensive Care Medicine (ESICM)," Eur Heart J. 29(19):2388-2442, 55 pages.

Go, A. S. et al. (Jan. 1, 2013, e-pub. Dec. 12, 2012). "Heart Disease and Stroke Statistics—2013 Update: A Report From the American Heart Association," Circulation 127(1):e6-e245, 489 pages.

Greenberg, B. H. et al. (Jan. 2015, e-pub. Nov. 11, 2014). "Safety and Tolerability of Omecamtiv Mecarbil During Exercise in Patients With Ischemic Cardiomyopathy and Angina," JACC Heart Fail. 3(1):22-29.

Greene, S. J. et al. (Apr. 2015, e-pub. Feb. 10, 2015). "The Vulnerable Phase After Hospitalization for Heart Failure," Nat Rev Cardiol. 12(4):220-229.

Hampton, J. R. et al. (Apr. 5, 1997). "Randomised Study of Effect of Ibopamine on Survival in Patients With Advanced Severe Heart Failure. Second Prospective Randomised Study of Ibopamine on Mortality and Efficacy (PRIME II) Investigators," Lancet. 349(9057):971-977.

Hasenfuss, G. et al. (Aug. 2011, e-pub. Mar. 8, 2011). "Cardiac Inotropes: Current Agents and Future Directions," Eur Heart J. 32(15):1838-1845.

Hicks, K. A. et al. (Jul. 28, 2015, e-pub. Dec. 29, 2014). "2014 ACC/AHA Key Data Elements and Definitions for Cardiovascular Endpoint Events in Clinical Trials: A Report of the American College of Cardiology/American Heart Association Task Force on Clinical Data Standards (Writing Committee to Develop Cardiovascular Endpoints Data Standards)," J Am Coll Cardiol. 66(4):403-469.

Hilfiker-Kleiner, D. et al. (Nov. 7, 2006). "Molecular Mechanisms in Heart Failure: Focus on Cardiac Hypertrophy, Inflammation, Angiogenesis, and Apoptosis," J Am Coll Cardiol. 48(9 Suppl. A):A56-A66.

International Preliminary Report on Patentability mailed on May 16, 2023, for PCT Application No. PCT/US2021/058988, filed on Nov. 11, 2021, 7 pages.

International Preliminary Report on Patentability, issued on Dec. 31, 2019, for PCT Application No. PCT/US2018/040181, filed on Jun. 29, 2018, 7 pages.

International Search Report and Written Opinion mailed on Feb. 2, 2024, for PCT Application PCT/US2023/076419, filed on Oct. 10, 2023, 14 pages.

International Search Report and Written Opinion of the International Searching Authority, mailed Sep. 27, 2018, for PCT Application No. PCT/US2018/040181, filed on Jun. 29, 2018, 10 pages.

Jencks, S. F. et al. (Apr. 2, 2009). "Rehospitalizations Among Patients in the Medicare Fee-For-Service Program," N Engl J Med. 360(14):1418-1428.

Jessup, M. et al. (May 15, 2003). "Heart Failure," N Engl J Med. 348(20):2007-2018.

Kang, J. S. et al. (Mar. 2009). "Overview of Therapeutic Drug Monitoring," Korean J Intern Med. 24(1):1-10.

(56) References Cited

OTHER PUBLICATIONS

Kannankeril, P.J. et al. (Nov. 15, 2002). "Usefulness of Troponin I as a Marker of Myocardial Injury After Pediatric Cardiac Catheterization," Am J Cardiol. 90(10):1128-1132.

Kawashima, Y. et al. (Nov. 1, 1999). "Pulmonary Delivery of Insulin With Nebulized DL-Lactide/Glycolide Copolymer (PLGA) Nanospheres to Prolong Hypoglycemic Effect," J Control Release 62(1-2):279-287.

Klinkenberg, L. J. J. et al. (May 6, 2014, e-pub. Feb. 26, 2014). "Circulating Cardiac Troponin T Exhibits A Diurnal Rhythm," J Am Coll Cardiol. 63(17):1788-1795.

Krum, H. et al. (Aug. 20, 2011). "Medical Therapy for Chronic Heart Failure," Lancet. 378(9792):713-721.

Levy, W. C. et al. (Mar. 21, 2006, e-pub. Mar. 13, 2006). "The Seattle Heart Failure Model: Prediction of Survival in Heart Failure," 113(11):1424-1433.

Liu, F. Y. et al. (Feb. 1993). "Pulmonary Delivery of Free and Liposomal Insulin," Pharm Res. 10(2):228-232.

Lopez-Sendon, J. (Jan. 2011). "The Heart Failure Epidemic," Medicographia 33(4):363-369.

Malik, F.I. et al. (Oct. 2011, e-pub. May 17, 2011). "Cardiac Myosin Activation Part 1: From Concept to Clinic," J Mol Cell Cardiol. 51(4):454-461.

McLlvennan, C. K. et al. (Dec. 2014, e-pub. Aug. 20, 2014). "Outcomes in Acute Heart Failure: 30-Day Readmission Versus Death," Curr Heart Fail Rep. 11(4):445-452.

Mozaffarian, D. et al. (Jul. 24, 2007, e-pub. Jul. 9, 2007). "Prediction of Mode of Death in Heart Failure: the Seattle Heart Failure Model," Circulation 116(4):392-398.

Nagy, L. et al. (Sep. 2014). "Inotropes and Inodilators for Acute Heart Failure: Sarcomere Active Drugs in Focus," J Cardiovasc Pharmacol. 64(3):199-208.

Packer, M. (Jul. 15, 1993). "The Search for the Ideal Positive Inotropic Agent," N Engl J Med. 329(3):201-202.

Packer, M. et al. (Nov. 21, 1991). "Effect of Oral Milrinone on Mortality in Severe Chronic Heart Failure. The Promise Study Research Group," N Engl J Med. 325(21):1468-1475.

Palaparthy, R. et al. (Mar. 1, 2016, e-pub. Dec. 28, 2015). "Relative Bioavailability, Food, Effect and Safety of the Single-Dose Pharmacokinetics of Omecamtiv Mecarbil Following Administration of Different Modified-Release Formulations in Healthy Subjects," International Journal of Clinical Pharmacology and Therapeutics 54(3):217-227.

Ponikowski, P. et al. (Aug. 2016, e-pub. May 20, 2016). "2016 ESC Guidelines for the Diagnosis and Treatment of Acute and Chronic Heart Failure: The Task Force for the Diagnosis and Treatment of Acute and Chronic Heart Failure of the European Society of Cardiology (ESC). Developed With the Special Contribution of the Heart Failure Association (HFA) of the ESC," Eur J Heart Fail. 18(8):891-975.

Qian, F. et al. (Jan. 21, 2009, e-pub. Nov. 5, 2008). "Pulmonary Delivery of a GLP-1 Receptor Agonist, BMS-686117," Int J Pharm 366(1-2):218-220.

Qian, F. et al. (Jun. 5, 2009, e-pub. Mar. 19, 2009). "Sustained Release Subcutaneous Delivery of BMS-686117, a GLP-1 Receptor Peptide Agonist, via a Zinc Adduct," Int J Pharm. 374(1-2):46-52.

Rahimi, K. et al. (Oct. 2014, e-pub. Sep. 3, 2014). "Risk Prediction in Patients With Heart Failure: A Systematic Review and Analysis," JACC Heart Fail 2(5):440-446.

Shave, R. et al. (Jul. 13, 2010). "Exercise-Induced Cardiac Troponin Elevation: Evidence, Mechanisms, and Implications," J Am Coll Cardiol. 56(3):169-176.

Shih, J. H. (Dec. 1995). "Sample Size Calculation for Complex Clinical Trials With Survival Endpoints," Control Clin Trials. 16(6):395-407.

Solomon, S. D. et al. (Oct. 12, 2004, e-pub. Oct. 4, 2004). "Effect of Candesartan on Cause-Specific Mortality in Heart Failure Patients: The Candesartan in Heart Failure Assessment of Reduction in Mortality and Morbidity (CHARM) Program," Circulation 110(15):2180-2183.

Solomon, S. D. et al. (Sep. 7, 2010, e-pub. Aug. 23, 2010). "Effect of Cardiac Resynchronization Therapy on Reverse Remodeling and Relation to Outcome: Multicenter Automatic Defibrillator Implantation Trial: Cardiac Resynchronization Therapy," Circulation 122(10):985-992.

Steijns, L. S. W. et al. (Jun. 2002). "Evaluation of Fluorescence Polarization Assays for Measuring Valproic Acid, Phenytoin, Carbamazepine and Phenobarbital in Serum," Ther Drug Monit. 24(3):432-435.

Tacon, C. L. et al. (Mar. 2012, e-pub. Dec. 8, 2011). "Dobutamine for Patients With Severe Heart Failure: A Systematic Review and Meta-Analysis of Randomised Controlled Trials," Intensive Care Med. 38(3):359-367.

Teerlink, J.R. et al. (2016). "Online Appendix: Acute Treatment With Omecamtiv Mecarbil to Increase Contractility in Acute Heart Failure: the ATOMIC AHF Study," J. Am. Coll. Cardiol. 67:1444-1455, Appendix, 16 pages.

Teerlink, J.R. et al. (May 2014). "Chronic Oral Study of Myosin Activation to Increase Contractility in Heart Failure (COSMIC-HF): Improved Contractility and Evolution of Ventricular Remodelling Through Time," European Society of Cardiology—Heart Failure, 1 pages.

Thygesen, K. et al. (Oct. 16, 2012, e-pub. Sep. 5, 2012). "Third Universal Definition of Myocardial Infarction," J Am Coll Cardiol 60(16):1581-1598.

Trissel, L. A. et al. (1986). "Intravenous Infusion Solutions," ASHP Handbook on Injectable Drugs, 4th ed., pp. 622-630.

U.S. Appl. No. 15/898,303, filed Feb. 16, 2018, by William Brett Caldwell et al. (U.S. Patent Application is not submitted herewith pursuant to the waiver of 37 C.F.R. § 1.98(a)(2)(iii) issued by the Office on Sep. 21, 2004.).

U.S. Appl. No. 17/176,003, filed Feb. 15, 2021, by Sheng Cui et al. (U.S. Patent Application is not submitted herewith pursuant to the waiver of 37 C.F.R. § 1.98(a)(2)(iii) issued by the Office on Sep. 21, 2004.).

U.S. Appl. No. 18/342,387, filed Jun. 27, 2023, by Fady Malik et al. (U.S. Patent Application is not submitted herewith pursuant to the waiver of 37 C.F.R. § 1.98(a)(2)(iii) issued by the Office on Sep. 21, 2004.).

U.S. Appl. No. 18/416,741, filed Jan. 18, 2024, by Henry Morrison et al. (U.S. Patent Application is not submitted herewith pursuant to the waiver of 37 C.F.R. § 1.98(a)(2)(iii) issued by the Office on Sep. 21, 2004.).

U.S. Appl. No. 18/421,849, filed Jan. 24, 2024, by Shang Cui et al. (U.S. Patent Application is not submitted herewith pursuant to the waiver of 37 C.F.R. § 1.98(a)(2)(iii) issued by the Office on Sep. 21, 2004.).

U.S. Appl. No. 18/531,424, filed Dec. 6, 2023, by Mingda Bi et al. (U.S. Patent Application is not submitted herewith pursuant to the waiver of 37 C.F.R. § 1.98(a)(2)(iii) issued by the Office on Sep. 21, 2004.).

Vu, T. et al. (Nov. 2015, e-pub. Jul. 14, 2015). "Population Pharmacokinetic-Pharmacodynamic Modeling of Omecamtiv Mecarbil, a Cardiac Myosin Activator, in Healthy Volunteers and Patients With Stable Heart Failure," J Clin Pharmacol. 55(11):1236-1247.

Waldenstrom, A. et al. (Jan. 17, 2014). "Role of Exosomes in Myocardial Remodeling," Circ Res. 114(2):315-324.

Wang, G-F. et al. (Nov. 2008). "Measurement of Plasma Concentration and Bioavailability of Nolatrexed Dihydrochloride in Mice," J South Med Univ 28(11):1993-1995, with English Abstract.

Weissler, A. M. et al. (Feb. 1968). "Systolic Time Intervals in Heart Failure in Man," Circulation 37(2):149-159.

Wu, S-N. et al. (2022). "Omecamtiv Mecarbil Treatment Improves Post-Resuscitation Cardiac Function and Neurological Outcome in a Rat Model," Plos One 17(2):e0264165, 12 pages.

Yancy, C. W. et al. (Oct. 15, 2013, e-pub. Jun. 5, 2013). "2013 ACCF/AHA Guideline for the Management of Heart Failure: A Report of the American College of Cardiology Foundation/American Heart Association Task Force on Practice Guidelines," Circulation 128(16):e240-e327.

Yancy, C. W. et al. (Sep. 27, 2016, e-pub. May 20, 2016). "2016 ACC/AHA/HFSA Focused Update on New Pharmacological Therapy for Heart Failure: An Update of the 2013 ACCF/AHA Guideline for

(56) References Cited

OTHER PUBLICATIONS the Management of Heart Failure: A Report of the American College of Cardiology/American Heart Association Task Force on Clinical Practice Guidelines and the Heart Failure Society of America," Circulation 134(13):e282-e293.
Biering-Sorensen, T. et al. (Nov. 11, 2019). "The Effect of the Cardiac Myosin Activator, Omecamtiv Mecarbil, on Diastolic Filling and Function in Chronic Systolic Heart Failure (COSMIC-HF)", Circ. 140(Suppl1): A14405, 2 pages.
Butzner, M. et al. (May 2020). "Medical Therapy Side Effects Across Heart Failure Patients With Reduced Ejection Fraction: A Systematic Literature Review", Value in Health 23(Suppl1):S91, 1 page.
Chen, P. et al. (Sep. 6, 2021). "Model-based Analysis of Omecamtiv Mecarbil Pharmacokinetics Properties," Presented at 2021 Annual Meeting American College of Clinical Pharmacology, Sep. 13, 2021, Poster 100, Clin Pharmacol Drug Dev. 10(S1):83-84.
Cohen, S.S. et al. (Oct. 2020). "Characteristics and Outcomes of a Real-world Population with Heart Failure with Reduced Ejection Fraction Representative of Clinical Trial Patients", J Card. Fail. 26(10):S82, p. 1.
Desai, N.R. et al. (Mar. 8, 2022). "Healthcare Resource Use, Intensity and Costs Among Patients with Heart Failure with Reduced Ejection Fraction Treated with Omecamtiv Mecarbil in GALACTIC-HF", J. Am. Coll Cardiol. 79(9):309, Abstract, 1 page.
Desai, N.R. et al. (Oct. 30, 2022). "Healthcare Resource Use, Early Benefit and Cost for North American Patients With HFrEF Most Likely to Benefit From Omecamtiv Mecarbil", Circ. 146(Suppl1):Abstract 11481, 2 pages.
Docherty, K.F. et al. (Mar. 8, 2022). "The Effect of Omecamtiv Mecarbil in Hospitalized Patients as Compared with Outpatients: a Prespecified Analysis of GALACTIC-HF," J. Am. Coll. Cardiol. 79(9):310, Abstract, 1 page.
European Examination Report dated Apr. 17, 2024, for European Examination No. 18745732.0, filed on Jan. 17, 2020, 4 pages.
Morgan, B. et al. (Aug. 19, 2018). "Discovery and Development of Omecamtiv Mecarbil—a Novel Cardiac Myosin Activator for the Potential Treatment of Systolic Heart Failure," Abstract, ACS Fall 2018, as posted on https://scimeetings.acs.org/exhibit/Discovery-development-omecamtiv-mecarbilnovel-cardiac/2974670, last visited on Jun. 5, 2024, 1 page.
Pabon, M et al. (Oct. 30, 2022). "Sex Differences in Heart Failure with Reduced Ejection Fraction in the GALACTIC-HF Trial," Circ. 146(Suppl1): Abstract 13640, 1 page.
Riskin, D. et al. (Nov. 12, 2020). "Enabling Advanced Real-world Evidence in Heart Failure: A Pilot Study Defining Preferred Approaches to Electronic Health Record Data Use," Circ. 142(Suppl3): Abstract 13797, 2 pages.
Teerlink, J.R. et al. (Dec. 21, 2021). "The Effect of Omecamtiv Mecarbil on Stroke in Patients With Heart Failure and Reduced Ejection Fraction in GALACTIC-HF," Circ. 144(25):e582, Abstract 16605, 1 page.
Teerlink, J.R. et al. (Jan. 14, 2021, e-pub. Nov. 13, 2020). "Supplementary Appendix. Cardiac Myosin Activation with Omecamtiv Mecarbil in Systolic Heart Failure," N Engl J Med. 384(2):1-55.
Teerlink, J.R. et al. (Mar. 12, 2019). "Effect of Omecamtiv Mecarbil in Patients with Atrial Fibrillation and Heart Failure with Reduced Ejection Fraction: Results from COSMIC-HF," JACC 73(9):691.
Trivedi, A. et al. (Sep. 6, 2021). "Effect of Varying Degrees of Hepatic Impairment on the Pharmacokinetics of Omecamtiv Mecarbil," Presented at 2021 Annual Meeting American College of Clinical Pharmacology, Sep. 13, 2021, Poster 111, Clin Pharmacol Drug Dev. 10(S1):94.

Trivedi, A. et al. (Sep. 6, 2021). "Effect of Varying Degrees of Renal Impairment on the Pharmacokinetics of Omecamtiv Mecarbil," Presented at 2021 Annual Meeting American College of Clinical Pharmacology, Sep. 13, 2021, Poster 112, Clin Pharmacol Drug Dev. 10(S1):94-95.
Trivedi, A. et al. (Sep. 6, 2021). "Omecamtiv Mecarbil Does Not Prolong QTc Intervals at Therapeutic Concentrations," Presented at 2021 Annual Meeting American College of Clinical Pharmacology, Sep. 13, 2021, Poster 021, Clin Pharmacol Drug Dev. 10(S1):17-18.
Trivedi, A. et al. (Sep. 6, 2021). "Pharmacokinetic Drug-Drug Interaction Study of Ome-camtiv Mecarbil With MATE1/MATE2-K Substrate Metformin in Healthy Subjects," Presented at 2021 Annual Meeting American College of Clinical Pharmacology, Sep. 13, 2021, Poster 034, Clin Pharmacol Drug Dev. 10(S1):26.
Trivedi, A. et al. (Sep. 6, 2021). "Pharmacokinetic Drug-Drug Interaction Study of Omecamtiv Mecarbil With Amiodarone in Healthy Subjects," Presented at 2021 Annual Meeting American College of Clinical Pharmacology, Sep. 13, 2021, Poster 032, Clin Pharmacol Drug Dev. 10(S1):25.
Trivedi, A. et al. (Sep. 6, 2021). "Pharmacokinetic Drug-Drug Interaction Study of Omecamtiv Mecarbil with Breast Cancer Resistance Protein Substrate, Rosuvastatin, in Healthy Subjects," Presented at 2021 Annual Meeting American College of Clinical Pharmacology, Sep. 13, 2021, Poster 033, Clin Pharmacol Drug Dev. 10 (S1):25-26.
Trivedi, A. et al. (Sep. 6, 2021). "Pharmacokinetic Drug-Drug Interaction Study of Omecamtiv Mecarbil With Midazolam, a CYP3A4 Sensitive Index Substrate, in Healthy Subjects," Presented at 2021 Annual Meeting American College of Clinical Pharmacology, Sep. 13, 2021, Poster 035, Clin Pharmacol Drug Dev. 10(S1):26-27.
Trivedi, A. et al. (Sep. 6, 2021). "Pharmacokinetic Drug-Drug Interaction Study of Omecamtiv Mecarbil with P-glycoprotein Substrate Digoxin in Healthy Subjects," Presented at 2021 Annual Meeting American College of Clinical Pharmacology, Sep. 13, 2021, Poster 036, Clin Pharmacol Drug Dev. 10(S1):27.
Trivedi, A. et al. (Sep. 6, 2021). "Pharmacokinetic Drug-Drug Interaction Study of Omecamtiv Mecarbil With Proton Pump Inhibitor, Omeprazole in Healthy Subjects," Presented at 2021 Annual Meeting American College of Clinical Pharmacology, Sep. 13, 2021, Poster 022, Clin Pharmacol Drug Dev. 10(S1):18-19.
Trivedi, A. et al. (Sep. 6, 2021). "Pharmacokinetics, Disposition & Biotransformation of [14C]-Omecamtiv Mecarbil in Healthy Male Subjects After a Single Intravenous or Oral Dose," Presented at 2021 Annual Meeting American College of Clinical Pharmacology, Sep. 13, 2021, Poster 084, Clin Pharmacol Drug Dev. 10(S1):69.
Trivedi, A. et al. (Sep. 6, 2021). "Relative Bioavailability of Omecamtiv Mecarbil Pediatric Minitablet Formulations in Healthy Subjects," Presented at 2021 Annual Meeting American College of Clinical Pharmacology, Sep. 13, 2021, Poster 015, Clin Pharmacol Drug Dev. 10(S1):13-14.
Trivedi, A. et al. (Sep. 6, 2021). "Switchability & Minimal Effect of Food on Pharmacokinetics of Modified-release Tablet Strengths of Omecamtiv Mecarbil, a Cardiac Myosin Activator," Presented at 2021 Annual Meeting American College of Clinical Pharmacology, Sep. 13, 2021, Poster 016, Clin Pharmacol Drug Dev. 10(S1):14-15.
U.S. Appl. No. 18/642,005, filed Apr. 22, 2024, by Fady Malik et al. (U.S. Patent Application is not submitted herewith pursuant to the waiver of 37 C.F.R. § 1.98(a)(2)(iii) issued by the Office on Sep. 21, 2004.).
International Search Report mailed on Jul. 19, 2024, for PCT Application No. PCT/US2024/025668, filed on Apr. 22, 2024, 15 pages.
MSD Manual Editorial Staff. "New York Heart Association (NYHA) Classification of Heart Failure," XP93180881, MSD Manual Professional Version, Retrieved from Internet: https://www.msdmanuals.com/professional/multimedia/table/new-york-heart-association-nyha-classification-of-heart-failure, last visited Jul. 2, 2024, 3 pages.

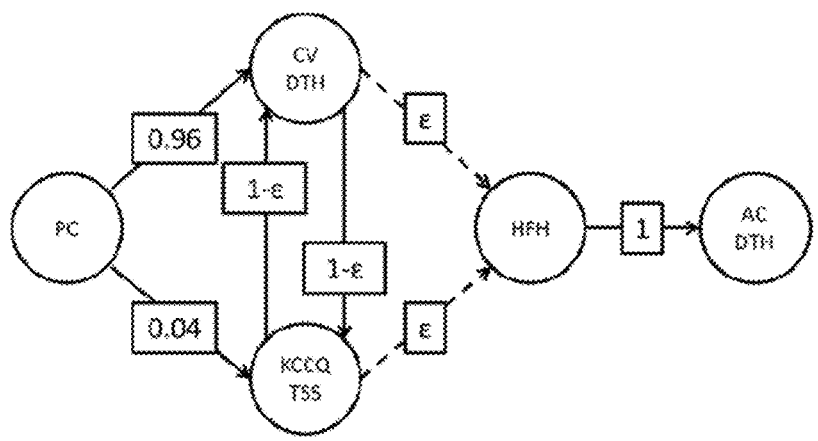

PC = primary composite endpoint; CV DTH = time to CV death; KCCQ TSS = Kansas City Cardiomyopathy Questionnaire Total Symptom Score; HFH = time to first heart failure hospitalization; AC DTH = time to all-cause death.

Each circle represents a hypothesis test. The values in boxes on the arrows indicate the fraction of α propagated in the direction of the arrow to the next hypothesis test(s). ε = 0.0001, a small value to complete the graph while prioritizing the CV death and KCCQ TSS endpoints over the time to first heart failure hospitalization and all-cause death endpoints. Dashed arrows used to emphasize this prioritization.

No multiplicity adjustment will be made for exploratory or sensitivity analyses.

FIGURE 3

BID = twice a day; ED = emergency department; EOS = end of study; ER = emergency room; HF = heart failure; HFrEF = heart failure with reduced ejection fraction; IP = investigational product; PK = pharmacokinetics; PO = by mouth; Q16W = every 16 weeks; SoC = standard of care;

METHODS OF TREATING HEART FAILURE BY ADMINISTERING OMECAMTIV MECARBIL

CROSS-REFERENCE TO RELATED APPLICATIONS

This application claims priority to and benefit of U.S. Provisional Patent Application No. 63/112,995, filed Nov. 12, 2020, U.S. Provisional Patent Application No. 63/154,077, filed Feb. 26, 2021, U.S. Provisional Patent Application No. 63/187,084, filed May 11, 2021, U.S. Provisional Patent Application No. 63/202,873, filed Jun. 28, 2021, and U.S. Provisional Patent Application No. 63/203,436, filed Jul. 22, 2021, the disclosures of which are hereby incorporated herein by reference in their entireties.

BACKGROUND

The cardiac sarcomere is the basic unit of muscle contraction in the heart. The cardiac sarcomere is a highly ordered cytoskeletal structure composed of cardiac muscle myosin, actin and a set of regulatory proteins. The discovery and development of small molecule cardiac muscle myosin activators would lead to promising treatments for acute and chronic heart failure. Cardiac muscle myosin is the cytoskeletal motor protein in the cardiac muscle cell. It is directly responsible for converting chemical energy into the mechanical force, resulting in cardiac muscle contraction.

Current positive inotropic agents, such as beta-adrenergic receptor agonists or inhibitors of phosphodiesterase activity, increase the concentration of intracellular calcium, thereby increasing cardiac sarcomere contractility. However, the increase in calcium levels increase the velocity of cardiac muscle contraction and shortens systolic ejection time, which has been linked to potentially life-threatening side effects. In contrast, cardiac muscle myosin activators work by a mechanism that directly stimulates the activity of the cardiac muscle myosin motor protein, without increasing the intracellular calcium concentration. They accelerate the rate-limiting step of the myosin enzymatic cycle and shift it in favor of the force-producing state. Rather than increasing the velocity of cardiac contraction, this mechanism instead lengthens the systolic ejection time, which results in increased cardiac muscle contractility and cardiac output in a potentially more oxygen-efficient manner.

A characteristic of heart failure with reduced ejection fraction is decreased systolic function leading to reduce cardiac output and increased filling pressures. To date, no drugs directly addressing systolic function have improved outcomes. Cardiac myosin activators are a class of myotropes that improve myocardial function by directly augmenting cardiac sarcomere function. Omecamtiv mecarbil, augments cardiac contractility by selectively binding to cardiac myosin increasing the number of force generators (myosin heads) that can bind to the actin filament and undergo a powerstroke once the cardiac cycle starts. In early clinical studies using short-term intravenous administration, omecamtiv mecarbil improved cardiac performance. In patients with chronic heart failure with reduced ejection fraction, treatment with omecamtiv mecarbil for 20 weeks increased left ventricular systolic function, decreased left ventricular systolic and diastolic volumes suggestive of beneficial reverse cardiac remodeling, and reduced natriuretic peptide concentrations and heart rate.

U.S. Pat. No. 7,507,735, herein incorporated by reference, discloses a genus of compounds, including omecamtiv mecarbil (AMG 423, CK-1827452), having the structure:

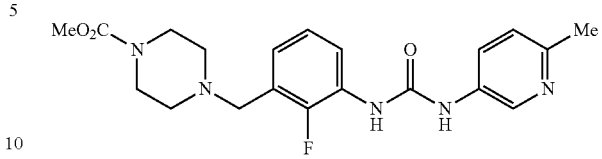

Omecamtiv mecarbil (OM) is a first in class direct activator of cardiac myosin that directly targets the contractile mechanisms of cardiac myocytes intended to enhance efficiency of myocardial contraction in patients suffering from a cardiovascular condition, such as heart failure.

Many therapies have been developed that improve cardiovascular outcomes in patients with heart failure with reduced ejection fraction (HFrEF). However, none of the currently available drugs directly improve the central defect of HFrEF, reduced systolic function. Moreover, severe impairment of systolic function is often associated with lower blood pressure and greater difficulty tolerating target doses of guideline-directed medical therapies. Myotropes represent a new class of drugs that improve myocardial function by directly augmenting cardiac sarcomere function. The cardiac myosin activator, omecamtiv mecarbil, is the first of this class and it increases systolic function by selectively facilitating the actin-myosin interaction, increasing contractile force without altering the cardiomyocyte calcium transient.

Despite significant improvements in prognosis with contemporary medical therapy, HF with reduced ejection fraction (HFrEF) remains a progressive clinical syndrome and many patients develop worsening over time despite optimal guideline-based treatment. The nomenclature to describe such patients is varied and includes "advanced HF", "severe HF", "refractory HF", or "Stage D HF". Regardless of terminology, these patients have a high burden of symptoms, recurrent HF hospitalizations, high mortality, and account for a large proportion of the total costs of HF care. As HF progresses, many patients become progressively intolerant of neuro-hormonal blockade with beta-blockers or renin-angiotensin-aldosterone system (RAAS) modulators due to hypotension or renal dysfunction, limiting their options for medical therapy. Selected patients with advanced HF may be candidates for other therapies such as cardiac transplantation or mechanical cardiac support, but these therapies are costly, highly invasive, and have limited availability. Intravenous inotropic therapy can be used for palliation of symptoms in selected patients but may be associated with increased mortality. Thus, there is a clear unmet need for effective and safe chronic medical therapies for patients with more advanced stages of HF.

The identification of safe drugs that increase cardiac performance has been a goal of heart failure therapeutics for more than a century, yet those that have been developed have consistently increased the incidence of myocardial ischemia, ventricular arrhythmias, or death due to their mechanism increasing intracellular calcium transients. As a selective cardiac myosin activator, omecamtiv mecarbil has been shown to have no effect on these transients.

Despite prior developments in this area, there remains a need for treating heart failure in patients.

SUMMARY

Provided herein are methods of treating heart failure in a patient having a left ventricular ejection fraction (LVEF) of less than 35% (such as less than 30%, less than 28%, less than 25%, or less than 22%) comprising administering to the patient a therapeutically effective amount of omecamtiv mecarbil as described herein.

Also provided herein are methods of treating heart failure in a patient who does not exhibit atrial fibrillation or atrial flutter comprising administering to the patient a therapeutically effective amount of omecamtiv mecarbil as described herein.

Also provided herein are methods of treating heart failure in a patient having heart failure classified as Class III or IV as determined using the New York Heart Association (NYHA) classification comprising administering to the patient a therapeutically effective amount of omecamtiv mecarbil as described herein.

Also provided herein are methods of treating heart failure in a patient having advanced heart failure comprising administering to the patient a therapeutically effective amount of omecamtiv mecarbil as described herein.

The disclosure further provides methods of treating ischemic heart failure in a patient comprising administering to the patient a therapeutically effective amount of omecamtiv mecarbil as described herein.

Also provided herein are methods of treating heart failure in a patient who has had a myocardial infarction comprising administering to the patient a therapeutically effective amount of omecamtiv mecarbil as described herein.

Also provided herein are methods of treating heart failure in a patient having a NT-proBNP level of at least 2,000 pg/mL prior to start of omecamtiv mecarbil treatment comprising administering to the patient a therapeutically effective amount of omecamtiv mecarbil as described herein.

Also provided herein are methods of treating heart failure in a patient who has low blood pressure, symptomatic hypotension, impaired renal function, or bradycardia comprising administering to the patient a therapeutically effective amount of omecamtiv mecarbil as described herein.

Also provided herein are methods of treating heart failure in a patient who is unable to tolerate one or more of angiotensin-converting enzyme inhibitors, angiotensin II receptor blockers, beta blockers, diuretics, aldosterone antagonists, inotropes, neprilysin inhibitors, digitalis, and digoxin comprising administering to the patient a therapeutically effective amount of omecamtiv mecarbil as described herein.

Also provided herein is a method of preventing stroke in a patient suffering from heart failure with reduced ejection fraction (HFrEF) comprising administering to the patient a therapeutically effective amount of omecamtiv mecarbil as described herein.

BRIEF DESCRIPTION OF THE FIGURES

FIG. 10 shows the incidence of heart failure events in the patient population evaluated.

FIG. 3 shows a multiplicity testing propagation approach.

DETAILED DESCRIPTION

Figure 1A:
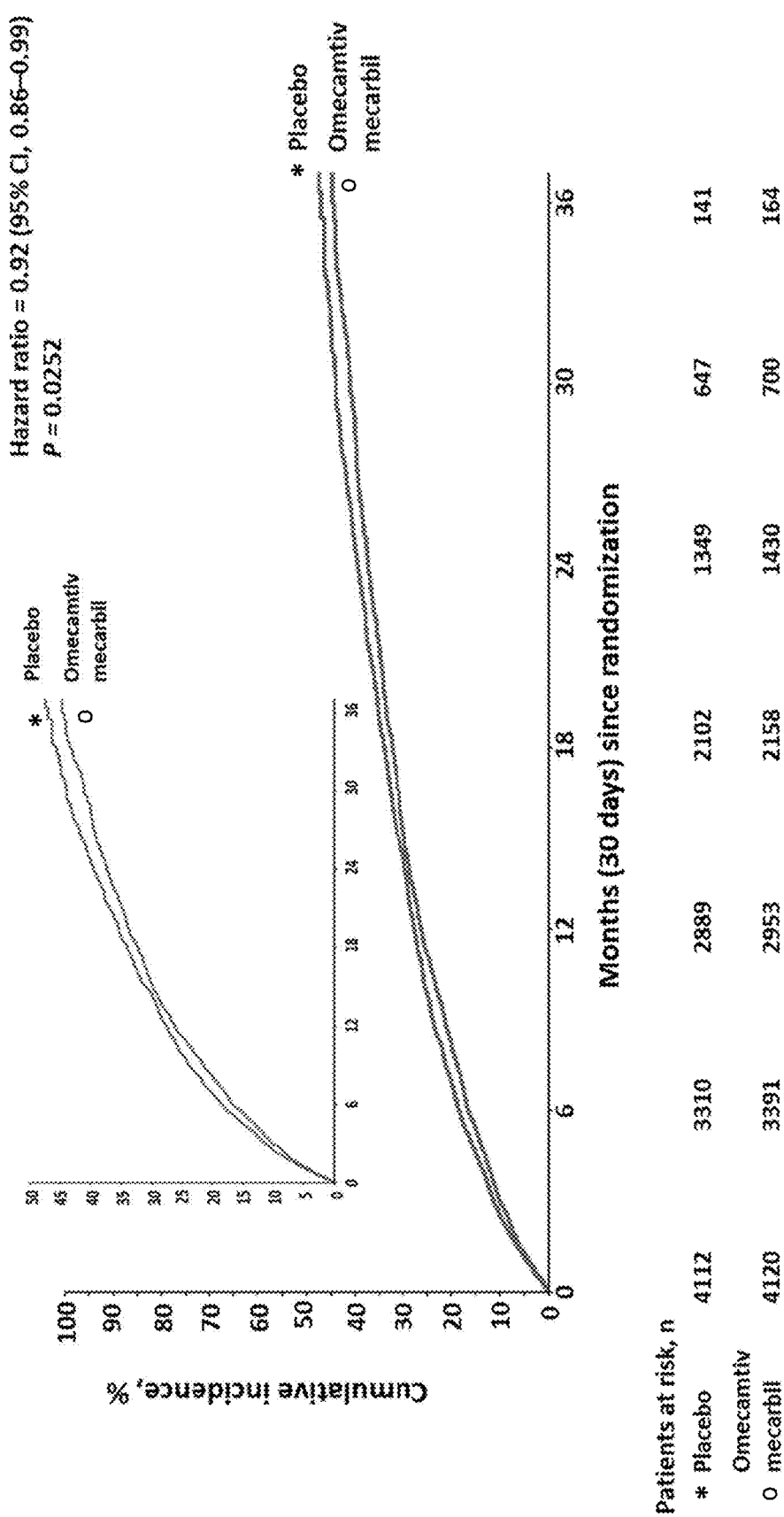
FIG. 1A shows the primary endpoint in the patient population evaluated, wherein the primary endpoint was the composite of time to a heart failure event or cardiovascular death, whichever occurred first.

The present disclosure provides methods of treating heart failure in a patient comprising administering to the patient a therapeutically effective amount of omecamtiv mecarbil as described herein. In various cases, the methods disclosed herein include, e.g., treating heart failure in patients having other cardiovascular conditions, such as patients having left ventricular ejection fraction (LVEF) of less than 28%, patients who do not exhibit atrial fibrillation or atrial flutter, patients having heart failure classified as Class III or IV as determined by New York Heart Association classification, patients having ischemic heart failure, patients who have had a myocardial infarction, patients having a NT-proBNP level greater than median, or patients having reduced ejection fraction (HFrEF).

The present disclosure provides methods of treating patients with heart failure and reduced ejection fraction receiving guideline-based medical and device therapy. In addition, the disclosed methods provide a statistically significant reduction in the risk of the primary composite outcome of a heart failure event or death from cardiovascular causes. This effect is evident after approximately 3 months of treatment and persists for a period of time (e.g., 3 years post treatment) without evidence of an increase in the risk of myocardial ischemic events, ventricular arrhythmias or death from cardiovascular or all causes. As described herein, a patient undergoing a method as disclosed herein can exhibit a reduction in NT-proBNP levels, compared to placebo.

The patients treated by the disclosed methods exhibit approximately the same rates of myocardial ischemia, ventricular arrhythmias and death between treatment groups through almost 7,500 patient-years of follow-up, which suggests that treatment with omecamtiv mecarbil does not increase the risk of these clinical adverse effects. Combined with a lack of detrimental effects on blood pressure, heart rate, creatinine or potassium concentrations, this supports the finding that the mechanism of selectively targeting the cardiac sarcomere with omecamtiv mecarbil is a safe approach to improving cardiac function.

As used herein, "treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of preventative treatment, such as, for example, chronic heart failure.

As used herein, the term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

Patient Populations

The present disclosure provides methods of treating heart failure in patients in need thereof. The disclosed methods provide a reduction in the composite of heart failure events or cardiovascular deaths without evidence of adverse safety signals in a broad range of patients, including patients with moderate to severe heart failure symptoms and lower ejection fraction, systolic blood pressure and renal function. In various cases, a patient with heart failure exhibits an 8% overall risk reduction when administered omecamtiv mecarbil as disclosed herein, compared to placebo control.

In some embodiments, treatment of heart failure in patients in need thereof may result in reduction of risk of heart failure hospitalization and/or cardiovascular death as well as other benefits, including reduction in heart rate, stroke, and/or natriuretic peptide concentrations.

In another aspect, the present disclosure also provides methods for reducing heart rate, reducing risk of stroke, reducing risk of heart failure hospitalization, reducing risk of cardiovascular death, and/or reducing/decreasing natriuretic peptide concentrations (e.g., NT-proBNP levels) in patients having heart failure.

While multiple drugs have been developed to improve inotropy, omecamtiv mecarbil is the first drug to specifically increase systolic function by targeting the sarcomere without any direct vascular, electrophysiologic, or neurohormonal effects and without increasing mortality. It exerts this effect by selectively binding to myosin, stabilizing its lever arm in a primed position resulting in accumulation of cardiac myosin heads in the pre-powerstroke state prior to onset of cardiac contraction. This mechanism increases the number of force generators (myosin heads) that can bind to the actin filament and undergo a powerstroke once the cardiac cycle starts without altering the cardiomyocyte calcium transient.

Furthermore, treatment with omecamtiv mecarbil was associated with greater reductions in heart failure events in patients with lower baseline ejection fraction. Combined with the high risk of heart failure events in these patients, patients treated with omecamtiv mecarbil displayed an even greater relative treatment effect and a progressively larger absolute risk reduction for the primary composite endpoint of heart failure events and cardiovascular death with lower baseline ejection fraction. These findings support the concept that certain subpopulations of heart failure patients, such as patients with more severe heart failure, may derive greater clinical benefit from cardiac myosin activator therapy.

Patients with left ventricular ejection fraction (LVEF) of less than 35%: In some cases, the patient with heart failure is one that also exhibits lower ejection fraction (ejection fraction 35%), prior to start of omecamtiv mecarbil therapy as described herein. In some embodiments, in conjunction with embodiments above or below, the patients have left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%). In some embodiments, in conjunction with embodiments above or below, the patients have left ventricular ejection of less than or equal to 22%, less than or equal to 28%, or between 23% and 28%.

Lower ejection fraction may be correlated with other patient characteristics. In a large clinical trial, when assessed by quartiles, patients with lower ejection fractions were younger, more likely to be male and non-white, and less likely to be enrolled in Eastern Europe or Russia and more likely to be enrolled in the United States, Canada, Western Europe, South Africa, or Australasia. Patients with lower ejection fraction were more likely to have a non-ischemic etiology of heart failure, NYHA III/IV functional class, lower body mass index, lower systolic blood pressure, higher heart rate, higher NT-proBNP, higher cardiac troponin I, and were less likely to have coronary artery disease, hypertension, type 2 diabetes mellitus, or atrial fibrillation/flutter. Lower ejection fraction was associated with greater symptom burden in patients enrolled as inpatients (lower KCCQ-TSS), but there was no meaningful difference in the outpatients. Patients with lower ejection fractions had higher use of ARNi, ivabradine, digitalis glycosides, cardiac resynchronization therapy and implantable cardioverter defibrillators compared to patients with higher ejection fractions. Accordingly, in any of the embodiments provided herein, the patients may have one or more of the aforementioned characteristics.

In one aspect, provided herein is a method of treating heart failure in a patient having heart failure who also exhibits lower ejection fraction. In some embodiments, provided herein is a method of treating heart failure in a patient having heart failure who also exhibits lower ejection fraction by administering omecamtiv mecarbil, wherein administration results in a risk reduction, for example, in occurrence or time to heart failure event or cardiovascular death. In a large clinical trial, selectively increasing systolic function in patients with HFrEF improved cardiovascular outcomes (primary composite endpoint: HR, 0.92; p=0.025), predominantly through reducing heart failure events. Omecamtiv mecarbil provided progressively greater benefit by reducing heart failure events in patients with lower baseline ejection fraction such that patients with an ejection fraction below the median (≤28%) had a 16% reduction in the primary endpoint. Patients with ejection fraction in the lowest quartile had a relative risk reduction of 17% and an absolute risk reduction of 7.4 events per 100 patient-years (NNT for 3 years=11.8) for the primary composite endpoint.

In some embodiments, treatment in patients with lower ejection fraction is effective to provide risk reduction compared to placebo. The risk reduction may be relative risk reduction and/or absolute risk reduction. In some embodiments, risk reduction is measured as event rates per 100 patient years. An event may be a first heart failure event or cardiovascular death. In various cases, patients with LVEF of less than or equal to 28% had a 16% reduction in time-to-first heart failure event or cardiovascular death. In some embodiments, the risk reduction may be an absolute risk reduction and/or relative risk reduction, in patients with EF of less than about 28% or less than about 22%. In some embodiments, the absolute risk reduction is at least about 5 events per 100-patient years (e.g., 5, 5.5, 6, 6.5, 7, 7.5, 8, 8.5, 9, 9.5, 10, 10.5 events per 100 patient years). In some embodiments, the absolute risk reduction is about 7.4 events per 100 patient years. In some embodiments, the treatment is effective to provide a relative risk reduction of at least 10% (e.g., 11%, 12%, 13%, 14%, 15%, 16%, 17%, 18%, 19%, 20%, etc.) In some embodiments, the relative risk reduction is 15%.

In some embodiments, the relative risk reduction is 17%. In some embodiments, provided is a method of reducing the time-to-first heart failure event in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein. In particular embodiments, the patient has LVEF of less than or equal to (e.g., less than) 28%. In particular embodiments, the patient has LVEF of less than or equal to (e.g., less than) 22%.

In some embodiments, provided is a method of reducing the number or frequency of heart failure events (e.g., heart failure hospitalizations) in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein. In particular embodiments, the patient has LVEF of less than or equal to (e.g., less than) 28%. In particular embodiments, the patient has LVEF of less than or equal to (e.g., less than) 22%. In some embodiments, provided is a method of reducing risk of cardiovascular death in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein. In particular embodiments, the patient has LVEF of less than or equal to (e.g., less than) 28%. In particular embodiments, the patient has LVEF of less than or equal to (e.g., less than) 22%.

It was also observed that patients with a lower ejection fraction exhibited a greater reduction in NT-proBNP upon treatment with omecamtiv mecarbil. In a large clinical trial, administration of omecamtiv mecarbil resulted in greater reductions in NT-proBNP with decreasing ejection fraction, with a 22% reduction of NT-proBNP at week 24 in the lowest EF quartile (22%). Accordingly, provided herein are methods of treating heart failure in patients, having LVEF of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%), wherein administration of omecamtiv mecarbil reduces the patient's NTproBNP level as compared to baseline. In particular embodiments, the patient has LVEF of less than or equal to (e.g., less than) 28%. In particular embodiments, the patient has LVEF of less than or equal to (e.g., less than) 22%. In some such embodiments the patient's NT-proBNP level is reduced by at least 5%, 10%, 15%, 20%, 25%, 30%, 35%, 40%, 45%, or 50%. In some embodiments, the NT-proBNP level is reduced to less than 2500, 2400, 2300, 2200, 2100, 2000, 1900, 1800, 1700, 1600, or 1500 pg/ml in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%). In some embodiments, the reduction in NT-proBNP occurs over a period of 1, 2, 3, 4, 5, 6, 7, 8, 9, 10, 12, 14, 16, 18, 20, 22, 24, 36, or 48 weeks.

In other embodiments, provided herein is a method of reducing NT-proBNP in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, In some embodiments, the NT-proBNP level is reduced by at least 5%, 10%, 15%, 20%, 25%, 30%, 35%, 40%, 45%, or 50% in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%). In some embodiments, the NT-proBNP level is reduced to less than 2500, 2400, 2300, 2200, 2100, 2000, 1900, 1800, 1700, 1600, or 1500 pg/ml in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%). In some embodiments, the reduction in NT-proBNP occurs over a period of 1, 2, 3, 4, 5, 6, 7, 8, 9, 10, 12, 14, 16, 18, 20, 22, 24, 36, or 48 weeks. In some embodiments, provided is a method of decreasing NT-proBNP in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein.

In a large clinical trial, there was no significant effect on systolic blood pressure, serum potassium or creatine across ejection fraction quartiles observed with administration of omecamtiv mecarbil as compared to placebo. There were also no significant differences noted in the incidence of most adverse events between the omecamtiv mecarbil and placebo treated groups. However, notably there was an apparent reduction in the incidence of adjudicated stroke for patients treated with omecamtiv mecarbil. Thus, in some embodiments, provided is a method for reducing risk of stroke in a patient with heart failure (e.g., HFrEF) comprising administering omecamtiv mecarbil as described herein.

In some embodiments, provided herein is a method of treating heart failure in a patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, wherein the administration of omecamtiv mecarbil reduces the patient's risk of stroke as compared to placebo. In some embodiments, provided is a method of preventing or reducing risk of stroke in a patient with heart failure (e.g., HFrEF). In some embodiments, the patient has LVEF of less than or equal to (e.g., less than) 35%. In certain embodiments, the patient has LVEF of less than or equal to (e.g., less than) 28%. In particular embodiments, the patient has LVEF of less than or equal to (e.g., less than) 22%. In some embodiments, the risk reduction may be an absolute risk reduction and/or relative risk reduction. In some embodiments, the risk reduction is a relative reduction of the risk of stroke as compared to placebo. In some such embodiments the patient's relative risk of stroke is reduced by at least 5%, 10%, 15%, 20%, 25%, 30%, 35%, 40%, 45%, or 50%. In some embodiments wherein the patient has LVEF of less than or equal to (e.g., less than) 35%, the patient's relative risk of stroke is reduced by at least 5%, 10%, 15%, 20%, or 25%. In other embodiments wherein the patient has LVEF of less than or equal to (e.g., less than) 28%, the patient's relative risk of stroke is reduced by at least 5%, 10%, 15%, 20%, 25%, 30%, 35%, 40%, or 45%. In some embodiments wherein the patient has LVEF of less than or equal to (e.g., less than) 22%, the patient's relative risk of stroke is reduced by at least 5%, 10%, 15%, 20%, 25%, 30%, or 35%. In some embodiments, in conjunction with embodiments above or below, the stroke is fatal. In some embodiments, in conjunction with embodiments above or below, the stroke is non-fatal. In some embodiments, in conjunction with embodiments above or below, the stroke is ischemic or nonhemorrhagic. In some embodiments, in conjunction with embodiments above or below, the stroke is ischemic with hemorrhagic transformation. In some embodiments, in conjunction with embodiments above or below, the stroke is hemorrhagic. In some embodiments, in conjunction with embodiments above or below, the patient has no history of stroke. In some embodiments, in conjunction with embodiments above or below, the patient has a history of stroke. In some embodiments, in conjunction with embodiments above or below, the patient has no history of atrial fibrillation. In some embodiments, in conjunction with embodiments above or below, the patient has a history of atrial fibrillation. In some embodiments, in conjunction with embodiments above or below, the patient has no atrial fibrillation/flutter at the time of initial administration of omecamtiv mecarbil. In some embodiments, in conjunction with embodiments above or below, the patient has no history of atrial fibrillation/flutter.

In a large clinical trial, omecamtiv mecarbil had no adverse effect on blood pressure, heart rate, potassium homeostasis or renal function when assessed by ejection fraction quartile. A small reduction in heart rate, believed to be due to the secondary effect of sympathetic withdrawal, was consistently observed across the ejection fraction groups.

In some embodiments, provided herein is a method of treating heart failure in a heart failure patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, wherein administration results in a reduction of heart rate. In some embodiments, provided herein is a method of reducing heart rate in a heart failure patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, as compared to placebo. In some embodiments, the patient has LVEF of less than or equal to (e.g., less than) 35%. In certain embodiments, the patient has LVEF of less than or equal to (e.g., less than) 28%. In particular embodiments, the patient has LVEF of less than or equal to (e.g., less than) 22%. In some embodiments, the reduction in heart rate is a reduction of about 1, 2, 3, 4 or 5 beats per minute (bpm), In certain embodiments, the reduction in heart rate is a reduction of about 1-5, 1-4, 1-3, 1-2, 2-5, 2-4, 2-4, 3-5, 3-4 or 4-5 bpm. In still other embodiments, the reduction in heart rate is a reduction of about 1-2 bpm.

In some embodiments, provided herein is a method of treating heart failure in a heart failure patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, wherein administration results in a reduction in the risk of stroke. In certain embodiments, provided herein is a method of reducing risk of stroke in a heart failure patient having left ventricular ejection of less than or equal to (e.g., less than) 35%, less than or equal to (e.g., less than) 30%, less than or equal to (e.g., less than) 28%, less than or equal to (e.g., less than) 25%, or less than or equal to (e.g., less than) 22% (e.g., 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%, or less than any of 34%, 33%, 32%, 31%, 30%, 29%, 27%, 26%, 25%, 24%, 23%, 22%, 21%, 20%, 19%, 18%, 17%, 16%, 15%, 14%, 13%, 12%, 11%, or 10%) by administering omecamtiv mecarbil as described herein, as compared to placebo. In some embodiments, the patient has LVEF of less than or equal to (e.g., less than) 35%. In certain embodiments, the patient has LVEF of less than or equal to (e.g., less than) 28%. In particular embodiments, the patient has LVEF of less than or equal to (e.g., less than) 22%. In some embodiments, the risk reduction may be an absolute risk reduction and/or relative risk reduction. In some embodiments, the risk reduction is a relative reduction of the risk of stroke as compared to placebo. In some such embodiments the patient's relative risk of stroke is reduced by at least 5%, 10%, 15%, 20%, 25%, 30%, 35%, 40%, 45%, or 50%. In some embodiments wherein the patient has LVEF of less than or equal to (e.g., less than) 35%, the patient's relative risk of stroke is reduced by at least 5%, 10%, 15%, 20%, or 25%. In other embodiments wherein the patient has LVEF of less than or equal to (e.g., less than) 28%, the patient's relative risk of stroke is reduced by at least 5%, 10%, 15%, 20%, 25%, 30%, 35%, 40%, or 45%. In some embodiments wherein the patient has LVEF of less than or equal to (e.g., less than) 22%, the patient's relative risk of stroke is reduced by at least 5%, 10%, 15%, 20%, 25%, 30%, or 35%.

Patients who do not exhibit atrial fibrillation or atrial flutter (AFF): As is understood, atrial fibrillation and atrial flutter are types of tachyarrhythmias, wherein atrial fibrillation presents as a rapid and chaotic beating of the atria and atrial flutter results in a rapid but regular heartbeat. Atrial fibrillation and atrial flutter can be diagnosed using any suitable method (e.g., electrocardiogram echocardiogram, transesophageal echocardiogram, chest X-rays, MRI scans, CT scans, exercise stress test, etc.). In some embodiments, in conjunction with embodiments above or below, the patient with heart failure does not exhibit atrial fibrillation or atrial flutter, prior to start of omecamtiv mecarbil therapy as described herein.

In one aspect, provided herein is a method of treating heart failure in a patient having heart failure who does not exhibit AFF. In some embodiments, the patient with heart failure does not exhibit AFF. In some embodiments, the patient without AFF is receiving digoxin. In some embodiments, the patient without AFF is not receiving digoxin. In some embodiments, treatment in patients without AFF by administering omecamtiv mecarbil is effective to provide risk reduction compared to placebo. The risk reduction may be relative risk reduction and/or absolute risk reduction. In some embodiments, risk reduction is measured as event rates per 100 patient years. An event may be a first heart failure event or cardiovascular death. In some embodiments, the risk reduction may be an absolute risk reduction and/or relative risk reduction, in patients having heart failure who do not exhibit AFF. In some embodiments, the treatment is effective to provide a relative risk reduction of at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%. In some embodiments, treatment with omecamtiv mecarbil results in a reduction in the risk of cardiovascular death and/or heart failure events (e.g., heart failure hospitalization) in patients without AFF. In some embodiments, provided is a method of reducing the time-to-first heart failure event in a patient without AFF by administering omecamtiv mecarbil as described herein. In some embodiments, provided is a method of reducing the number or frequency of heart failure events (e.g., heart failure hospitalizations) in a patient without AFF by administering omecamtiv mecarbil as described herein. In some embodiments, provided is a method of reducing risk of cardiovascular death in a patient without AFF by administering omecamtiv mecarbil as described herein.

In some embodiments, provided is a method of reducing the time-to-first heart failure event in a heart failure patient who does not exhibit AFF by administering omecamtiv mecarbil as described herein. In some embodiments, provided is a method of reducing the number or frequency of heart failure events (e.g., heart failure hospitalizations) in a heart failure patient who does not exhibit AFF by administering omecamtiv mecarbil as described herein. In some embodiments, provided is a method of reducing risk of cardiovascular death in a heart failure patient who does not exhibit AFF by administering omecamtiv mecarbil as described herein. In some embodiments, provided is a method of reducing risk of all-cause death in a heart failure patient who does not exhibit AFF by administering omecamtiv mecarbil as described herein. In some embodiments, the relative risk reduction is at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%.

In some embodiments, provided is a method of reducing the time-to-first heart failure event in a heart failure patient without AFF, wherein the patient is not receiving digoxin, by administering omecamtiv mecarbil as described herein. In some embodiments, provided is a method of reducing the number or frequency of heart failure events (e.g., heart failure hospitalizations) in a heart failure patient who does not exhibit AFF, wherein the patient is not receiving digoxin, by administering omecamtiv mecarbil as described herein. In other embodiments, provided herein is a method of reducing risk of cardiovascular death in a heart failure patient having without AFF, wherein the patient is not receiving digoxin, by administering omecamtiv mecarbil as described herein. In other embodiments, provided herein is a method of reducing risk of all-cause death in a heart failure patient having without AFF, wherein the patient is not receiving digoxin, by administering omecamtiv mecarbil as described herein. In some embodiments, the relative risk reduction for the heart failure patient without AFF who is not receiving digoxin is at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%.

In other embodiments, provided is a method of reducing the time-to-first heart failure event in a heart failure patient without AFF, wherein the patient is receiving digoxin, by administering omecamtiv mecarbil as described herein. In some embodiments, provided is a method of reducing the number or frequency of heart failure events (e.g., heart failure hospitalizations) in a heart failure patient who does not exhibit AFF, wherein the patient is receiving digoxin, by administering omecamtiv mecarbil as described herein. In other embodiments, provided herein is a method of reducing risk of cardiovascular death in a heart failure patient having without AFF, wherein the patient is receiving digoxin, by administering omecamtiv mecarbil as described herein. In other embodiments, provided herein is a method of reducing risk of all-cause death in a heart failure patient having without AFF, wherein the patient is receiving digoxin, by administering omecamtiv mecarbil as described herein. In some embodiments, the relative risk reduction for the heart failure patient without AFF who is not receiving digoxin is at least 10% (e.g., 11%, 12%, 13%, 14%, 15%, 16%, 17%, 18%, 19%, 20%, 21%, 22%, 23%, 24%, or 25%, etc.). In some embodiments, the relative risk reduction is 12%. In some embodiments, the relative risk reduction is 15%. In some embodiments, the relative risk reduction is 17%. In still other embodiments, 20%. In some embodiments, the relative risk reduction is 22%. In yet other embodiments, the relative risk reduction is 25%.

Patients who exhibit atrial fibrillation or atrial flutter (AFF): Treatment with omecamtiv mecarbil may reduce the occurrence of serious adverse events in patients with AFF. In some aspects, provided herein is a method of reducing the risk of serious adverse events in heart failure patients with AFF, wherein the patient is receiving digoxin, by administering omecamtiv mecarbil as described herein. In some embodiments, the treatment is effective to provide a relative risk reduction of at least 10% (e.g., 11%, 12%, 13%, 14%, 15%, 16%, 17%, 18%, 19%, 20%, etc.) In some embodiments, the relative risk reduction is 15%.

Patients having heart failure classified as Class III or IV: The New York Heart Association (NYHA) classification is a paradigm describing patients suffering from heart failure, wherein patients are placed into one of four categories based on the extent the patient is limited during physical activity. Class I patients are not limited during physical activity, that is, ordinary physical activity does not cause undue fatigue, palpitation, or shortness of breath. Class II patients are slightly limited during physical activity such that ordinary physical activity results in fatigue, palpitation, or shortness of breath. Class III patients suffer from marked limitation during physical activity, wherein less than ordinary activity causes fatigue, palpitation, or shortness of breath. The Class IV heart failure patient experiences symptoms of heart failure at rest and is unable to carry on any physical activity without increasing discomfort. In some embodiments, in conjunction with embodiments above or below, the patient with heart failure is classified as Class III or IV as determined using the New York Heart Association (NYHA) classification.

Patients having more advanced heart failure (HF): In some aspects, provided is a method of treating a patient having more advanced HF by administering omecamtiv mecarbil as described herein. More advanced HF, also referred to as severe HF, refractory HF, or Stage D HF, can be determined based on a number of criteria recognized in the medical field. In some embodiments, more advanced HF refers to the published criteria from the 2018 ESC-HFA position statement (European journal of heart failure. 2018; 20:1505-1535). For the ESC-HFA criteria, patients were required to have all of 1) NYHA class III-IV symptoms, 2) a left ventricular ejection fraction 30%, 3) 2 or more hospitalizations for HF within the prior 12 months, and 4) evidence of severe functional impairment as defined by cardiopulmonary exercise testing or 6-minute walk test. In some embodiments, the hospitalization criteria is modified to one HF hospitalization within the prior 6 months In some embodiments, more advanced HF refers to patients having all of 1) NYHA class III-IV symptoms, 2) a left ventricular ejection fraction 30%, and 3) 1 or more hospitalizations for HF within the prior 6 months.

On the other hand, patients with true end-stage HF who may require mechanical support, cardiac transplant, or hospice care, referred to as Stage D patients in the AHA/ACC guidelines, represents a very small proportion of the HF population (approximately 2% in an unselected community cohort). In some embodiments, patients having advanced HF as described herein do not include patients with true end-stage HF who may require mechanical support, cardiac transplant, or hospice care, referred to as Stage D patients in the AHA/ACC guidelines. In still other embodiments, patients having advanced HF do not include patients requiring IV inotropic therapy or mechanical ventilatory or circulatory support. A much larger population of ambulatory HF patients have significant symptoms, severely impaired cardiac performance, and frequent hospitalizations, but do not yet require advanced HF therapies such mechanical support or cardiac transplant. In some embodiments, patients having advanced heart failure include patients who have significant symptoms, severely impaired cardiac performance, and frequent hospitalizations, but do not yet require advanced HF therapies such mechanical support or cardiac transplant. In some embodiments, patients having advanced HF as described herein may include patients having NYHA class ejection fraction 30%, and HF hospitalization within the prior 6 months.

In some embodiments, the patient receiving treatment has heart failure classified as Class III or IV as determined using the NYHA classification. In some embodiments, the patient has a LVEF of less than 30% (e.g., 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, and 1%). In some embodiments, the patient is hospitalized for heart failure or one or more (e.g., 1, 2, 3, 4, 5, etc.) hospitalization for heart failure within 6 months prior to treatment. In some embodiments, the patient has severe functional impairment as defined by cardiopulmonary exercise testing or 6-minute walk test. In some embodiments, the patient meets one or more of the following: 1) NYHA class III-IV symptoms, 2) a left ventricular ejection fraction 30%, 3) one or more hospitalizations for HF within the prior 6 months (including those hospitalized at the time of study enrollment), and 4) evidence of severe functional impairment as defined by cardiopulmonary exercise testing or 6-minute walk test. In some embodiments, the patient meets all of the following: 1) NYHA class III-IV symptoms, 2) a left ventricular ejection fraction 30%, 3) one or more hospitalizations for HF within the prior 6 months (including those hospitalized at the time of study enrollment), and 4) evidence of severe functional impairment as defined by cardiopulmonary exercise testing or 6-minute walk test. In some embodiments, the patient meets one or more of the following: 1) NYHA class III-IV symptoms, 2) a left ventricular ejection fraction 30%, and 3) 1 or more hospitalizations for HF within the prior 6 months. In some embodiments, the patient meets all of the following: 1) NYHA class III-IV symptoms, 2) a left ventricular ejection fraction 30%, and 3) 1 or more hospitalizations for HF within the prior 6 months.

Despite substantial improvements in medical therapy for HFrEF, patients with more advanced HF continue to experience a high burden of symptoms, frequent HF hospitalizations, and high mortality. As HF worsens, the economic costs of care increase dramatically, and these patients account for disproportionate share of HF costs. With the progression of HF, the pathologic manifestations of severely impaired systolic function and low cardiac output often begin to predominate, including hypotension and progressive renal insufficiency. These features progressively limit the ability to tolerate guideline recommended HF therapy such as beta-blockers, RAAS modulators, or mineralocorticoid receptor antagonists, creating a mismatch between patient risk and intensity of medical therapy. Omecamtiv mecarbil differs from other HF therapies in that it directly targets systolic performance rather than modulating associated neuro-hormonal perturbations. Unlike other HFrEF treatments, omecamtiv mecarbil does not lower blood pressure, affect renal function, or alter potassium homeostasis, allowing its use even in patients with cardio-renal limitations to other HF therapies. In a large clinical trial, in patients classified as advanced HF, there was no significant difference in systolic blood pressure, serum creatinine, or serum potassium at 24 weeks between patients treated with omecamtiv mecarbil or placebo. These data support both the efficacy and tolerability of omecamtiv mecarbil in a patient population that is difficult to treat effectively with other HF drugs.

In patients with more advanced HF defined by NYHA class, EF, and recent HF hospitalization, omecamtiv mecarbil therapy provided a clinically significant reduction in the composite of HF hospitalizations and cardiovascular death. These data support the possible role of omecamtiv mecarbil in patients for whom current treatment options are limited.

In a large clinical trial, it was found that treatment with omecamtiv mecarbil provided a clinically important improvement in outcomes in the patients meeting an accepted definition of advanced HF, e.g., one or more of the following: 1) NYHA class III-IV symptoms, 2) a left ventricular ejection fraction ≤30%, 3) one or more hospitalizations for HF within the prior 6 months (including those hospitalized at the time of study enrollment), and 4) evidence of severe functional impairment as defined by cardiopulmonary exercise testing or 6-minute walk test. Given that patients with more advanced HF have higher baseline risk, the 20% relative risk reduction translated into a significant absolute risk reduction of 8.3 events/100-patient-years (NNT=12) for the primary endpoint of time to first HF event or death from cardiovascular causes.

In some embodiments, treatment in patients with more advanced HF with omecamtiv mecarbil is effective to provide risk reduction as compared to placebo. In some embodiments, the risk reduction is an absolute risk reduction. In some embodiments, the risk reduction is a relative risk reduction of about 20% (e.g., 20%, 19%, 18%, 17%, 16%, 15%, 14%, 13%, 12%, 11%, 10%, 9%, 8%, 7%, 6%, 5%, etc.). For example, absolute risk reduction may be at least 2 events per 100 patient years (e.g., 3, 4, 5, 6, 7, 8, 9, 10 events/100-patient-years). In some embodiments, absolute risk reduction is about 8 events per 100 patient years (e.g., 8.1, 8.2, 8.3, 8.4, 8.5, 8.6, 8.7, 8.8, 8.9 events/100-patient-years). In some embodiments, treatment in patients with more advanced HF shows no significant increase in treatment emergent serious adverse events. In some embodiments, treatment in patients with more advanced HF shows no significant increase in serious adverse events related to ventricular tachyarrhythmia. In some embodiments, treatment with omecamtiv mecarbil results in a reduction in the risk of cardiovascular death and/or heart failure events (e.g., heart failure hospitalization) in patients with more advanced HF. In some embodiments, provided is a method of reducing the time-to-first heart failure event in a patient with advanced HF by administering omecamtiv mecarbil as described herein. In some embodiments, provided is a method of reducing the number or frequency of heart failure events (e.g., heart failure hospitalizations) in a patient with more advanced HF by administering omecamtiv mecarbil as described herein. In some embodiments, provided is a method of reducing risk of cardiovascular death in a patient with more advanced HF by administering omecamtiv mecarbil as described herein.

In the more advanced HF population, treatment with omecamtiv mecarbil has been observed to be associated with a significant decrease in NT-proBNP. In some embodiments, the NT-proBNP level is reduced by at least 5%, 10%, 15%, 20%, 25%, 30%, 35%, 40%, 45%, or 50% in a patient with more advanced HF. In some embodiments, the NT-proBNP level is reduced to less than 2500, 2400, 2300, 2200, 2100, 2000, 1900, 1800, 1700, 1600, or 1500 pg/ml in a patient with more advanced HF. IN some embodiments, the reduction in NT-proBNP occurs over a period of 1, 2, 3, 4, 5, 6, 7, 8, 9, 10, 12, 14, 16, 18, 20, 22, 24, 36, or 48 weeks. In some embodiments, provided is a method of decreasing NT-proBNP in a patient with more advanced HF by administering omecamtiv mecarbil as described herein.

Patients having Ischemic Heart Failure: In some embodiments, in conjunction with embodiments above or below, the patient with heart failure exhibits ischemic heart failure. As is understood, ischemic heart failure refers to heart failure characterized by inadequate blood supply and oxygen delivery in tissues due to, for example, narrowing of arteries from a blood clot or vessel constriction (e.g., plaque buildup). Ischemic heart disease, also known as coronary heart disease (CHD) can be diagnosed in several ways. For example, patients with documented (prior) myocardial infarction or coronary artery revascularization (either with percutaneous coronary interventions (PCI) or coronary artery bypass (CABG) surgery have CHD. Moreover, the presence of typical angina suggests a clinical diagnosis of CHD, but most often requires confirmation by additional diagnostic tests, such as coronary angiography.

Patients having myocardial infarction: As is understood, myocardial infarction or heart attack, occurs when blood flow to the heart is blocked. Typically, the blockage is due to arterial plaques in coronary arteries. A myocardial infarction, or damage therefrom, can be diagnosed using any suitable method (e.g., electrocardiogram, blood tests, chest x-rays, echocardiogram, angiogram, cardiac CT or MRI, etc.). In some embodiments, in conjunction with embodiments above or below, the patient with heart failure also has had a myocardial infarction.

Patients having reduced ejection fraction: In some embodiments, in conjunction with embodiments above or below, the patient with heart failure also has reduced ejection fraction (HFrEF). As is understood, HFrEF is characterized by diminished ability of the left ventricle to pump, such that the ejection fraction is 40% or less, wherein normal ejection fraction is more than 55%. In some cases of HFrEF, the left ventricle is enlarged, and thus cannot pump normally. In other cases, HFrEF can be caused by coronary heart disease, heart attack, cardiomyopathy, high blood pressure, aortic stenosis, mitral regurgitation, viral myocarditis, and/or arrhythmia.

In addition, it is understood that the risk of stroke in a patient increases with decreasing ejection fraction. Accordingly, the disclosed method provides a method of preventing or reducing the risk of stroke in a patient suffering from HFrEF comprising administering to the patient a therapeutically effective amount of omecamtiv mecarbil, as described herein.

Patients having a pretreatment level of NT-proBNP of at least 2000 pg/mL: In some aspects, provided is a method of treating a patient having heart failure with elevated NT-proBNP levels, by administering omecamtiv mecarbil as described herein. NT-proBNP levels are understood to be a marker for heart failure (e.g., higher levels indicate a progression of heart failure). Patients with very high natriuretic peptide levels are at especially high risk and often have other clinical features such as low blood pressure and poor renal function causing intolerance of some recommended therapies. Any additional therapeutic option is attractive for these individuals and it is often in these patients that inotropic therapy is resorted to, or even use of mechanical support or transplantation. Omecamtiv mecarbil may one such treatment possibility. Omecamtiv mecarbil was found to result in higher treatment efficacy in populations having higher NT-proBNP levels at baseline. In contrast, for another new therapy, vericiguat, treatment efficacy declined at higher NT-proBNP concentrations. Plasma natriuretic peptide concentrations reflect cardiac chamber wall stress, blood volume, heart rhythm and kidney function. Therefore, in patients with HFrEF, natriuretic peptides provide an integrated measure of cardiac preload and afterload, chamber size, wall thickness and systolic function, as well as the systemic consequences of pump dysfunction. Moreover, by reflecting multiple aspects of cardiac structure and physiology, natriuretic peptides give a more complete assessment of cardiac performance than left ventricular ejection fraction, the most widely used measure of contractile function. It is not surprising, therefore, that selectively targeting the cardiac sarcomere to improve pump function might have most benefit in those with elevated NT-proBNP levels, by identifying the individuals with greatest cardiac dysfunction.

In some embodiments, in conjunction with embodiments above or below, the patient with heart failure has an N-terminal-pro hormone B-type natriuretic peptide (BNP) (NT-proBNP) of at least 2000 pg/mL prior to start of omecamtiv mecarbil treatment as described herein. In some cases, the patient exhibits a NT-proBNP level of at least 2000 pg/mL. In some embodiments, the patient as a pretreatment level of NT-proBNP of 2000 to 150,000 pg/mL. For example, in some cases, the patient has a NT-proBNP level of 1,700, 1,800, 1,900, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 55,000, 60,000, 65,000, 70,000, 75,000, 80,000, 85,000, 90,000, 95,000, 100,000, 105,000, 110,000, 115,000, 120,000, 125,000, 130,000, 135,000, 140,000, 145,000, or 150,000 pg/mL, prior to omecamtiv mecarbil therapy as described herein. Thus, the patient prior to treatment can exhibit a NT-proBNP level bounded by, and including any of the aforementioned values. For example, in some cases, the patient has a NT-proBNP level of 2000 to 150,000 pg/mL prior to omecamtiv mecarbil therapy as described herein, e.g., 2000 to 125,000 pg/mL, or 2500 to 150,000 pg/mL, or 3000 to 125,000 pg/mL, or 3000 to 100,000 pg/mL. In various cases, the disclosed methods reduce NT-proBNP levels in a patient upon omecamtiv mecarbil therapy as described herein. The levels of NT-proBNP can be measured using any suitable method. In various cases, the patient's NT-proBNP levels decrease by at least 5%, or at least 10%, e.g., 5% to 15%, upon treatment with omecamtiv mecarbil as disclosed herein.

It was observed that omecamtiv mecarbil reduced the risk of the primary endpoint to a greater extent in patients without AF/F who had higher NT-proBNP levels, compared to lower NT-proBNP levels, at baseline. Omecamtiv mecarbil reduced the risk of both components of the primary endpoint in patients with higher NT-proBNP levels. Omecamtiv mecarbil also reduced the risk of the primary endpoint in the overall patient population, but to a lesser extent compared to participants without AF/F.

In the population of patients without AF/F, treatment with omecamtiv mecarbil led to a relative risk reduction of 18% (95% CI 10-27%) in the primary endpoint, with a somewhat larger reduction in heart failure hospitalization (21, 11-30%) than in cardiovascular mortality (13, 0-25%), in patients with a baseline NT-proBNP>median, with no benefit in patients with NT-proBNP≤median. Analyses examining the effect of omecamtiv mecarbil using NT-proBNP as a continuous measure suggested a linear interaction, with a steadily increasing benefit of omecamtiv mecarbil as NT-proBNP level increased. The favorable effect of omecamtiv mecarbil emerged at a NT-proBNP threshold of around 2,000 pg/mL and increased in size with increasing NT-proBNP level across the remaining range of baseline values (up to approximately 20,000 pg/mL). The benefits of omecamtiv mecarbil were consistent in both inpatients and outpatients.

The benefits of omecamtiv mecarbil in the overall trial population were smaller than seen in participants without AF/F. This reflected an attenuation, or absence, of the effect of omecamtiv mecarbil in patients with AF/F, who accounted for 37% of the patients with a NT-proBNP level greater than the median. The reasons for this lack of benefit of omecamtiv mecarbil in patients with AF/F are not yet clear. However, atrial arrhythmias themselves elevate natriuretic peptides and, for a given natriuretic peptide level, the degree of left ventricular systolic dysfunction is less in patients with AF/F than in patients in sinus rhythm. Consequently, patients with AF/F may have "diluted" the prevalence of significant left ventricular systolic dysfunction in the overall trial population with a NT-proBNP greater than the median, compared to participants without AF/F with a NT-proBNP greater than the median. Just as natriuretic peptides increase with cardiac chamber dilatation, elevated wall stress and reduced systolic function, reversal of these abnormalities with effective therapy results in a decrease in natriuretic peptides.

In some embodiments, the patient receiving treatment has a pretreatment level of NT-proBNP of at least about 2,000 pg/ml (e.g., 2000, 2500, 3000, 3500, 4000, 4500, 5000, 5500, 6000, 7000, 8000, 9000, 10,000, 15,000, and 20,000 pg/ml). In some embodiments, the patient has a pretreatment level of NT-proBNP of below about 20,000 pg/ml. In some embodiments, the patient is without AF/F. In some embodiments, treatment in patients without AF/F is effective to achieve a risk reduction, wherein the risk reduction is a relative risk reduction of about 18% (e.g., about 10%, 11%, 12%, 13%, 14%, 15%, 16%, 17%, 18%, 19%, 20%, etc.). In some embodiments, the patient receiving treatment has a pretreatment level of NT-proBNP of at least about 2,000 pg/ml (e.g., 2000, 2500, 3000, 3500, 4000, 4500, 5000, 5500, 6000, 7000, 8000, 9000, 10,000, 15,000, and 20,000 pg/ml). In some embodiments, the patient has a pretreatment level of NT-proBNP of below about 20,000 pg/ml. In some embodiments, the patient is without AF/F. In some embodiments, treatment in patients without AF/F is effective to achieve a risk reduction, wherein the risk reduction is a relative risk reduction of about 18% (e.g., about 10%, 11%, 12%, 13%, 14%, 15%, 16%, 17%, 18%, 19%, 20%, etc.).

In one aspect, provided herein is a method of treating heart failure in a patient with heart failure having no atrial fibrillation or flutter (without AFF) and who exhibits a NT-proBNP level of at least 2000 pg/mL, by administering omecamtiv mecarbil. In some embodiments, treatment in patients without AFF by administering omecamtiv mecarbil is effective to provide risk reduction compared to placebo. The risk reduction may be relative risk reduction and/or absolute risk reduction. In some embodiments, risk reduction is measured as event rates per 100 patient years. An event may be a first heart failure event or cardiovascular death. In some embodiments, the risk reduction may be an absolute risk reduction and/or relative risk reduction, in patients having heart failure who do not exhibit AFF. In some embodiments, the treatment is effective to provide a relative risk reduction of at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%. In some embodiments, treatment with omecamtiv mecarbil results in a reduction in the risk of cardiovascular death and/or heart failure events (e.g., heart failure hospitalization) in patients without AFF and who exhibit a NT-proBNP level of at least 2000 pg/mL. In some embodiments, provided is a method of reducing the time-to-first heart failure event in a patient without AFF and who exhibits a NT-proBNP level of at least 2000 pg/mL by administering omecamtiv mecarbil as described herein. In some embodiments, provided is a method of reducing the number or frequency of heart failure events (e.g., heart failure hospitalizations) in a patient without AFF and who exhibits a NT-proBNP level of at least 2000 pg/mL by administering omecamtiv mecarbil as described herein. In some embodiments, provided is a method of reducing risk of cardiovascular death in a patient without AFF and who exhibits a NT-proBNP level of at least 2000 pg/mL by administering omecamtiv mecarbil as described herein.

In some embodiments, provided is a method of reducing the time-to-first heart failure event in a heart failure patient without AFF who exhibits a NT-proBNP level of at least 2000 pg/mL by administering omecamtiv mecarbil as described herein. In some embodiments, provided is a method of reducing the number or frequency of heart failure events (e.g., heart failure hospitalizations) in a heart failure patient who does not exhibit AFF by administering omecamtiv mecarbil as described herein. In some embodiments, provided is a method of reducing risk of cardiovascular death in a heart failure patient without AFF who exhibits a NT-proBNP level of at least 2000 pg/mL by administering omecamtiv mecarbil as described herein. In some embodiments, the relative risk reduction is at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%.

It was also observed that patients without AFF exhibited a greater reduction in NT-proBNP upon treatment with omecamtiv mecarbil. In a large clinical trial, omecamtiv mecarbil also reduced NT-proBNP to a significantly greater extent in those with a baseline concentration greater than the median, compared to those with a baseline NT-proBNP level less than or equal to the median. In other words, it appeared that NT-proBNP concentration at baseline identified patients likely to respond more favorably to omecamtiv mecarbil (i.e., those with a high baseline level) and reduction in NT-proBNP represented a surrogate for the efficacy of omecamtiv mecarbil, as seen with other treatments.

Accordingly, in one aspect, provided herein is a method of treating heart failure in a patient who does not exhibit AFF and who exhibits a higher NT-proBNP level at baseline (e.g. patient exhibits a NT-proBNP level of at least 2000 pg/mL), by administering omecamtiv mecarbil as described herein, wherein the administration results in a reduction of NT-proBNP levels relative to baseline. In another aspect, provided herein is a method of reducing NT-proBNP in a heart failure patient who does not exhibit AFF and who exhibits a higher NT-proBNP level at baseline (e.g. patient exhibits a NT-proBNP level of at least 2000 pg/mL) by administering omecamtiv mecarbil as described herein. In one aspect, provided herein is a method of reducing NT-proBNP levels in a heart failure patient without AFF who exhibits a higher NT-proBNP level at baseline (e.g. patient exhibits a NT-proBNP level of at least 2000 pg/mL at baseline).

In some embodiments, the NT-proBNP level is reduced by at least 5%, 10%, 15%, 20%, 25%, 30%, 35%, 40%, 45%, or 50% in a patient without AFF who exhibits a NT-proBNP level of at least 2000 pg/mL at baseline. In some embodiments, the NT-proBNP level is reduced to less than 2500, 2400, 2300, 2200, 2100, 2000, 1900, 1800, 1700, 1600, or 1500 pg/ml in a patient without AFF who exhibits a NT-proBNP level of at least 2000 pg/mL at baseline. In some embodiments, the reduction in NT-proBNP occurs over a period of 1, 2, 3, 4, 5, 6, 7, 8, 9, 10, 12, 14, 16, 18, 20, 22, 24, 36, or 48 weeks. In some embodiments, provided is a method of decreasing NT-proBNP in a patient without AFF who exhibits a NT-proBNP level of at least 2000 pg/mL at baseline by administering omecamtiv mecarbil as described herein.

In patients with a NT-proBNP greater than the median at baseline, the proportional reduction in NT-proBNP in the omecamtiv mecarbil, compared with placebo, group was approximately 17%. In a prior analysis of 18 therapeutic interventions in heart failure, a 17% reduction in natriuretic peptide concentration was associated with an approximately 20% relative risk reduction in heart failure hospitalization and 13% reduction in mortality, estimates close to the actual reductions observed in a large clinical trial of omecamtiv mecarbil.

In yet another aspect, provided herein is a method of treating heart failure in a patient without AFF who exhibits a NT-proBNP level of at least 2000 pg/mL at baseline, by administering omecamtiv mecarbil as described herein, wherein the administration results in a reduction of the risk of heart failure event or cardiovascular death and reduction in the level of NT-proBNP as compared to baseline. In still yet another aspect, provided herein is a method of reducing risk of heart failure event or cardiovascular death and reducing NT-proBNP level in a patient without AFF who exhibits a NT-proBNP level of at least 2000 pg/mL at baseline. In some embodiments, treatment with omecamtiv mecarbil results in a reduction in the risk of heart failure event or cardiovascular death, as well as a reduction in NT-proBNP levels. In some embodiments, the reduction in the risk of heart failure event or cardiovascular death is a relative risk reduction of about 20% (e.g., 20%, 19%, 18%, 17%, 16%, 15%, 14%, 13%, 12%, 11%, 10%, 9%, 8%, 7%, 6%, 5%, etc.). In some embodiments, the reduction of NT-proBNP level is a reduction of at least 5%, 10%, 15%, 20%, 25%, 30%, 35%, 40%, 45%, or 50%. In other embodiments, the NT-proBNP level is reduced to less than 2500, 2400, 2300, 2200, 2100, 2000, 1900, 1800, 1700, 1600, or 1500 pg/mL. In certain embodiments, treatment with omecamtiv mecarbil results in a reduction in the risk of heart failure event or cardiovascular death is a relative risk reduction of about 20% (e.g., 20%, 19%, 18%, 17%, 16%, 15%, 14%, 13%, 12%, 11%, 10%, 9%, 8%, 7%, 6%, 5%, etc.) and a reduction of NT-proBNP level at least 5%, 10%, 15%, 20%, 25%, 30%, 35%, 40%, 45%, or 50%. In certain other embodiments, treatment with omecamtiv mecarbil results in a reduction in the risk of heart failure event or cardiovascular death is a relative risk reduction of about 20% (e.g., 20%, 19%, 18%, 17%, 16%, 15%, 14%, 13%, 12%, 11%, 10%, 9%, 8%, 7%, 6%, 5%, etc.) and a reduction of NT-proBNP levels to less than 2500, 2400, 2300, 2200, 2100, 2000, 1900, 1800, 1700, 1600, or 1500 pg/mL.

Patients having a baseline systolic blood pressure (SBP): In some aspects, provided is a method of treating a patient having heart failure with low systolic blood pressure (e.g., less than or equal to 100 mmHg), by administering omecamtiv mecarbil as described herein. Typical HFrEF therapies may not be well-tolerated by patients having SBP less than or equal to 100 mmHg without increased incidence of adverse events or worsening renal function. Any additional therapeutic option is attractive for these individuals. Omecamtiv mecarbil may one such treatment possibility. Omecamtiv mecarbil was found to result in higher treatment efficacy in populations having lower baseline systolic blood pressure (e.g., less than or equal to 100 mmHg) at baseline.

In some embodiments, the patient exhibits a systolic blood pressure at baseline of less than or equal to about 120 mmHg, less than or equal to about 115 mmHg, less than or equal to about 110 mmHg, less than or equal to about 105 mmHg, less than or equal to about 100 mmHg, less than or equal to about 95 mmHg, less than or equal to about 90 mmHg, between about 85 mmHg and about 120 mmHg, or between about 110 mmHg and about 100 mmHg. In some embodiments, the patient with heart failure has a systolic blood pressure less than or equal to 100 mmHg prior to start of omecamtiv mecarbil treatment as described herein. In certain embodiments, the patient having heart failure exhibits a systolic blood pressure at baseline of between about 85 mmHg and about 100 mmHg, between about 85 mmHg and about 95 mmHg, between about 85 mmHg and about 90 mmHg, between about 90 mmHg and about 100 mmHg, between about 90 mmHg and about 95 mmHg, or between about 95 mmHg and about 100 mmHg.

It was observed that omecamtiv mecarbil reduced the risk of the primary endpoint to a greater extent in patients with lower SBP, demonstrating a linear inverse relation to baseline SBP. In some embodiments, patient receiving treatment exhibits a systolic blood pressure at baseline of less than or equal to about 100 mmHg, less than or equal to about 95 mmHg, less than or equal to about 90 mmHg, between about 85 mmHg and about 100 mmHg, between about 85 mmHg and about 95 mmHg, between about 85 mmHg and about 90 mmHg, between about 90 mmHg and about 100 mmHg, between about 90 mmHg and about 95 mmHg, or between about 95 mmHg and about 100 mmHg.

In some embodiments, treatment is effective to achieve a risk reduction, wherein the risk reduction is a relative risk reduction of about 18% (e.g., about 10%, 11%, 12%, 13%, 14%, 15%, 16%, 17%, 18%, 19%, 20%, etc.). In some embodiments, the patient receiving treatment exhibits a SBP at baseline of less than or equal to about 100 mmHg. In some embodiments, treatment in patients who exhibit a SBP at baseline of less than or equal to about 100 mmHg is effective to achieve a risk reduction, wherein the risk reduction is a relative risk reduction of about 18% (e.g., about 10%, 11%, 12%, 13%, 14%, 15%, 16%, 17%, 18%, 19%, 20%, etc.).

In one aspect, provided herein is a method of treating heart failure in a patient with heart failure who exhibits a SBP at baseline of less than or equal to about 100 mmHg, by administering omecamtiv mecarbil. In some embodiments, treatment in patients who exhibit a SBP at baseline of less than or equal to about 100 mmHg, by administering omecamtiv mecarbil is effective to provide risk reduction compared to placebo. The risk reduction may be relative risk reduction and/or absolute risk reduction. In some embodiments, risk reduction is measured as event rates per 100 patient years. An event may be a first heart failure event or cardiovascular death. In some embodiments, the risk reduction may be an absolute risk reduction and/or relative risk reduction, in patients having heart failure who exhibits a SBP at baseline of less than or equal to about 100 mmHg. In some embodiments, the treatment is effective to provide a relative risk reduction of at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%. In some embodiments, treatment with omecamtiv mecarbil results in a reduction in the risk of cardiovascular death and/or heart failure events (e.g., heart failure hospitalization) in patients who exhibit a SBP at baseline of less than or equal to about 100 mmHg. In some embodiments, provided is a method of reducing the time-to-first heart failure event in a patient who exhibits a SBP at baseline of less than or equal to about 100 mmHg by administering omecamtiv mecarbil as described herein. In some embodiments, provided is a method of reducing the number or frequency of heart failure events (e.g., heart failure hospitalizations) in a patient who exhibits a SBP at baseline of less than or equal to about 100 mmHg by administering omecamtiv mecarbil as described herein. In some embodiments, provided is a method of reducing risk of cardiovascular death in a patient who exhibits a SBP at baseline of less than or equal to about 100 mmHg by administering omecamtiv mecarbil as described herein.

In some embodiments, provided is a method of reducing the time-to-first heart failure event in a heart failure patient who exhibits a SBP at baseline of less than or equal to about 100 mmHg by administering omecamtiv mecarbil as described herein. In some embodiments, provided is a method of reducing the number or frequency of heart failure events (e.g., heart failure hospitalizations) in a heart failure patient who exhibits a SBP at baseline of less than or equal to about 100 mmHg by administering omecamtiv mecarbil as described herein. In some embodiments, provided is a method of reducing risk of cardiovascular death in a heart failure patient who exhibits a SBP at baseline of less than or equal to about 100 mmHg by administering omecamtiv mecarbil as described herein. In some embodiments, the relative risk reduction is at least 10% (e.g., 11%, 12%, 13%, 14%, 15%, 16%, 17%, 18%, 19%, 20%, etc.). In some embodiments, the relative risk reduction is 12%. In some embodiments, the relative risk reduction is 15%. In some embodiments, the relative risk reduction is 17%.

Patients unable to tolerate other standard of care medications: In some embodiments, in conjunction with embodiments above or below, the patient with heart failure is unable to tolerate other standard of care medications. Illustrative standard of care medications for treating heart failure include, for example, angiotensin-converting enzyme inhibitors, angiotensin II receptor blockers, beta blockers, diuretics, aldosterone antagonists, inotropes, neprilysin inhibitors, digitalis, and/or digoxin. In some instances, these patients have an inability to tolerate other standard of care medications due to, for example, low blood pressure, symptomatic hypotension, impaired renal function, or bradycardia. In some embodiments, the disclosure provides a method for treating a patient with heart failure having symptomatic hypotension, impaired renal functions, or bradycardia comprising administering omecamtiv mecarbil, as disclosed herein. Further, in some embodiments, the treated patient has not been previously treated with one or more of an angiontensin-converting enzyme inhibitor, an angiotension II receptor blocker, a beta blocker, a diuretic, an aldosterone antagonist, an inotrope, neprilysin inhibitors, digitalis, and/or digoxin. Moreover, in some embodiments, in conjunction with embodiments above or below, the patient treated herein has low blood pressure, symptomatic hypotension, impaired renal function, and/or bradycardia.

In some instances, the patient with heart failure has undergone or is undergoing, at the time of omecamtiv mecarbil treatment, one or more additional therapies (e.g., antihypertensive) and/or intervention strategies (e.g., implantable device). In some embodiments, in conjunction with embodiments above or below, the patient has undergone cardiac resynchronization therapy (CRT) prior to treatment. In some embodiments, in conjunction with embodiments above or below, the patient has an implantable cardioverter defibrillator (ICD) device. In some instances, the patient is administered sacubitril/valsartan.

Patients with chronic heart failure: in some embodiments, provided is a method of reducing the risk of heart failure events or death from cardiovascular causes in a heart failure patient, such as a patient with chronic heart failure, by administering omecamtiv mecarbil, or a hydrate, a salt, or a salt of a hydrate thereof, as described herein. A heart failure event includes, but is not limited to, urgent clinic visit, emergency department visit, and hospitalization for worsening heart failure. In some embodiments, in conjunction with embodiments above or below, a heart failure event is an urgent clinic visit, an emergency department visit, or hospitalization for worsening heart failure leading to treatment intensification beyond changed oral diuretic therapy.

In some embodiments, in conjunction with embodiments above or below, treatment is effective to reduce the risk of heart failure events in a heart failure patient, such as a patient with chronic heart failure. In some embodiments, the patent with chronic heart failure also has one or more of the following: reduced ejection fraction, LVEF of less than 30%, LVEF of less than 28%, LVEF of less than 25%, LVEF of less than 22%, advanced heart failure, heart failure classified as Class III or IV as determined using the NYHA classification, or at least one heart failure hospitalization within 6 months prior to the treatment. In some embodiments, the heart failure patient, such as a patient with chronic heart failure, is an inpatient.

In some embodiments, in conjunction with embodiments above or below, treatment is effective to reduce the risk of death, such as fatal stroke in a heart failure patient. In some embodiments, treatment is effective to reduce the risk of fatal stroke or non-fatal stroke in a heart failure patient (e.g., patient with chronic heart failure).

Administration Route and Dosing

The OM can be administered via any suitable route. In some embodiments, in conjunction with other above or below embodiments, omecamtiv mecarbil is administered orally. In some embodiments, in conjunction with other above or below embodiments, OM is administered as a tablet.

OM can be administered in any suitable amount. In some embodiments, in conjunction with other above or below embodiments, OM is administered at a dosage of 10 mg or more (e.g., 15 mg, 20 mg, 25 mg, 30 mg, 35 mg, or 40 mg or more). Alternatively, or in addition, OM can be administered at a dosage of 75 mg or less (e.g., 70 mg, 65 mg, 60 mg, 55 mg, 50 mg, or 45 mg or less).

It will be understood that descriptions herein regarding the amount of omecamtiv mecarbil, a pharmaceutically acceptable salt thereof, or a pharmaceutically acceptable hydrate of a pharmaceutically acceptable salt thereof, is relative to the salt or hydrate form of the active ingredient. The amount of omecamtiv mecarbil described herein refers to the amount (or the equivalent amount) of omecamtiv mecarbil free base. For example, when a tablet formulation is indicated to have 1 mg of omecamtiv mecarbil, the tablet formulation comprises 1.22 mg of omecamtiv mecarbil dihydrochloride monohydrate (molecular weight (MW) of 492.37 g/mol) which provides 1 mg of omecamtiv mecarbil (MW of 401.43 g/mol).

The disclosed method comprises administering OM using a suitable dosing schedule (e.g., once-a-day or twice daily). In some embodiments, in conjunction with other above or below embodiments, OM is administered twice daily.

In some embodiments, in conjunction with other above or below embodiments, OM is administered in a dosage of 25 mg twice daily, or 37.5 mg twice daily, or 50 mg twice daily. Plasma concentrations of omecamtiv mecarbil may be assessed after 2 weeks of treatment at a given dose and the dose adjusted so patients are in the target plasma concentration range according to the following: 1) if plasma concentration is <300 ng/mL, then increase to next higher dose; 2) if plasma concentration is 300-750 ng/mL, no change; and 3) if plasma concentration is >750 ng/mL, then decrease to next lower dose (if >750 ng/mL on starting dose of 25 mg BID, then 25 mg QD may be appropriate). Plasma concentrations of omecamtiv mecarbil may be assessed approximately 12 hours after the last dose of omecamtiv mecarbil. In some embodiments, the target plasma concentration range of omecamtiv mecarbil is 300 ng/mL to 750 ng/mL.

Omecamtiv mecarbil is a CYP3A4 substrate. Concomitant use of strong CYP3A4 inhibitors such as ketoconazole, or regimens containing ritonavir-or cobicistat may increase plasma concentrations of omecamtiv mecarbil. Concomitant use of strong CYP3A4 inducers, such as rifampin or carbamazepine may decrease plasma concentrations of omecamtiv mecarbil. Plasma concentrations of omecamtiv mecarbil may be re-checked following 2 weeks of initiation or discontinuation of a strong inhibitor or inducer of CYP3A4 to assess whether dose adjustment of omecamtiv mecarbil are warranted.

Omecamtiv Mecarbil, Salts, Hydrates, and Polymorphs Thereof

Omecamtiv mecarbil used in the disclosed methods can be present as a pharmaceutically acceptable salt, hydrate, or salt hydrate form, and can be formulated into any suitable pharmaceutical formulation.

As used herein, the term "pharmaceutically acceptable salts" include, but are not limited to salts with inorganic acids, such as hydrochloride, phosphate, diphosphate, sulfate, and like; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, $HOOC-(CH_2)_nCOOH$ where n is 0-4, and like. Those skilled in the art will recognize various synthetic methodologies that may be used to prepare non-toxic pharmaceutically acceptable addition salts. In some embodiments, the pharmaceutically acceptable salt is a dihydrochloride salt.

As used herein, the term "hydrate" refers to the chemical entity formed by the interaction of water and a compound, including, for example, hemi-hydrates, monohydrates, dihydrates, trihydrates, etc. In some embodiments, the omecamtiv mecarbil hydrate or salt thereof, is omecamtiv mecarbil monohydrate or salt thereof. In some cases, omecamtiv mecarbil is present as omecamtiv mecarbil dihydrochloride monohydrate.

As used herein, the term "crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. In some embodiments, in conjunction with other above or below embodiments, the disclosed methods comprise administering omecamtiv mecarbil dihydrochloride monohydrate salt. In some embodiments, in conjunction with other above or below embodiments, the methods comprise administering omecamtiv mecarbil dihydrochloride hydrate Form A. In some embodiments, in conjunction with other above or below embodiments, the omecamtiv mecarbil used herein is a solvate.

Figure 5:
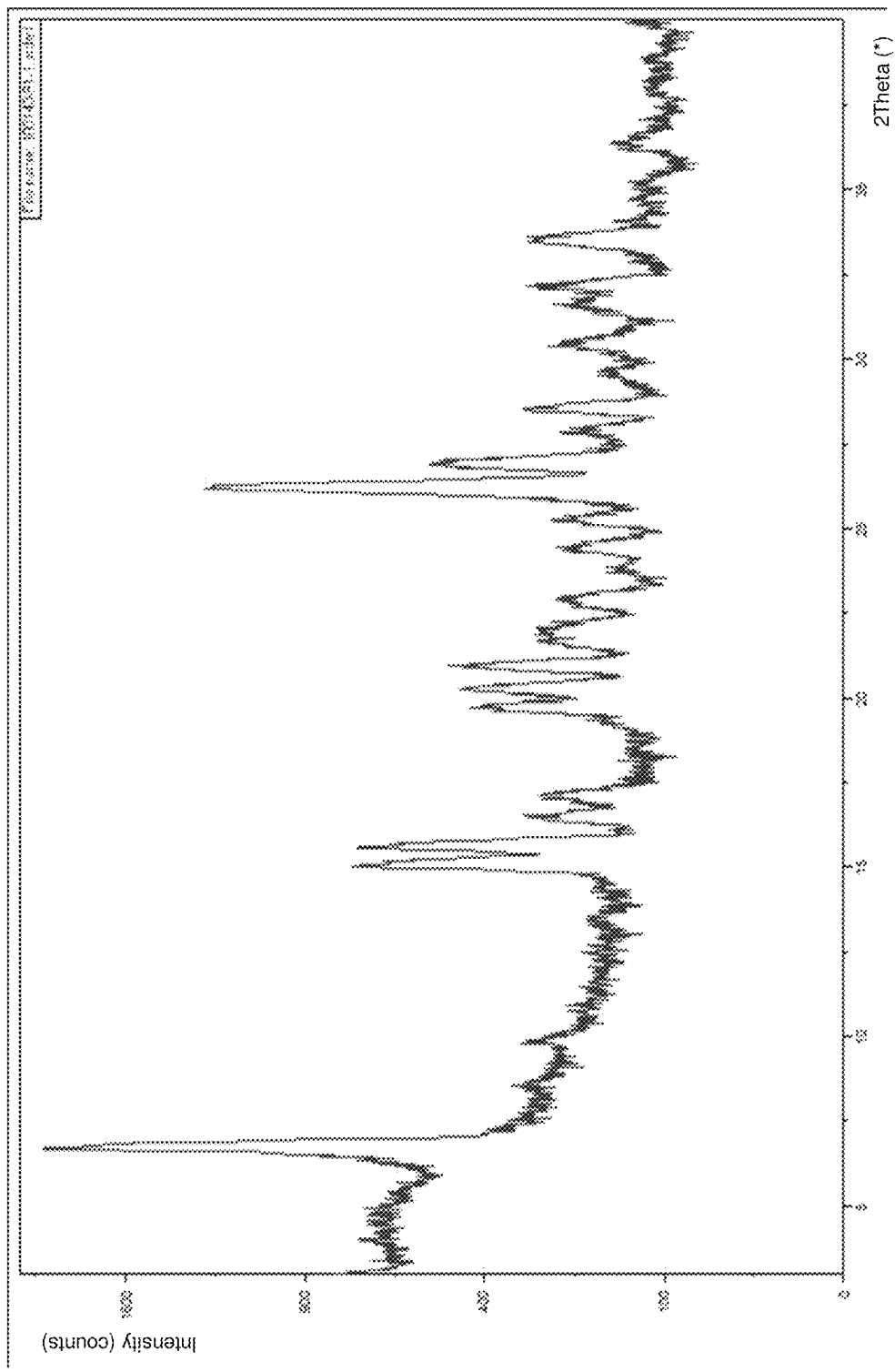
FIG. 5 shows a X-ray powder diffraction pattern (XRPD) for Form A of omecamtiv mecarbil dihydrochloride monohydrate.

Form A can be characterized by an X-ray powder diffraction (XRPD) pattern, obtained as set forth in WO2014/152270A1, having peaks at 6.6, 14.9, 20.1, 21.4, and 26.8±0.2° 2θ using Cu Kα radiation. Form A optionally can be further characterized by an XRPD pattern having additional peaks at 8.4, 24.2, 26.0, 33.3±0.2° 2θ using Cu Kα radiation. Form A optionally can be even further characterized by an XRPD pattern having additional peaks at 6.2, 9.7, 13.2, 14.3, 15.4, 16.3, 16.9, 18.9, 19.5, 20.7, 21.8, 22.8, 23.6, 25.1, 27.3, 27.7, 28.4, 29.4, 30.2, 31.2, 31.5, 31.9, 33.9, 34.5, 34.9, 36.1, 36.8, 37.7, 38.5, and 39.7±0.2° 2θ using Cu Kα radiation. In various cases, Form A can be characterized by an XRPD pattern having peaks at 6.2, 6.6, 8.4, 9.7, 13.2, 14.3, 14.9, 15.4, 16.3, 16.9, 18.9, 19.5, 20.1, 20.7, 21.4, 21.8, 22.8, 23.6, 24.3, 25.1, 26.0, 26.8, 27.3, 27.7, 28.4, 29.4, 30.2, 31.2, 31.5, 31.9, 33.3, 33.9, 34.5, 34.9, 36.1, 36.8, 37.7, 38.5, and 39.7±0.2° 2θ using Cu Kα radiation. In some embodiments, Form A can be characterized by an X-ray powder diffraction pattern substantially as depicted in FIG. 5 wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

In some embodiments, the omecamtiv mecarbil used in the described methods comprises omecamtiv mecarbil dihydrochloride Form B. In some embodiments, the omecamtiv mecarbil used in the described methods comprises omecamtiv mecarbil dihydrochloride Form C. Form B and Form C polymorphs of omecamtiv mecarbil are metastable anhydrous dihydrochloride forms, and can be formed under varied conditions and temperatures, as described in detail in WO2014/152270, the disclosure of which is incorporated by reference in its entirety.

Figure 6:
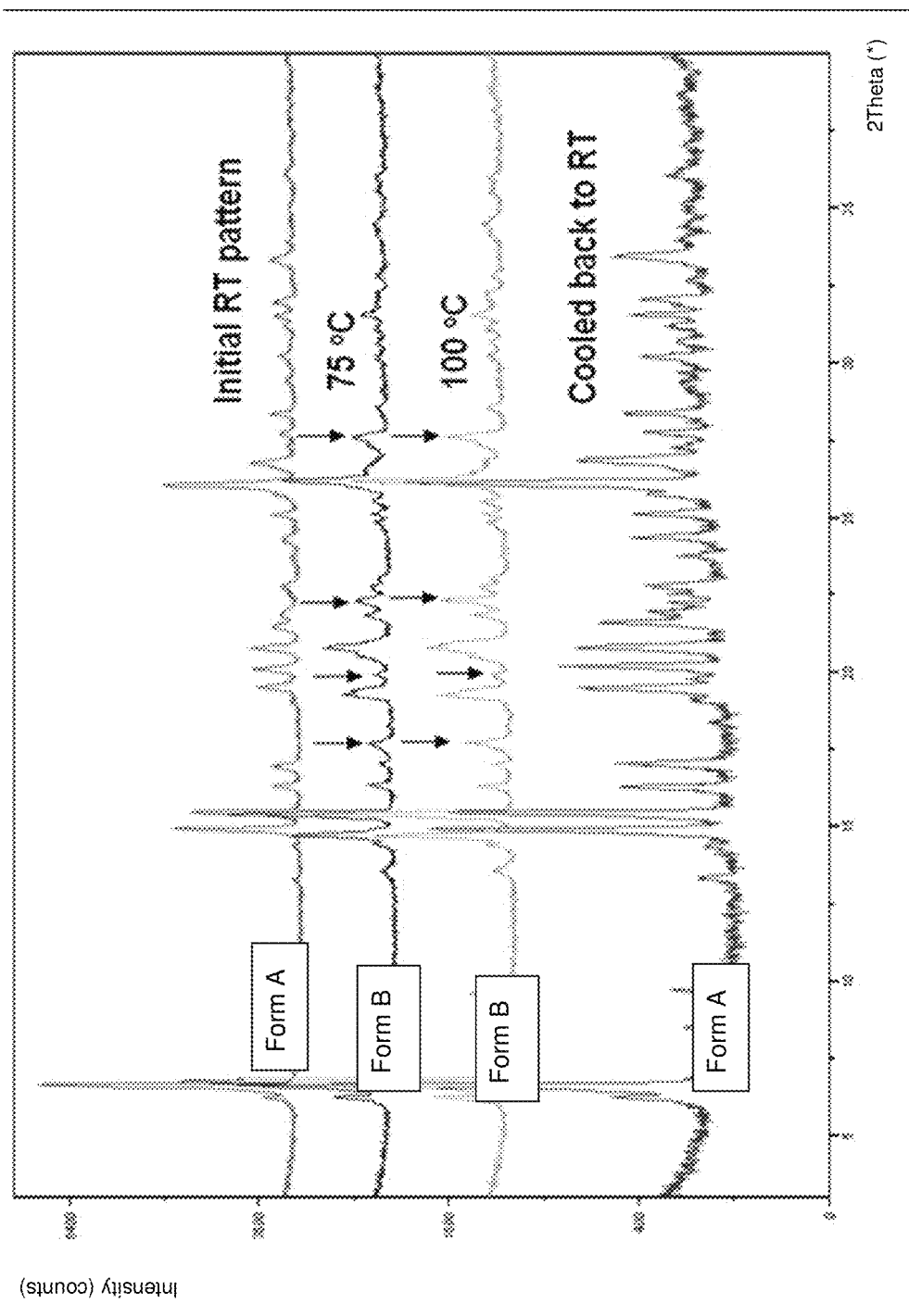
FIG. 6 shows a XRPD of a omecamtiv mecarbil dihydrochloride hydrate salt form, including Form B, at varying temperatures.

Form B can be characterized by an XRPD pattern having peaks at 6.8, 8.8, 14.7, 17.7, and 22.3±0.2° 2θ using Cu Kα radiation. Form B optionally can be further characterized by an XRPD pattern having additional peaks at 9.6, 13.5, 19.2, 26.2±0.2° 2θ using Cu Kα radiation. Form B can be characterized by an XRPD pattern having peaks at 6.2, 6.8, 8.8, 9.6, 13.5, 14.4, 14.7, 15.4, 16.3, 17.0, 17.7, 18.3, 19.2, 19.9, 20.5, 20.8, 21.8, 22.3, 22.7, 23.0, 24.8, 25.1, 25.5, 26.2, 26.4, 26.8, 27.5, 28.5, 30.2, 30.6, 31.1, 31.5, 32.1, 32.7, 34.1, 34.4, 35.5, 35.9, 38.1, 38.9±0.2° 2θ using Cu Kα radiation. In some embodiments, Form B can be characterized by an XRPD pattern substantially as depicted in FIG. 6, wherein by "substantially" is meant that the reported peaks can vary by ±0.2°.

Figure 7:
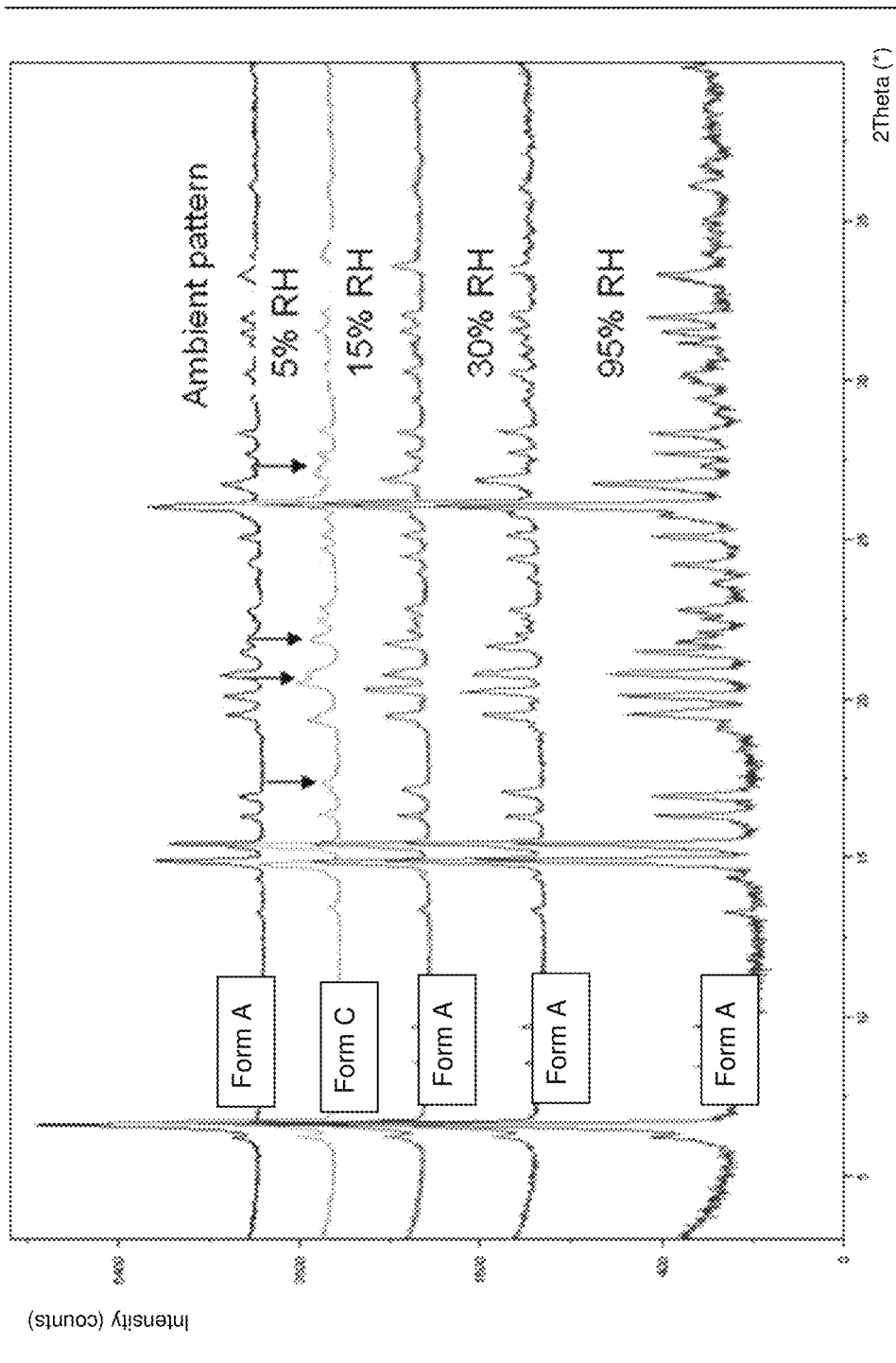
FIG. 7 shows a XRPD of a omecamtiv mecarbil dihydrochloride hydrate salt form, including Form C, at varying relative humidity conditions.

Form C can be characterized by an XRPD pattern having peaks at 6.7, 14.8, 17.4, 20.6, and 26.2±0.2° 2θ using Cu Kα radiation. Form C optionally can be further characterized by an XRPD pattern having additional peaks at 8.7, 22.0, 27.1, and 27.7±0.2° 2θ using Cu Kα radiation. Form C can be characterized by an XRPD pattern having peaks at 6.2, 6.7, 8.7, 9.6, 13.5, 14.5, 14.8, 15.4, 16.4, 17.1, 17.4, 18.4, 19.3, 19.5, 19.9, 20.6, 20.8, 21.8, 22.0, 22.5, 22.8, 24.3, 24.7, 25.1, 25.6, 26.2, 26.5, 27.1, 27.3, 27.7, 28.5, 30.0, 30.5, 31.0, 31.5, 32.2, 32.8, 34.1, 35.2, 36.0, 36.9, and 38.8±0.2° 2θ using Cu Kα radiation. In some embodiments, Form C can be characterized by an XRPD pattern substantially as depicted in FIG. 7, wherein by "substantially" is meant that the reported peaks can vary by ±0.2°.

Omecamtiv Mecarbil Formulations

The disclosed methods comprise administering a therapeutically effective amount omecamtiv mecarbil, or a pharmaceutically acceptable salt, a pharmaceutically acceptable hydrate, or a pharmaceutically acceptable hydrate of a pharmaceutically acceptable salt thereof, such as omecamtiv mecarbil dihydrochloride monohydrate in a suitable formulation.

Exemplary pharmaceutical formulations administered to patients in the methods disclosed herein include modified release matrix tablets capable of releasing omecamtiv mecarbil evenly at a pace controlled by the diffusion of omecamtiv mecarbil through a gel layer formed by the hydration of the control release agents in the tablets. In some embodiments, in conjunction with other above or below embodiments, the present modified release matrix tablets demonstrate a minimal pH-dependent release in-vitro. In some embodiments, in conjunction with other above or below embodiments, complete release of omecamtiv mecarbil is achieved in both pH 2 and 6.8 dissolution medium within 24 hours, possibly resulting in less inter- and intra-subject variability and food effect. It is found that the present modified release matrix tablet dosage form is superior to the former immediate release dosage form in minimizing the plasma peak-trough ratio. As a result, the present modified release matrix tablets reduce plasma concentration fluctuation, leading to reduced side effects, and improved safety and efficacy. It is also expected that the present modified release matrix tablets will improve patient compliance by reducing the dosing frequency. Additionally, the present modified release matrix tablets are physicochemically stable—resulting in no physical attribute, assay, impurity, or dissolution profile changes after storage at 40° C./75% RH for 6 months. Modified release may, in some embodiments, be extended release.

In some embodiments, in conjunction with other above or below embodiments, the exposure of omecamtiv mecarbil from two to twelve hours after dosing in humans is between 40 and 70 ng/mL. In some embodiments, in conjunction with other above or below embodiments, the exposure of omecamtiv mecarbil from two to twelve hours after dosing in humans remains between 40 and 55 ng/mL.

In some embodiments, in conjunction with other above or below embodiments, the omecamtiv mecarbil is released in the following intervals: 30% dose dissolved at 1 hour; 30-75% dose dissolved at 3 hours; and 80% dose dissolved at 12 hours.

In some embodiments, in conjunction with other above or below embodiments, the omecamtiv mecarbil is released in the following intervals: 30% dose dissolved at 2 hours; 30-75% dose dissolved at 6 hours; and 80% dose dissolved at 16 hours.

A typical pharmaceutical formulation as administered in the methods disclosed herein comprises omecamtiv mecarbil, or a pharmaceutically acceptable salt, a pharmaceutically acceptable hydrate, or a pharmaceutically acceptable hydrate of a pharmaceutically acceptable salt thereof; a control release agent; a pH modifying agent; a filler; and a lubricant.

In some embodiments, omecamtiv mecarbil can be administered as a tablet. For example, the tablet excipients may include one or more of fumaric acid, hypromellose, lactose monohydrate, microcrystalline cellulose, and magnesium stearate. The tablet may also comprise a film coating that may include one or more of polyethylene glycol, polyvinyl alcohol, talc, and titanium dioxide.

In some embodiments, in conjunction with other above or below embodiments, the pharmaceutical formulation administered comprises about 3-30% w/w of omecamtiv mecarbil, or a pharmaceutically acceptable salt, a pharmaceutically acceptable hydrate, or a pharmaceutically acceptable hydrate of a pharmaceutically acceptable salt thereof; 15-35% w/w control release agent; 20-45% w/w pH modifying agent; 25-65% w/w filler; and 0.1-1.0% w/w lubricant.

In some embodiments, in conjunction with other above or below embodiments, the pharmaceutical formulation administered comprises about 12-25 (w/w %) omecamtiv mecarbil Di-HCl hydrate; 25-35 (w/w %) Methocel™ K100 M Prem CR; 20-30 (w/w %) microcrystalline cellulose, PH 102; 5-10 (w/w %) lactose monohydrate, FF 316; 12-25 (w/w %) fumaric acid; 0.1-2 (w/w %) intra-granular magnesium stearate; and 0.1-2 (w/w %) extra-granular magnesium stearate. As used herein throughout, Methocel™ K100 M Prem CR is hypromellose having a viscosity of 100,000 mPa·s at 2% concentration in water at 20° C.

In some embodiments, in conjunction with other above or below embodiments, the pharmaceutical formulation administered comprises about 3-10 (w/w %) omecamtiv mecarbil Di-HCl hydrate; 20-40 (w/w %) Methocel™ K100 M Prem CR; 30-42 (w/w %) microcrystalline cellulose, PH 102; 12-25 (w/w %) lactose monohydrate, FF 316; 4-11 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation administered comprises about 12-25 (w/w %) omecamtiv mecarbil Di-HCl hydrate; 1-10 (w/w %) Methocel™ K100 M Prem CR; 12-27 (w/w %) Methocel™ K100 LV Prem CR; 20-35 (w/w %) microcrystalline cellulose, PH 102; 4-15 (w/w %) lactose monohydrate, FF 316; 12-25 (w/w %) fumaric acid; 0.1-2 (w/w %) intra-granular magnesium stearate; and 0.1-2 (w/w %) extra-granular magnesium stearate. As used herein throughout, Methocel™ K100 LV Prem CR is hypromellose having a viscosity of 100 mPa·s at 2% concentration in water at 20° C.

In some embodiments, in conjunction with other above or below embodiments, the pharmaceutical formulation administered comprises about 3-10 (w/w %) omecamtiv mecarbil Di-HCl hydrate; 1-10 (w/w %) Methocel™ K100 M Prem CR; 12-27 (w/w %) Methocel™ K100 LV Prem CR; 30-50 (w/w %) microcrystalline cellulose, PH 102; 15-25 (w/w %) lactose monohydrate, FF 316; 3-11 (w/w %) fumaric acid; 0.1-2 (w/w %) intra-granular magnesium stearate; and 0.1-2 (w/w %) extra-granular magnesium stearate.

In some embodiments, in conjunction with other above or below embodiments, the pharmaceutical formulation administered comprises about 18-19 (w/w %) omecamtiv mecarbil Di-HCl hydrate; 28-32 (w/w %) Methocel™ K100 M Prem CR; 23-26 (w/w %) microcrystalline cellulose, PH 102; 7-9 (w/w %) lactose monohydrate, FF 316; 17-20 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation administered comprises about 5-7 (w/w %) omecamtiv mecarbil Di-HCl hydrate; 27-33 (w/w %) Methocel™ K100 M Prem CR; 35-38 (w/w %) microcrystalline cellulose, PH 102; 17-20 (w/w %) lactose monohydrate, FF 316; 6-9 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation administered comprises about 17-20 (w/w %) omecamtiv mecarbil Di-HCl hydrate; 3-7 (w/w %) Methocel™ K100 M Prem CR; 18-22 (w/w %) Methocel™ K100 LV Prem CR; 26-30 (w/w %) microcrystalline cellulose, PH 102; 8-11 (w/w %) lactose monohydrate, FF 316; 17-20 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation administered comprises about 5-7 (w/w %) omecamtiv mecarbil Di-HCl hydrate; 3-7 (w/w %) Methocel™ K100 M Prem CR; 18-22 (w/w %) Methocel™ K100 LV Prem CR; 37-43 (w/w %) microcrystalline cellulose, PH 102; 18-22 (w/w %) lactose monohydrate, FF 316; 6-9 (w/w %) fumaric acid; 0.1-1 (w/w %) intra-granular magnesium stearate; and 0.1-1 (w/w %) extra-granular magnesium stearate.

In some embodiments, in conjunction with other above or below embodiments, the pharmaceutical formulation administered comprises about 18.37 (w/w %) omecamtiv mecarbil Di-HCl hydrate; 30 (w/w %) Methocel™ K100 M Prem CR; 24.20 (w/w %) microcrystalline cellulose, PH 102; 8.07 (w/w %) lactose monohydrate, FF 316; 18.37 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation administered comprises about 6.13 (w/w %) omecamtiv mecarbil Di-HCl hydrate; 30 (w/w %) Methocel™ K100 M Prem CR; 36.81 (w/w %) microcrystalline cellulose, PH 102; 18.40 (w/w %) lactose monohydrate, FF 316; 7.66 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation administered comprises about 18.37 (w/w %) omecamtiv mecarbil Di-HCl hydrate; 5 (w/w %) Methocel™ K100 M Prem CR; 20 (w/w %) Methocel™ K100 LV Prem CR; 27.95 (w/w %) microcrystalline cellulose, PH 102; 9.31 (w/w %) lactose monohydrate, FF 316; 18.37 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation administered comprises about 6.13 (w/w %) omecamtiv mecarbil Di-HCl hydrate; 5 (w/w %) Methocel™ K100 M Prem CR; 20 (w/w %) Methocel™ K100 LV Prem CR; 40.14 (w/w %) microcrystalline cellulose, PH 102; 20.07 (w/w %) lactose monohydrate, FF 316; 7.66 (w/w %) fumaric acid; 0.5 (w/w %) intra-granular magnesium stearate; and 0.5 (w/w %) extra-granular magnesium stearate.

In some embodiments, in conjunction with other above or below embodiments, the pharmaceutical formulation administered comprises about 6.13 (w/w %) omecamtiv mecarbil Di-HCl hydrate; 30 (w/w %) Methocel™ K100 M Prem CR; 27.94 (w/w %) microcrystalline cellulose, PH 102; 27.94 (w/w %) lactose monohydrate, FF 316; 6.74 (w/w %) fumaric acid; 0.5 (w/w %) intra-granular magnesium stearate; and 0.75 (w/w %) extra-granular magnesium stearate.

In some embodiments, in conjunction with other above or below embodiments, the pharmaceutical formulation administered comprises about 9.20 (w/w %) omecamtiv mecarbil Di-HCl hydrate; 30 (w/w %) Methocel™ K100 M Prem CR; 24.72 (w/w %) microcrystalline cellulose, PH 102; 24.71 (w/w %) lactose monohydrate, FF 316; 10.12 (w/w %) fumaric acid; 0.5 (w/w %) intra-granular magnesium stearate; and 0.75 (w/w %) extra-granular magnesium stearate.

In some embodiments, in conjunction with other above or below embodiments, the pharmaceutical formulation administered comprises about 12.27 (w/w %) omecamtiv mecarbil Di-HCl hydrate; 30 (w/w %) Methocel™ K100 M Prem CR; 21.49 (w/w %) microcrystalline cellulose, PH 102; 21.49 (w/w %) lactose monohydrate, FF 316; 13.50 (w/w %) fumaric acid; 0.5 (w/w %) intra-granular magnesium stearate; and 0.75 (w/w %) extra-granular magnesium stearate.

In some embodiments, in conjunction with other above or below embodiments, the pharmaceutical formulation administered comprises about 6.13 (w/w %) omecamtiv mecarbil Di-HCl hydrate; 30 (w/w %) Methocel™ K100 M Prem CR; 27.82 (w/w %) microcrystalline cellulose, PH 102; 27.81 (w/w %) lactose monohydrate, FF 316; 6.74 (w/w %) fumaric acid; 0.5 (w/w %) intra-granular magnesium stearate; and 1.0 (w/w %) extra-granular magnesium stearate.

In some embodiments, in conjunction with other above or below embodiments, the pharmaceutical formulation administered comprises about 9.20 (w/w %) omecamtiv mecarbil Di-HCl hydrate; 30 (w/w %) Methocel™ K100 M Prem CR; 24.59 (w/w %) microcrystalline cellulose, PH 102; 24.59 (w/w %) lactose monohydrate, FF 316; 10.12 (w/w %) fumaric acid; 0.5 (w/w %) intra-granular magnesium stearate; and 1.0 (w/w %) extra-granular magnesium stearate.

In some embodiments, in conjunction with other above or below embodiments, the pharmaceutical formulation administered comprises about 12.27 (w/w %) omecamtiv mecarbil Di-HCl hydrate; 30 (w/w %) Methocel™ K100 M Prem CR; 21.37 (w/w %) microcrystalline cellulose, PH 102; 21.36 (w/w %) lactose monohydrate, FF 316; 13.50 (w/w %) fumaric acid; 0.5 (w/w %) intra-granular magnesium stearate; and 1.0 (w/w %) extra-granular magnesium stearate.

In some embodiments, in conjunction with other above or below embodiments, the pharmaceutical formulation administered comprises about 12.27 (w/w %) omecamtiv mecarbil Di-HCl hydrate; 30 (w/w %) Methocel™ K100 M Prem CR; 31.04 (w/w %) microcrystalline cellulose, PH 102; 10.35 (w/w %) lactose monohydrate, FF 316; 15.34 (w/w %)

fumaric acid; 0.5 (w/w %) intra-granular magnesium stearate; and 0.5 (w/w %) extra-granular magnesium stearate.

Combination Therapy

In some embodiments, in conjunction with embodiments above or below, the disclosed methods can comprise administering one or more additional therapeutics suitable for treating/ameliorating one or more cardiovascular conditions. In some embodiments, in conjunction with embodiments above or below, the disclosed methods comprise administering to the patient a therapeutically effective amount of an angiotensin-converting enzyme (ACE) inhibitor. In some embodiments, in conjunction with embodiments above or below, the disclosed methods comprise administering to the patient a therapeutically effective amount of a mineralocorticoid receptor antagonist (MRA).

In some cases, the ACE inhibitor comprises one or more agents selected from benazepril, captopril, enalapril, fosinopril, lisinopril, moexipril, perindopril, quinapril, ramipril, and trandolapril.

In some cases, the MRA comprises one or more agents selected from spironolactone, eplerenone, canrenoic acid, canrenone, and drospirenone.

Embodiments

1. A method of treating heart failure in a patient having a left ventricular ejection fraction (LVEF) of less than 35% comprising administering to the patient a therapeutically effective amount of omecamtiv mecarbil, or a hydrate, a salt, or a salt of a hydrate thereof.

2. The method of embodiment 1, wherein the patient has a LVF of less than 30%.

3. The method of embodiment 1, wherein the patient has a LVF of less than 28%.

4. The method of embodiment 1, wherein the patient has a LVF of less than 25%.

5. The method of embodiment 1, wherein the patient has a LVEF of less than 22%.

6. A method of treating heart failure in a patient who does not exhibit atrial fibrillation or atrial flutter comprising administering to the patient a therapeutically effective amount of omecamtiv mecarbil, or a hydrate, a salt, or a salt of a hydrate thereof.

7. The method of embodiment 6, wherein the patient has a LVEF of less than 35%.

8. The method of embodiment 6, wherein the patient has a LVEF of less than 30%.

9. The method of embodiment 6, wherein the patient has a LVEF of less than 28%.

10. The method of embodiment 6, wherein the patient has a LVEF of less than 25%.

11. The method of embodiment 6, wherein the patient has a LVEF of less than 22%.

12. A method of treating heart failure in a patient having heart failure classified as Class III or IV as determined using the New York Heart Association (NYHA) classification comprising administering to the patient a therapeutically effective amount of omecamtiv mecarbil, or a hydrate, a salt, or a salt of a hydrate thereof.

13. A method of treating heart failure in a patient having advanced heart failure comprising administering to the patient a therapeutically effective amount of omecamtiv mecarbil, or a hydrate, a salt, or a salt of a hydrate thereof.

14. The method of embodiment 13, wherein the patient has heart failure classified as Class III or IV as determined using the New York Heart Association (NYHA) classification.

15. The method of embodiment 13 or 14, wherein the patient has a LVEF of less than 30%.

16. The method of any one of embodiments 13-15, wherein the patient has had at least one heart failure hospitalization within 6 months prior to the treatment.

17. The method of any one of embodiments 13-16, wherein the patient does not exhibit atrial fibrillation or atrial flutter.

18. A method of treating ischemic heart failure in a patient comprising administering to the patient a therapeutically effective amount of omecamtiv mecarbil, or a hydrate, a salt, or a salt of a hydrate thereof.

19. A method of treating heart failure in a patient who has had a myocardial infarction comprising administering to the patient a therapeutically effective amount of omecamtiv mecarbil, or a hydrate, a salt, or a salt of a hydrate thereof.

20. A method of treating heart failure in a patient who has a pretreatment level of NT-proBNP of at least 2,000 pg/mL comprising administering to the patient a therapeutically effective amount of omecamtiv mecarbil, or a hydrate, a salt, or a salt of a hydrate thereof.

21. The method of embodiment 20, wherein the patient has a LVEF of less than 35%.

22. The method of embodiment 20, wherein the patient has a LVEF of less than 30%.

23. The method of embodiment 20, wherein the patient has a LVEF of less than 28%.

24. The method of embodiment 20, wherein the patient has a LVEF of less than 25%.

25. The method of embodiment 20, wherein the patient has a LVEF of less than 22%.

26. The method of any one of embodiments 20-25, wherein the patient does not exhibit atrial fibrillation or atrial flutter.

27. A method of treating heart failure in a patient who has low blood pressure, symptomatic hypotension, impaired renal function, or bradycardia comprising administering to the patient a therapeutically effective amount of omecamtiv mecarbil, or a hydrate, a salt, or a salt of a hydrate thereof.

28. The method of embodiment 27, wherein the patient has not previously been treated with one or more of an angiotensin-converting enzyme inhibitor, an angiotensin II receptor blocker, a beta blocker, a diuretic, an aldosterone antagonist, an inotrope, neprilysin inhibitors, digitalis, and digoxin.

29. A method of treating heart failure in a patient who is unable to tolerate one or more of angiotensin-converting enzyme inhibitors, angiotensin II receptor blockers, beta blockers, diuretics, aldosterone antagonists, inotropes, neprilysin inhibitors, digitalis, and digoxin comprising administering to the patient a therapeutically effective amount of omecamtiv mecarbil, or a hydrate, a salt, or a salt of a hydrate thereof.

30. The method of embodiment 29, wherein the patient has low blood pressure, symptomatic hypotension, impaired renal function, or bradycardia.

31. A method of preventing stroke in a patient suffering from heart failure with reduced ejection fraction (HFrEF) comprising administering to the patient a therapeutically effective amount of omecamtiv mecarbil, or a hydrate, a salt, or a salt of a hydrate thereof.

32. The method of claim 31, wherein the stroke is non-fatal.

33. The method of claim 31, wherein the stroke is fatal.

34. The method of any one of claims 31 to 33, wherein the stroke is ischemic.

35. The method of any one of claims 31 to 33, wherein the stroke is ischemic with hemorrhagic transformation.

36. The method of any one of claims 31 to 33, wherein the stroke is hemorrhagic.

37. A method of reducing the risk of heart failure events or death from cardiovascular causes in a heart failure patient comprising administering to the patient a therapeutically effective amount of omecamtiv mecarbil, or a hydrate, a salt, or a salt of a hydrate thereof.

38. The method of claim 37, wherein the method reduces the risk of heart failure events in the patient.

39. The method of claim 37 or 38, wherein the patient has chronic heart failure with reduced ejection fraction.

40. The method of any one of claims 37-39, wherein the heart failure events are an urgent clinic visit, emergency department visit or hospitalization for worsening heart failure leading to treatment intensification beyond changed oral diuretic therapy.

41. The method of any one of claims 37-40, wherein the patient has a LVEF of less than 30%.

42. The method of any one of claims 37-40, wherein the patient has a LVEF of less than 28%.

43. The method of any one of claims 37-40, wherein the patient has a LVEF of less than 25%.

44. The method of any one of claims 37-40, wherein the patient has a LVEF of less than 22%.

45. The method of any one of claims 37-44, wherein the patient does not exhibit atrial fibrillation or atrial flutter.

46. The method of any one of claims 37-45, wherein the patient has advanced heart failure.

47. The method of any one of claims 37-46, wherein the patient has heart failure classified as Class III or IV as determined using the New York Heart Association (NYHA) classification.

48. The method of any one of claims 37-47, wherein the patient has had at least one heart failure hospitalization within 6 months prior to the treatment.

49. The method of any one of claims 1-48, wherein the patient is an inpatient.

50. The method of any one of claims 1-48, wherein the patient is an outpatient.

51. The method of any one of claims 1-50, wherein omecamtiv mecarbil is administered orally.

52. The method of claim 51, wherein omecamtiv mecarbil is administered as a tablet.

53. The method of any one of claims 1-52, comprising administering to the patient a therapeutically effective amount of omecamtiv mecarbil dihydrochloride hydrate.

54. The method of any one of claims 1-53, wherein omecamtiv mecarbil, or a hydrate, a salt, or a salt of a hydrate thereof is administered as a modified release matrix tablet.

55. The method of any one of claims 1-54, wherein omecamtiv mecarbil is administered twice daily.

56. The method of claim 55, wherein omecamtiv mecarbil is administered in a dosage of 25 mg twice daily.

57. The method of claim 55, wherein omecamtiv mecarbil is administered in a dosage of 37.5 mg twice daily.

58. The method of claim 55, wherein omecamtiv mecarbil is administered in a dosage of 50 mg twice daily.

59. The method of any one of claims 1-58, wherein the patient has undergone cardiac resynchronization therapy (CRT) prior to treatment.

60. The method of any one of claims 1-59, wherein the patient has an implantable cardioverter defibrillator (ICD) device.

61. The method of any one of claims 1-60, further comprising administering to the patient a therapeutically effective amount of an angiotensin-converting enzyme inhibitor.

62. The method of any one of claims 1-61, further comprising administering to the patient a therapeutically effective amount of a mineralocorticoid receptor antagonist.

Examples

The following examples further illustrate the disclosed methods of treatment, but of course, should not be construed as in any way limiting its scope.

The following abbreviations are used in the Examples: ACEi refers to angiotensin-converting enzyme inhibitor; ARB refers to angiotensin receptor blocker; ARNi refers to angiotensin receptor-neprilysin inhibitor; BB refers to beta blocker; CRT refers to cardiac resynchronization therapy; ED refers to emergency department; eGFR refers to estimated glomerular filtration rate; HF refers to heart failure; hsTn refers to high-sensitivity troponin I; ICD refers to implantable cardioverter-defibrillator; KCCQ refers to Kansas City Cardiomyopathy Questionnaire; LVEF refers to left ventricular ejection fraction; MAGGIC refers to Meta-Analysis Global Group in Chronic HF; MRA refers to mineralocorticoid receptor antagonist; NEJM refers to The New England Journal of Medicine; NT-proBNP refers to N-terminal pro-B-type natriuretic peptide; NYHA refers to New York Heart Association; SBP refers to systolic blood pressure; and SGLT2 refers to sodium-glucose co-transporter 2.

The endpoints of studies and event definitions were based on ACC/AHA standards for endpoint definitions in cardiovascular clinical trials as described in Hicks et al. 2017 Cardiovascular and Stroke Endpoint Definitions for Clinical Trials, J Am Coll Cardiol 2018; 71:1021-34.

Patient Eligibility

Patient eligibility requirements included age 18-85 years, New York Heart Association functional class (NYHA) II-IV symptoms, and ejection fraction of 35% or less. Participants were currently hospitalized for heart failure (in-patients) or had either an urgent visit to the emergency department or a hospitalization for heart failure (outpatients) within one year prior to randomization. Participants had N-terminal pro-B-type natriuretic peptide (NT-proBNP) concentration ≥400 pg/mL or BNP≥125 pg/mL at screening (if in atrial fibrillation/flutter: NT-proBNP≥1,200 pg/mL or BNP≥375 pg/mL). Patients were required to receive standard drug and device therapy for heart failure consistent with regional clinical practice guidelines and doses optimized according to investigator judgment.

Key exclusion criteria for patients included current hemodynamic or clinical instability requiring mechanical or intravenous medication, systolic blood pressure (SBP)<85 mmHg, estimated glomerular filtration rate (eGFR)<20 mL/min/1.73 m$^2$, recent acute coronary syndrome events or cardiovascular procedures (including planned), and other conditions that would adversely affect participation in the trial.

Study Procedures

All eligible participants were randomized 1:1 to oral administration of either placebo or omecamtiv mecarbil (pharmacokinetic-guided dosing: 25, 37.5 or 50 mg) twice daily. Pre-dose plasma concentrations of omecamtiv mecarbil were measured at weeks 2 and 6 with respective dose adjustments on weeks 4 and 8. The patient and investigator were blinded to the plasma concentrations and dispensed dose. The full schedule of assessments is provided in the protocol available at NEJM.org. Study drug was temporarily withheld if the participant experienced clinical signs or symptoms consistent with acute myocardial infarction or ischemia.

Study Outcomes

The primary outcome was a composite of the time to a heart failure event or cardiovascular death, whichever occurred first. A heart failure event was defined as an urgent clinic visit, emergency department visit or hospitalization for subjectively and objectively worsening heart failure leading to treatment intensification beyond changed oral diuretic therapy. Secondary outcomes were: the time to cardiovascular death; change in KCCQ Total Symptom Score (TSS) from baseline to Week 24 (scale from 0 to 100; higher score indicates fewer symptoms); time to first heart failure hospitalization; and time to all-cause death. All deaths, HF events, major cardiac ischemic events (myocardial infarction/unstable angina hospitalization, and coronary revascularization), and strokes were adjudicated by a blinded external Clinical Events Committee (Duke Clinical Research Institute) using standardized definitions.

Summary of Results

Over a median of 21.8 months, the primary outcome occurred in 1523 of 4120 patients (37.0%) in the omecamtiv mecarbil group and in 1607 of 4112 patients (39.1%) in the placebo group (hazard ratio, 0.92; 95% CI 0.86, 0.99; P=0.025); 808 patients (19.6%) receiving omecamtiv mecarbil and 798 patients (19.4%) receiving placebo died from cardiovascular causes (hazard ratio, 1.01; 95% CI, 0.92 to 1.11; P=0.86), 1177 (28.6%) and 1236 (30.1%) experienced a first heart failure event (hazard ratio, 0.93; 95% CI, 0.86 to 1.00; P=0.063), and 1067 (25.9%) and 1065 (25.9%) died from any cause (hazard ratio 1.00; 95% CI, 0.92 to 1.09). The frequency of cardiac ischemic and ventricular arrhythmia events did not differ between treatment groups.

Patients enrolled as in patients were more symptomatic as suggested by their lower KCCQ total symptom score at baseline; those receiving omecamtiv mecarbil had a 2.5 point improvement in this score compared to those on placebo.

Statistical Analysis

A sample size of approximately 8,000 patients was chosen to provide 90% power to detect a hazard ratio of 0.8 for cardiovascular death assuming the following: a 10% annualized rate of cardiovascular death in the first year and 7% thereafter; a 24-month enrollment period; total study duration set to 48 months; a 3-month treatment lag with a treatment effect hazard ratio of 0.8 thereafter, 10% annual rate of study drug discontinuation, and 10% of subjects lost to endpoint determination either through non-cardiovascular death or study discontinuation over the course of the trial. The study was event-driven and was ended after approximately 1590 cardiovascular deaths. The overall type I error was 0.05 for 2-sided testing across primary and secondary endpoints with control for multiplicity testing. A single interim efficacy analysis was conducted after approximately two-thirds of the targeted number of cardiovascular deaths accrued with a one-sided alpha of 0.0005. Given the negligible impact of this interim on the final alpha, the full 0.05 was used in the final analysis consistent with the Haybittle-Peto approach. Efficacy analyses were performed according to randomized treatment group assignment (intention-to-treat) on the full analysis set which included all randomized patients except for 24 subjects from a single site excluded due to Good Clinical Practice violations. Time-to-event data were evaluated with Kaplan-Meier estimates and Cox proportional-hazards models stratified by randomization setting and region with treatment group and baseline eGFR as covariates. The mean differences in the KCCQ TSS change from baseline to Week 24 were estimated using a mixed model stratified by randomization setting (inpatient and outpatient) containing baseline TSS value, region, baseline eGFR, scheduled visit, treatment group, and the interaction of treatment group with scheduled visit. A joint omnibus F-test was used to test the treatment effect for the KCCQ TSS. An overall pooled estimate for the KCCQ TSS treatment difference to placebo were conducted using a likelihood based approach. The prespecified safety analyses included: serious adverse events; adverse events associated with discontinuation of study treatment; "adverse events of interest" i.e., ventricular arrhythmias requiring treatment and positively adjudicated major cardiac ischemic events (including myocardial infarction, hospitalization for unstable angina, coronary revascularization). The safety analyses were performed in patients who underwent randomization and received at least one dose of omecamtiv mecarbil or placebo with the same exclusion of the 24 subjects as in the full analysis set. All analyses were performed with the use of SAS software, version 9.4 (SAS Institute).

Enrollment, Randomization, Treatment and Follow-Up 8,256 participants were randomized and 24 patients were excluded prior to database lock due to Good Clinical Practice violations. Accordingly, 8,232 patients were included in the efficacy analysis. At the end of the trial, 16 patients had unknown vital status (omecamtiv mecarbil: nine patients withdrew consent; placebo: six patients withdrew consent and one lost to follow-up). The baseline characteristics were balanced between the two treatment groups (Table 1). The overall median duration of follow-up was 21.8 months (Q1, Q3; 15.4, 28.6 months).

TABLE 1

Baseline characteristics of patients

| Demographics | OM (N = 4120) | Placebo (N = 4112) |
|---|---|---|
| Age (years), median (Q1, Q3) | 66 (58, 73) | 66 (58, 73) |
| Age (years), mean (SD) | 64.5 (11.3) | 64.5 (11.4) |
| Sex, female, n (%) | 875 (21.2) | 874 (21.3) |
| Race, n (%)* | | |
| White | 3196 (77.6) | 3201 (77.8) |
| Asian | 355 (8.6) | 355 (8.6) |
| Black or African American | 285 (6.9) | 277 (6.7) |
| Other | 284 (6.9) | 279 (6.8) |
| Ethnicity, Hispanic/Latino n (%) | 886 (21.5) | 885 (21.5) |
| Geographic Region, n (%) | | |
| Eastern Europe/Russia | 1344 (32.6) | 1337 (32.5) |
| Western Europe/South Africa/Australasia | 961 (23.3) | 960 (23.3) |
| Latin and South America | 787 (19.1) | 787 (19.1) |
| US and Canada | 693 (16.8) | 693 (16.9) |
| Asia | 335 (8.1) | 335 (8.1) |
| Clinical Characteristics | | |
| Medical Conditions, n (%) | | |
| Coronary artery disease | 2568 (62.3) | 2560 (62.3) |
| Myocardial infarction | 1693 (41.1) | 1742 (42.4) |
| Percutaneous coronary intervention | 1232 (29.9) | 1206 (29.3) |
| Coronary artery bypass grafting | 639 (15.5) | 678 (16.5) |
| Peripheral artery disease | 418 (10.1) | 429 (10.4) |
| Stroke | 377 (9.2) | 377 (9.2) |
| Atrial fibrillation or flutter at screening | 1146 (27.8) | 1099 (26.7) |
| Hypertension | 2910 (70.6) | 2874 (69.9) |
| Type 2 diabetes mellitus | 1652 (40.1) | 1657 (40.3) |
| Chronic kidney disease | 1475 (35.8) | 1519 (36.9) |
| Chronic Obstructive Pulmonary Disease | 665 (16.1) | 680 (16.5) |
| Asthma | 218 (5.3) | 222 (5.4) |
| Heart Failure History | | |
| LVEF (%), median (Q1, Q3) | 28 (22, 32) | 27 (21, 32) |
| LVEF (%), mean (SD) | 26.6 (6.3) | 26.5 (6.3) |
| MAGGIC Score, mean (SD) | 23.3 (6.3) | 23.4 (6.4) |
| MAGGIC Score, median (Q1, Q3) | 23 (19, 28) | 23 (19, 28) |
| NYHA classification, n (%) | | |
| Class II | 2195 (53.3) | 2173 (52.8) |
| Class III | 1801 (43.7) | 1815 (44.1) |

TABLE 1-continued

Baseline characteristics of patients

| Demographics | OM (N = 4120) | Placebo (N = 4112) |
|---|---|---|
| Class IV | 124 (3.0) | 124 (3.0) |
| Ischemic heart failure etiology, n (%) | 2193 (53.2) | 2222 (54.0) |
| KCCQ Total Symptom Score, median (Q1, Q3) | 68.8 (49, 87.5) | 68.8 (49, 87.5) |
| Vitals and Laboratory Parameters | | |
| Body mass index (kg/m$^2$), mean (SD) | 28.5 (6.3) | 28.4 (6.1) |
| Body mass index (kg/m$^2$), median (Q1, Q3) | 27.6 (24.2, 31.7) | 27.6 (24.2, 31.6) |
| SBP (mmHg), median (Q1, Q3) | 116 (105, 128) | 117 (105, 128) |
| SBP (mmHg), mean (SD) | 116.3 (15.4) | 116.6 (15.3) |
| Heart rate (beats/min), median (Q1, Q3) | 71 (64, 80) | 71 (64, 80) |
| Heart rate (beats/min), mean (SD) | 72.4 (12.2) | 72.3 (12.1) |
| NT-proBNP (pg/mL), median (Q1-Q3) | 1977 (980, 4061) | 2025 (1000, 4105) |
| hsTnI (ng/mL), median (Q3) | 0.027 (0.052) | 0.027 (0.052) |
| eGFR (mL/min/1.73 m$^2$), median (Q1-Q3) | 58.8 (44.3, 74.3) | 58.7 (43.8, 73.7) |
| G≤2: >60 | 1964 (47.7) | 1947 (47.3) |
| G3: 30-59 | 1882 (45.7) | 1912 (46.5) |
| G4: 15-29 | 270 (6.6) | 252 (6.1) |
| G5: <15 | 4 (<0.1) | 1 (<0.1) |
| Medications and Cardiac Devices, n (%) | | |
| ACEi, ARB or ARNi | 3583 (87.0) | 3576 (87.0) |
| ARNi | 819 (19.9) | 782 (19.0) |
| BB | 3881 (94.2) | 3883 (94.4) |
| MRA | 3199 (77.6) | 3198 (77.8) |
| (ACEi, ARB, or ARNi) + MRA + BB | 2709 (65.8) | 2716 (66.1) |
| Digitalis Glycosides | 687 (16.7) | 698 (16.7) |
| SGLT2 Inhibitors | 104 (2.5) | 114 (2.8) |
| Ivabradine | 255 (6.2) | 278 (6.8) |
| Cardiac Resynchronization Therapy | 592 (14.4) | 566 (13.8) |
| Implantable Cardioverter Defibrillator | 1326 (32.2) | 1288 (31.3) |

Outcomes

Figure 1B:
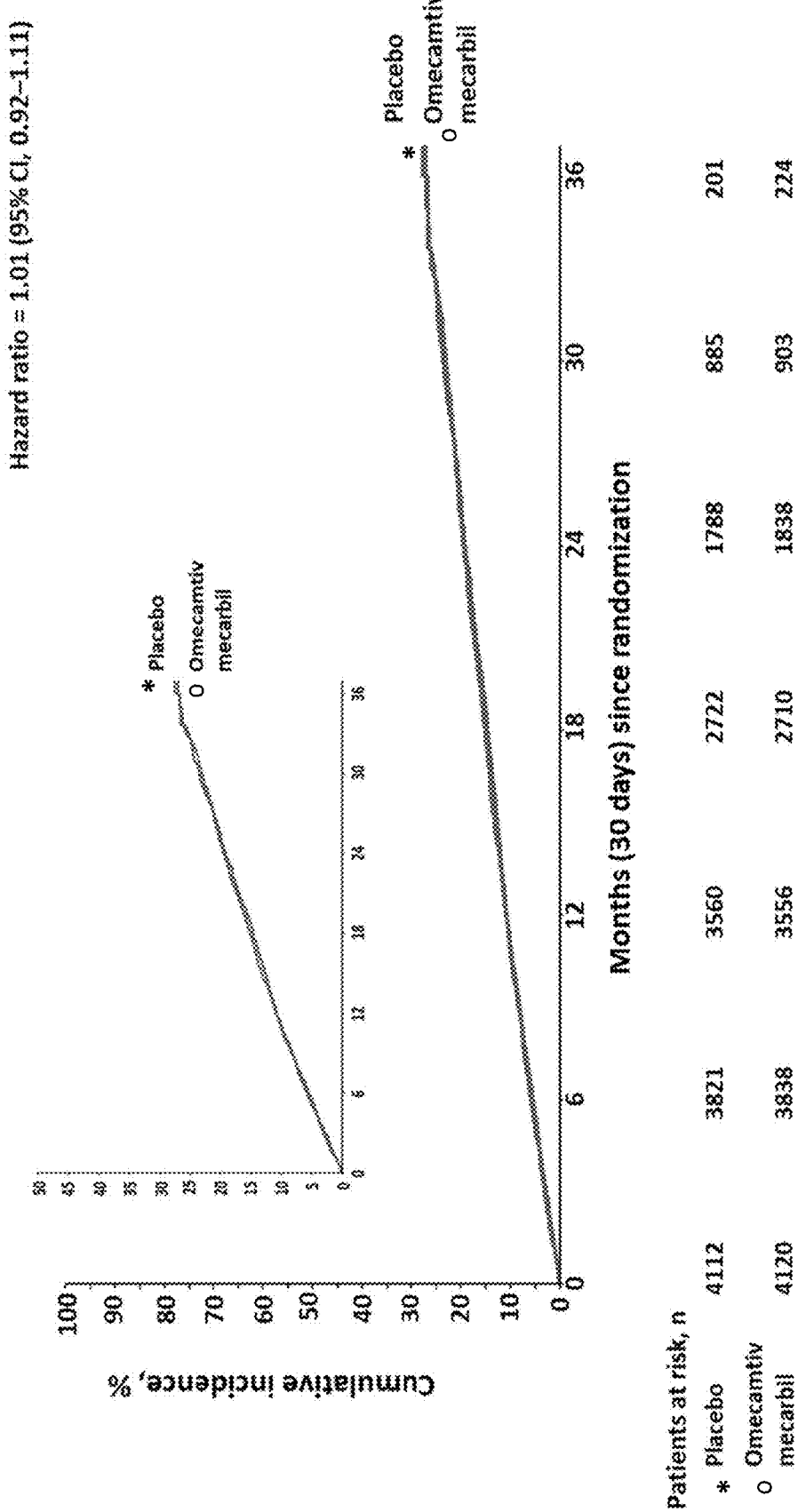
FIG. 1B shows the incidence of cardiovascular death in the patient population evaluated.
Figure 1C:
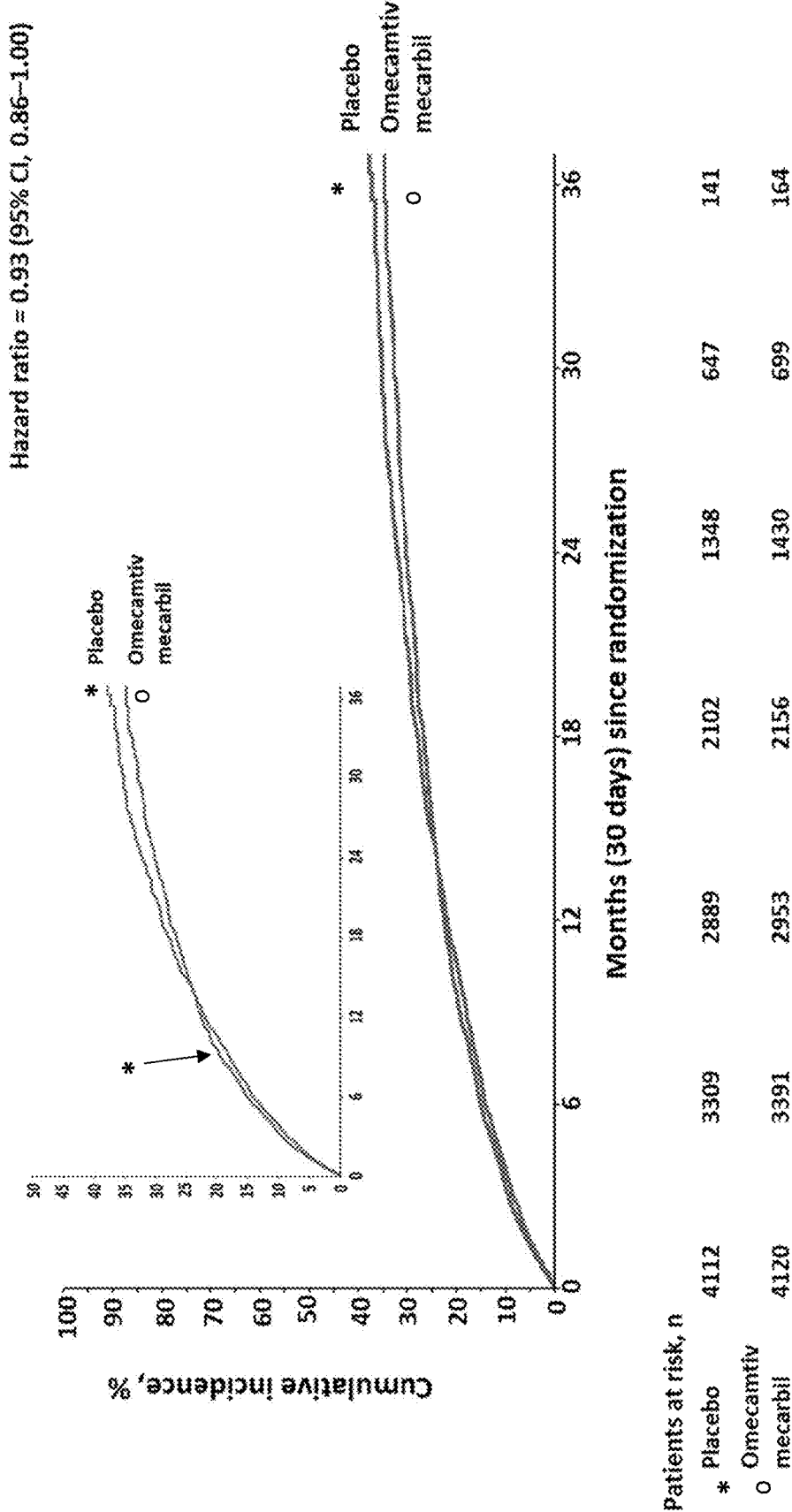
FIG. 1D shows the incidence of all deaths in the patient population evaluated.

A first heart failure event or death from cardiovascular causes occurred in 1523 of 4120 patients (37.0%) in the omecamtiv mecarbil group and in 1607 of 4112 patients (39.1%) in the placebo group (hazard ratio, 0.92; 95% confidence interval [CI] 0.86, 0.99; P=0.025; FIG. 1A and Table 2). For the two components of this time-to-first event composite, 1177 (28.6%) in patients receiving omecamtiv mecarbil and 1236 (30.1%) in the placebo group experienced a first heart failure event (hazard ratio, 0.93; 95% CI, 0.86 to 1.00; P=0.063; FIG. 1B and Table 2); death from cardiovascular causes contributed 346 events (8.4%) and 371 events (9.0%) (Table 2). The effect of omecamtiv mecarbil was generally consistent across most prespecified subgroups with statistically the largest potential interaction observed for the ejection fraction subgroup (interaction effect p=0.003; FIG. 3).

Figure 1D:
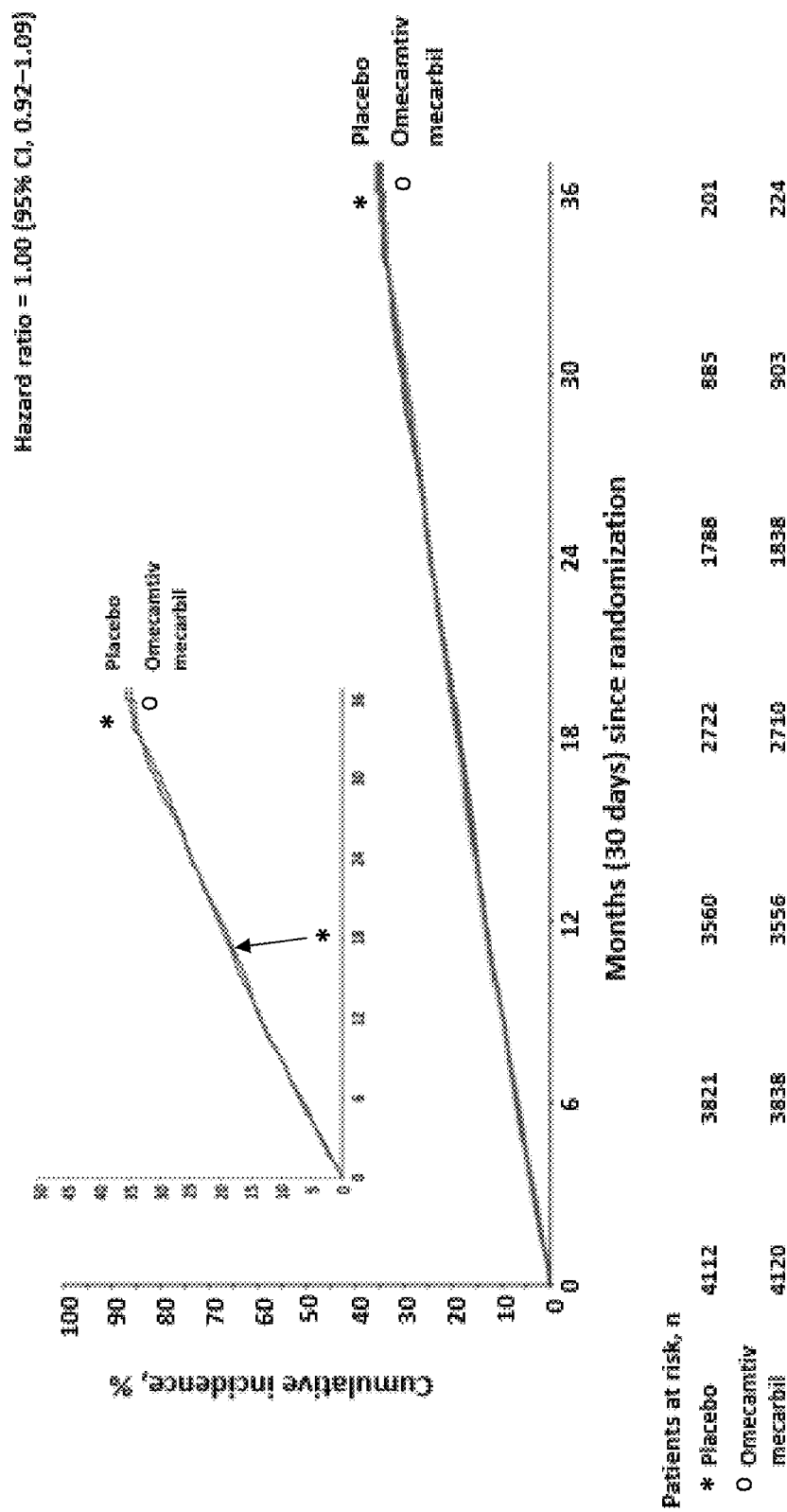
Figure 2A:
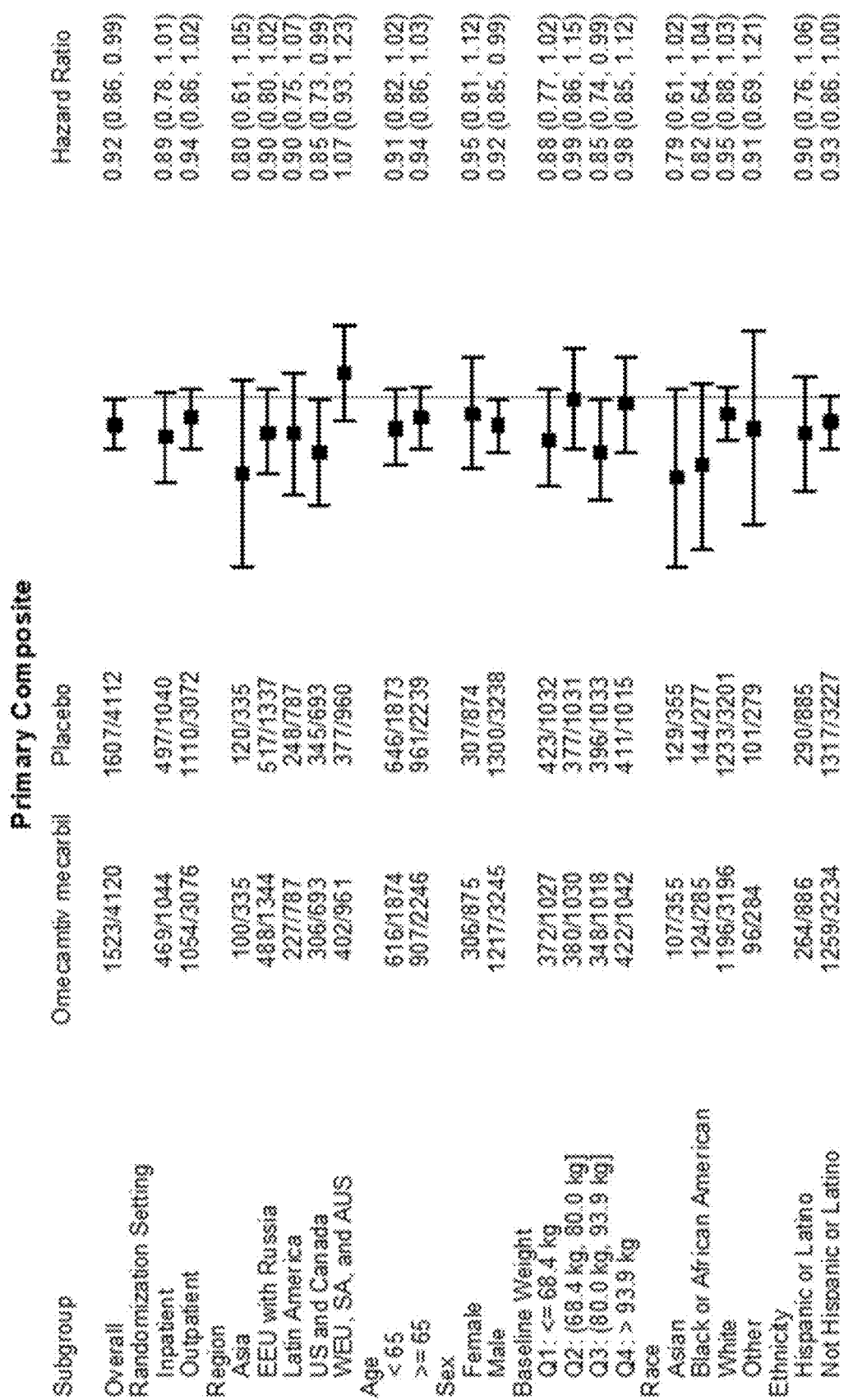
FIGS. 2A, 2B, and 2C show the primary outcome of the trial as a composite of heart failure event or cardiovascular death, according to subgroups that were prespecified in the protocol. Race was self-reported by patients. Baseline NT-proBNP subgroups exclude subjects in atrial fibrillation/flutter at screening.
Figure 2B:
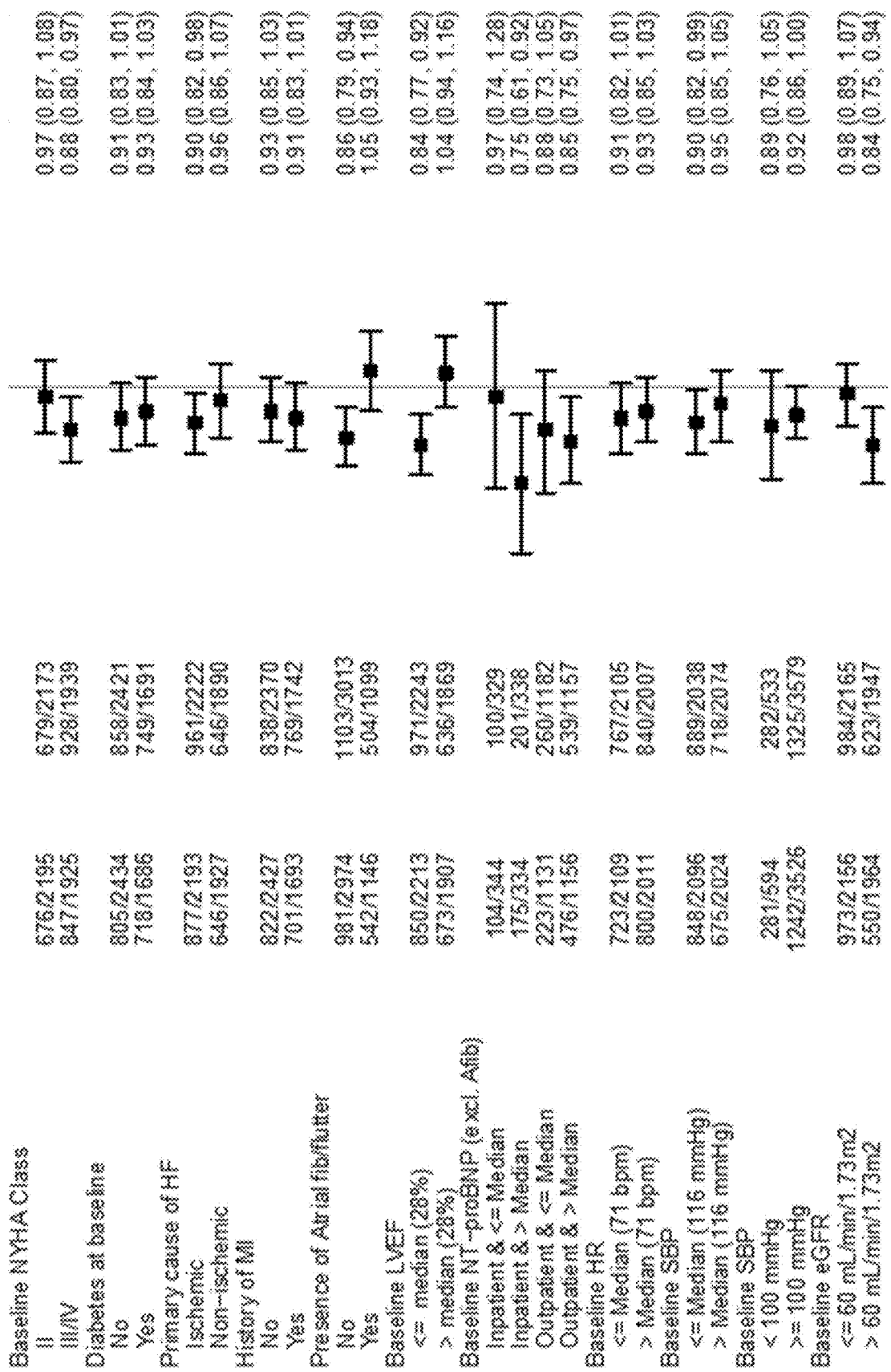
Figure 2C:
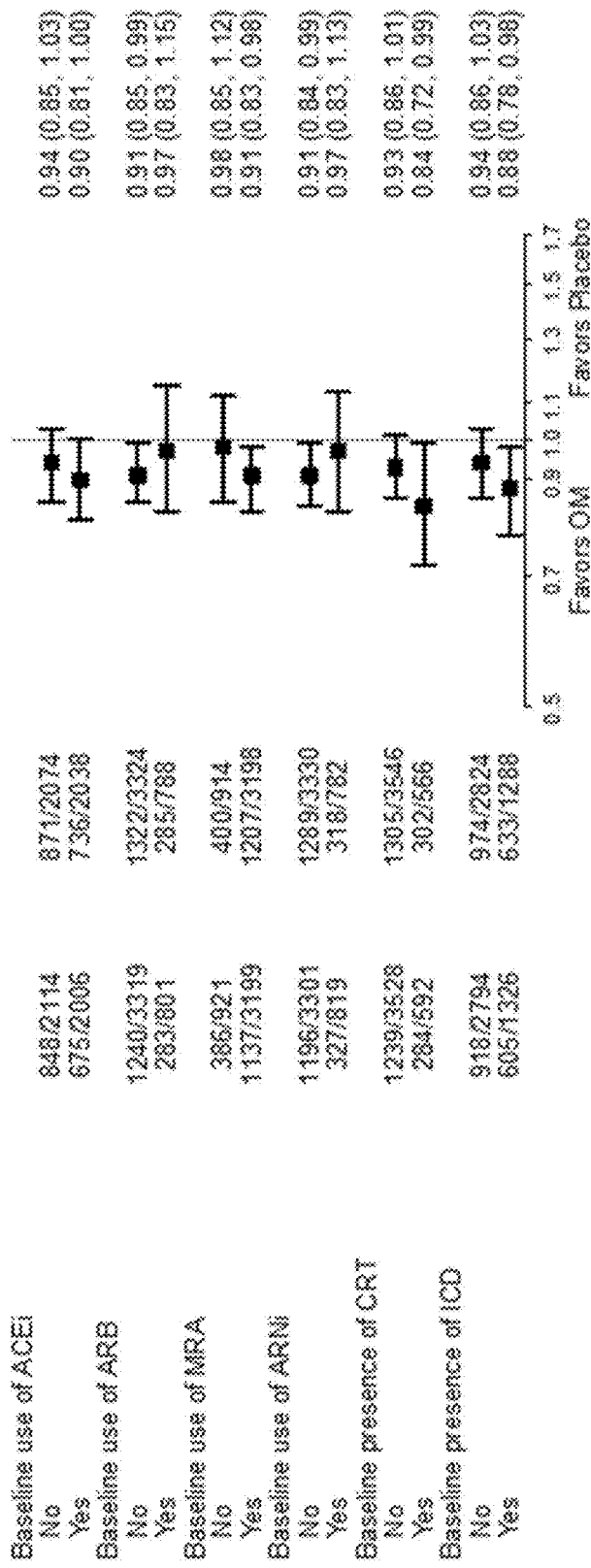
Figure 4:
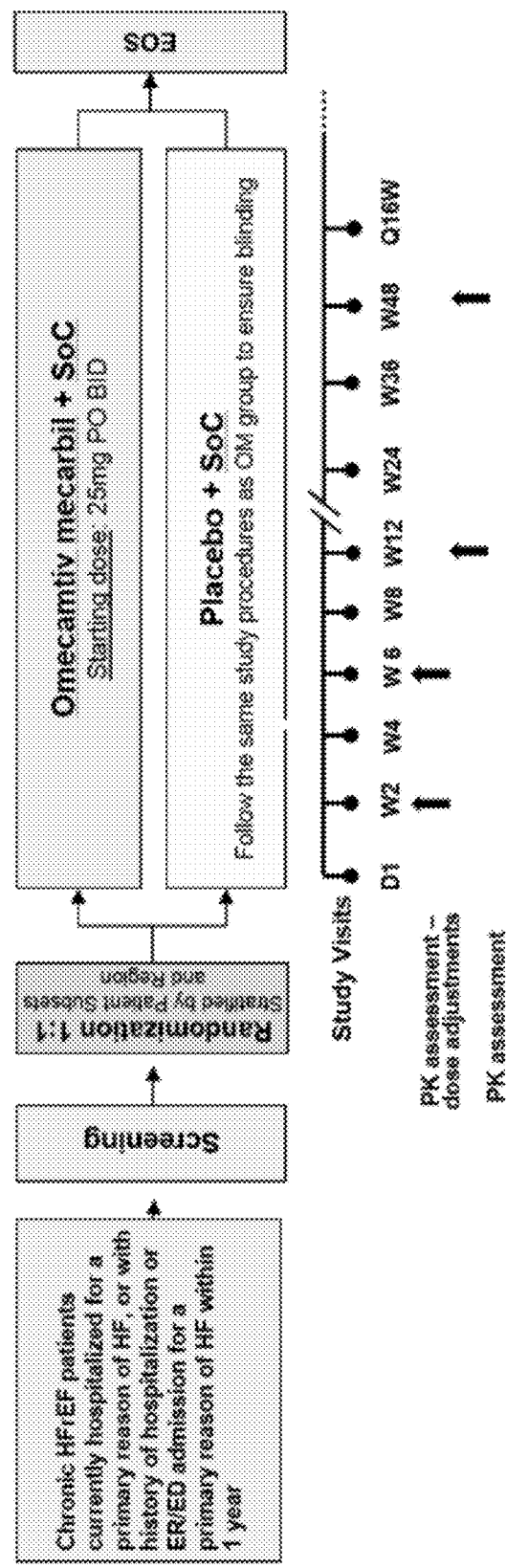
FIG. 4 shows a design of a clinical trial of omecamtiv mecarbil.
Figure 10A:
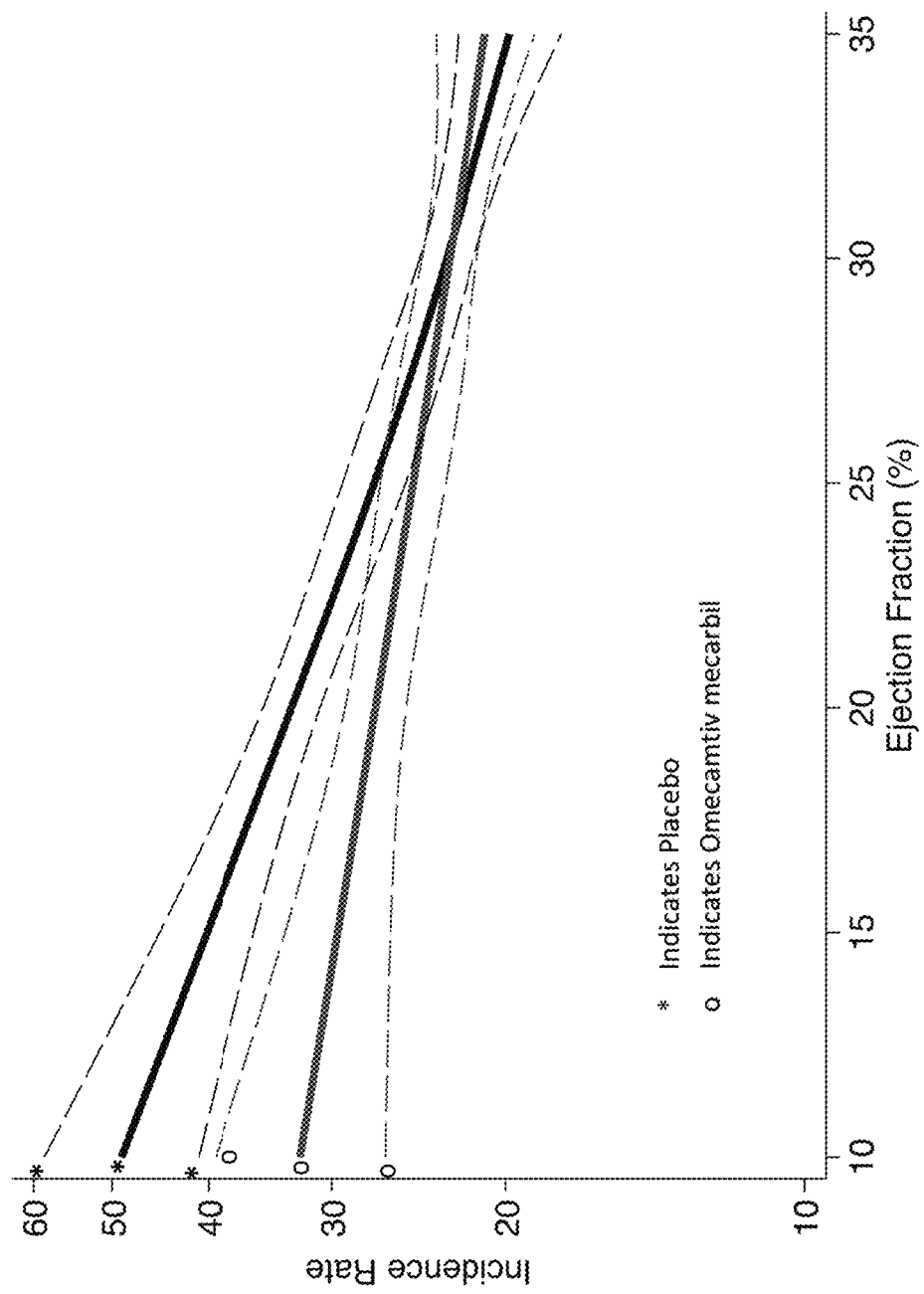
FIG. 10A shows The difference in the incidence of the primary composite endpoint increased disproportionately between the placebo (stars) and omecamtiv mecarbil (circles) treatment groups with lower ejection fractions.

The secondary outcome of time to death from cardiovascular causes occurred in 808 (19.6%) patients receiving omecamtiv mecarbil and 798 patients (19.4%) receiving placebo (hazard ratio, 1.01; 95% CI, 0.92 to 1.11; P=0.86; FIG. 10 and Table 2). The pre-specified analysis of change from baseline to week 24 KCCQ total symptom score improvement by randomization setting (inpatient mean difference [95% CI]: 2.50 [0.54, 4.46], outpatient: −0.46 [−1.40, 0.48], joint p=0.028) did not meet the threshold of p=0.002 based upon the multiplicity control testing procedure, thus it and the other two secondary outcomes are considered exploratory. A first hospitalization for heart failure occurred in 1142 patients (27.7%) in the omecamtiv mecarbil group and in 1179 (28.7%) in the placebo group (hazard ratio 0.95; 95% CI, 0.87 to 1.03; Table 2), while death due to all causes occurred in 1067 (25.9%) and 1065 (25.9%) patients, respectively (hazard ratio 1.00; 95% CI, 0.92 to 1.09; FIG. 1D and Table 2).

The cumulative incidences of the primary outcome, heart failure events, death from cardiovascular causes and death from any cause were estimated with the use of the Kaplan-Meier method. Hazard ratios and 95% confidence intervals were estimated with the use of Cox regression models stratified by randomization location and region and treatment with omecamtiv mecarbil or placebo as explanatory variables. Analyses are based upon all participants who underwent randomization. The inset in each panel of FIGS. 1A-1D shows the same data on an enlarged y axis.

Other outcomes of interest included the effects of omecamtiv mecarbil on vital signs and selected laboratory values (Table 3). There was no significant difference in the change in systolic blood pressure at 24 or 48 weeks between the omecamtiv mecarbil and placebo groups; there was a small but significant decrease in heart rate in participants assigned to omecamtiv mecarbil compared to placebo at both timepoints. Omecamtiv mecarbil significantly decreased NT-proBNP concentrations at Week 24 compared to placebo.

TABLE 2

Primary and Secondary Cardiovascular Outcomes

| Variable | Omecamtiv Mecarbil (N = 4120) | | Placebo (N = 4112) | | Hazard or Rate | |
|---|---|---|---|---|---|---|
| | Values | Events/100 patient-yrs | Values | Events/100 patient-yrs | Ratio or Difference (95% CI) | P value |
| Primary composite outcome-no. (%) | 1523 (37.0) | 24.2 | 1607 (39.1) | 26.3 | 0.92 (0.86, 0.99) | 0.025 |
| Cardiovascular death as first event | 346 (8.4) | NA | 371 (9.0) | NA | NA | NA |
| Heart failure event | 1177 (28.6) | 18.7 | 1236 (30.1) | 20.3 | 0.93 (0.86, 1.00) | NA |

TABLE 2-continued

Primary and Secondary Cardiovascular Outcomes

| Variable | Omecamtiv Mecarbil (N = 4120) | | Placebo (N = 4112) | | Hazard or Rate Ratio or Difference (95% CI) | P value |
|---|---|---|---|---|---|---|
| | Values | Events/100 patient-yrs | Values | Events/100 patient-yrs | | |
| Secondary outcomes | | | | | | |
| Cardiovascular death | 808 (19.6) | 10.9 | 798 (19.4) | 10.8 | 1.01 (0.92, 1.11) | 0.86† |
| Change in KCCQ total symptom score at week 24, least squares mean (SE) | | | | | | |
| Inpatients | 23.7 (0.70) | — | 21.2 (0.71) | — | 2.5 (0.54, 4.46) | 0.028† |
| Outpatients | 5.8 (0.34) | — | 6.3 (0.34) | — | −0.5 (−1.40, 0.48) | |
| Heart failure hospitalization | 1142 (27.7) | 18.0 | 1179 (28.7) | 19.1 | 0.95 (0.87, 1.03) | NA |
| All-cause death | 1067 (25.9) | 14.4 | 1065 (25.9) | 14.4 | 1.00 (0.92, 1.09) | NA |

NA denotes not applicable because P values for efficacy outcomes are reported only for outcomes that were included in the hierarchical-testing strategy *The primary outcome was a composite of heart failure events (hospitalization or an urgent visit resulting in intravenous therapy for heart failure) or death from cardiovascular causes. The total symptom score on the Kansas City Cardiomyopathy Questionnaire (KCCQ) ranges from 0 to 100, with higher scores indicating fewer symptoms and physical limitations associated with heart failure. †Non-significant. After statistical significance on the primary endpoint, CV death was tested against an alpha of 0.048 and change from baseline in the KCCQ TSS was tested against an alpha of 0.002.

Figure 8A:
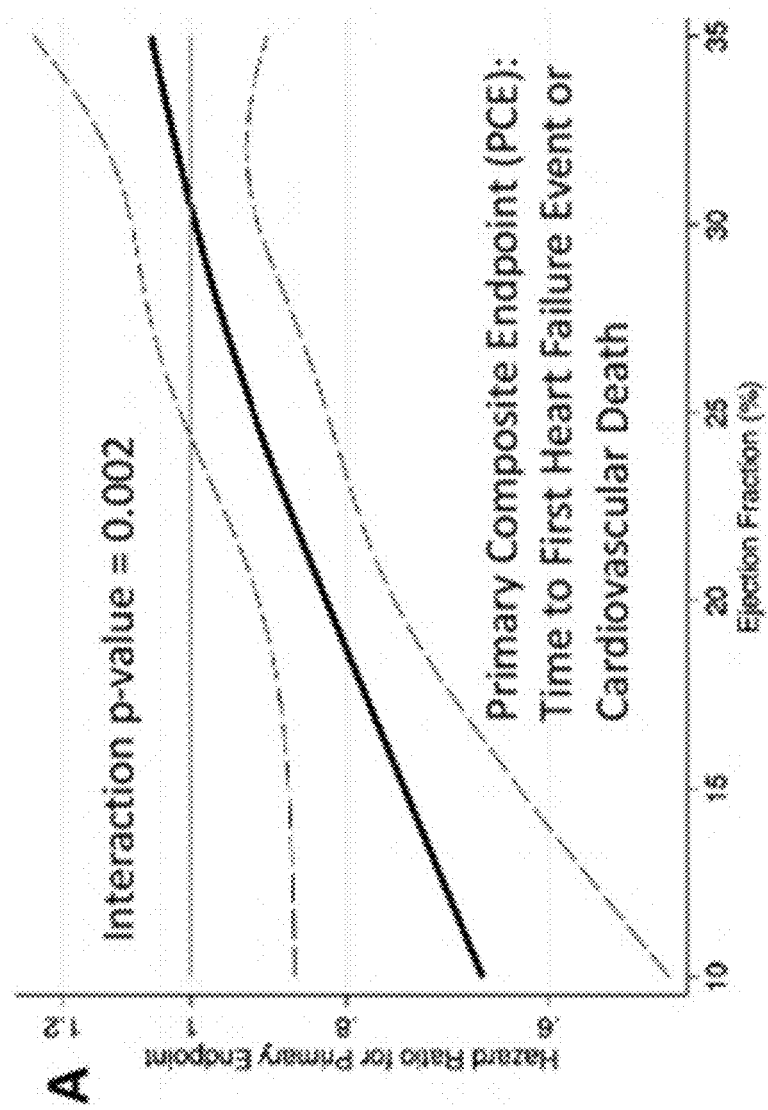
FIG. 8A shows progressively greater improvement in the primary composite endpoint (PCE) with decreasing left ventricular ejection fraction (LVEF) as indicated by the continuously improving hazard ratio.
Figure 8B:
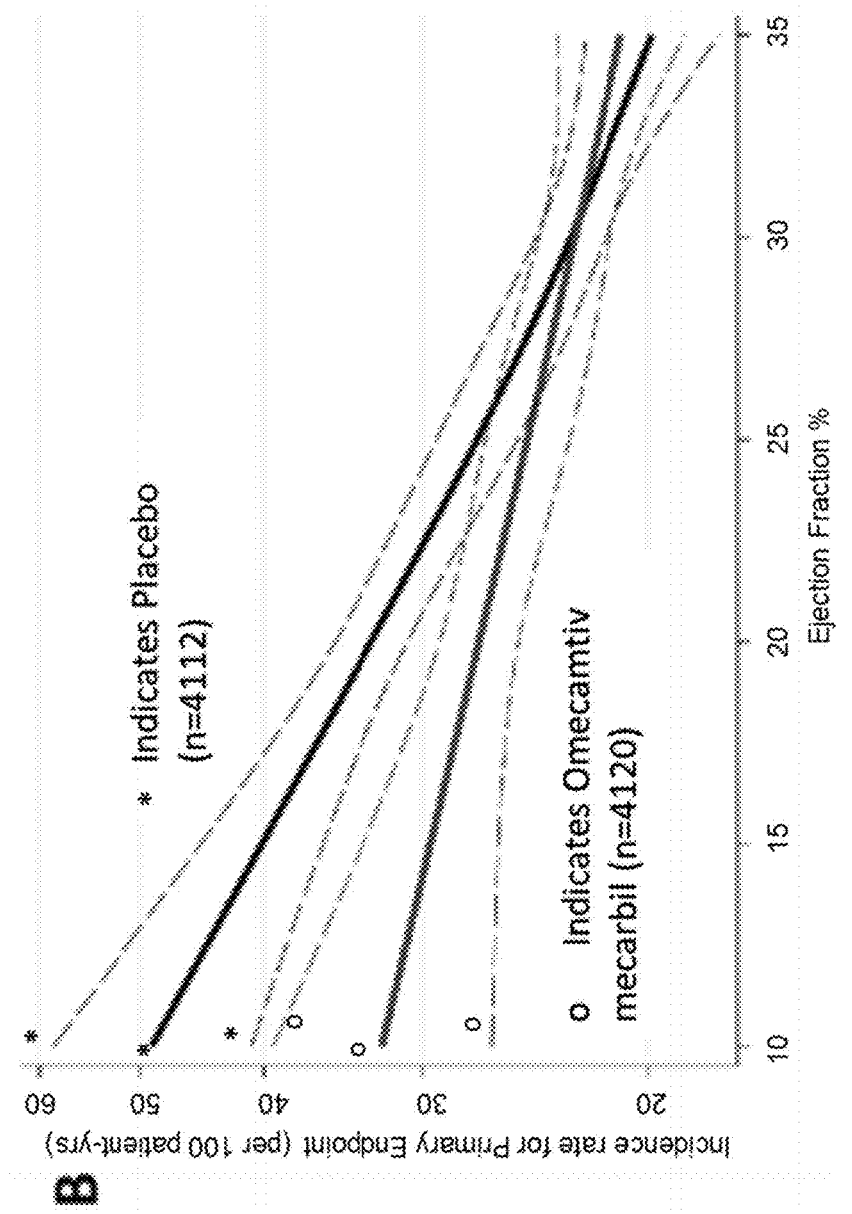
FIG. 8B shows the incidence of the primary composite endpoint (PCE) increased with decreasing ejection fraction (EF) and omecamtiv mecarbil (circles) producing increasing greater absolute reductions in the PCE with decreasing EF as compared to placebo (stars).

In addition, the impact of LVEF on the therapeutic effect of omecamtiv mecarbil in cardiovascular outcomes was analyzed. The patient population data demonstrated that patients with more severely reduced ejection fraction were more likely to be younger, male, non-white, from the Americas or Western Europe, had ischemic cardiomyopathy, normal sinus rhythm, and other clinical markers of more severe HFrEF when compared to patients with less severely reduced ejection fraction. There was a significant heterogeneity in the effect of omecamtiv mecarbil on the primary composite endpoint with respect to LVEF (continuous interaction, p=0.002). Omecamtiv mecarbil had progressively greater improvement in the primary composite endpoint with decreasing LVEF as demonstrated by the continuously improving hazard ratio (FIG. 8A). The incidence of the PCE increased with decreasing EF and omecamtiv mecarbil produced increasingly greater absolute reductions in the PCE with decreasing EF (FIG. 8B).

Safety

Excluding the discontinuations due to death, the study drug was stopped in 847 patients (20.6%) receiving omecamtiv mecarbil and 897 patients (21.9%) receiving placebo with 371 (9.0%) in the omecamtiv mecarbil group and 382 (9.3%) receiving placebo discontinuing due to an adverse event. Patients receiving omecamtiv mecarbil had no change in potassium or creatinine concentrations during the course of the trial compared to placebo. Patients receiving omecamtiv mecarbil had increased median concentrations of high sensitivity troponin-I from baseline of 0.004 ng/mL (lower limit of quantification, 0.010 ng/mL) compared to placebo at week 24. A total of 200 (4.9%) of participants receiving omecamtiv mecarbil had a positively adjudicated major cardiac ischemic event compared to a total of 188 (4.6%) receiving placebo, with myocardial infarction consisting of 122 (3.0%) and 118 (2.9%) of these events. Ventricular arrhythmias were similar in patients receiving omecamtiv mecarbil compared to placebo (Table 3).

TABLE 3

Laboratory Parameters and Safety Outcomes

| Variable | Omecamtiv Mecarbil (N = 4110) | Placebo (N = 4101) | Relative Risk or Difference (95% CI) |
|---|---|---|---|
| Laboratory measures, change from baseline | | | |
| Systolic blood pressure-mmHg, mean (SD) | | | |
| Week 24 | 1.4 (15.3) | 1.5 (15.6) | −0.13 (−0.85, 0.58) |
| Week 48 | 2.0 (16.1) | 1.9 (16.0) | 0.16 (−0.63, 0.96) |
| Heart rate-bpm, mean (SD) | | | |
| Week 24 | −2.1 (12.6) | −0.5 (12.8) | −1.61 (−2.19, −1.02) |
| Week 48 | −2.0 (13.1) | −0.2 (13.2) | −1.75 (−2.40, −1.10) |
| Potassium-mmol/L, mean (SD) | | | |
| Week 24 | −0.01 (0.57) | −0.01 (0.57) | 0.002 (−0.025, 0.028) |
| Week 48 | −0.03 (0.59) | −0.02 (0.58) | −0.007 (−0.036, 0.022) |

TABLE 3-continued

Laboratory Parameters and Safety Outcomes

| Variable | Omecamtiv Mecarbil (N = 4110) | Placebo (N = 4101) | Relative Risk or Difference (95% CI) |
|---|---|---|---|
| Creatinine-mg/dL, mean (SD) | | | |
| Week 24 | 0.03 (0.33) | 0.02 (0.32) | 0.007 (−0.008, 0.022) |
| Week 48 | 0.06 (0.39) | 0.05 (0.38) | 0.010 (−0.009, 0.029) |
| NT-proBNP-pg/mL, median (Q1, Q3) | | | |
| Week 24 | −251 (−1180, 295) | −180 (−915, 441) | 0.90 (0.86, 0.94)† |
| Troponin-ng/mL, median(Q1, Q3) | | | |
| Week 24 | 0.004 (−0.002, 0.021) | 0.000 (−0.009, 0.008) | 0.004 (0.003, 0.005) |
| Week 48 | 0.002 (−0.004, 0.018) | 0.000 (−0.009, 0.008) | 0.002 (0.001, 0.003) |
| Safety Outcomes | | | |
| Drug discontinuation due to an adverse event-no. (%) | 371 (9.0) | 382 (9.3) | 0.97 (0.85, 1.11) |
| Serious adverse events-no. (%) | 2373 (57.7) | 2435 (59.4) | 0.97 (0.94, 1.01) |
| Adverse events of interest-no. (%) | | | |
| Ventricular tachyarrhythmias (narrow SMQ) | 290 (7.1) | 304 (7.4) | 0.95 (0.82, 1.11) |
| Torsade de pointes/QT prolongation (narrow SMQ) | 176 (4.3) | 195 (4.8) | 0.90 (0.74, 1.10) |
| Serious adverse ventricular arrhythmia requiring treatment | 119 (2.9) | 127 (3.1) | 0.93 (0.73, 1.20) |
| Adjudicated major cardiac ischemic events-no. (%) | 200 (4.9) | 188 (4.6) | 1.06 (0.87, 1.29) |
| Myocardial infarction | 122 (3.0) | 118 (2.9) | |
| Hospitalized for unstable angina | 25 (0.6) | 12 (0.3) | |
| Coronary revascularization | 115 (2.8) | 117 (2.9) | |
| Stroke | 76 (1.8) | 112 (2.7) | 0.68 (0.51, 0.91) |

Continuous variables were summarized as means±standard deviations (SD) or medians and first and third quartiles (Q1, Q3), as appropriate. Categorical variables were summarized as counts and percentages. The safety population included all patients who underwent randomization and received at least one dose of omecamtiv mecarbil or placebo. The change from baseline on NT-proBNP analysis included all participants who underwent randomization. The difference column is the exponentiated change from baseline on the log scale using a mixed model containing the log baseline value, region, baseline eGFR, scheduled visit, treatment group and interaction of treatment with scheduled visit.

Adverse Events

Table 4 summarizes the adverse events reported in 1% or more of patients.

TABLE 4

Treatment-emergent serious adverse events by preferred term report.

| Preferred Term | Placebo (N = 4101) n (%) | Omcamtiv Mecarbil (N = 4110) n (%) |
|---|---|---|
| Number of subjects reporting treatment-emergent serious adverse events | 2435 (59.4) | 2373 (57.7) |
| Cardiac failure | 1045 (25.5) | 988 (24.0) |
| Cardiac failure acute | 251 (6.1) | 212 (5.2) |
| Pneumonia | 179 (4.4) | 171 (4.2) |
| Cardiac failure chronic | 170 (4.1) | 156 (3.8) |
| Cardiac failure congestive | 154 (3.8) | 147 (3.6) |
| Acute kidney injury | 138 (3.4) | 129 (3.1) |
| Ventricular tachycardia | 129 (3.1) | 106 (2.6) |
| Atrial fibrillation | 113 (2.8) | 94 (2.3) |
| Cardiogenic shock | 68 (1.7) | 75 (1.8) |
| Acute myocardial infarction | 64 (1.6) | 71 (1.7) |
| Death | 49 (1.2) | 65 (1.6) |
| Angina unstable | 49 (1.2) | 63 (1.5) |
| Chronic obstructive pulmonary disease | 38 (0.9) | 63 (1.5) |
| Sudden death | 58 (1.4) | 52 (1.3) |
| Sepsis | 60 (1.5) | 51 (1.2) |
| Cardiac arrest | 64 (1.6) | 50 (1.2) |
| Hypotension | 37 (0.9) | 49 (1.2) |
| Syncope | 46 (1.1) | 42 (1.0) |
| Angina pectoris | 40 (1.0) | 41 (1.0) |
| Septic shock | 32 (0.8) | 37 (0.9) |
| Myocardial infarction | 54 (1.3) | 36 (0.9) |
| Ischaemic stroke | 38 (0.9) | 36 (0.9) |
| Chronic kidney disease | 36 (0.9) | 36 (0.9) |
| Ventricular fibrillation | 49 (1.2) | 30 (0.7) |
| Sudden cardiac death | 37 (0.9) | 27 (0.7) |
| Renal failure | 31 (0.8) | 25 (0.6) |
| Renal impairment | 29 (0.7) | 25 (0.6) |
| Respiratory tract infection | 24 (0.6) | 15 (0.4) |

Outcomes by Ejection Fraction
Baseline Characteristics for Patients were Further Evaluated by Quartiles of EF Continuous variables were summarized via means and standard deviations or medians and interquartile ranges, as appropriate. Categorical variables are summarized with counts and percentages. Tests of trend across categories were conducted via linear regression, Cuzick's non-parametric trend test, and Chi-squared tests of trend, respectively. Treatment effects on continuous outcomes were assessed via linear regression models adjusted for the corresponding baseline value of the parameter of interest. Survival analyses were conducted using Poisson regression models to estimate incidence rates, rate differences, and rate ratios and Cox proportional hazards models to estimate hazard ratios. Treatment effect hazard ratios were adjusted for eGFR and stratified by region and inpatient status as in the primary GALACTIC-HF analysis. To allow for potentially non-linear associations between ejection fraction and time-to-event outcomes, restricted cubic splines were utilized in the Poisson regression models with 3 knots. All analyses were conducted using STATA 16 (College Station, Tex.). P-values <0.05 were considered statistically significant. Due to the exploratory nature of these analyses, no adjustments were made for multiple comparisons.

Figure 13A:
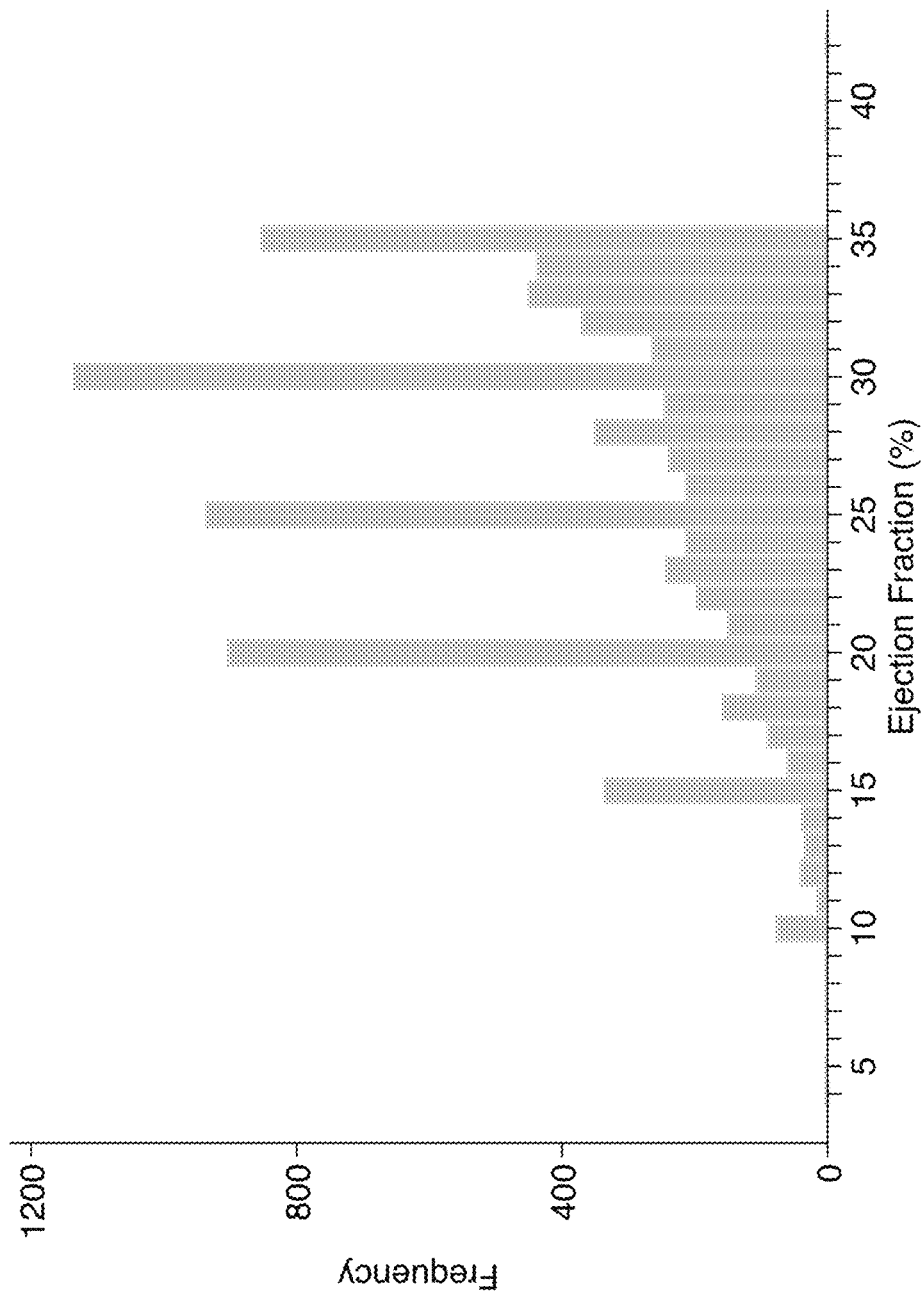
FIG. 13A shows the distribution of baseline ejection fractions in GALACTIC-HF.
Figure 13B:
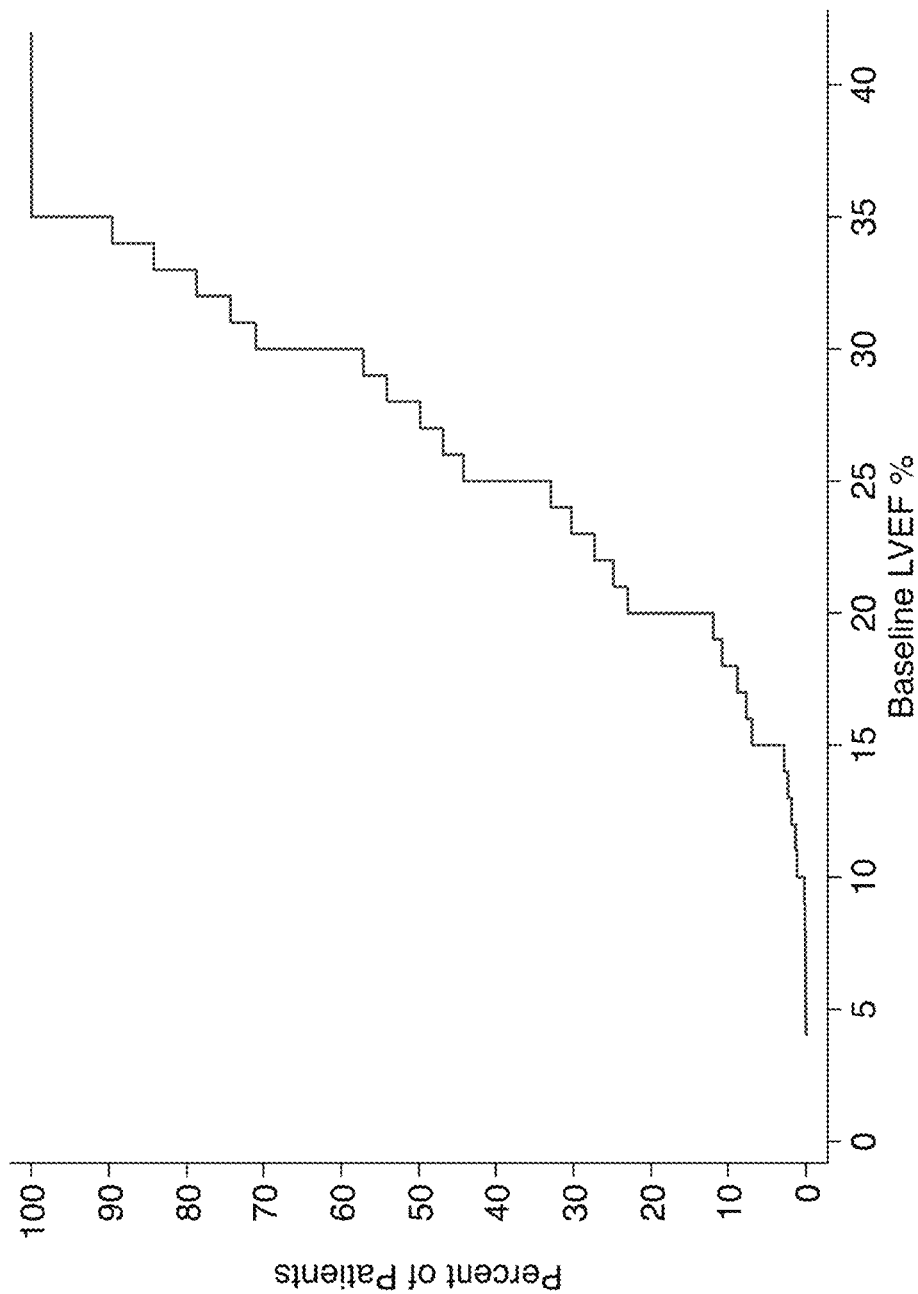
FIG. 13B shows the distribution of ejection fractions in GALACTIC-HF.

Of the 8,232 participants analyzed, there were 4,456 patients with an EF 28%, the median ejection fraction in the trial (Tables 5 and 6; FIGS. 13A and 13B). Method of ejection fraction measurement is shown in Table 19.

TABLE 5

Baseline characteristics of GALACTIC-HF patients Ejection Fraction Quartiles

|  | EF ≤22% (N = 2246) | EF 23-28% (N = 2210) | EF 29-32% (N = 2026) | EF ≥33% (N = 1750) | p-Value |
|---|---|---|---|---|---|
| Demographics | | | | | |
| Age (years), mean (SD) | 62.5 (11.8) | 64.1 (11.6) | 65.7 (10.9) | 66.4 (10.5) | <0.001 |
| Sex, female, n (%) | 422 (18.8%) | 451 (20.4%) | 455 (22.5%) | 421 (24.1%) | <0.001 |
| Race, n (%) | | | | | <0.001 |
| Asian | 171 (7.6%) | 224 (10.1%) | 179 (8.8%) | 136 (7.8%) | |
| Black or African American | 243 (10.8%) | 156 (7.1%) | 95 (4.7%) | 68 (3.9%) | |
| Other* | 200 (8.9%) | 162 (7.3%) | 118 (5.8%) | 83 (4.7%) | |
| White | 1632 (72.7%) | 1668 (75.5%) | 1634 (80.7%) | 1463 (83.6%) | |
| Geographic Region, n (%) | | | | | <0.001 |
| Asia | 152 (6.8%) | 214 (9.7%) | 174 (8.6%) | 130 (7.4%) | |
| Eastern Europe/Russia | 476 (21.2%) | 617 (27.9%) | 783 (38.6%) | 805 (46.0%) | |
| Latin and South America | 438 (19.5%) | 504 (22.8%) | 364 (18.0%) | 268 (15.3%) | |
| US and Canada | 581 (25.9%) | 341 (15.4%) | 259 (12.8%) | 205 (11.7%) | |
| Western Europe/South Africa/Australasia | 599 (26.7%) | 534 (24.2%) | 446 (22.0%) | 342 (19.5%) | |
| Radomization Setting: In-patient | 592 (26.4%) | 552 (25.0%) | 487 (24.0%) | 453 (25.9%) | 0.50 |
| Clincal Characteristics | | | | | |
| Medical Conditions, n (%) | | | | | |
| Coronary artery disease | 1267 (56) | 1320 (60) | 1323 (65) | 1218 (70) | <0.001 |
| Stroke | 214 (10) | 194 (9) | 250 (12) | 161 (9) | 0.80 |
| Atrial fibrillation or flutter history | 912 (41) | 884 (40) | 889 (44) | 790 (45) | <0.001 |
| Atrial fibrillation or flutter at Screening | 547 (24.4%) | 561 (25.4%) | 609 (30.1%) | 528 (30.2%) | <0.001 |
| Hypertension | 1431 (64) | 1483 (67) | 1503 (74) | 1367 (78) | <0.001 |
| Type 2 diabetes mellitus | 869 (39) | 880 (40) | 817 (40) | 743 (43) | <0.001 |
| Chronic Obstructive Pulmonary Disease | 352 (16) | 360 (16) | 332 (16) | 301 (17) | 0.21 |
| Heart Failure History | | | | | |
| LVEF (%), median [Q1, Q3] | 20 [15, 20] | 25 [25, 27] | 30 [30, 31] | 34 [33, 35] | N/A |
| Time from last HF event (months), median (Q1, Q3; Outpatients only) | 2.9 [1.6, 5.8] | 3.1 [1.6, 6.1] | 3.3 [1.6, 6.5] | 3.4 [1.5, 6.8] | 0.039 |
| Time from last HF Hospitalization (months), median (Q1, Q3; Outpatients only) | 3.0 [1.6, 5.9] | 3.2 [1.6, 6.2] | 3.4 [1.7, 6.6] | 3.6 [1.6, 6.9] | 0.043 |
| MAGGIC Score, median (Q1, Q3) | 25 (21, 30) | 24 (20, 28) | 22 (17, 26) | 21 (17, 25) | <0.001 |
| NYHA classification, n (%) | | | | | 0.016 |
| Class II | 1160 (52) | 1164 (53) | 1085 (54) | 959 (55) | |
| Class III | 1007 (45) | 968 (44) | 889 (44) | 752 (43) | |
| Class IV | 79 (4) | 78 (4) | 52 (3) | 39 (2) | |
| Ischemic heart failure etiology, n (%) | 1033 (46) | 1153 (52) | 1141 (56) | 1088 (62) | <0.001 |
| KCCQ Total Symptom Score, median [Q1, Q3] | 69 [48, 88] | 70 [49, 88] | 71 [50, 88] | 69 [49, 85] | 0.77 |
| Outpatient | 75 [56, 92] | 75 [54, 92] | 75 [56, 92] | 73 [54, 90] | 0.05 |
| Inpatient | 51 [29, 69] | 53 [33, 73] | 55 [35, 72] | 54 [31, 74] | 0.022 |

TABLE 5-continued

Baseline characteristics of GALACTIC-HF patients Ejection Fraction Quartiles

| | EF ≤22% (N = 2246) | EF 23-28% (N = 2210) | EF 29-32% (N = 2026) | EF ≥33% (N = 1750) | p-Value |
|---|---|---|---|---|---|
| Vitals and Laboratory Parameters | | | | | |
| Body mass index (kg/m²), mean (SD) | 27.9 (6.3) | 28.2 (6.2) | 28.9 (6.0) | 29.1 (6.1) | <0.001 |
| SBP (mmHg), mean (SD) | 112 (15) | 115 (15) | 119 (15) | 121 (14) | <0.001 |
| Heart rate (beats/min), mean (SD) | 74 (12) | 72 (12) | 72 (12) | 72 (12) | <0.001 |
| NT-proBNP (pg/mL), median [Q1-Q3] | 2524 [1250, 5296] | 2035 [1057, 4157] | 1866 [924, 3655] | 1615 [755, 3245] | <0.001 |
| hsTnI (ng/L), median [Q3] | 31 [58] | 29 [55] | 26 [48] | 23 [43] | <0.001 |
| eGFR (mL/min/1.73 m²), median [Q1, Q3] | 59 [44, 74] | 59 [44, 75] | 59 [43, 74] | 58 [45, 74] | 0.72 |
| Medications and Cardiac Devices, n (%) | | | | | |
| ACEi, ARB or ARNi | 1900 (85) | 1933 (88) | 1787 (88) | 1539 (88) | <0.001 |
| ARNi | 534 (24) | 468 (21) | 351 (17) | 248 (14) | <0.001 |
| BB | 2086 (93) | 2101 (95) | 1922 (95) | 1655 (95) | 0.022 |
| MRA | 1715 (76) | 1792 (81) | 1585 (78) | 1305 (75) | 0.10 |
| (ACEi, ARB, or ARNi) + MRA + BB | 1413 (63) | 1511 (68) | 1387 (68) | 1114 (64) | 0.37 |
| Digitalis Glycosides | 450 (20) | 380 (17) | 304 (15) | 251 (14) | <0.001 |
| SGLT2 Inhibitors | 64 (3) | 67 (3) | 44 (2) | 43 (3) | 0.19 |
| Ivabradine | 172 (8) | 165 (8) | 106 (5) | 90 (5) | <0.001 |
| Cardiac Resynchronization Therapy | 454 (20) | 321 (15) | 231 (11) | 152 (9) | <0.001 |
| Implantable Cardioverter Defibrillator | 972 (43) | 745 (34) | 534 (26) | 363 (21) | <0.001 |

*Includes American Indian or Alaska Native, Native Hawaiian or Other Pacific Islander, or Multiple self-identified races
ACEi indicates angiotensin-converting enzyme inhibitor; ARB, angiotensin receptor blocker; ARNi, angiotension receptor-neprilysin inhibitor; BB, beta blocker; CRT, cardiac resynchronization therapy; ED, emergency department; eGFR, estimated glomerular filtration rate; hsTnI, high-sensitivity troponin I; ICD, implantable cardioverter-defibrillator; KCCQ, Kansas City Cardiomyopathy Questionnaire; LVEF, left ventricular ejection fraction; MAGGIC, Meta-Analysis Global Group in Chronic HF; MRA, mineralcorticoid receptor antagonist; NT-proBNP, N-terminal pro-B-type natriuretic perptide; NYHA, New York Heart Association; SBP, systolic blood pressure; SGLT2, sodium-glucose co-transporter 2.

TABLE 6

Baseline Characteristics by Ejection Fraction Quartile:

| | EF ≤22% (N = 2246) | | EF 23-28% (N = 2210) | | EF 29-32% (N = 2026) | | EF ≥33% (N = 1750) | |
|---|---|---|---|---|---|---|---|---|
| | OM n = 1127 | Placebo n = 1119 | OM n = 1086 | Placebo n = 1124 | OM n = 1015 | Placebo n = 1011 | OM n = 892 | Placebo n = 858 |
| Demographics | | | | | | | | |
| Age in years | 62.1 (±11.9) | 62.9 (±11.6) | 64.2 (±11.5) | 64.0 (±11.8) | 65.8 (±11.0) | 65.6 (±10.8) | 66.6 (±10.1) | 66.1 (±11.0) |
| Sex, Female | 215 (19.1%) | 207 (18.5%) | 205 (18.9%) | 246 (21.9%) | 228 (22.5%) | 227 (22.5%) | 227 (25.4%) | 194 (22.6%) |
| Race | | | | | | | | |
| Asian | 91 (8.1%) | 80 (7.1%) | 114 (10.5%) | 110 (9.8%) | 86 (8.5%) | 93 (9.2%) | 64 (7.2%) | 72 (8.4%) |
| Black | 118 (10.5%) | 125 (11.2%) | 77 (7.1%) | 79 (7.0%) | 49 (4.8%) | 46 (4.5%) | 41 (4.6%) | 27 (3.1%) |
| Other | 102 (9.1%) | 98 (8.8%) | 79 (7.3%) | 83 (7.4%) | 65 (6.4%) | 53 (5.2%) | 38 (4.3%) | 45 (5.2%) |
| White | 816 (72.4%) | 816 (72.9%) | 816 (75.1%) | 852 (75.8%) | 815 (80.3%) | 819 (81.0%) | 749 (84.0%) | 714 (83.2%) |
| Geographic Region | | | | | | | | |
| Asia | 82 (7.3%) | 70 (6.3%) | 109 (10.0%) | 105 (9.3%) | 84 (8.3%) | 90 (8.9%) | 60 (6.7%) | 70 (8.2%) |
| Eastern Europe/Russia | 232 (20.6%) | 244 (21.8%) | 304 (28.0%) | 313 (27.8%) | 397 (39.1%) | 386 (38.2%) | 411 (46.1%) | 394 (45.9%) |
| Latin America | 228 (20.2%) | 210 (18.8%) | 235 (21.6%) | 269 (23.9%) | 196 (19.3%) | 168 (16.6%) | 128 (14.3%) | 140 (16.3%) |
| US And Canada | 287 (25.5%) | 294 (26.3%) | 171 (15.7%) | 170 (15.1%) | 121 (11.9%) | 138 (13.6%) | 114 (12.8%) | 91 (10.6%) |

TABLE 6-continued

| | | | | | | | | |
|---|---|---|---|---|---|---|---|---|
| Western Europe/South Africa/Australasia | 298 (26.4%) | 301 (26.9%) | 267 (24.6%) | 267 (23.8%) | 217 (21.4%) | 229 (22.7%) | 179 (20.1%) | 163 (19.0%) |
| Randomization Setting: In-patient | 289 (25.6%) | 303 (27.1%) | 266 (24.5%) | 286 (25.4%) | 241 (23.7%) | 246 (24.3%) | 248 (27.8%) | 205 (23.9%) |
| Clinical Characteristics | | | | | | | | |
| Atrial Fibrillation or Flutter at Screening | 276 (24.5%) | 271 (24.2%) | 274 (25.2%) | 287 (25.5%) | 310 (30.5%) | 299 (29.6%) | 286 (32.1%) | 242 (28.2%) |
| Hypertension Hx | 712 (63.2%) | 719 (64.3%) | 753 (69.3%) | 730 (64.9%) | 737 (72.6%) | 766 (75.8%) | 708 (79.4%) | 659 (76.8%) |
| Type 2 diabetes mellitus | 420 (37.3%) | 449 (40.1%) | 430 (39.6%) | 450 (40.0%) | 411 (40.5%) | 406 (40.2%) | 391 (43.8%) | 352 (41.0%) |
| History of stroke | 103 (9.1%) | 111 (9.9%) | 96 (8.8%) | 98 (8.7%) | 99 (9.8%) | 86 (8.5%) | 79 (8.9%) | 82 (9.6%) |
| Ischemic heart failure etiology | 497 (44.1%) | 536 (47.9%) | 566 (52.1%) | 587 (52.2%) | 570 (56.2%) | 571 (56.5%) | 560 (62.8%) | 528 (61.5%) |
| History of Myocardial Infarction | 377 (33.5%) | 452 (40.4%) | 443 (40.8%) | 461 (41.0%) | 441 (43.4%) | 443 (43.8%) | 432 (48.4%) | 386 (45.0%) |
| History of Coronary Artery Bypass Surgery | 152 (13.5%) | 174 (15.5%) | 166 (15.3%) | 187 (16.6%) | 164 (16.2%) | 171 (16.9%) | 157 (17.6%) | 146 (17.0%) |
| History of Percutaneous Coronary Revascularization | 272 (24.1%) | 320 (28.6%) | 333 (30.7%) | 330 (29.4%) | 328 (32.3%) | 295 (29.2%) | 299 (33.5%) | 261 (30.4%) |
| LVEF-% | 18.3 (±3.1) | 18.1 (±3.2) | 25.5 (±1.5) | 25.5 (±1.5) | 30.4 (±0.9) | 30.4 (±0.9) | 34.2 (±0.9) | 34.2 (±0.8) |
| NYHA Classification | | | | | | | | |
| Class II | 587 (52.1%) | 573 (51.2%) | 570 (52.5%) | 594 (52.8%) | 546 (53.8%) | 539 (53.3%) | 492 (55.2%) | 467 (54.4%) |
| Class III | 503 (44.6%) | 504 (45.0%) | 474 (43.6%) | 494 (44.0%) | 445 (43.8%) | 444 (43.9%) | 379 (42.5%) | 373 (43.5%) |
| Class IV | 37 (3.3%) | 42 (3.8%) | 42 (3.9%) | 36 (3.2%) | 24 (2.4%) | 28 (2.8%) | 21 (2.4%) | 18 (2.1%) |
| KCCQ Total Symptom Score | 68.8 [47.9, 87.5] | 67.7 [47.9, 87.5] | 68.8 [49.0, 87.5] | 70.8 [49.0, 89.6] | 70.8 [50.0, 88.5] | 70.8 [50.0, 87.5] | 69.8 [47.9, 85.4] | 66.7 [49.0, 85.4] |
| Outpatient | 75.0 [56.2, 91.7] | 75.0 [56.2, 91.7] | 74.0 [54.2, 90.6] | 77.1 [56.2, 91.7] | 75.0 [54.7, 91.7] | 75.0 [57.3, 91.7] | 73.4 [54.2, 87.5] | 72.9 [54.2, 89.6] |
| Inpatient | 50.0 [32.3, 68.8] | 52.1 [27.1, 67.7] | 54.7 [34.4, 75.0] | 53.1 [33.3, 70.8] | 58.3 [38.5, 74.0] | 52.1 [33.3, 68.8] | 55.2 [33.3, 77.1] | 52.1 [29.2, 69.3] |
| SBP-mmHg | 111.4 (±14.9) | 112.5 (±14.9) | 115.5 (±15.2) | 114.9 (±15.4) | 118.4 (±15.1) | 119.2 (±15.1) | 120.9 (±14.4) | 121.3 (±14.3) |
| Heart rate-(bpm) | 73.9 (±12.3) | 73.2 (±12.3) | 71.7 (±12.1) | 72.8 (±12.0) | 72.3 (±12.1) | 71.5 (±11.8) | 71.6 (±12.3) | 71.6 (±12.0) |
| NT-proBNP-pg/mL | 2512 [1318, 5406] | 2527 [1206, 5240] | 2072 [1108, 4250] | 1998 [1025, 4079] | 1800 [901, 3655] | 1932 [940, 3653] | 1569 [740, 3066] | 1650 [782, 3367] |
| Cardiac Troponin I (ng/L) | 32 [14, 57] | 31 [16, 59] | 29 [14, 55] | 28 [13, 55] | 26 [12, 49] | 26 [11, 47] | 23 [10, 41] | 23 [11, 45] |
| eGFR-mL/min/1.73 m² | 58.9 [44.5, 74.8] | 58.6 [43.8, 72.5] | 58.3 [43.4, 73.5] | 59.5 [44.3, 75.5] | 60.8 [44.3, 75.6] | 57.3 [42.6, 72.4] | 57.3 [45.1, 72.8] | 59.4 [45.0, 74.5] |
| Heart Failure Therapies | | | | | | | | |
| ACEi, ARB or ARNi | 942 (83.6%) | 958 (85.6%) | 949 (87.4%) | 984 (87.5%) | 901 (88.8%) | 886 (87.6%) | 791 (88.7%) | 748 (87.2%) |
| ARNi | 265 (23.5%) | 269 (24.0%) | 243 (22.4%) | 225 (20.0%) | 183 (18.0%) | 168 (16.6%) | 128 (14.3%) | 120 (14.0%) |
| BB | 1047 (92.9%) | 1039 (92.9%) | 1026 (94.5%) | 1074 (95.6%) | 954 (94.0%) | 968 (95.7%) | 853 (95.6%) | 802 (93.5%) |
| MRA | 868 (77.0%) | 847 (75.7%) | 876 (80.7%) | 916 (81.5%) | 797 (78.5%) | 788 (77.9%) | 658 (73.8%) | 647 (75.4%) |
| SGLT2 Inhibitors | 31 (2.8%) | 33 (2.9%) | 31 (2.9%) | 36 (3.2%) | 23 (2.3%) | 21 (2.1%) | 19 (2.1%) | 24 (2.8%) |
| Ivabradine | 90 (8.0%) | 82 (7.3%) | 77 (7.1%) | 88 (7.8%) | 49 (4.8%) | 57 (5.6%) | 39 (4.4%) | 51 (5.9%) |
| Digitalis glycosides | 226 (20.1%) | 224 (20.0%) | 191 (17.6%) | 189 (16.8%) | 142 (14.0%) | 162 (16.0%) | 128 (14.3%) | 123 (14.3%) |
| Cardiac Resynchronization Therapy | 233 (20.7%) | 221 (19.7%) | 164 (15.1%) | 157 (14.0%) | 108 (10.6%) | 123 (12.2%) | 87 (9.8%) | 65 (7.6%) |
| Implantable Cardioverter Defibrillator | 485 (43.0%) | 487 (43.5%) | 389 (35.8%) | 356 (31.7%) | 269 (26.5%) | 265 (26.2%) | 183 (20.5%) | 180 (21.0%) |

TABLE 19

Method of ejection fraction measurement:

| Method of Ejection Fraction Measurement | Omecamtiv mecarbil N (%) | Placebo N (%) |
|---|---|---|
| Echocardiogram | 4006 (97.2%) | 3997 (97.2%) |
| Cardiac MRI | 35 (0.8%) | 39 (0.9%) |
| SPECT Nuclear Imaging | 33 (0.8%) | 25 (0.6%) |
| Left vantriculography (Cineangiography) | 17 (0.4%) | 17 (0.4%) |
| Radionuclide ventriculography (MUGA) | 17 (0.4%) | 16 (0.4%) |
| Cardiac CT | 10 (0.2%) | 14 (0.3%) |
| Cardiac PET | 1 (0.0%) | 3 (0.1%) |
| Missing | 1 (0.0%) | 1 (0.0%) |

Due to digit preference for ejection fraction assessment, over 70% of the patients had an EF 30%. When assessed by quartiles, patients with lower ejection fractions were younger, more likely to be male and non-white, and less likely to be enrolled in Eastern Europe or Russia and more likely to be enrolled in the United States, Canada, Western Europe, South Africa, or Australasia. Patients with lower ejection fraction were more likely to have a non-ischemic etiology of heart failure, NYHA III/IV functional class, lower body mass index, lower systolic blood pressure, higher heart rate, higher NT-proBNP, higher cardiac troponin I, and were less likely to have coronary artery disease, hypertension, type 2 diabetes mellitus, or atrial fibrillation/flutter. Lower ejection fraction was associated with greater symptom burden in patients enrolled as inpatients (lower KCCQ-TSS), but there was no meaningful difference in the outpatients. There was no difference in the proportion of patients receiving triple therapy [(ACEi, ARB, or ARNi)+ MRA+BB] among the EF quartiles. Patients with lower ejection fractions had higher use of ARNi, ivabradine, digitalis glycosides, cardiac resynchronization therapy and implantable cardioverter defibrillators compared to patients with higher ejection fractions.

Relationship Between Ejection Fraction and Clinical Outcomes

Within the group of patients with HFrEF enrolled in GALACTIC-HF, the incidence of clinical outcomes increased with decreasing ejection fraction (Table 7).

TABLE 7

Clinical Outcomes

| Outcome by EF Quartiles | OM | | Placebo | | HR (95% CI); | |
|---|---|---|---|---|---|---|
| | n/N (%) | Rate[1] | n/N (%) | Rate[1] | p-value | ARR[1] |
| Primary Outcome | | | | | Interaction p = 0.013 | |
| EF ≥33% | 298/892 (33%) | 20.5 | 280/858 (33%) | 20.0 | 0.99 (0.84, 1.16) | −0.4 |
| EF 29-32% | 375/1015 (37%) | 23.8 | 356/1011 (35%) | 22.4 | 1.11 (0.96, 1.28) | −1.4 |
| EF 23-28% | 393/1086 (36%) | 24.0 | 449/1124 (40%) | 27.2 | 0.85 (0.74, 0.97) | 3.3 |
| EF ≤22% | 457/1127 (41%) | 28.3 | 522/1119 (47%) | 35.6 | 0.83 (0.73, 0.95) | 7.4 |
| First HF Event | | | | | Interaction p = 0.004 | |
| EF ≥33% | 236/892 (26%) | 16.2 | 208/858 (24%) | 14.9 | 1.04 (0.86, 1.25) | −1.3 |
| EF 29-32% | 286/1015 (28%) | 18.2 | 269/1011 (27%) | 16.9 | 1.13 (0.96, 1.33) | −1.3 |
| EF 23-28% | 304/1086 (28%) | 18.5 | 345/1124 (31%) | 20.9 | 0.84 (0.72, 0.98) | 2.4 |
| EF ≤22% | 351/1127 (31%) | 21.7 | 414/1119 (37%) | 28.3 | 0.81 (0.70, 0.93) | 6.6 |
| 1st HF Hospitalization | | | | | Interaction p = 0.004 | |
| EF ≥33% | 228/892 (26%) | 15.5 | 201/858 (23%) | 14.3 | 1.03 (0.85, 1.24) | −1.2 |
| EF 29-32% | 279/1015 (27%) | 17.6 | 251/1011 (25%) | 15.5 | 1.19 (1.01, 1.42) | −2.1 |
| EF 23-28% | 295/1086 (27%) | 17.8 | 327/1124 (29%) | 19.6 | 0.86 (0.74, 1.01) | 1.8 |
| EF ≤22% | 340/1127 (30%) | 20.9 | 400/1119 (36%) | 26.9 | 0.82 (0.71, 0.94) | 6.1 |
| CV Death | | | | | Interaction p = 0.14 | |
| EF ≥33% | 153/892 (17%) | 9.0 | 136/858 (16%) | 8.4 | 1.06 (0.84, 1.33) | −0.6 |
| EF 29-32% | 196/1015 (19%) | 10.5 | 162/1011 (16%) | 8.5 | 1.26 (1.02, 1.55) | −2.0 |
| EF 23-28% | 207/1086 (19%) | 10.8 | 235/1124 (21%) | 11.8 | 0.88 (0.73, 1.07) | 1.0 |
| EF ≤22% | 252/1127 (22%) | 13.0 | 265/1119 (24%) | 14.1 | 0.96 (0.80, 1.14) | 1.1 |
| All-cause Death | | | | | Interaction p = 0.38 | |
| EF ≥33% | 200/892 (22%) | 11.8 | 189/858 (22%) | 11.7 | 0.98 (0.80, 1.20) | −0.1 |
| EF 29-32% | 260/1015 (26%) | 13.9 | 226/1011 (22%) | 11.9 | 1.19 (0.99, 1.42) | −2.0 |
| EF 23-28% | 278/1086 (26%) | 14.4 | 315/1124 (28%) | 15.8 | 0.89 (0.76, 1.05) | 1.4 |
| EF 22% | 329/1127 (29%) | 17.0 | 335/1119 (30%) | 17.8 | 0.98 (0.84, 1.14) | 0.8 |

[1] per 100 patient years;
ARR = absolute risk reduction

As noted by the rates in the placebo group, the incidence of the primary outcome of first heart failure event or cardiovascular death in patients in the lowest EF quartile (EF 22%; 35.6 per 100 patient-years) was almost 80% greater than in the highest EF quartile (EF 33%; 20 per 100 patient-years). The incidence of first heart failure event was 90% greater (28.3 versus 14.9 events per 100 patient-years) and of cardiovascular death was 68% greater (14.1 versus 8.4 deaths per 100 patient-years) in the lowest EF compared to the highest EF quartile. Participants in the placebo group had significant improvements in the KCCQ-TSS at Week 24 compared to baseline, with greater improvements in those enrolled as inpatients, but there was no modification of this effect by EF quartile (Table 8).

TABLE 8

Change from baseline in KCCQ Total Symptom Score by Ejection Fraction Quartiles and Treatment Group

| KCCQ Total Symptom Score -- Least square mean (95% CI) | EF ≤22% | EF 23-28% | EF 29-32% | EF ≥33% |
| --- | --- | --- | --- | --- |
| Outpatient | | | | |
| Placebo | 6.37 | 6.30 | 5.95 | 6.60 |
| | (5.02, 7.73) | (5.00, 7.59) | (4.67, 7.22) | (5.21, 8.00) |
| Omecamtiv mecarbil | 7.08 | 5.61 | 5.30 | 5.18 |
| | (5.75, 8.40) | (4.30, 6.92) | (4.02, 6.58) | (3.78, 6.59) |
| Inpatient | | | | |
| Placebo | 23.59 | 21.35 | 18.14 | 21.31 |
| | (20.77, 26.40) | (18.60, 24.10) | (15.29, 21.00) | (18.49, 24.13) |
| Omecamtiv mecarbil | 27.70 | 21.51 | 22.34 | 22.09 |
| | (24.86, 30.54) | (18.71, 24.30) | (19.42, 25.25) | (19.61, 24.57) |

Within each randomization setting group least squares mean is from the mixed model which includes baseline total sympton score value, region, baseline eGFR, scheduled visit, treatment group and interaction of treatment with scheduled visit as covarites.

Within each randomization setting subgroup least squares mean is from the mixed model which includes baseline total symptom score value, region, baseline eGFR, scheduled visit, treatment group and interaction of treatment with scheduled visit as covariates.

Influence of Ejection Fraction on the Treatment Effect of Omecamtiv Mecarbil

Figure 9:
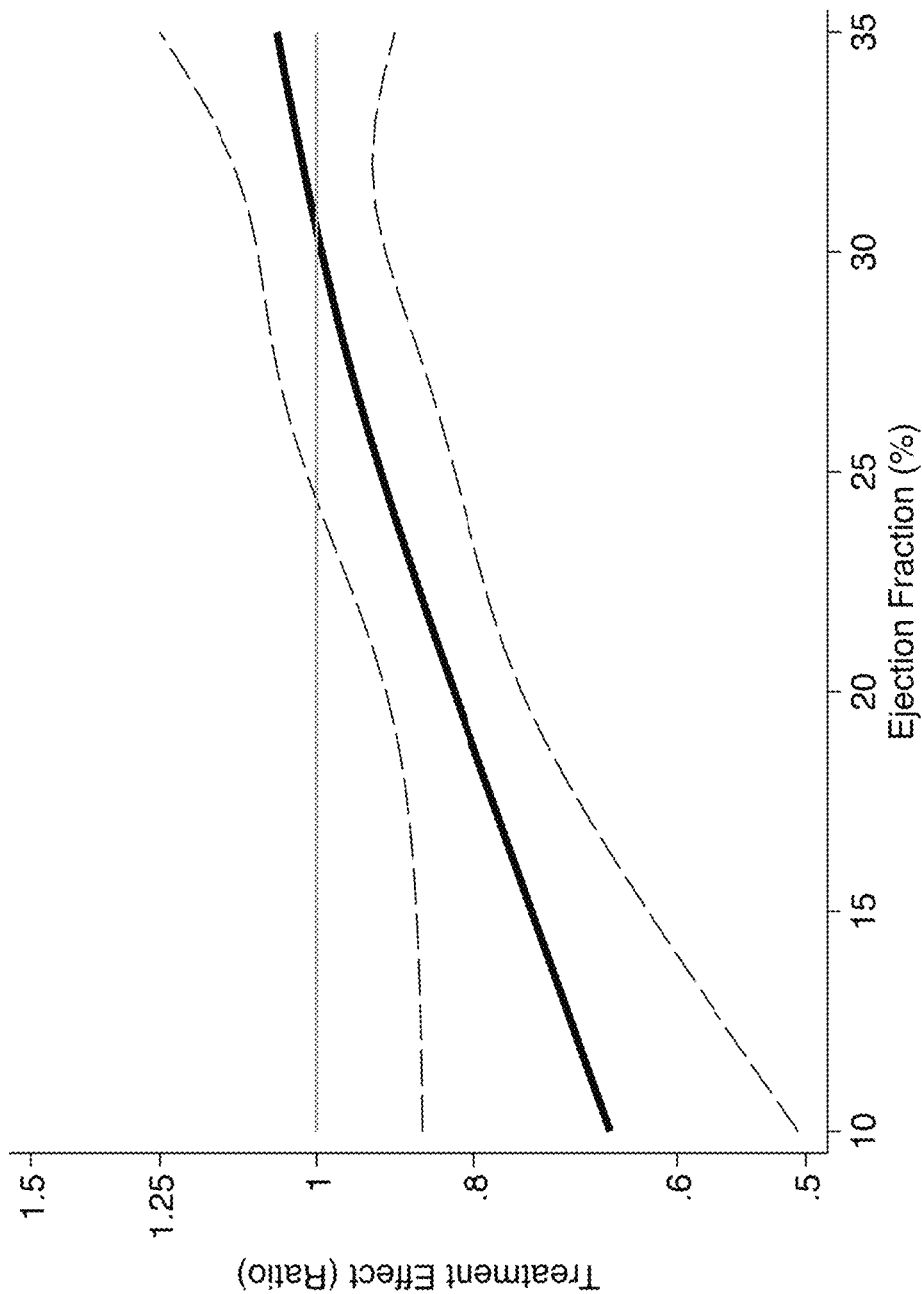
FIG. 9 shows analysis of ejection fraction as a continuous variable (interaction effect, p=0.004) demonstrated a progressively larger treatment effect of omecamtiv mecarbil with decreasing ejection fraction (EF).
Figure 10B:
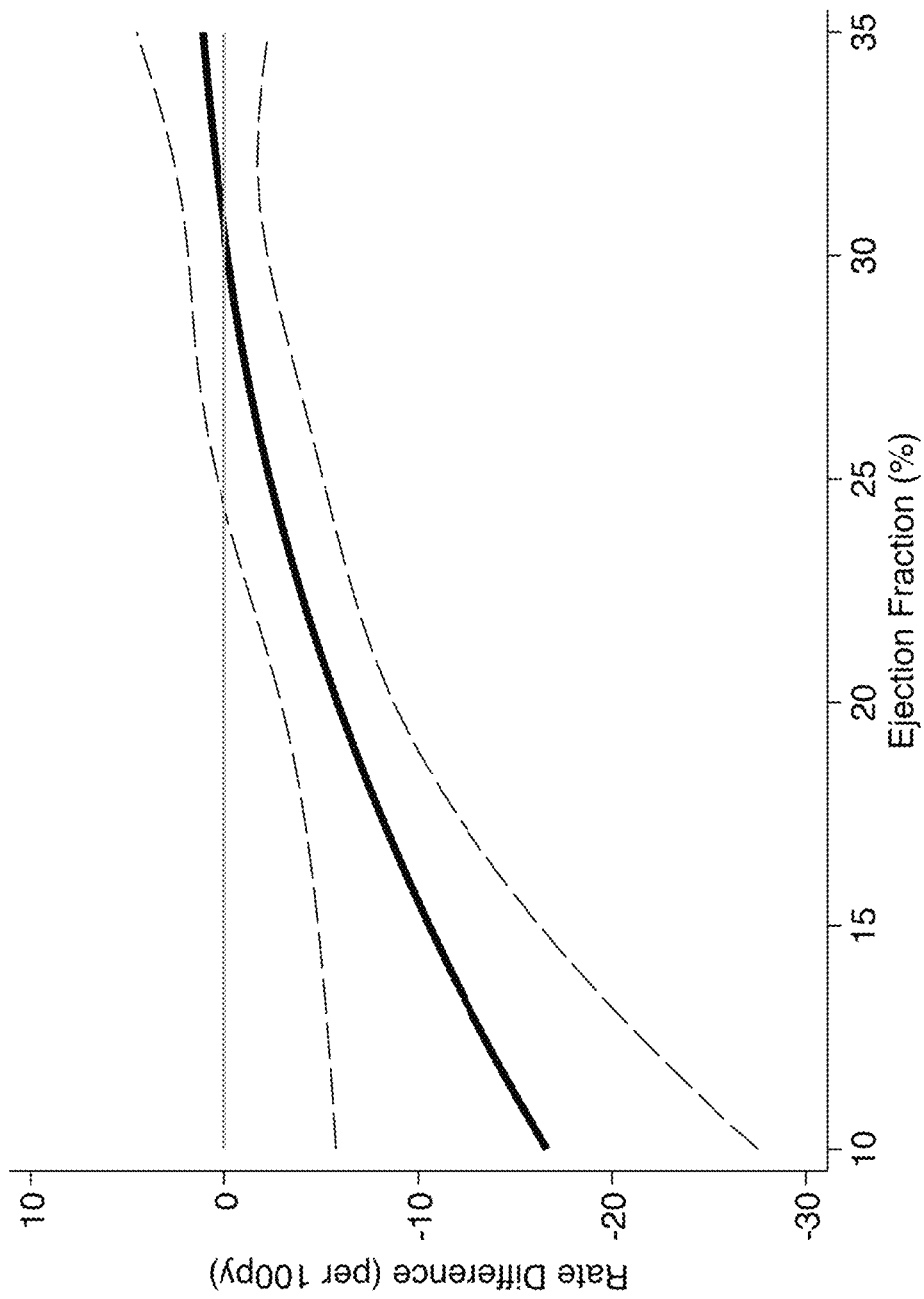
FIG. 10B shows that absolute risk reduction by omecamtiv mecarbil progressively increased with decreasing ejection fraction (EF).
Figure 22:
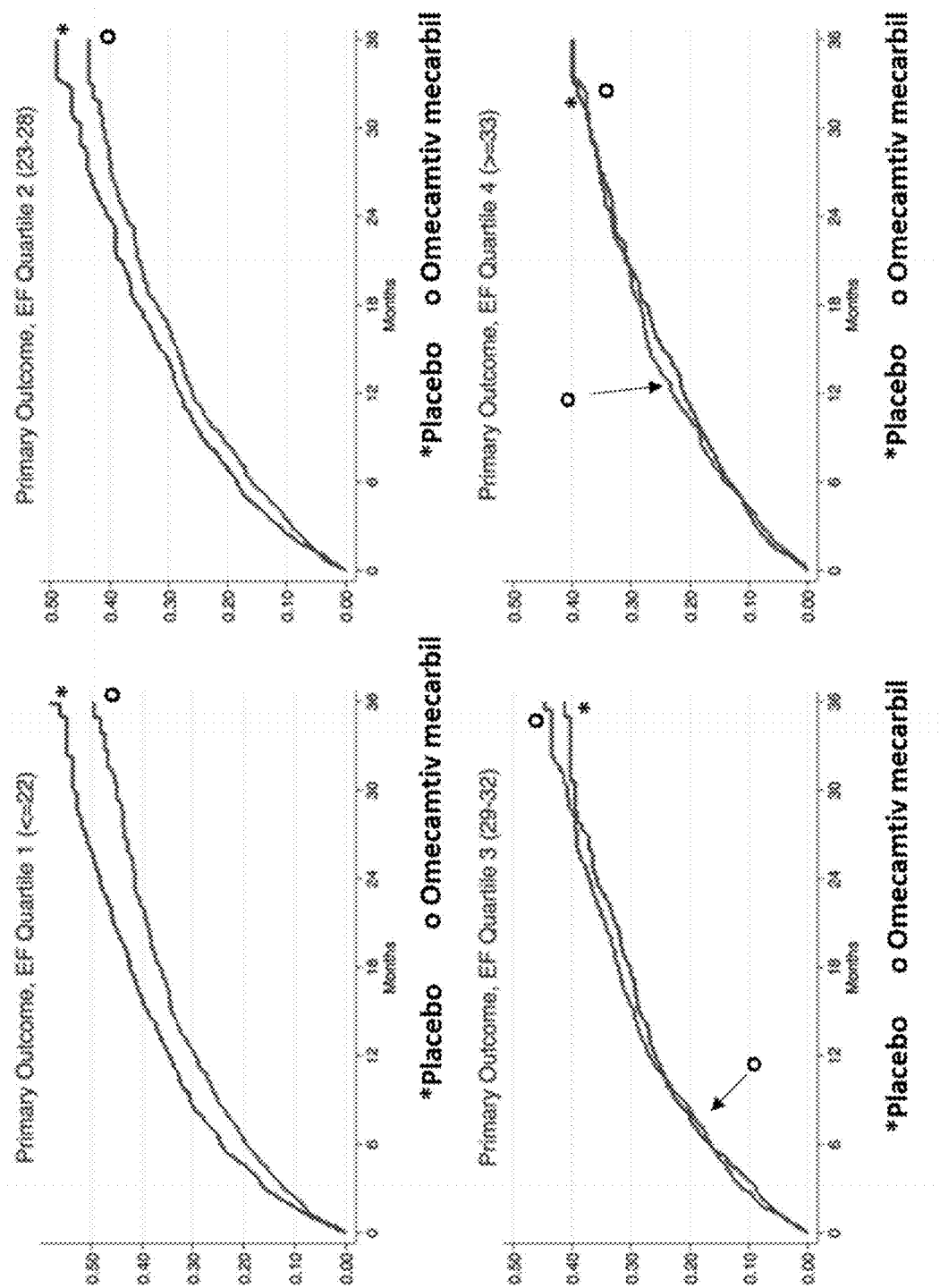
FIG. 22 shows Kaplan-Meier curves for primary composite endpoint by EF quartile.

Omecamtiv mecarbil significantly decreased the primary endpoint of the time-to-first heart failure event or cardiovascular death in the overall trial population (HR 0.92; p=0.025). The statistical analysis plan pre-specified the assessment of the primary endpoint in the ejection fraction subgroups above and below the median value (28%) and there was a significant modification of the treatment effect of omecamtiv mecarbil by ejection fraction (interaction effect, p=0.004). In patients with EF 28%, there was a 16% reduction in the time-to-first heart failure event or cardiovascular death (HR 0.84, 95% CI 0.77-0.92; p=0.0003) compared to no difference in patients with EF>28% (HF 1.04, 95% CI 0.94-1.16; p=0.45). Analysis by quartiles of ejection fraction of the modifying effect on the primary composite endpoint (interaction p=0.013; Table 7, FIG. 22) by treatment with omecamtiv mecarbil demonstrated a 15 and 17% relative risk reduction in the lower two quartiles of ejection fraction, respectively. Analysis of ejection fraction as a continuous variable (interaction effect, p=0.004) demonstrated a progressively larger treatment effect of omecamtiv mecarbil with decreasing ejection fraction (FIG. 9; Table 7). The difference in the incidence of the primary composite endpoint increased disproportionately between the placebo and omecamtiv mecarbil treatment groups with lower ejection fractions (FIG. 10A, such that absolute risk reduction by omecamtiv mecarbil progressively increased with decreasing ejection fraction (FIG. 10B). In the lowest ejection fraction quartile, omecamtiv mecarbil resulted in an absolute reduction of 7.4 events per 100 patient-years, with a number-needed-to-treat of 11.8 patients over 3-years necessary to prevent an event (Table 7).

Figure 11A:
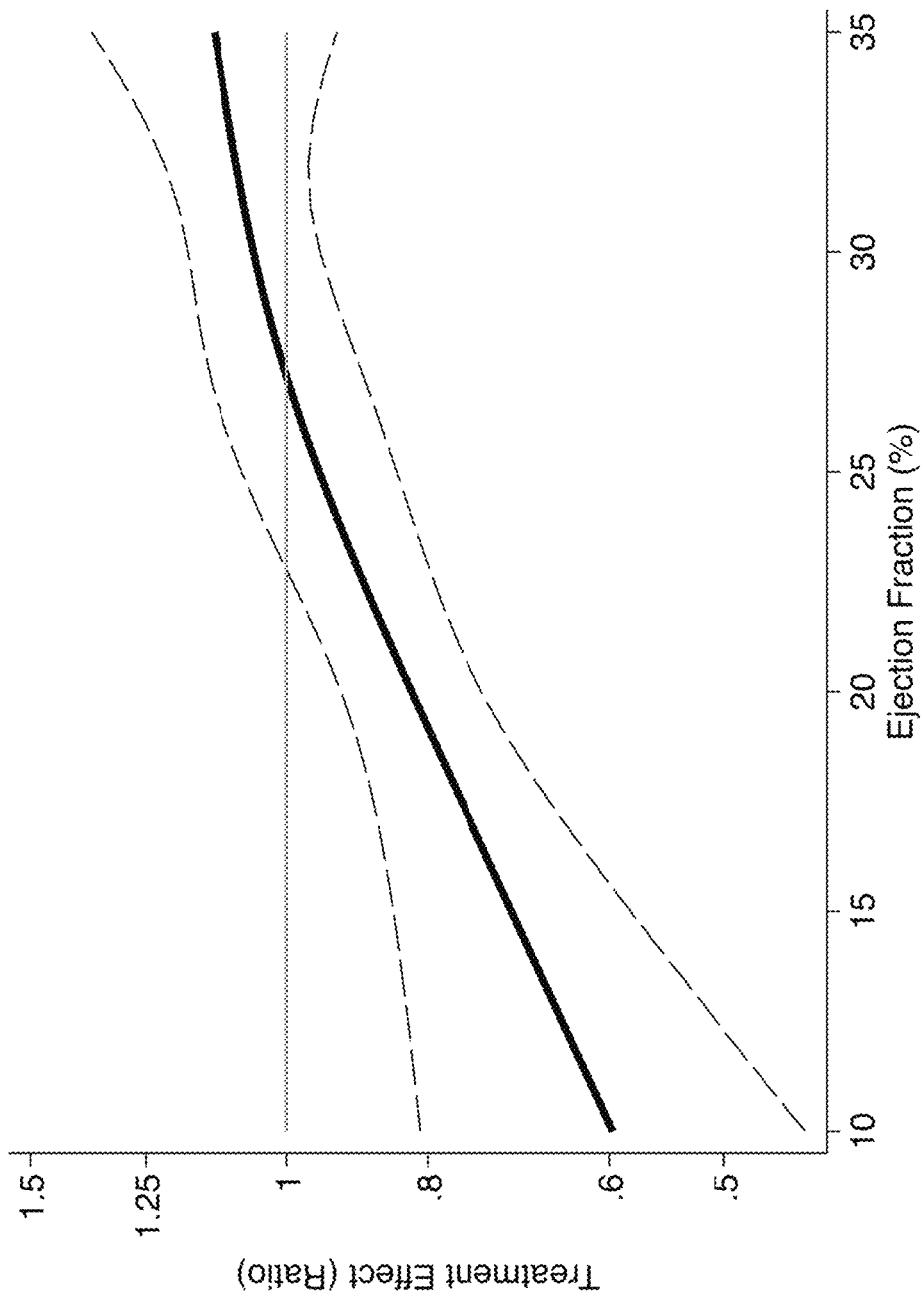
FIG. 11A shows The beneficial effect of treatment with omecamtiv mecarbil on the primary outcome was driven predominantly by the significant reduction in heart failure events.
Figure 11B:
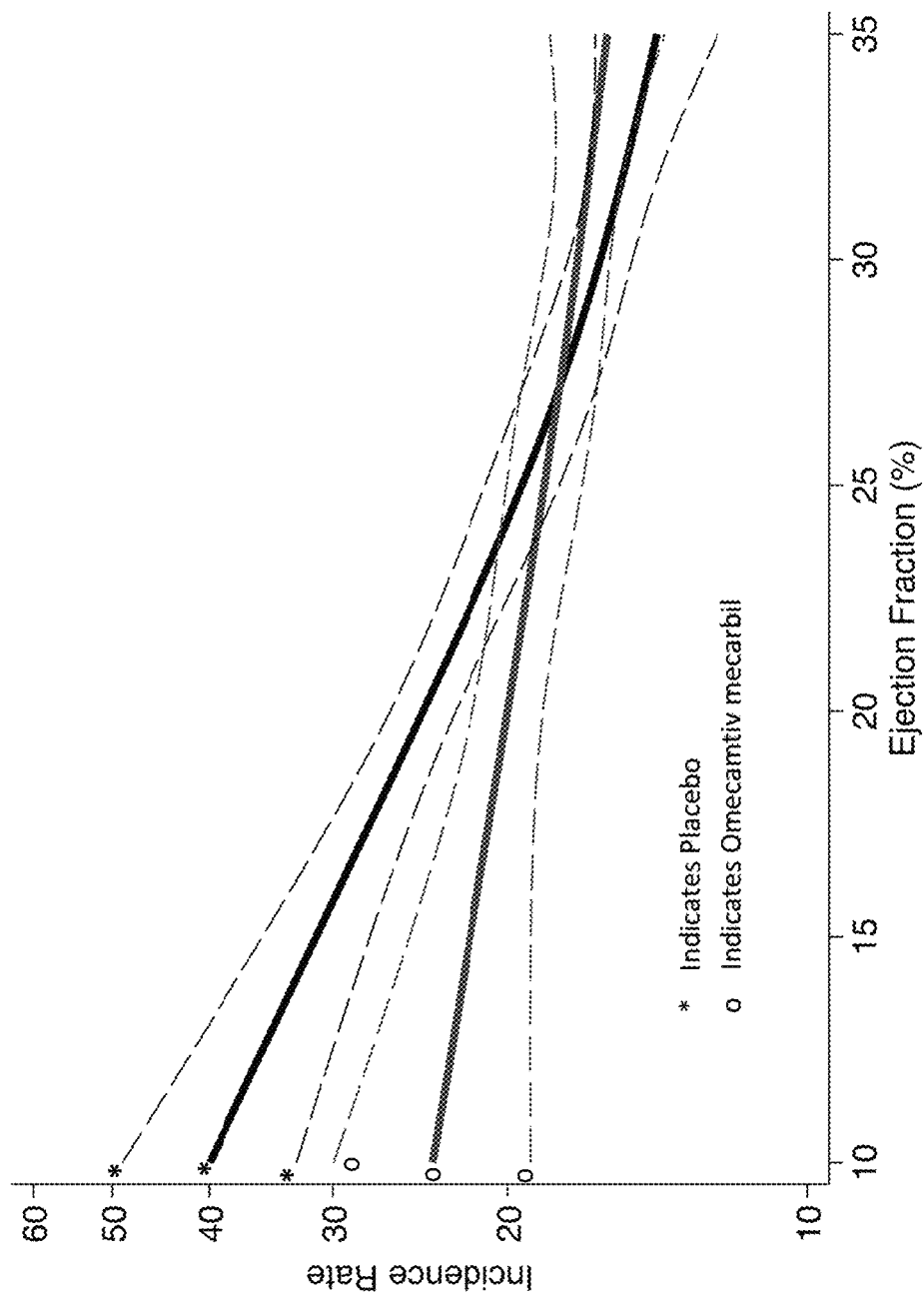
FIG. 11B shows the incidence rate of heart failure hospitalizations increases with decreasing ejection fraction in both the placebo (stars) and omecamtiv mecarbil (circles) treated patients, but was significantly impacted by treatment with omecamtiv mecarbil, and showed a progressively greater reduction in the absolute difference with decreasing ejection fraction.
Figure 12A:
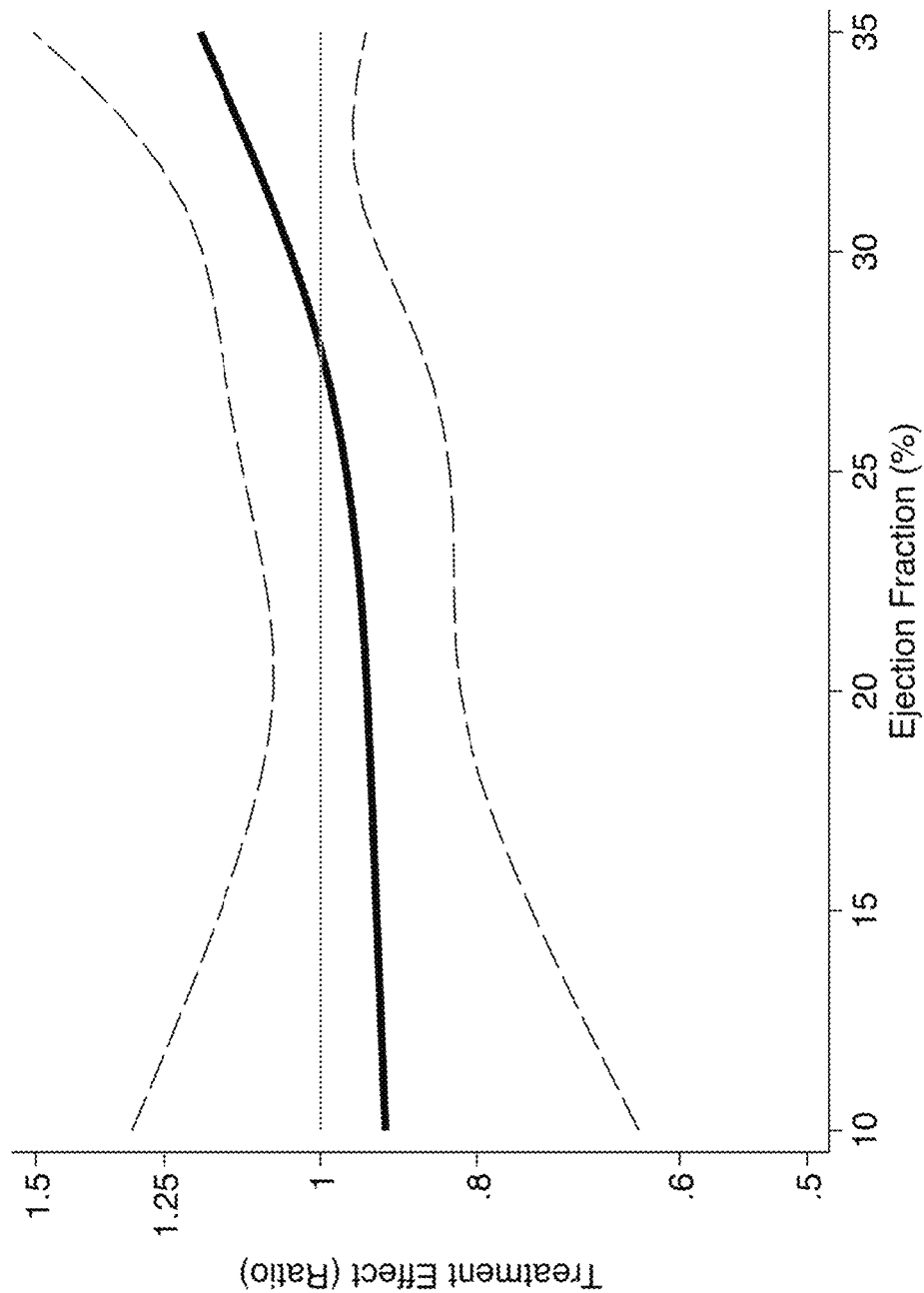
FIG. 12A shows OM had no overall effect on cardiovascular death, neither in the overall population, nor as a function of baseline ejection fraction (EF).
Figure 12B:
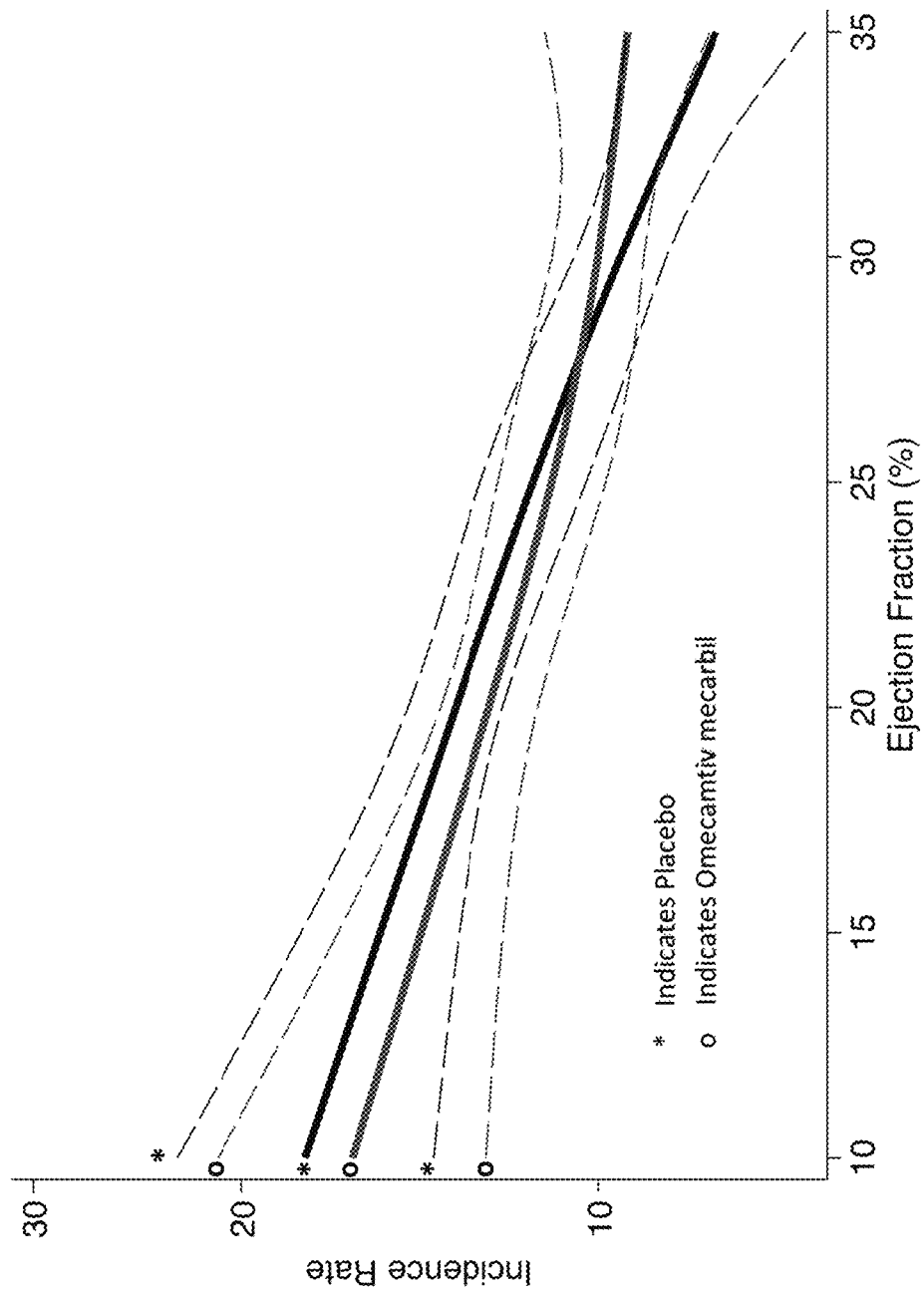
FIG. 12B shows OM the incidence of cardiovascular death increased comparably in both the placebo (stars) and omecamtiv mecarbil (circles) arms with decreasing ejection fraction (EF).

The beneficial effect of treatment with omecamtiv mecarbil on the primary outcome was driven predominantly by the significant reduction in heart failure events and ejection fraction was a significant modifier of this treatment effect (interaction p=0.004 by ejection fraction quartile, interaction p=0.001 by ejection fraction as continuous variable; Table 7). Ejection fraction had a similar modifying effect on the progressive reduction of heart failure hospitalizations by omecamtiv mecarbil (interaction p=0.004 by ejection fraction quartile, interaction p=0.001 by ejection fraction as continuous variable; FIG. 11A; Table 7). Consistent with the primary composite endpoint, the incidence rate of heart failure hospitalizations increases with decreasing ejection fraction in both the placebo and omecamtiv mecarbil treated patients (FIG. 11B), but was significantly impacted by treatment with omecamtiv mecarbil, and showed a progressively greater reduction in the absolute difference with decreasing ejection fraction. Ejection fraction significantly modified the treatment of effect of omecamtiv mecarbil on total heart failure events and hospitalizations as well (interaction p=0.006 and 0.009, respectively; Table 20). Omecamtiv mecarbil had no overall effect on cardiovascular death, neither in the overall population nor as a function of baseline ejection fraction (interaction p=0.14 by ejection fraction quartile; FIG. 12A, Table 7). As expected, the incidence of cardiovascular death increased comparably in both the placebo and omecamtiv mecarbil arms with decreasing ejection fraction (FIG. 12B, Table 7). Similarly, there was no effect of omecamtiv mecarbil on all-cause mortality (Table 7). The proportional hazards assumption was evaluated for all hazard ratios presented in Table 2 via a test of Schoenfeld residuals. No significant violations were detected (all p>0.2).

TABLE 20

Total heart failure events/hospitalizations by ejection fraction quartiles:

| Outcome by EF Quartiles | Omecamtiv Mecarbil | | Placebo | | Ratio (95% CI) | ARR (per 100 pt-yrs) |
|---|---|---|---|---|---|---|
| | Events | Rate (per 100 pt-yrs) | Events | Rate (per 100 pt-yrs) | | |
| Total HF Events | | | | | Interaction p = 0.006 | |
| EF ≥33% | 483 | 28.5 | 386 | 23.8 | 1.13 (0.90, 1.43) | −4.7 |
| EF 29-32% | 506 | 27.1 | 526 | 27.7 | 1.14 (0.93, 1.40) | 0.6 |
| EF 23-28% | 577 | 30.0 | 678 | 34.0 | 0.83 (0.68, 1.01) | 4.0 |
| EF ≤22% | 719 | 37.1 | 909 | 48.4 | 0.83 (0.70, 1.01) | 11.3 |
| Total HF Hospitalizations | | | | | Interaction p = 0.009 | |
| EF ≥33% | 449 | 26.5 | 372 | 22.9 | 1.12 (0.89, 1.43) | −3.6 |
| EF 29-32% | 472 | 25.3 | 478 | 25.2 | 1.18 (0.96, 1.46) | −0.1 |
| EF 23-28% | 541 | 28.1 | 624 | 31.3 | 0.84 (0.69, 1.02) | 3.2 |
| EF ≤22% | 679 | 35.1 | 846 | 45.0 | 0.84 (0.70, 1.01) | 9.9 |

Other Outcomes and Safety of Omecamtiv Mecarbil by Ejection Fraction

Despite the reduction in heart failure events with omecamtiv mecarbil, there was no consistent beneficial effect on symptoms as a function of EF as assessed by the KCCQ-TSS in either the subjects enrolled from the inpatient or outpatient settings. However, there was a greater reduction in NT-proBNP by omecamtiv mecarbil in patients with lower ejection fraction such that the lowest EF quartile had a 22% reduction (p<0.001) while the highest EF quartile showed only a 3% change (p=0.54; interaction p<0.001) (Table 9).

Omecamtiv mecarbil treatment resulted in a small reduction in heart rate (treatment difference of 1.1 to 1.9 bpm across the EF quartiles) and increase in troponin I (median 3-5 ng/L across the EF quartiles; limit of detection, 6 ng/L; upper reference limit, 40 ng/L) which did not differ by EF quartile. There was no significant effect on systolic blood pressure, serum potassium or creatine across the EF quartiles compared to placebo. There were also no significant differences noted in the incidence of adverse events between the omecamtiv mecarbil and placebo treated groups, except for

TABLE 9

Omecamtiv Mecarbil Treatment Effects from Baseline to> Week 24 of Selected Vital Signs and Laboratory Values

| Variable Treatment Difference (95% CI) p-value | EF ≤22% (N = 2246) | EF 23-28% (N = 2210) | EF 29-32% (N = 2026) | EF ≥33% (N = 1750) | p-value |
|---|---|---|---|---|---|
| KCCQ Total Symptom Score Least squares mean (95% CI) | +1.6 (−0.2, +3.3) 0.08 | −0.6 (−2.3, +1.2) 0.52 | +0.3 (−1.4, +2.0) 0.74 | −1.0 (−2.8, +0.9) 0.30 | 0.10 |
| Inpatient- Least squares mean (95% CI) | +4.9 (+0.8, +8.9) 0.018 | +0.2 (−3.7, +4.1) 0.91 | +4.8 (+0.6, +8.9) 0.024 | −0.0 (−3.9, +3.9) 0.99 | 0.33 |
| Outpatient- Least squares mean (95% CI) | +0.7 (−1.2, +2.6) 0.47 | −0.6 (−2.5, +1.2) 0.52 | −0.8 (−2.6, +1.1) 0.42 | −1.5 (−3.5, +0.5) 0.13 | 0.12 |
| Systolic BP (mmHg) | 0.9 (−0.4, 2.2) 0.19 | −0.6 (−1.9, 0.8) 0.40 | −0.6 (−1.9, 0.7) 0.34 | −1.2 (−2.7, 0.2) 0.09 | 0.038 |
| Heart rate (bpm) | −1.6 (−2.5, −0.6) 0.001 | −1.7 (−2.7, −0.8) 0.001 | −1.9 (−2.9, −0.9) <0.001 | −1.1 (−2.1, −0.1) 0.032 | 0.62 |
| Potassium (mmol/L) | 0.01 (−0.04, 0.05) 0.76 | −0.01 (−0.06, 0.03) 0.76 | −0.01 (−0.06, 0.03) 0.59 | 0.02 (−0.03, 0.06) 0.53 | 0.87 |
| Creatinine (mg/dL) | −0.01 (−0.04, 0.02) 0.53 | 0.01 (−0.02, 0.04) 0.53 | 0.01 (−0.02, 0.04) 0.58 | 0.02 (−0.01, 0.05) 0.24 | 0.22 |
| NT-proBNP (Ratio) | 0.78 (0.71, 0.85) <0.001 | 0.90 (0.83, 0.98) <0.001 | 0.95 (0.87, 1.04) 0.28 | 0.97 (0.89, 1.06) 0.54 | <0.001 |
| Troponin I (Ratio) | 1.19 (1.11, 1.27) <0.001 | 1.29 (1.21, 1.38) <0.001 | 1.27 (1.18, 1.36) <0.001 | 1.27 (1.18, 1.37) <0.001 | 0.22 |
| Troponin I (ng/L) | 5 (4, 6) <0.001 | 4 (3, 5) <0.001 | 4 (3, 5) <0.001 | 3 (2, 4) <0.001 | 0.055 |

*Values represent treatment effects as evaluated by between-group differences of change from baseline to Week 24. Least squares mean is from the mixed model which includes baseline total symptom score value, region, baseline eGFR, scheduled visit, treatment group and interaction of treatment with scheduled visit as covariates. Troponin I assay had limit of detection of 6 ng/L with an upper reference limit of 40 ng/L.

an apparent reduction in the incidence of adjudicated stroke for patients treated with omecamtiv mecarbil (Table 10 and Table 23A).

Figure 24:
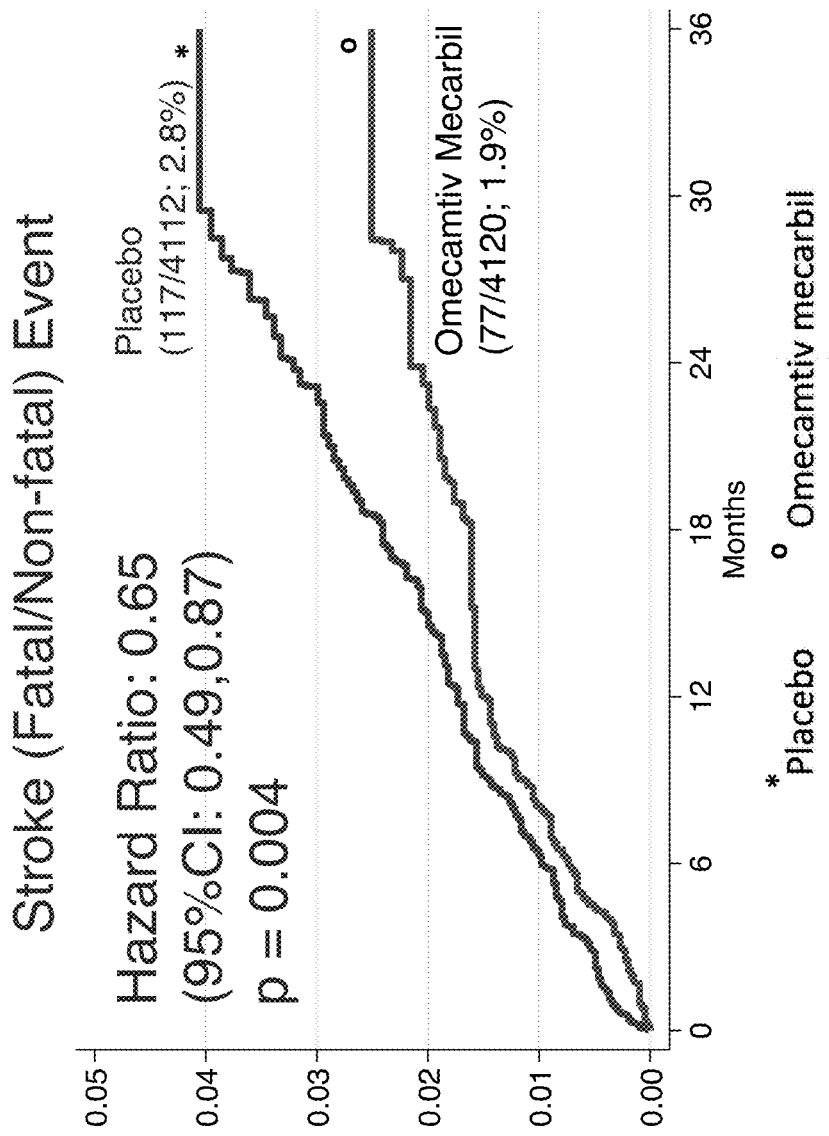
FIG. 24 shows the incidence of stroke (fatal and non-fatal stroke events) in all patients randomized.
Figure 25:
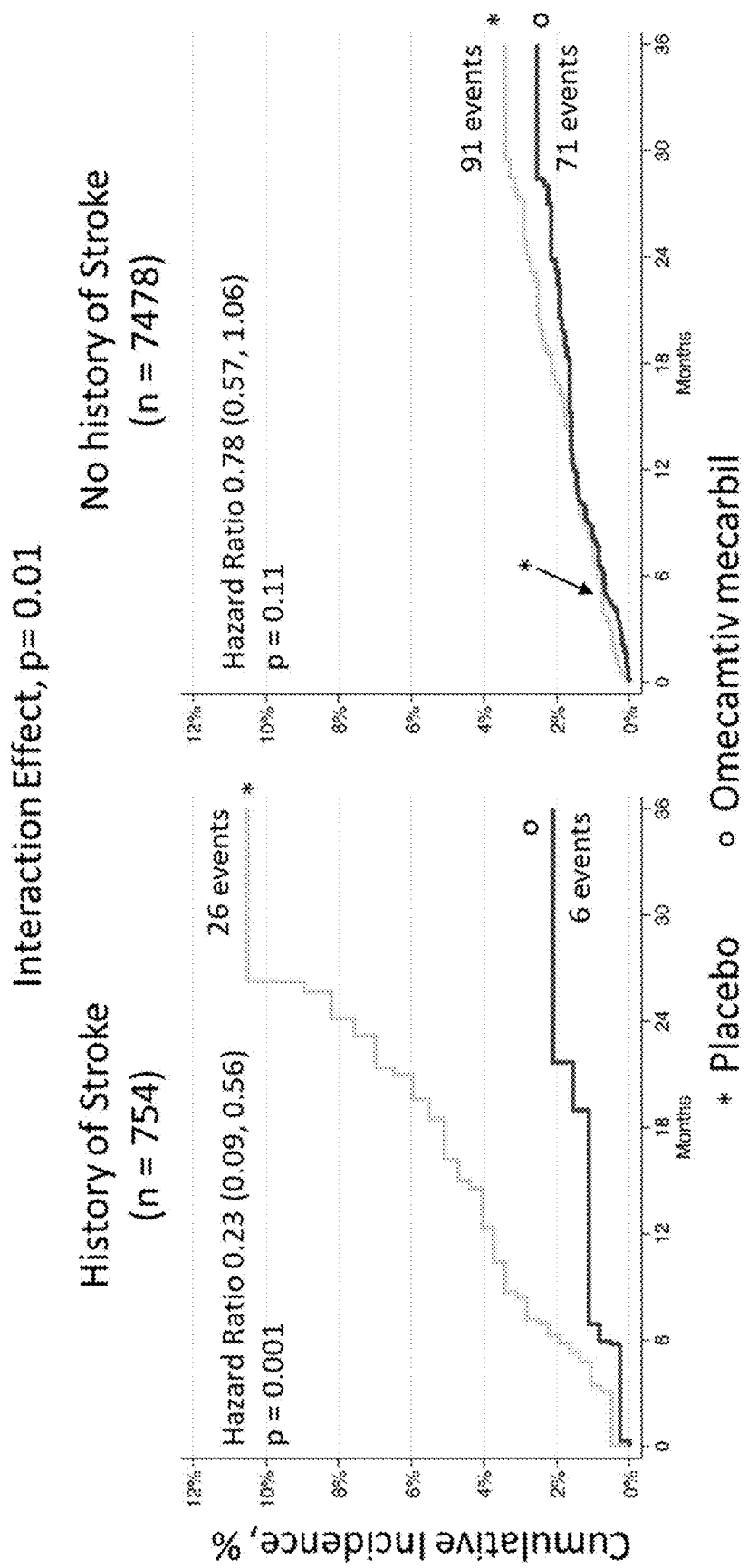
FIG. 25 shows the treatment effect of omecamtiv mecarbil in patients with or without a history of stroke as compared to placebo on the occurrence of stroke (fatal and non-fatal stroke events) (placebo—stars; omecamtiv mecarbil—circles).
Figure 26:
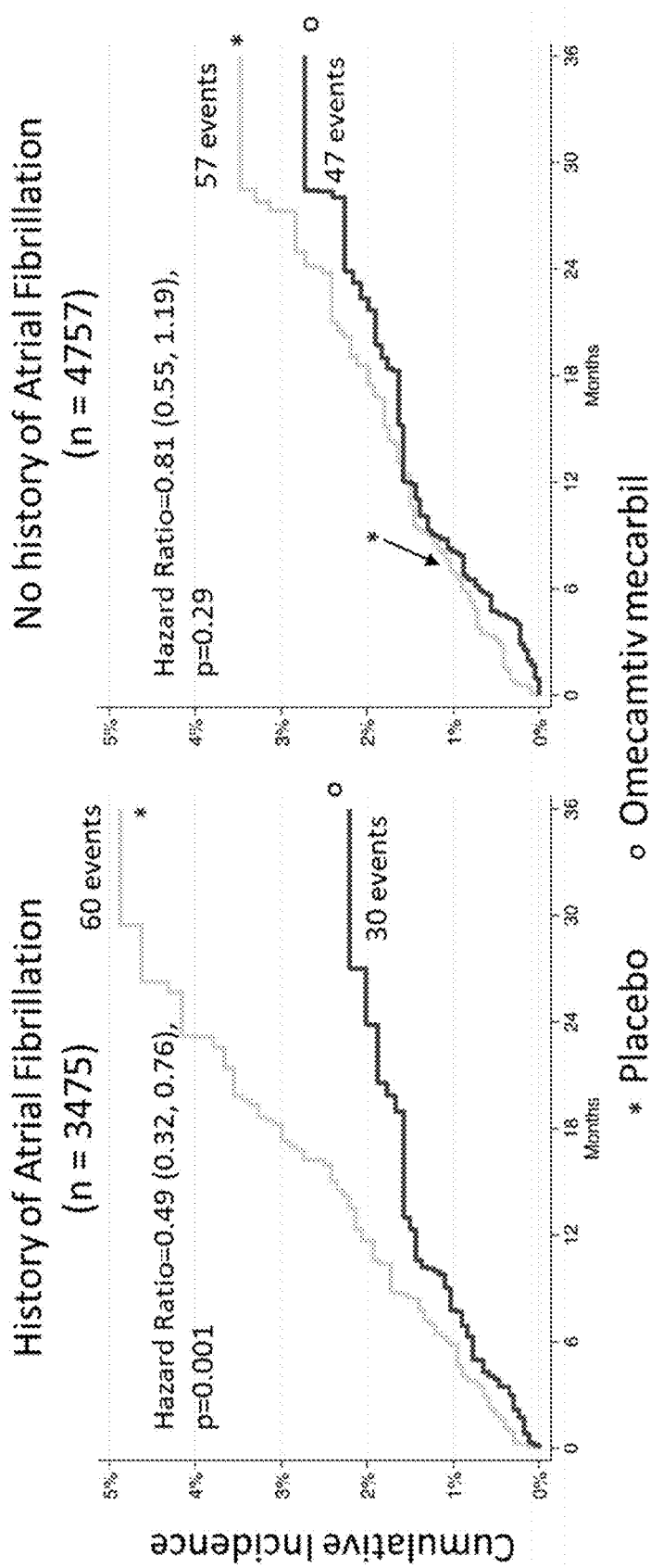
FIG. 26 shows the treatment effect of omecamtiv mecarbil in patients with or without a history of atrial fibrillation as compared to placebo on the occurrence of stroke (fatal and non-fatal stroke events) (placebo—stars; omecamtiv mecarbil—circles).
Figure 27:
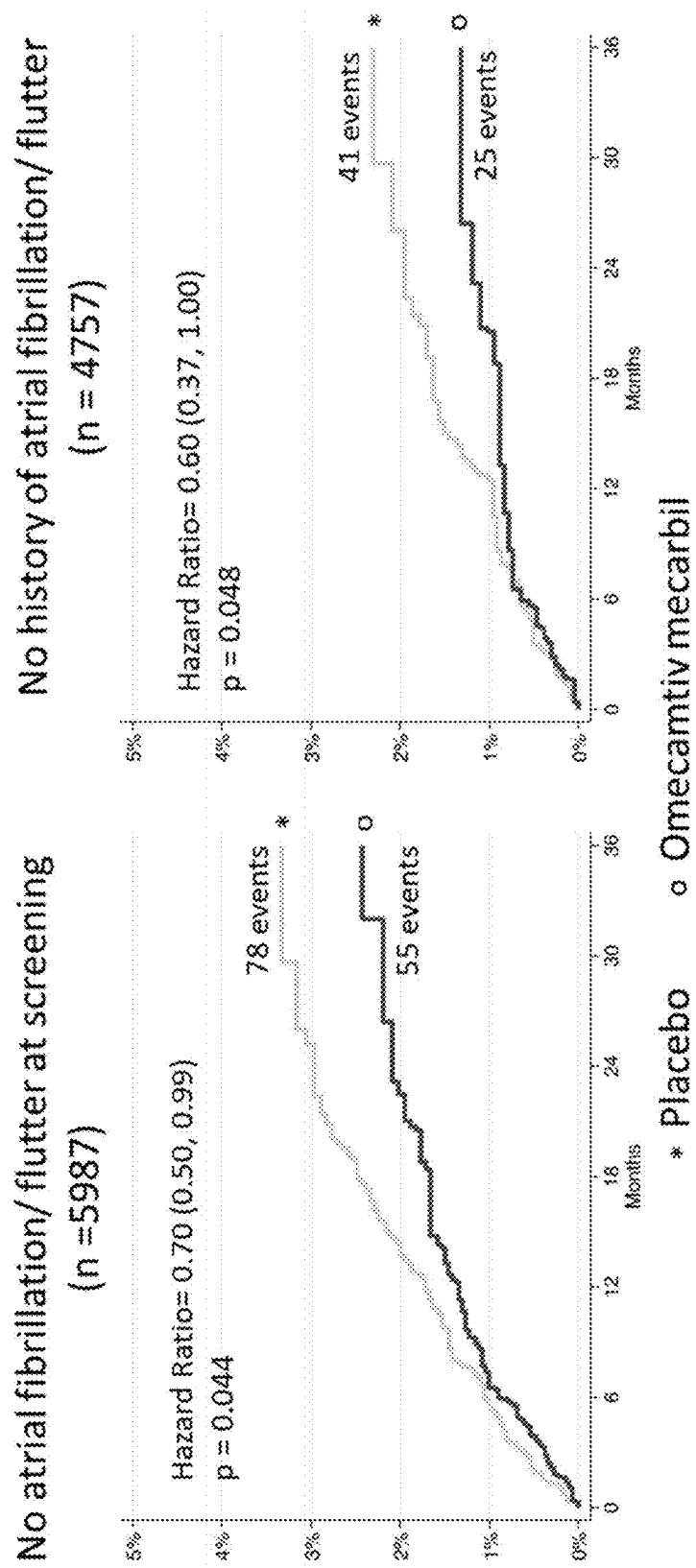
FIG. 27 shows the treatment effect of omecamtiv mecarbil in patients without an atrial fibrillation/atrial flutter (AFF) at screening and those without a history of AFF as compared to placebo on the occurrence of new-onset AFF (placebo—stars; omecamtiv mecarbil—circles).

Omecamtiv mecarbil provided similar benefit in patients with and without a history of stroke. The time to first stroke event was significantly reduced in patients allocated to omecamtiv mecarbil. A history of stroke was present in 754 (9.2%) participants, who were older and more likely to be non-White, have atrial fibrillation/flutter, hypertension, diabetes mellitus, or ischemic heart disease, worse NYHA class and eGFR, and higher baseline NT-proBNP or troponin. Patients with a history of stroke had similar beneficial effect of omecamtiv mecarbil on the primary endpoint (HR 0.86; 95% CI 0.70, 1.07; p=0.18) as in patients with no stroke (HR 0.93; 95% CI 0.87, 1.00; p=0.06). Multivariate predictors of the incident 194 first stroke events included non-White race, history of stroke or percutaneous coronary intervention (PCI), and elevated baseline troponin or systolic blood pressure (Table 24). Patients randomized to omecamtiv mecarbil had a significant 35% reduction in the risk of first fatal or non-fatal stroke (FIG. 24) and a 42% reduction in fatal stroke (HR: 0.56; 95% CI 0.31, 0.99; p=0.048). The effect of omecamtiv mecarbil on risk of non-fatal and fatal stroke by history of stroke is shown in FIG. 25 (with history of stroke—HR: 0.23; 95% CI 0.09, 0.56; p=0.001, and no history of stroke—HR: 0.78; 95% CI 0.57, 1.06; p=0.11). The effect of omecamtiv mecarbil on risk of non-fatal and fatal stroke by history of atrial fibrillation is shown in FIG. 26 (with history of atrial fibrillation—HR: 0.49; 95% CI 0.32, 0.76; p=0.001, and no history of atrial fibrillation—HR: 0.81; 95% CI 0.55, 1.19; p=0.29). The effect of omecamtiv mecarbil on new onset atrial fibrillation/flutter is shown in FIG. 27 (no AF/F at screening—HR: 0.70; 95% CI 0.50, 0.99; p=0.044, and no history of AF/F—HR: 0.60; 95% CI 0.37, 1.00; p=0.048). Omecamtiv mecarbil significantly reduced non-fatal and fatal strokes in patients with heart failure with reduced ejection fraction in the context of significantly reducing new onset atrial fibrillation. Characteristics by baseline history of stroke are shown in Table 25.

TABLE 10

Other Outcomes and Adverse Events of Special Interest

| Safety outcomes<br>Omecamtiv Mecarbil: n (%)<br>Placebo: n (%)<br>Relative Risk (95% CI)<br>p-value | EF22%<br>(N = 2246) | EF 23-28%<br>(N = 2210) | EF 29-32%<br>(N = 2026) | EF 33%<br>(N = 1750) |
|---|---|---|---|---|
| Any treatment Emergent Serious Adverse Events | OM: 683 (60.7%)<br>P: 719 (64.6%)<br>RR: 0.94 (0.88, 1.00)<br>p = 0.05 | OM: 616 (56.9%)<br>P: 666 (59.3%)<br>0.96 (0.89, 1.03)<br>0.26 | OM: 579 (57.3%)<br>P: 585 (58.0%)<br>0.99 (0.92, 1.07)<br>0.77 | OM: 495 (55.5%)<br>P: 465 (54.3%)<br>1.02 (0.94, 1.11)<br>0.62 |
| Adverse Event: Ventricular Tachyarrhythmia | OM: 97 (9.8%)<br>P: 99 (9.8%)<br>RR: 1.00 (0.76, 1.30)<br>p = 1.00 | OM: 80 (8.3%)<br>P: 85 (8.5%)<br>0.98 (0.73, 1.31)<br>0.98 | OM: 62 (6.9%)<br>P: 65 (7.2%)<br>0.96 (0.69, 1.34)<br>0.81 | OM: 51 (6.4%)<br>P: 55 (7.3%)<br>0.88 (0.61, 1.27)<br>0.48 |
| Serious Adverse Event: Ventricular Arrhythmia Requiring Treatment | OM: 41 (3.6%)<br>P: 46 (4.1%)<br>RR: 0.88 (0.58, 1.33)<br>p = 0.55 | OM: 35 (3.2%)<br>P: 35 (3.1%)<br>1.04 (0.65, 1.65)<br>0.87 | OM: 21 (2.1%)<br>P: 27 (2.7%)<br>0.78 (0.44, 1.37)<br>0.38 | OM: 22 (2.5%)<br>P: 19 (2.2%)<br>1.11 (0.61, 2.04)<br>0.73 |
| Adjudicated First Major Cardiac Ischemic Events | OM: 54 (4.8%)<br>P: 45 (4.0%)<br>RR: 1.19 (0.81, 1.75)<br>p = 0.39 | OM: 47 (4.3%)<br>P: 49 (4.4%)<br>1.00 (0.67, 1.47)<br>0.98 | OM: 41 (4.1%)<br>P: 38 (3.8%)<br>1.08 (0.70, 1.66)<br>0.73 | OM: 58 (6.5%)<br>P: 56 (6.5%)<br>0.99 (0.70, 1.42)<br>0.99 |
| Positively Adjudicated Myocardial Infarction | OM: 37 (3.3%)<br>P: 30 (2.7%)<br>RR: 1.22 (0.76, 1.96)<br>p = 0.41 | OM: 29 (2.7%)<br>P: 34 (3.0%)<br>0.89 (0.54, 1.44)<br>0.62 | OM: 22 (2.2%)<br>P: 22 (2.2%)<br>1.00 (0.56, 1.79)<br>1.00 | OM: 34 (3.8%)<br>P: 32 (3.7%)<br>1.02 (0.64, 1.64)<br>0.94 |
| Adjudicated First Stroke | OM: 17 (1.5%)<br>P: 26 (2.3%)<br>RR: 0.65 (0.35, 1.18)<br>p = 0.15 | OM: 19 (1.8%)<br>P: 37 (3.3%)<br>0.53 (0.31, 0.92)<br>0.022 | OM: 24 (2.4%)<br>P: 29 (2.9%)<br>0.83 (0.48, 1.41)<br>0.48 | OM: 16 (1.8%)<br>P: 20 (2.3%)<br>0.77 (0.40, 1.47)<br>0.42 |

TABLE 23A

| Adjudicated type of first stroke event | | |
|---|---|---|
| | Omecamtiv Mecarbil (n = 4110) | Placebo (n = 4101) |
| Ischemic (Non-hemorrhagic) | 65 (1.6%) | 84 (2.0%) |
| Ischemic with hemorrhagic transformation | 5 (0.1%) | 15 (0.4%) |
| Hemorrhagic | 3 (0.1%) | 9 (0.2%) |
| Undetermined | 3 (0.1%) | 4 (0.1%) |

TABLE 24

| Multivariate predictors of non-fatal and fatal stroke. | | |
|---|---|---|
| Covariates (n = 8120) | p-value | Hazard Ratio (95% CI) (n = 193 events) |
| Race (ref. = White) | <0.001 | |
| Asian | | 2.05 (1.33, 3.16) |
| Black | | 1.96 (1.20, 3.19) |
| Other | | 1.92 (1.17, 3.16) |
| History of stroke | 0.002 | 1.85 (1.26, 2.71) |
| PCI | 0.003 | 1.58 (1.17, 2.12) |
| Troponin (per doubling) | 0.006 | 1.15 (1.04, 1.26) |
| AFF | 0.008 | 1.51 (1.12, 2.05) |
| SBP (per 10 mmHg) | 0.015 | 1.12 (1.02, 1.23) |

CI = 95% confidence interval.
PCI = percutaneous coronary interventions.
AFF = atrial fibrillation or atrial flutter.
SBP = systolic blood pressure.

TABLE 25

| Characteristics by baseline history of stroke | | | |
|---|---|---|---|
| | No h/o Stroke (n = 7478) | H/o Stroke (n = 754) | p-value |
| Demographics | | | |
| Age-yr | 64.3 ± 11.4 | 67.0 ± 10.1 | p <0.001 |
| Sex, Female | 1595 (21.3%) | 154 (20.4%) | p = 0.56 |
| Race: Asian/ Black/ Other/ White | 8/7/7/78% | 12/8/4/77% | p <0.001 |
| Region: | | | p <0.001 |
| Asia | 587 (7.8%) | 83 (11.0%) | |
| E Europe/Russia | 2431 (32.5%) | 250 (33.2%) | |
| Latin America | 1474 (19.7%) | 100 (13.3%) | |
| US And Canada | 1234 (16.5%) | 152 (20.2%) | |
| W Europe/South Africa/Australasia | 1752 (23.4%) | 169 (22.4%) | |
| In-patient | 1886 (25.2%) | 198 (26.3%) | p = 0.53 |
| Clinical Characteristics | | | |
| A Fib/Flutter (Screening) | 1988 (26.6%) | 257 (34.1%) | p <0.001 |
| Hypertension Hx | 5185 (69.3%) | 599 (79.4%) | p <0.001 |
| Type 2 diabetes mellitus | 2951 (39.5%) | 358 (47.5%) | p <0.001 |
| History of stroke | 0 (0.0%) | 754 (100.0%) | p <0.001 |
| Ischemic HF etiology | 3943 (52.7%) | 472 (62.6%) | p <0.001 |
| H/o MI | 3051 (40.8%) | 384 (50.9%) | p <0.001 |
| H/o CABG | 1166 (15.6%) | 151 (20.0%) | p = 0.002 |
| H/o PCI | 2183 (29.2%) | 255 (33.8%) | p = 0.008 |
| LVEF-% | 26.6 ± 6.3 | 26.5 ± 6.3 | p = 0.84 |
| NYHA II/III/IV | 54/43/3% | 47/50/3% | p = 0.004 |
| KCCQ Total Symptom Score | 70 [49, 88] | 67 [49, 85] | p = 0.038 |
| SBP-mmHg | 117 ± 15 | 117 ± 16 | p = 0.99 |
| Heart rate-beats/min | 73 ± 12 | 72 ± 12 | p = 0.046 |
| NT-proBNP-pg/mL | 1961 [976, 4025] | 2388 [1272, 4505] | p <0.001 |
| Troponin I-ng/L | 26 [13, 50] | 30 [18, 58] | p <0.001 |
| eGFR-mUmin/1.73 m2 | 59 [44, 75] | 55 [43, 69] | p <0.001 |
| Baseline BMI (kg/m2) | 29 ± 6 | 28 ± 6 | p <0.001 |
| Heart Failure Therapies | | | |
| ACEi, ARB or ARNi | 6511 (87.1%) | 648 (85.9%) | p = 0.38 |
| ARNi | 1452 (19.4%) | 149 (19.8%) | p = 0.82 |
| BB | 7059 (94.4%) | 704 (93.4%) | p = 0.25 |

TABLE 25-continued

Characteristics by baseline history of stroke

|  | No h/o Stroke (n = 7478) | H/o Stroke (n = 754) | p-value |
|---|---|---|---|
| MRA | 5824 (77.9%) | 573 (76.0%) | p = 0.24 |
| SGLT2 Inhibitors | 198 (2.6%) | 20 (2.7%) | p = 0.99 |
| Ivabradine | 499 (6.7%) | 34 (4.5%) | p = 0.021 |
| Digitalis glycosides | 1256 (16.8%) | 129 (17.1%) | p = 0.83 |
| CRT | 1017 (13.6%) | 141 (18.7%) | p <0.001 |
| ICD | 2345 (31.4%) | 269 (35.7%) | p = 0.015 |

H/o = history of.
HF = heart failure.
MI = myocardial infarction.
CABG = coronary atery bypass.
PCI = percutaneous coronary interventions.
LVEF = left ventricular ejection fraction.
NYHA = New York Heart Association.
KCCQ - Kansas City Cardiomopathy Questionnnaire.
SBP = systolic blood pressure.
eGFR = estimated glomerular fitltration rate.
BMI = Body Mass Index.
ACEi = Angiotensin-converting enzyme inhibitors.
ARB = Angiotensin receptor blockers.
ARNi = Angiotensin receptor neprilysin inhibitor.
BB = Beta blockers.
MRA = Mineralicorticoid receptor antagonists.
SGLT2 = Sodium-glucose cotransporter 2.
CRT = Cardiac resynchronization therapy.
ICD = implantable cardioverter-defibillator.

The evaluation of EF by quartiles in the current analysis has subgroups of approximately 2,000 patients with 578 to 979 events in each quartile, subgroups in themselves larger than many studies. These investigations are supported by analyses of ejection fraction as a continuous variable incorporating the data from all 8,232 patients. While the statistical analysis plan from GALACTIC-HF pre-specified multiple sub-groups for evaluation and is subject to issues related to multiplicity testing, the univariate interaction p-value for the treatment-covariate interaction was 0.004, making it highly unlikely to be due to chance. In addition, there is biological plausibility for this effect modification and the findings are internally consistent.

Patients Having More Advanced Heart Failure
Statistical Approach

Baseline characteristics for patients classified as more advanced HF compared to those without were evaluated using appropriate summary statistics. Outcomes for patients with or without more advanced HF were compared using Cox proportional hazards models and Kaplan-Meier curves. Interaction terms were used to assess whether omecamtiv mecarbil had a differential effect on outcome by advanced HF status. Absolute event rates were described using rate per 100 patient-years. As a sensitivity analysis, the event rates and treatment effect of omecamtiv mecarbil for patients was assessed by specific advanced HF criteria met, as well as the total number of criteria met. For quality-of-life data as assessed by the Kansas City Cardiomyopathy Questionnaire Total Symptom Score (KCCQ TSS), linear regression adjusted for baseline scores was used to compare treatment effects of omecamtiv mecarbil compared to placebo. Safety and tolerability data for patients with advanced HF vs. those without were summarized using descriptive statistics. P value ≤0.05 was considered statistically significant for all analyses.

Results

Of patients enrolled in GALACTIC-HF, 2258 (27%) met the specified criteria for more advanced HF, of which 1106 were randomized to treatment with omecamtiv mecarbil and 1152 to placebo. Baseline characteristics stratified by those patients with or without more advanced HF are shown in Table 11.

TABLE 11

Baseline Characteristics by Advanced Heart Failure Classification

|  | n = 2258 | n = 5974 |  |
|---|---|---|---|
| Demographics |  |  |  |
| Age-yr | 64.5 ± 11.6 | 64.5 ± 11.3 | p = 0.75 |
| Sex, Female | 477 (21.1%) | 1272 (21.3%) | p = 0.87 |
| Race |  |  | p <0.001 |
| Asian | 153 (6.8%) | 557 (9.3%) |  |
| Black | 177 (7.8%) | 385 (6.4%) |  |
| Other | 129 (5.7%) | 434 (7.3%) |  |
| White | 1799 (79.7%) | 4598 (77.0%) |  |
| Geographic Region |  |  | p <0.001 |
| Asia | 141 (6.2%) | 529 (8.9%) |  |
| Eastern Europe/Russia | 810 (35.9%) | 1871 (31.3%) |  |
| Latin America | 324 (14.3%) | 1250 (20.9%) |  |
| US And Canada | 434 (19.2%) | 952 (15.9%) |  |

TABLE 11-continued

Baseline Characteristics by Advanced Heart Failure Classification

|  | n = 2258 | n = 5974 |  |
|---|---|---|---|
| Western Europe/South Africa/Australasia | 549 (24.3%) | 1372 (23.0%) |  |
| Randomization Setting: In-patient | 937 (41.5%) | 1147 (19.2%) | p <0.001 |
| Clinical Characteristics |  |  |  |
| Atrial Fibrillation or Flutter at Screening | 717 (31.8%) | 1528 (25.6%) | p <0.001 |
| Hypertension History | 1573 (69.7%) | 4211 (70.5%) | p = 0.46 |
| Type 2 diabetes mellitus | 954 (42.2%) | 2355 (39.4%) | p = 0.020 |
| History of stroke | 240 (10.6%) | 514 (8.6%) | p = 0.004 |
| Ischemic heart failure etiology | 1213 (53.7%) | 3202 (53.6%) | p = 0.92 |
| History of Myocardial Infarction | 960 (42.5%) | 2475 (41.4%) | p = 0.37 |
| LVEF-% | 23.4 ± 5.2 | 27.8 ± 6.2 | p <0.001 |
| NYHA Classification |  |  | p <0.001 |
| Class II | 0 (0.0%) | 4368 (73.1%) |  |
| Class III | 2085 (92.3%) | 1531 (25.6%) |  |
| Class IV | 173 (7.7%) | 75 (1.3%) |  |
| KCCQ Total Symptom Score | 56.2 [36.5, 77.1] | 74.0 [54.2, 90.6] | p <0.001 |
| Outpatient | 63.5 [44.8, 83.3] | 77.1 [58.3, 91.7] | p <0.001 |
| Inpatient | 47.4 [29.2, 66.7] | 57.3 [37.5, 76.0] | p <0.001 |
| SBP-mmHg | 113.8 ± 15.0 | 117.5 ± 15.4 | p <0.001 |
| Heart rate-beats/min | 74.3 ± 12.5 | 71.7 ± 11.9 | p <0.001 |
| NT-proBNP-pg/mL | 2804 [1450, 5795] | 1768 [878, 3521] | p <0.001 |
| Cardiac Troponin I-ng/L | 34 [18, 64] | 25 [11, 47] | p <0.001 |
| eGFR-mUmin/1.73 m$^2$ | 55.1 [41.8, 69.9] | 60.0 [45.4, 75.5] | p <0.001 |
| Heart Failure Therapies |  |  |  |
| ACEi, ARB or ARNi | 1873 (82.9%) | 5286 (88.5%) | p <0.001 |
| ARNi | 447 (19.8%) | 1154 (19.3%) | p = 0.62 |
| BB | 2093 (92.7%) | 5670 (94.9%) | p <0.001 |
| MRA | 1768 (78.3%) | 4629 (77.5%) | p = 0.43 |
| SGLT2 Inhibitors | 50 (2.2%) | 168 (2.8%) | p = 0.13 |
| Ivabradine | 188 (8.3%) | 345 (5.8%) | p <0.001 |
| Digitalis glycosides | 436 (19.3%) | 949 (15.9%) | p <0.001 |
| Cardiac Resynchronization Therapy | 372 (16.5%) | 786 (13.2%) | p <0.001 |
| Implantable Cardioverter Defibrillator | 807 (35.7%) | 1807 (30.2%) | p <0.001 |

LVEF = left ventricular ejection fraction,
NYHA = New York Heart Association,
KCCQ = Kansas City Cardiomyopathy Questionnaire,
SBP = systolic blood pressure,
NT-proBNP = amino-terminal-b-type natriuretic peptide,
eGFR = estimated glomerular filtration rate,
ACEi = angiotensin converting enzyme inhibitor,
ARB = angiotensin receptor blocker,
ARNi = angiotensin receptor neprilysin inhibitor,
BB = beta blocker,
MRA = mineralocorticoid receptor antagonists,
SGLT2 = sodium glucose co-transport-2

As anticipated, patients with more advanced HF had markers of more severe disease, including lower ejection fraction, greater NYHA class, higher NT-proBNP concentrations, lower systolic blood pressure, worse renal function, and worse quality of life as assessed by the KCCQ TSS. Patients with more advanced HF were less likely to be treated with renin-angiotensin-aldosterone system (RAAS) modulators and beta blockers at baseline but more likely to have cardiac resynchronization therapy (CRT) or an implantable cardioverter defibrillator (ICD). Patients with more advanced HF were at significantly higher risk, with event rates for placebo treated patients that were approximately twice those of patients without more advanced HF for the primary endpoint (42.6 events/100 pt-years vs. 21.3), cardiovascular mortality (17.3 events/100 patient-years vs. 8.5), and all-cause mortality (21.7 events/100 pt-years vs. 11.9).

Efficacy and Safety of Omecamtiv Mecarbil in More Advanced Heart Failure

Figure 14A:
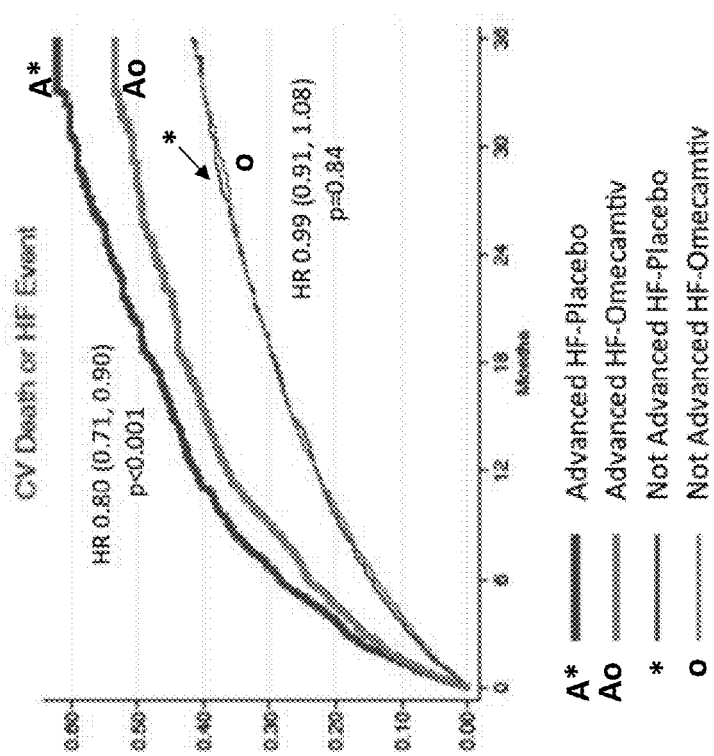
FIG. 14A shows Kaplan-Meier curves comparing patients with and without more advanced heart failure (HF) for each endpoint (CV Death or HF event)
Figure 14B:
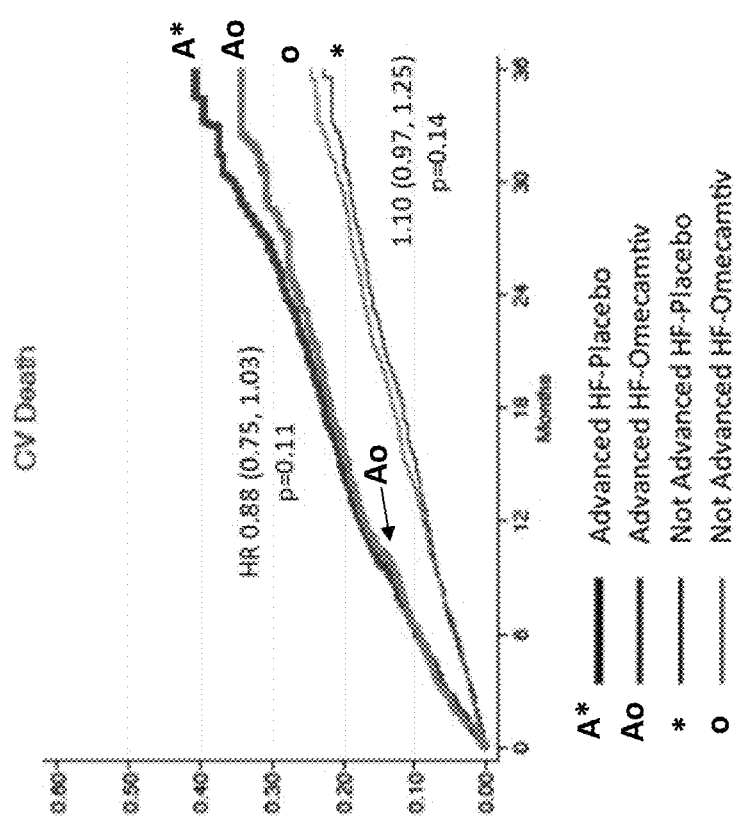
FIG. 14B shows Kaplan-Meier curves comparing patients with and without more advanced heart failure (HF) for each endpoint (CV Death).
Figure 15A:
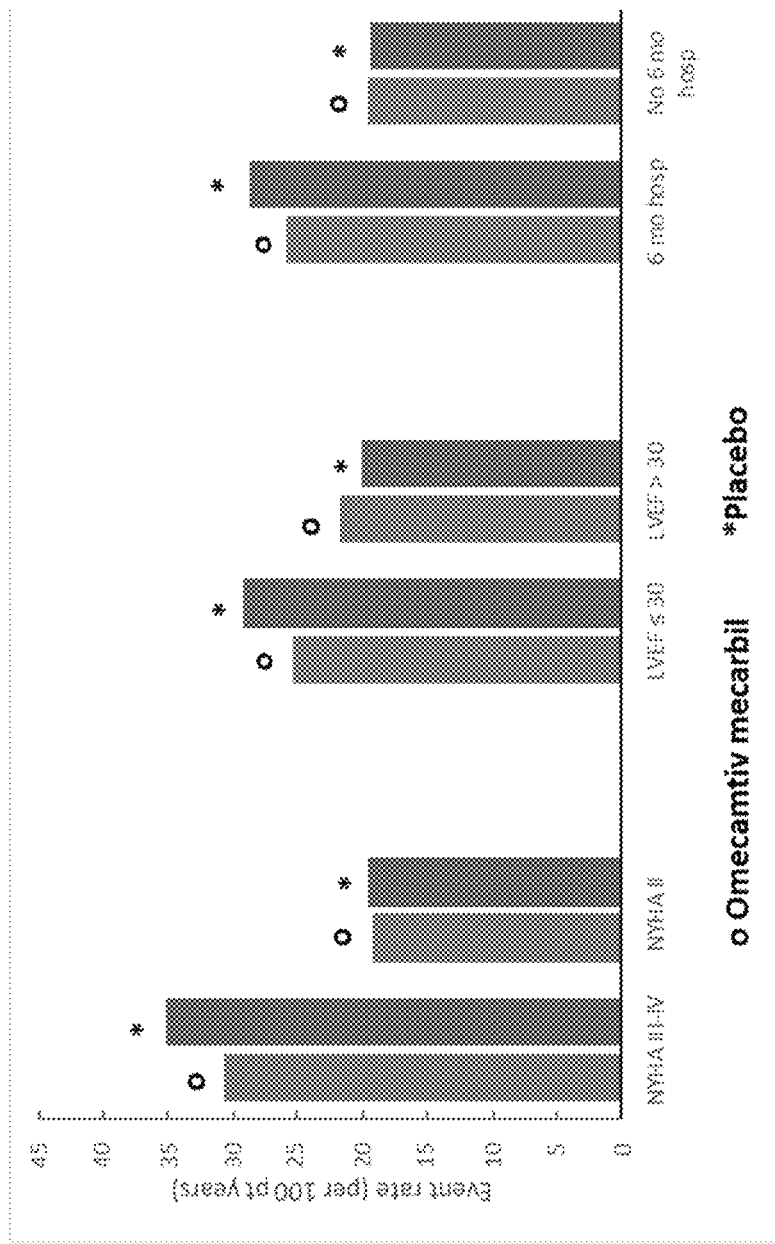
FIG. 15A shows event rates for primary endpoints by treatment assignment and advanced heart failure (HF) criteria met (specific advanced HF criteria).
Figure 15B:
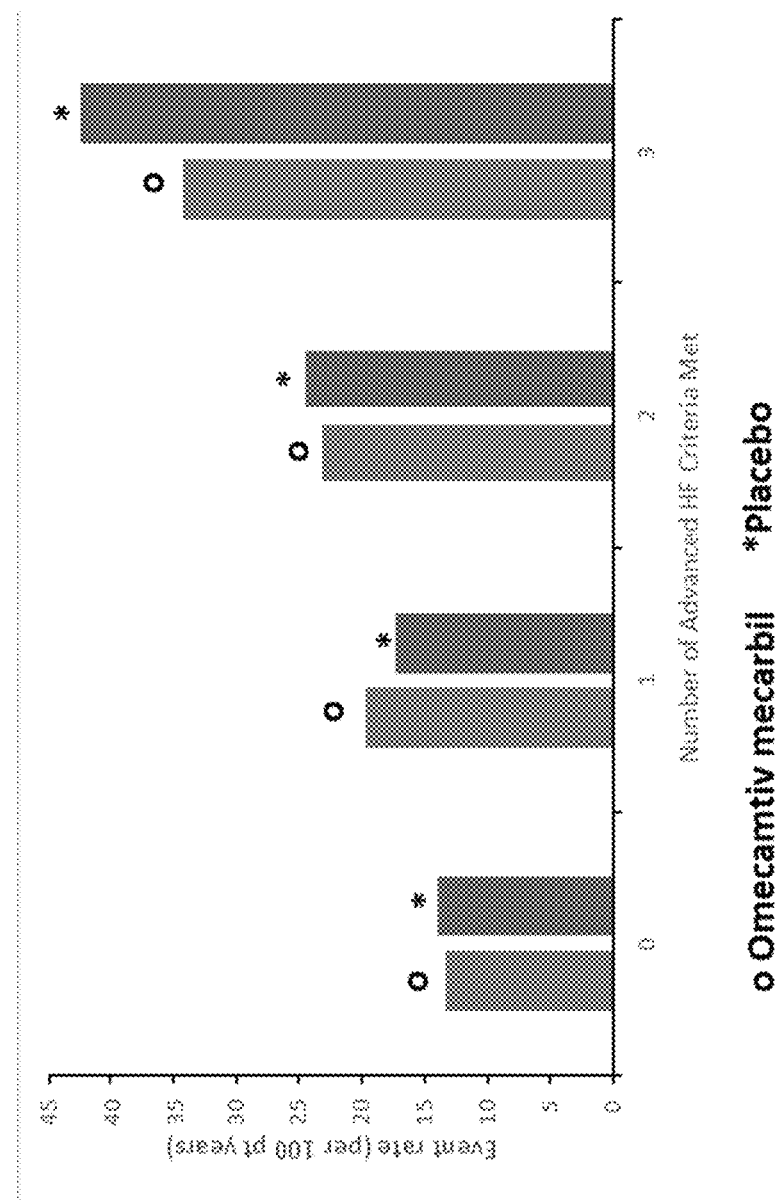
FIG. 15B shows event rates for primary endpoints by treatment assignment and advanced heart failure (HF) criteria met (total number of advanced HF criteria met).
Figure 16A:
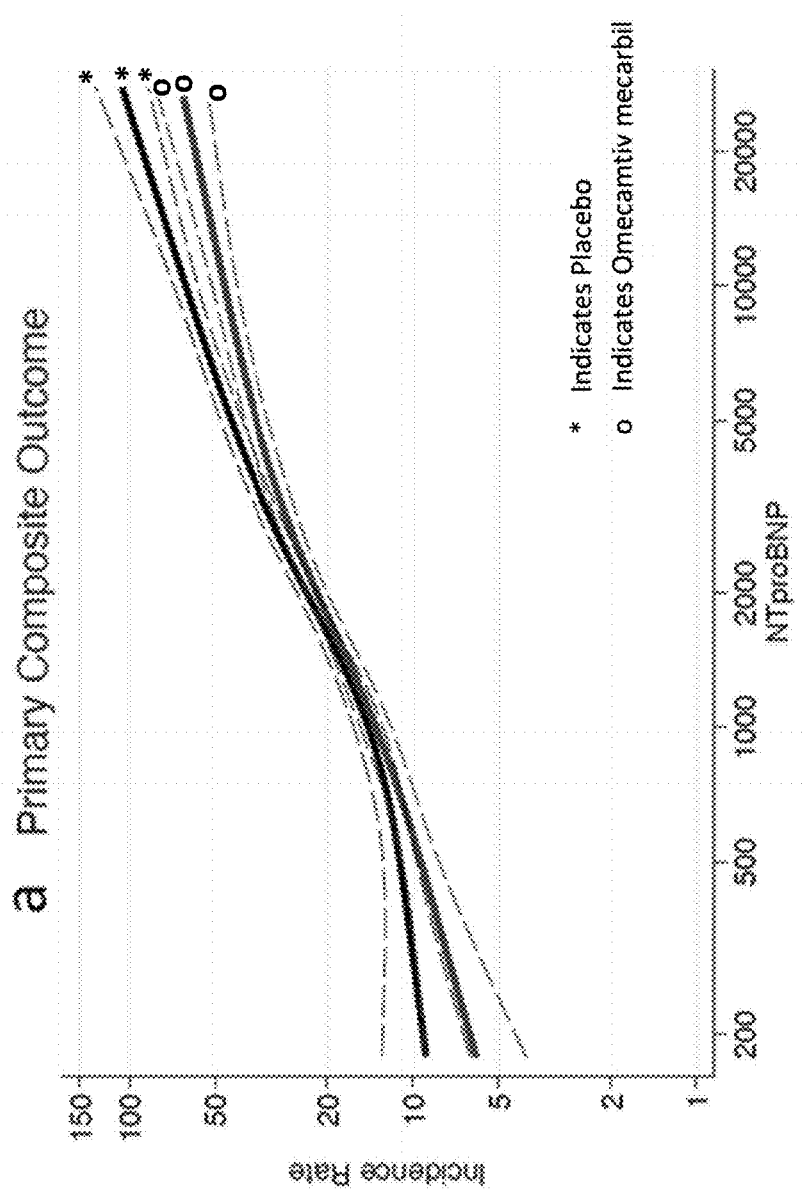
FIG. 16A shows outcomes according to baseline NT-proBNP in the prespecified analysis population (no atrial fibrillation/flutter at baseline) randomized (primary composite outcome) (placebo—stars; omecamtiv mecarbil—circles).
Figure 16B:
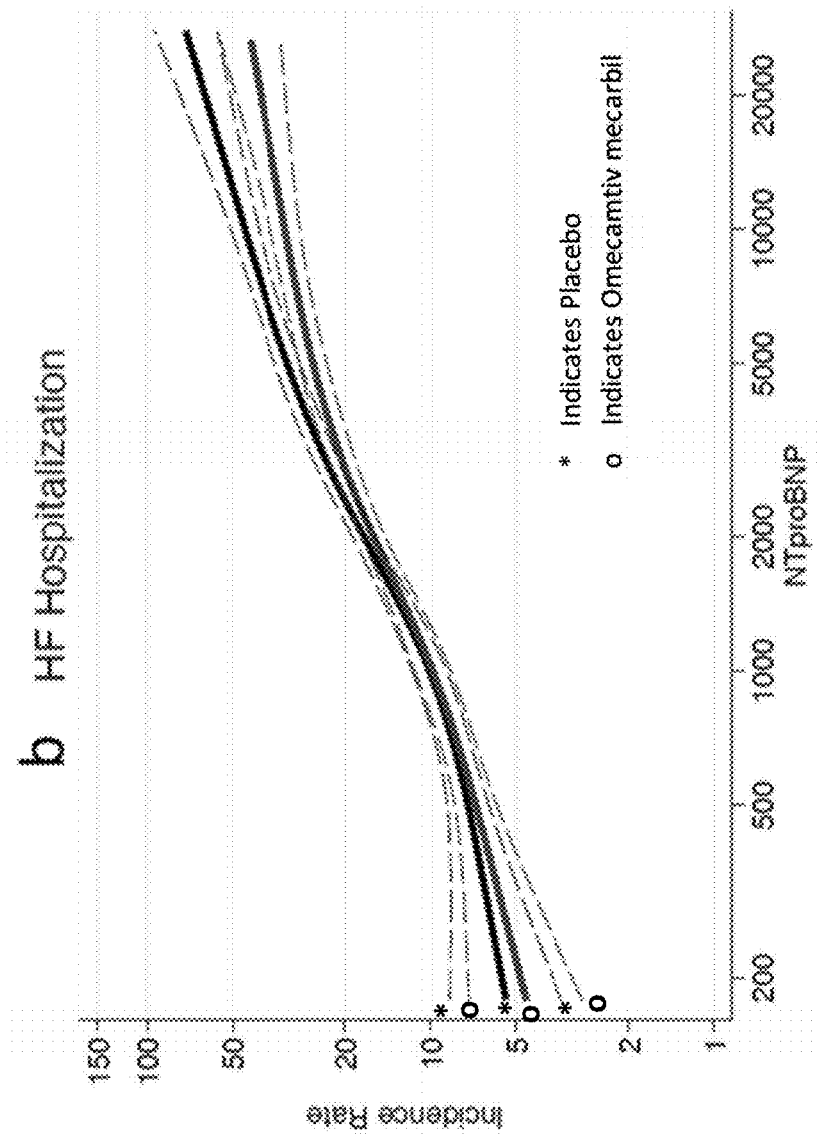
FIG. 16B shows outcomes according to baseline NT-proBNP in the prespecified analysis population (no atrial fibrillation/flutter at baseline) randomized (HF hospitalization) (placebo—stars; omecamtiv mecarbil—circles).
Figure 16C:
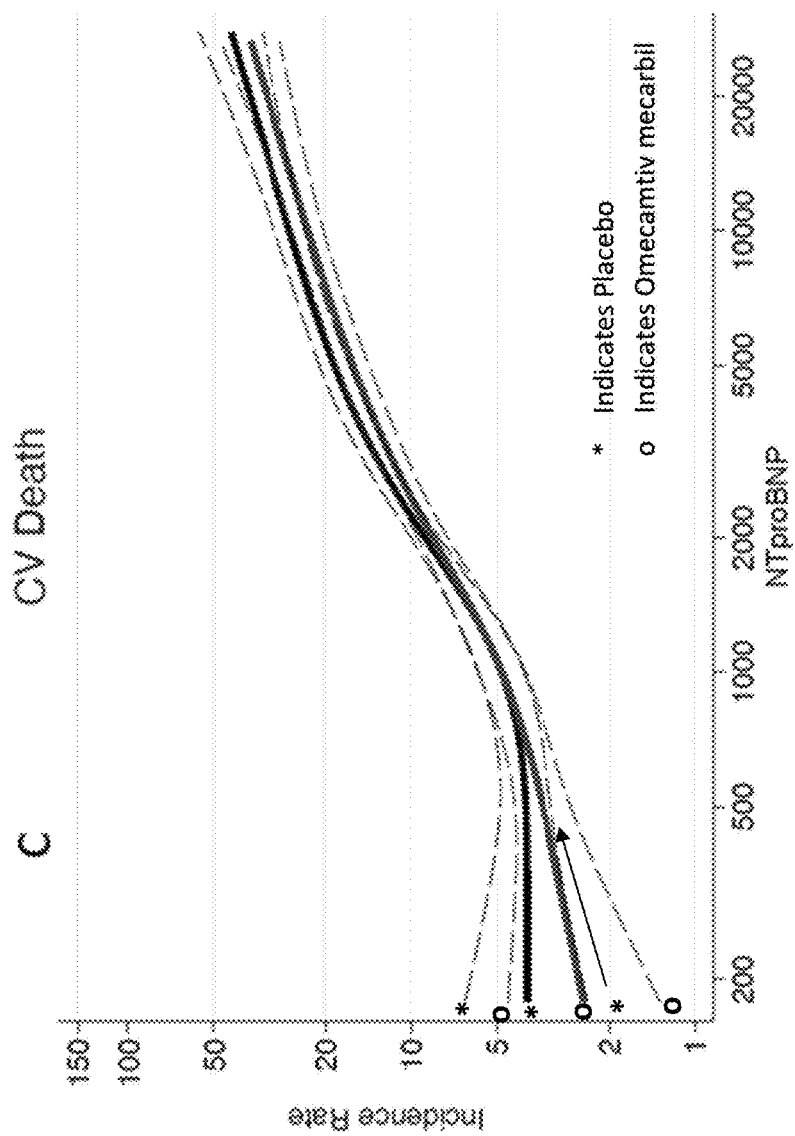
FIG. 16C shows outcomes according to baseline NT-proBNP in the prespecified analysis population (no atrial fibrillation/flutter at baseline) randomized (CV death) (placebo—stars; omecamtiv mecarbil—circles).
Figure 16D:
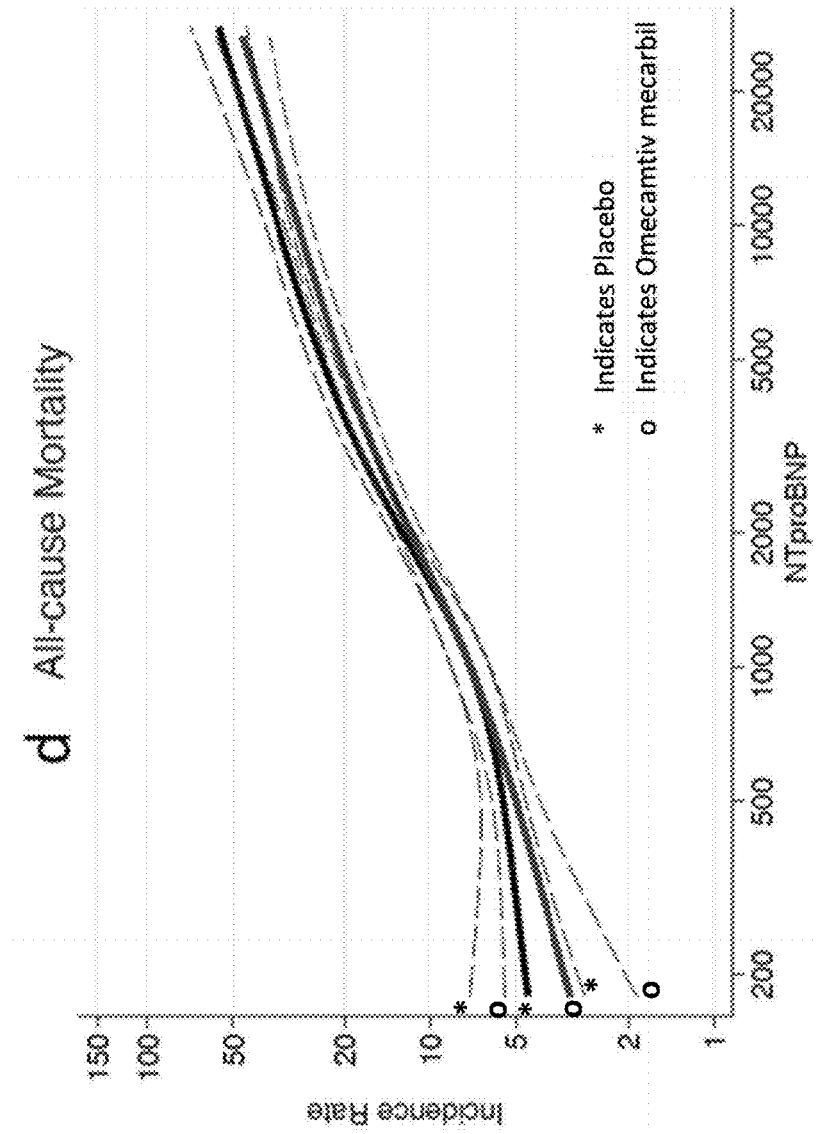
FIG. 16D shows outcomes according to baseline NT-proBNP in the prespecified analysis population (no atrial fibrillation/flutter at baseline) randomized (all-cause mortality) (placebo—stars; omecamtiv mecarbil—circles).
Figure 17A:
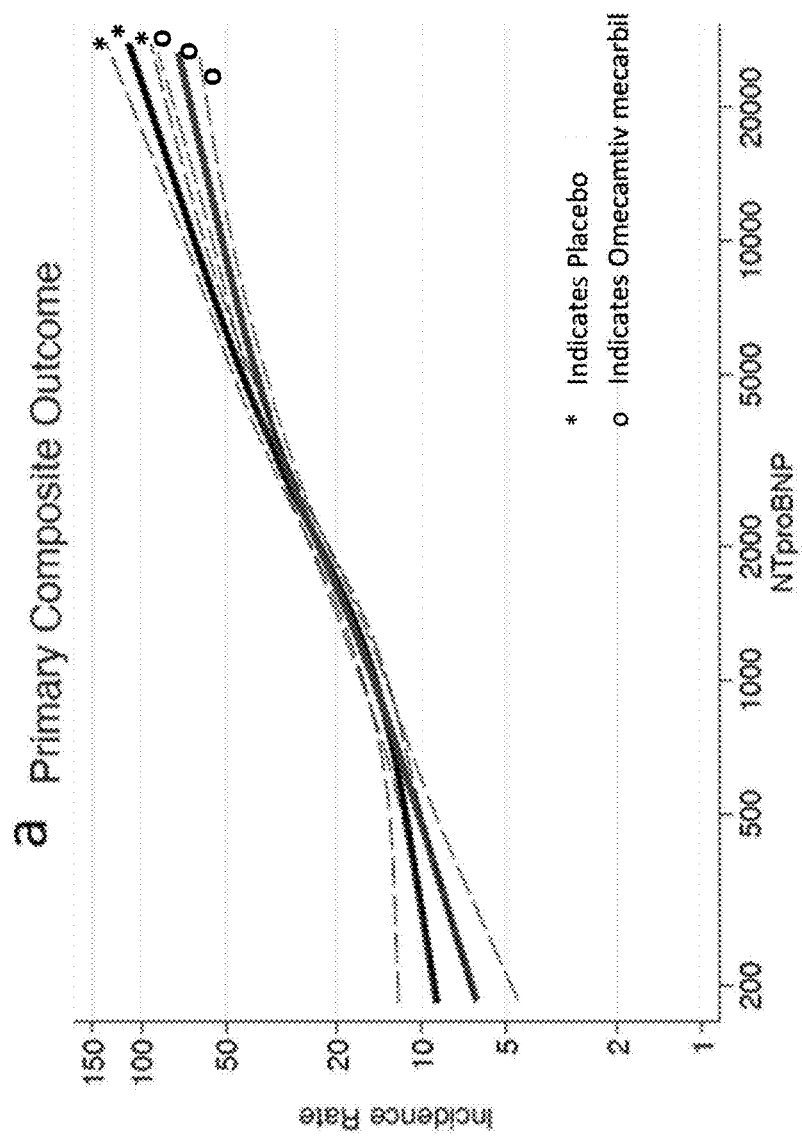
FIG. 17A shows outcomes according to baseline NT-proBNP in the prespecified analysis population in all patients randomized (primary composite outcome) (placebo—stars; omecamtiv mecarbil—circles).
Figure 17B:
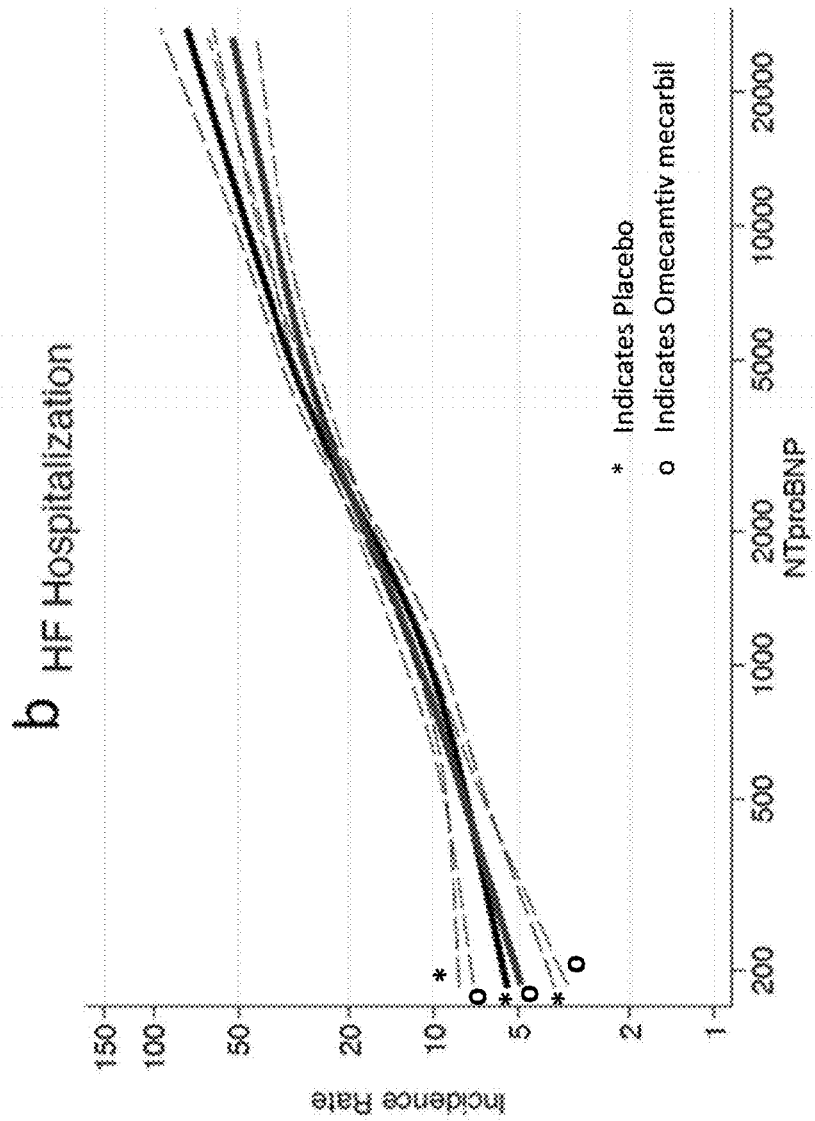
FIG. 17B shows outcomes according to baseline NT-proBNP in the prespecified analysis population in all patients randomized (HF hospitalization) (placebo—stars; omecamtiv mecarbil—circles).
Figure 17C:
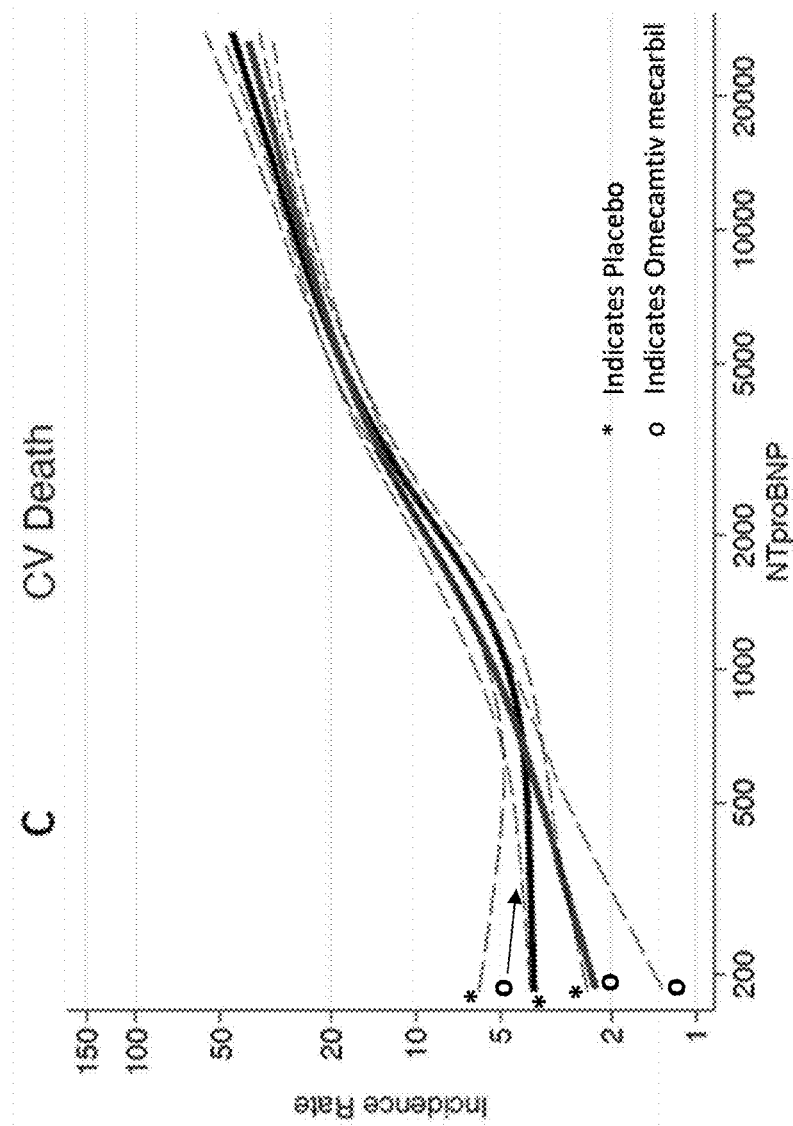
FIG. 17C shows outcomes according to baseline NT-proBNP in the prespecified analysis population in all patients randomized (CV death) (placebo—stars; omecamtiv mecarbil—circles).
Figure 17D:
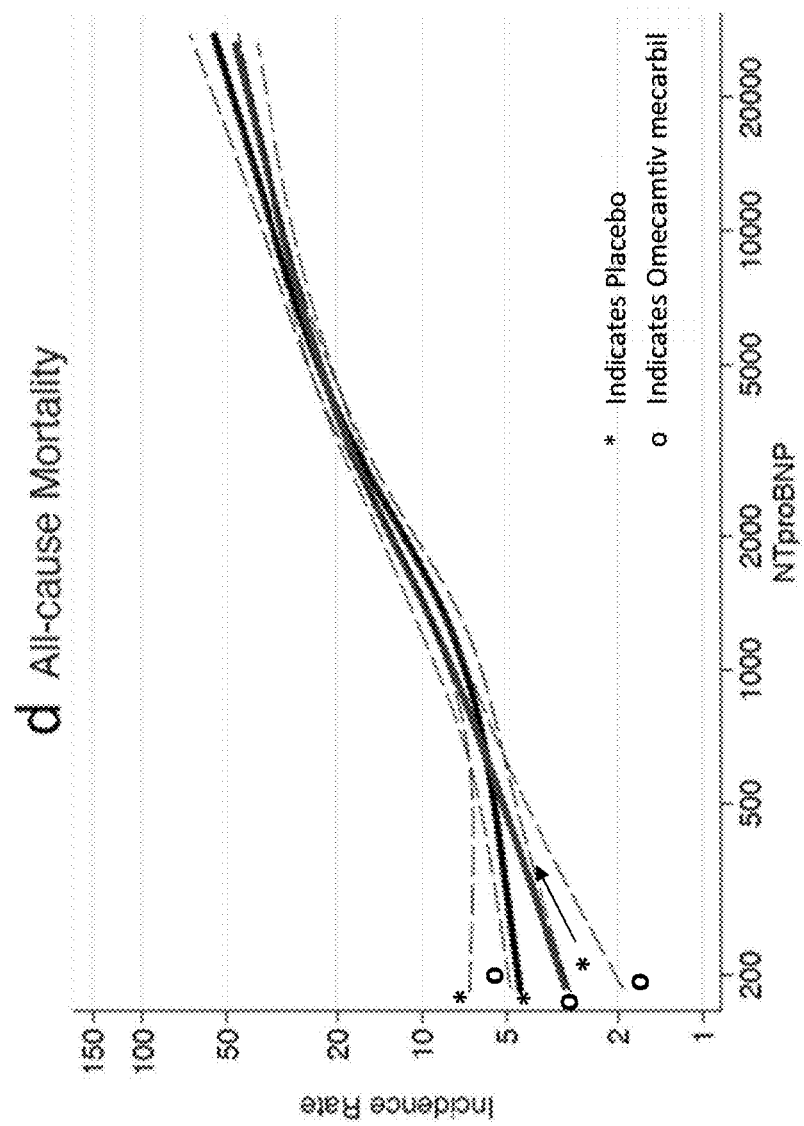
FIG. 17D shows outcomes according to baseline NT-proBNP in the prespecified analysis population in all patients randomized (all-cause mortality) (placebo—stars; omecamtiv mecarbil—circles).
Figure 18A:
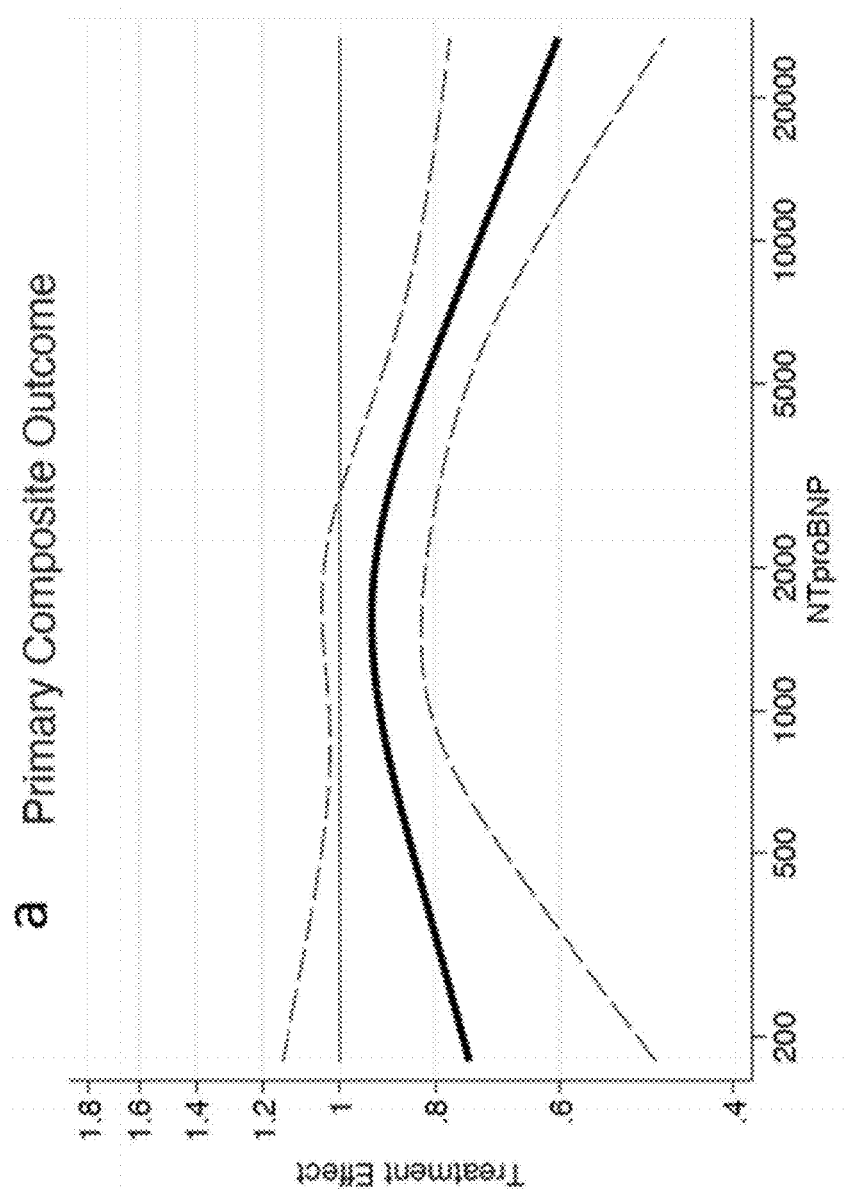
FIG. 18A shows effect of randomized treatment on outcomes according to baseline NT-proBNP concentration (shown as a continuous measure) in the prespecified analysis population (no atrial fibrillation/flutter at baseline) randomized (primary composite outcome).
Figure 18B:
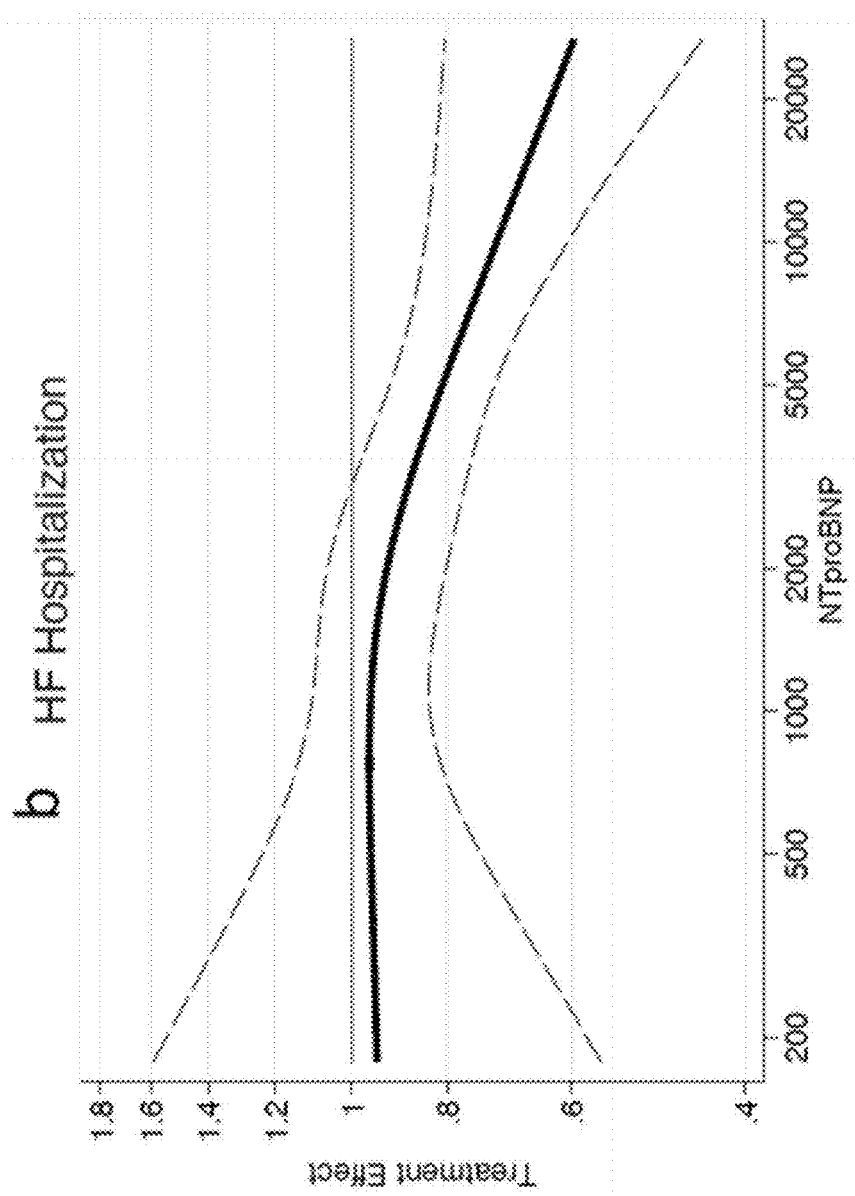
FIG. 18B shows effect of randomized treatment on outcomes according to baseline NT-proBNP concentration (shown as a continuous measure) in the prespecified analysis population (no atrial fibrillation/flutter at baseline) randomized (HF hospitalization).
Figure 18C:
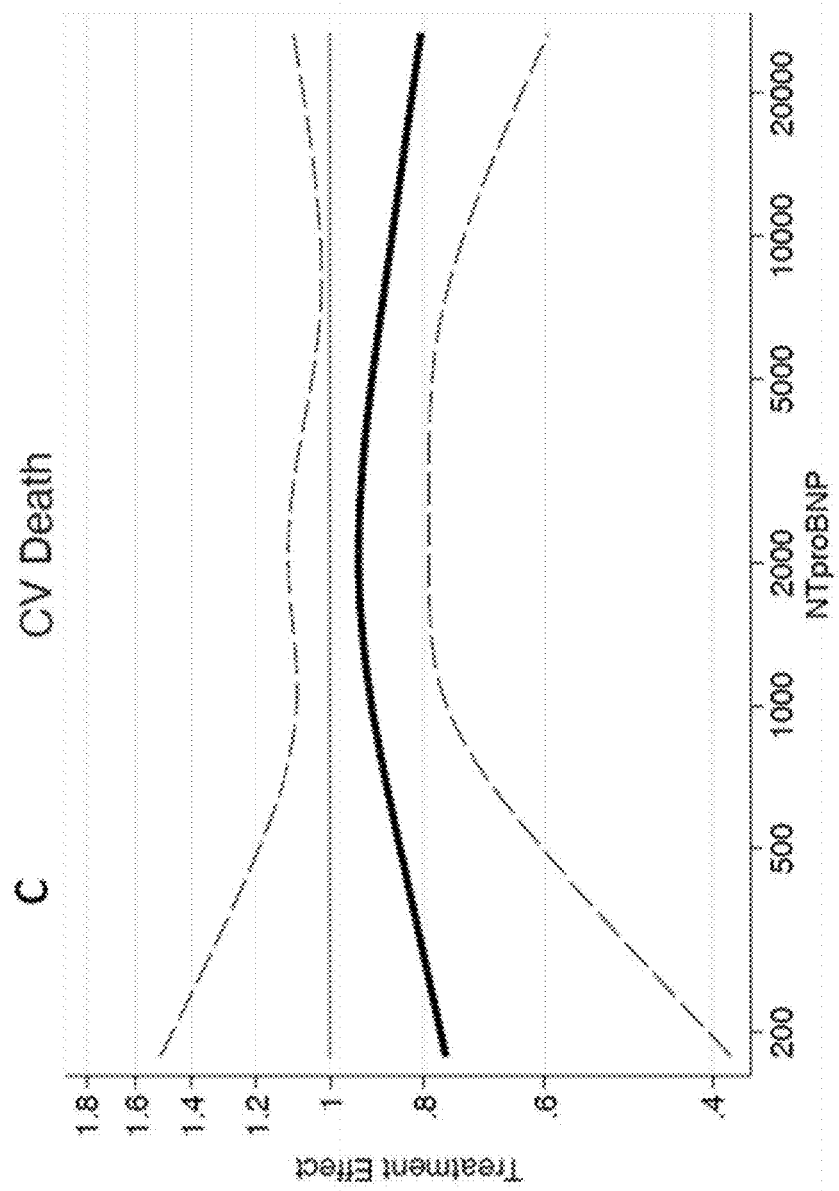
FIG. 18C shows effect of randomized treatment on outcomes according to baseline NT-proBNP concentration (shown as a continuous measure) in the prespecified analysis population (no atrial fibrillation/flutter at baseline) randomized (CV death).
Figure 18D:
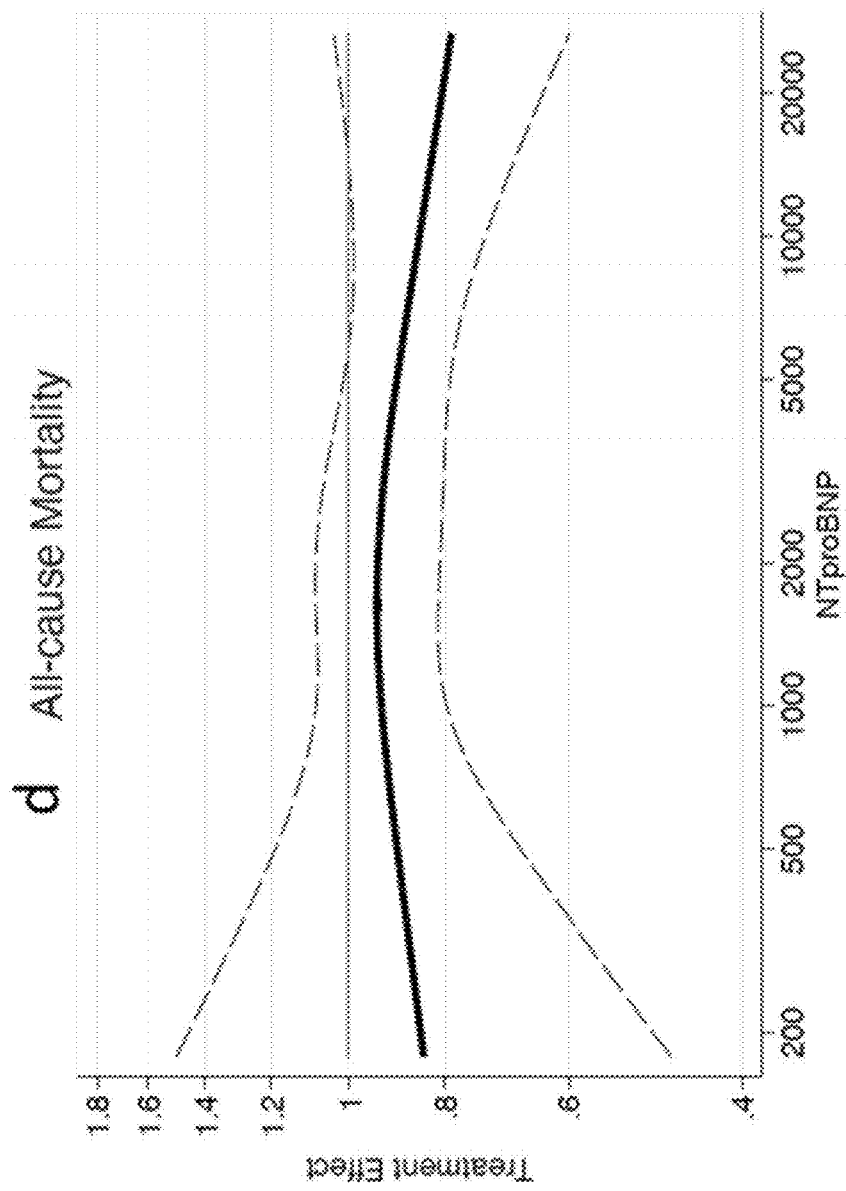
FIG. 18D shows effect of randomized treatment on outcomes according to baseline NT-proBNP concentration (shown as a continuous measure) in the prespecified analysis population (no atrial fibrillation/flutter at baseline) randomized (all cause mortality).
Figure 19A:
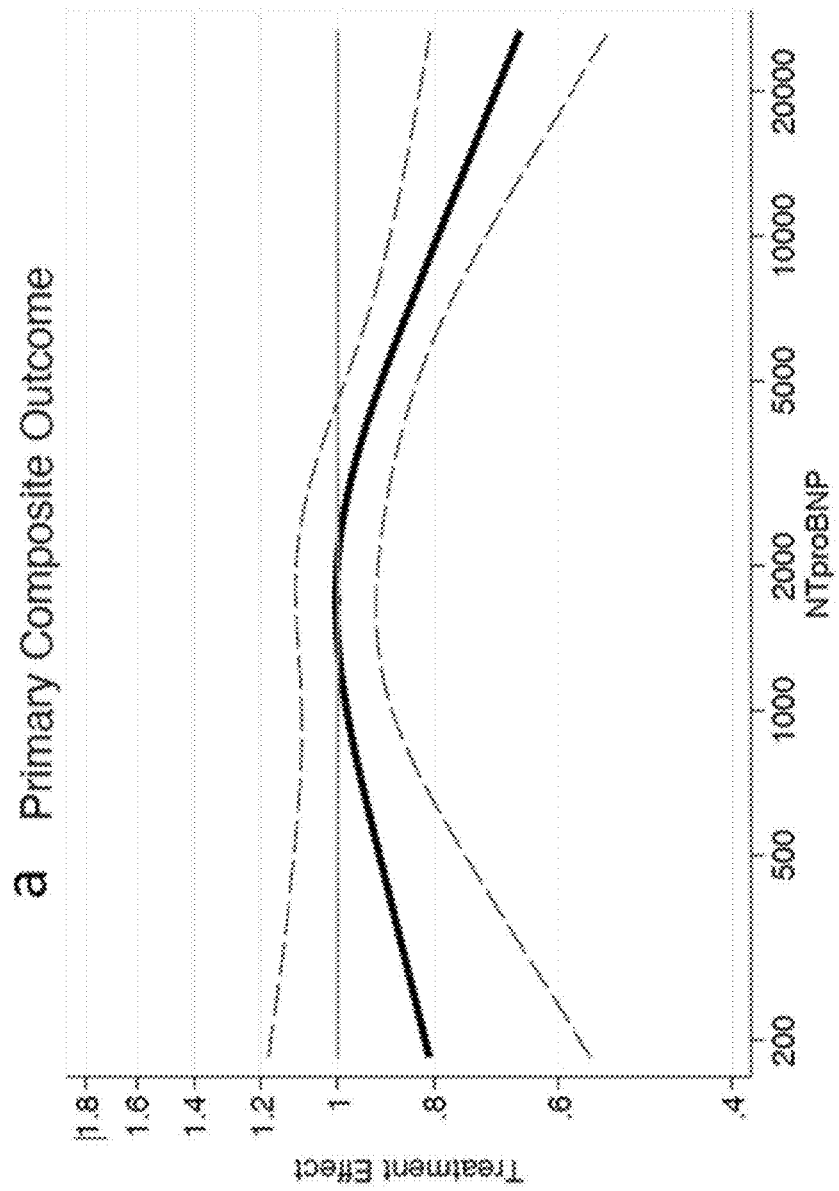
FIG. 19A shows effect of randomized treatment on outcomes according to baseline NT-proBNP concentration (shown as a continuous measure) in the prespecified analysis population in all patients randomized (primary composite outcome).
Figure 19B:
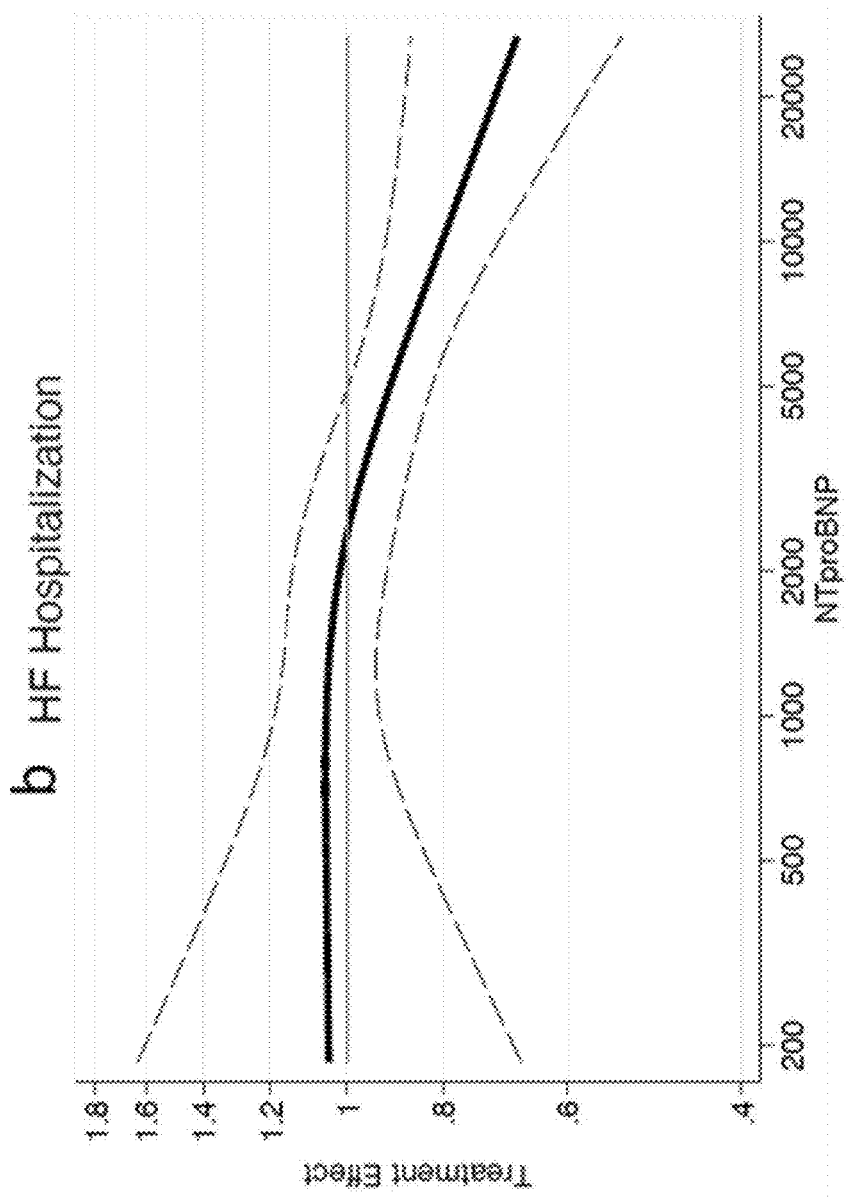
FIG. 19B shows effect of randomized treatment on outcomes according to baseline NT-proBNP concentration (shown as a continuous measure) in the prespecified analysis population in all patients randomized (HF hospitalization).
Figure 19C:
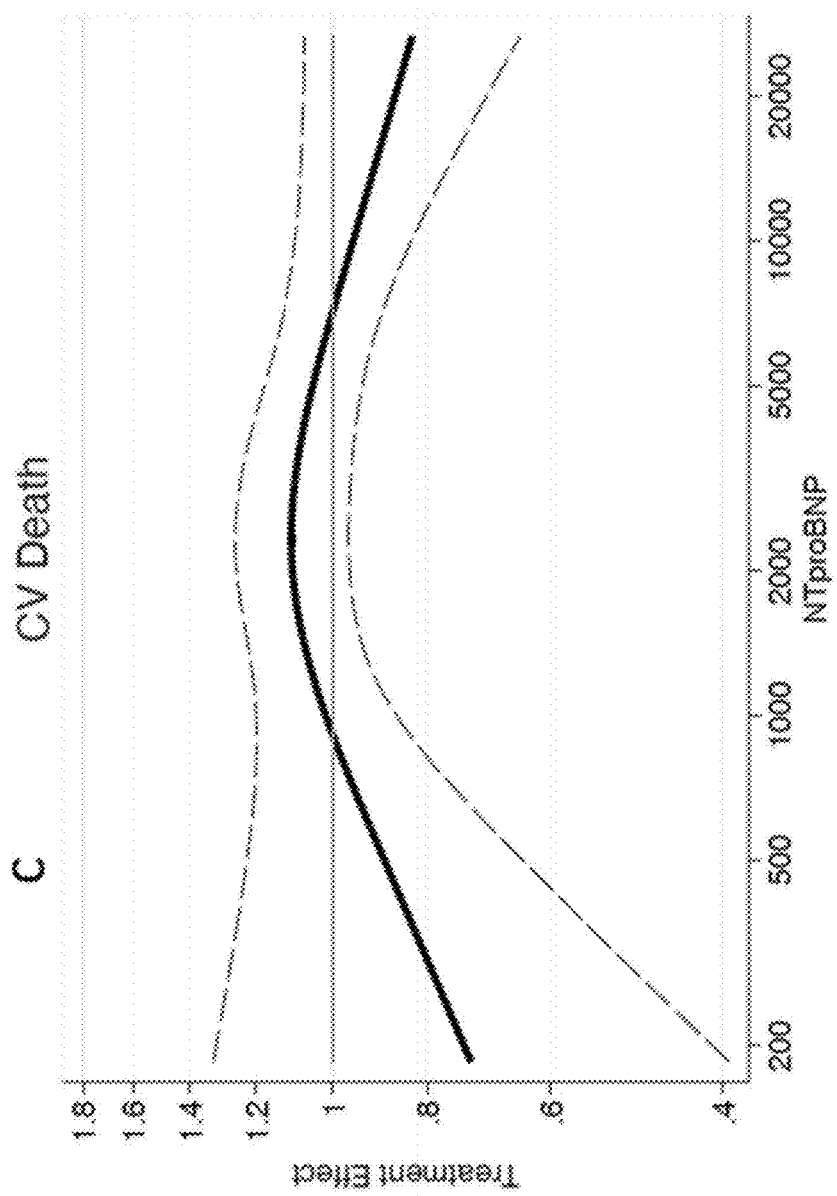
FIG. 19C shows effect of randomized treatment on outcomes according to baseline NT-proBNP concentration (shown as a continuous measure) in the prespecified analysis population in all patients randomized (CV death).
Figure 19D:
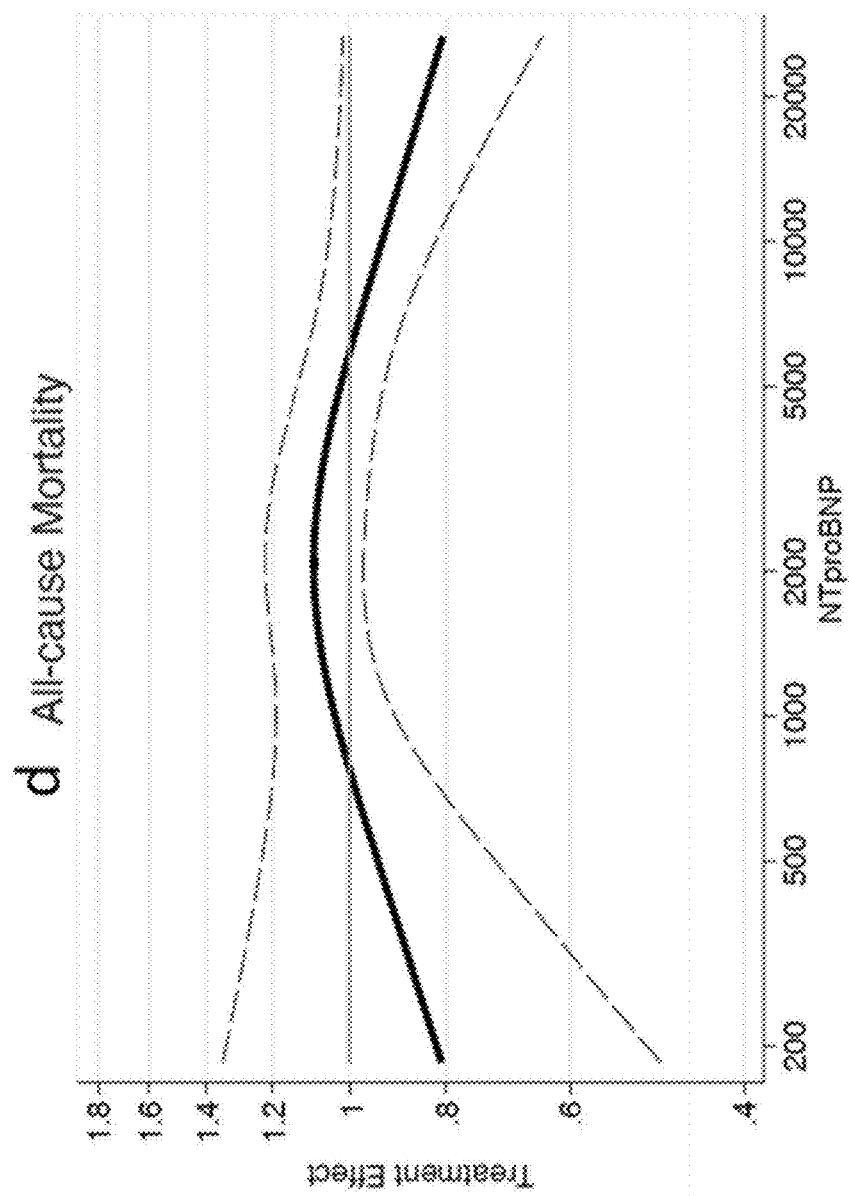
FIG. 19D shows effect of randomized treatment on outcomes according to baseline NT-proBNP concentration (shown as a continuous measure) in the prespecified analysis population in all patients randomized (all cause mortality).
Figure 20A:
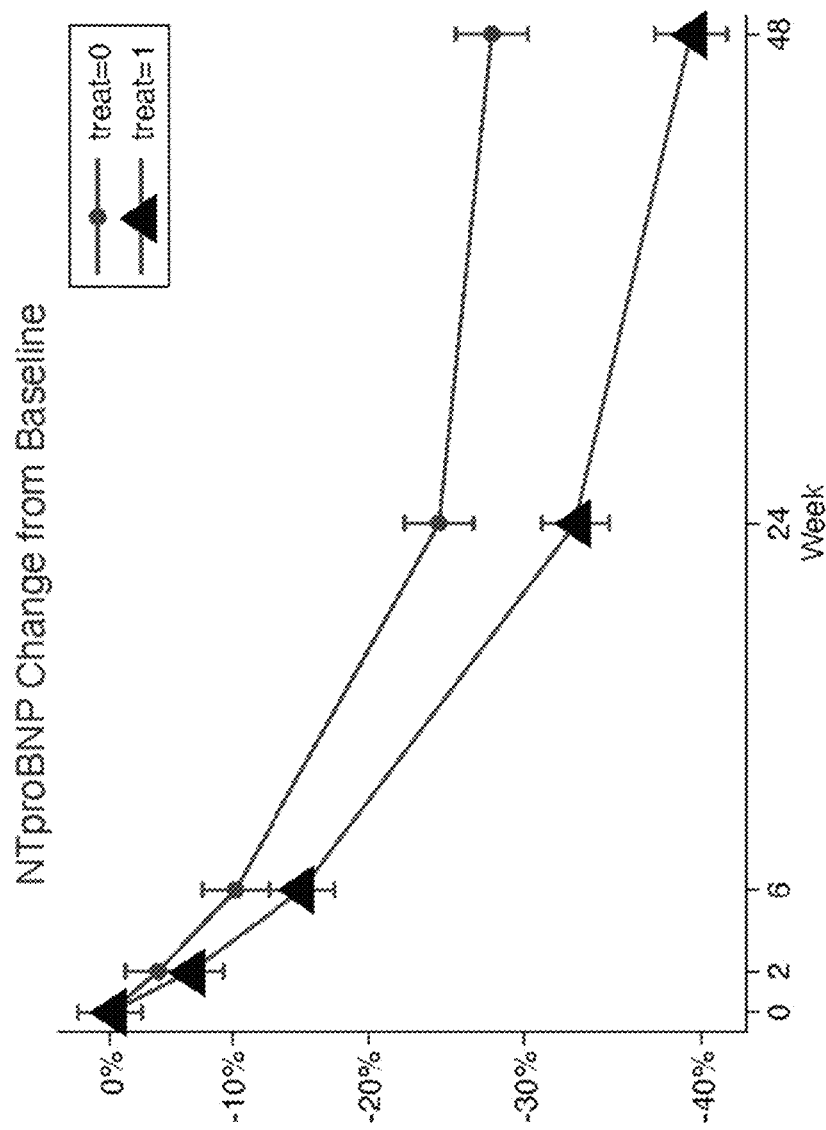
FIG. 20A shows effect of omecamtiv mecarbil, compared with placebo, on NT-proBNP after randomization in the prespecified analysis population (no atrial fibrillation/flutter at baseline and all NT-proBNP concentrations).
Figure 20B:
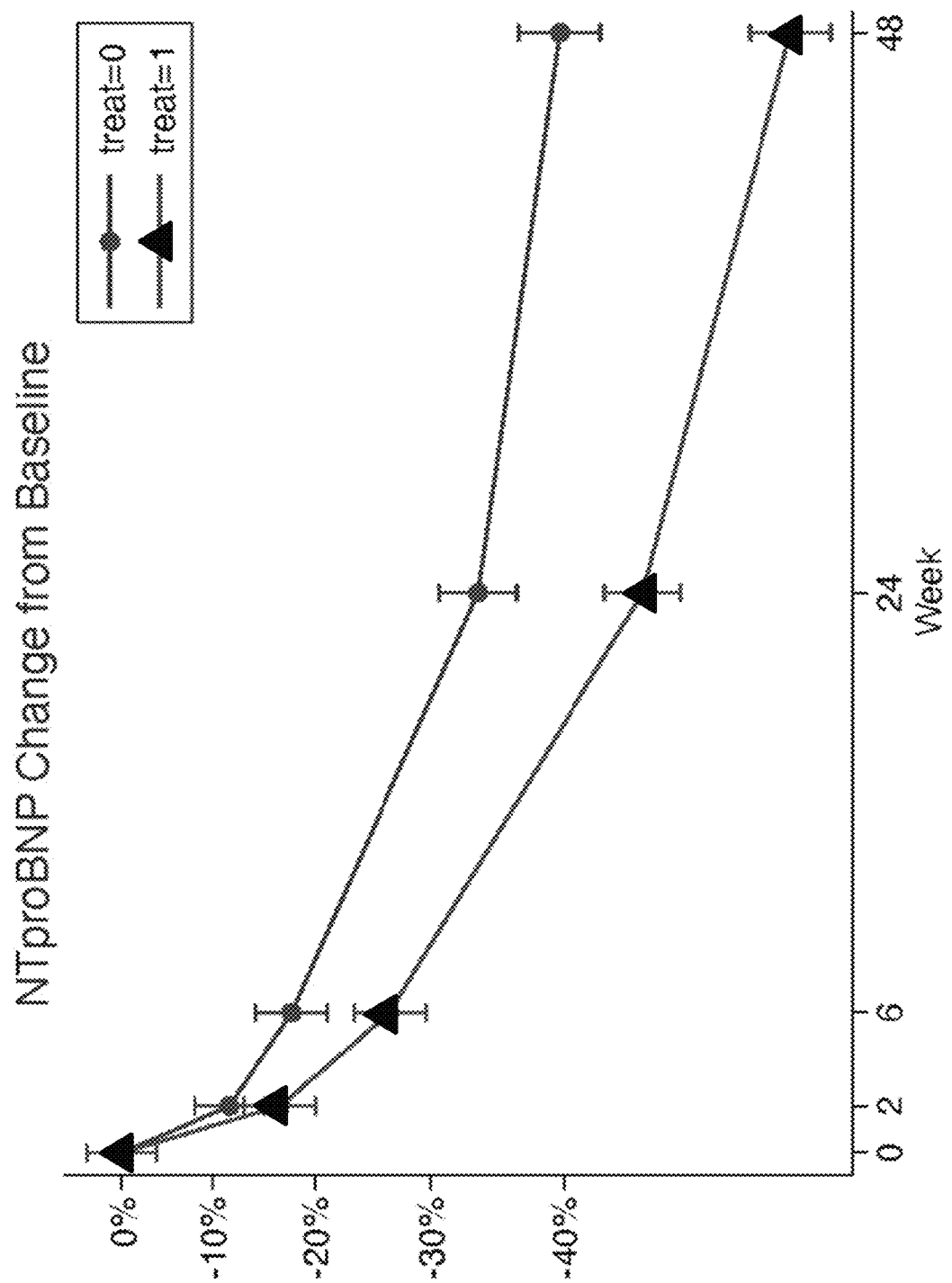
FIG. 20B shows effect of omecamtiv mecarbil, compared with placebo, on NT-proBNP after randomization in the prespecified analysis population (no atrial fibrillation/flutter at baseline, NT-proBNP>median).
Figure 20C:
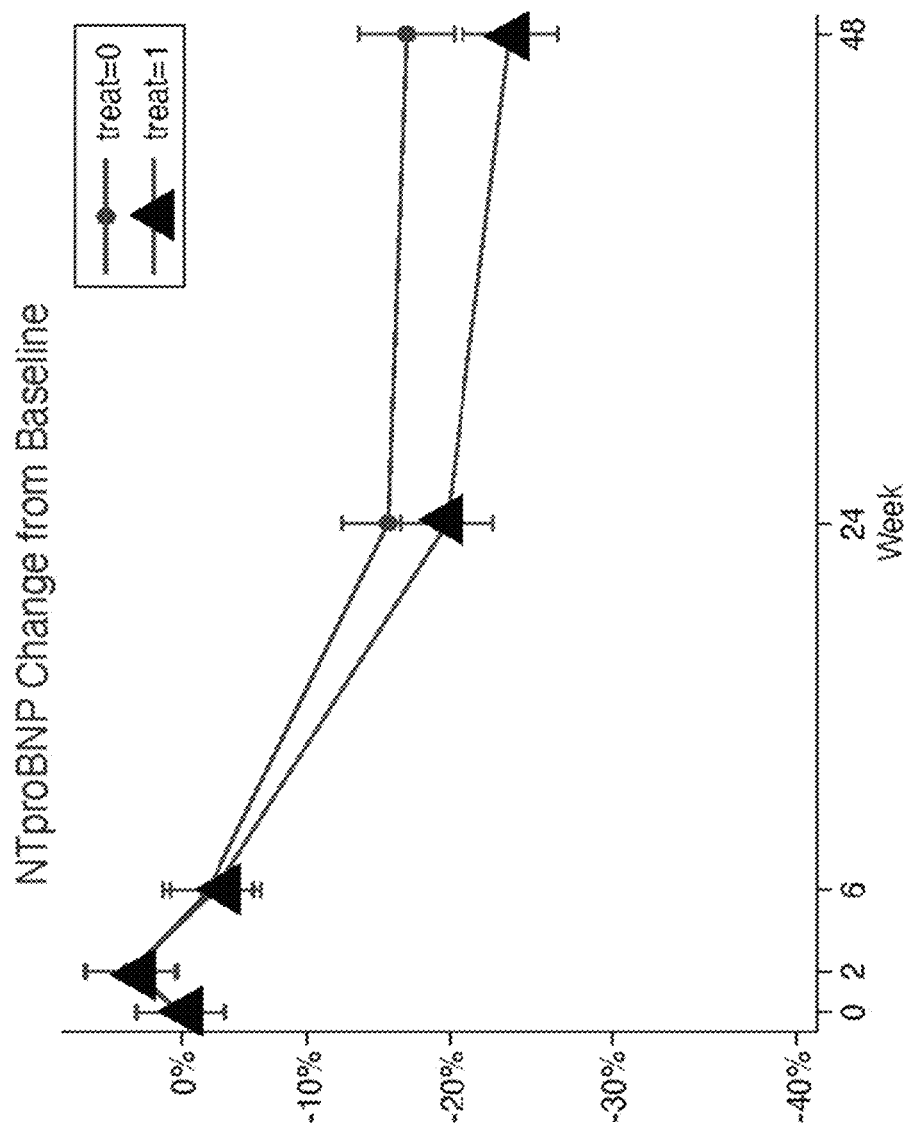
FIG. 20C shows effect of omecamtiv mecarbil, compared with placebo, on NT-proBNP after randomization in the prespecified analysis population (no atrial fibrillation/flutter at baseline, NT-proBNP≤median).
Figure 20D:
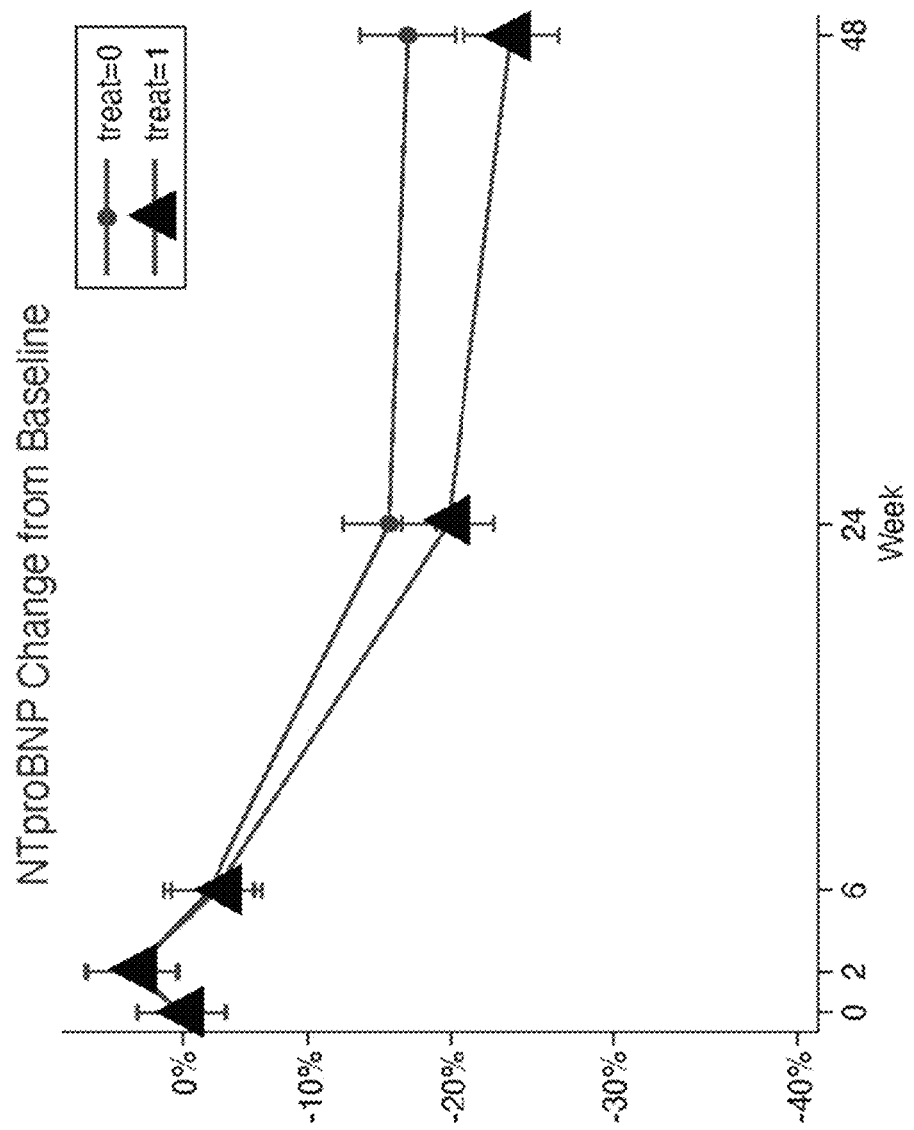
FIG. 20D shows effect of omecamtiv mecarbil, compared with placebo, on NT-proBNP in all patients randomized (all NT-proBNP concentrations).
Figure 20E:
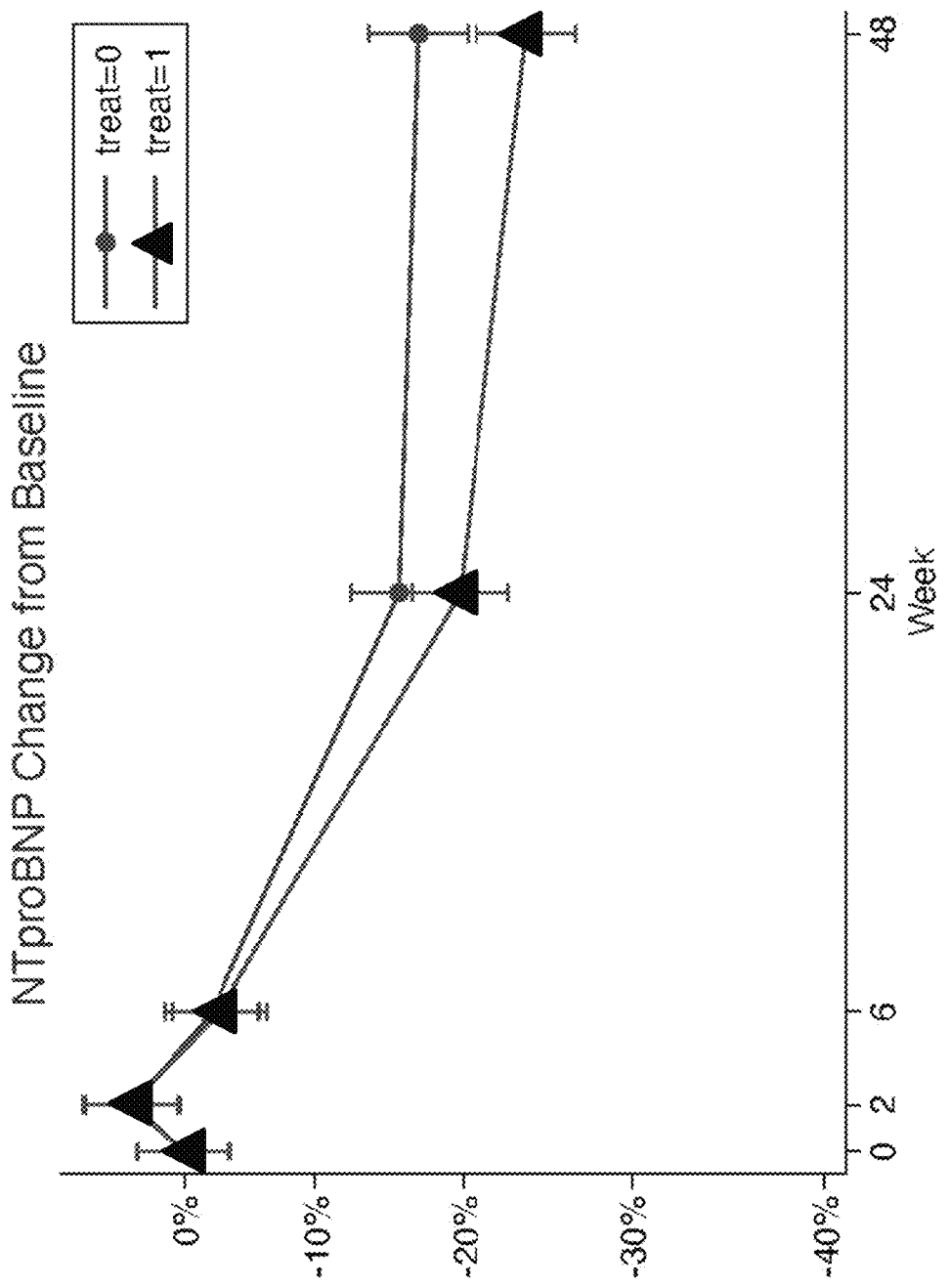
FIG. 20E shows effect of omecamtiv mecarbil, compared with placebo, on NT-proBNP in all patients randomized (NT-proBNP>median).
Figure 20F:
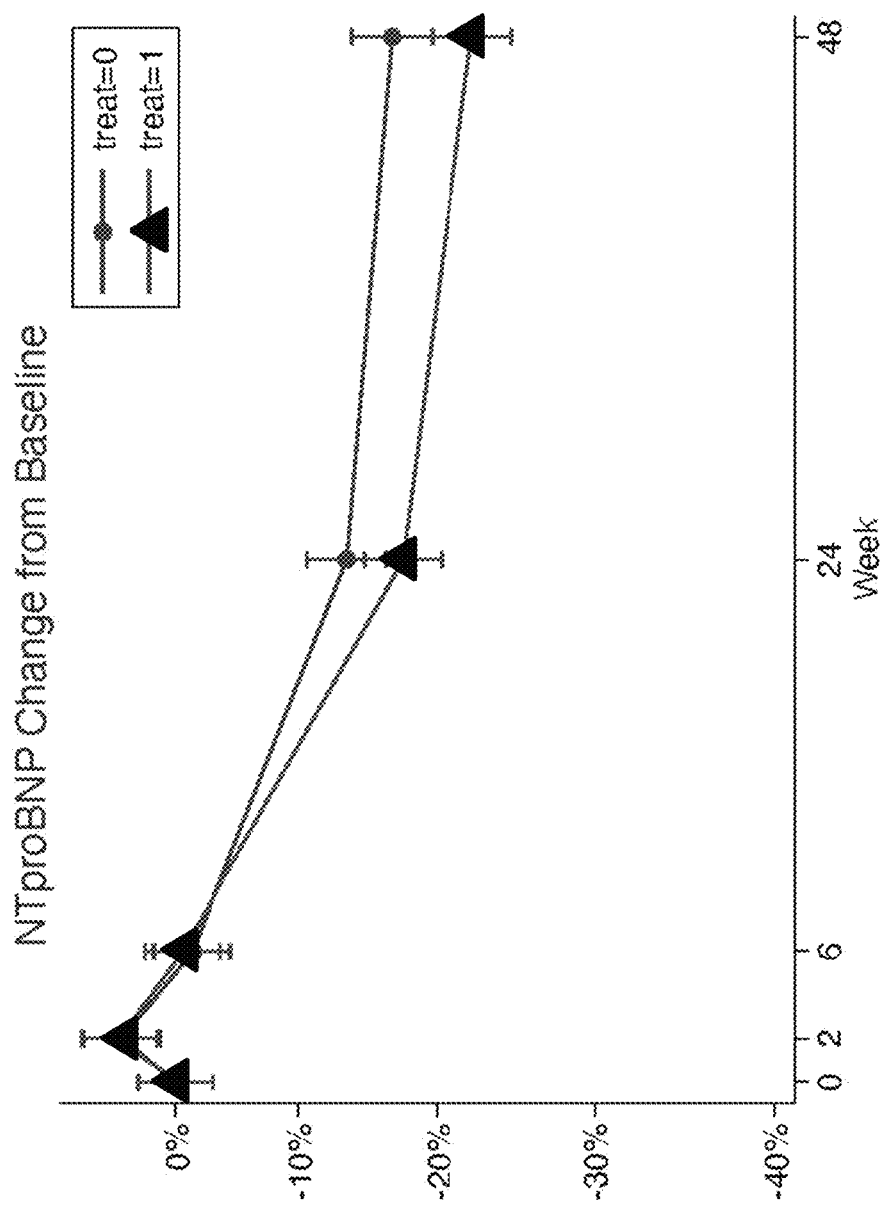
FIG. 20F shows effect of omecamtiv mecarbil, compared with placebo, on NT-proBNP in all patients randomized (NT-proBNP≤median).

Patients classified as more advanced HF had a greater treatment benefit from omecamtiv mecarbil treatment than those without more advanced HF. For the primary endpoint, patients with more advanced HF had a 20% risk reduction (HR=0.80, 95% CI 0.71 to 0.90), whereas patients without more advanced HF had no significant treatment effect (HR=0.99. 95% CI 0.91 to 1.08, p value for interaction=0.005). These results were similar for cardiovascular mortality (patients with more advanced HF (HR=0.88, 95% CI 0.75 to 0.1.03) compared to patients with less advanced HF (HR=1.10, 95% CI 0.97 to 1.25, p value for interaction=0.028)). Kaplan-Meier curves comparing patients with and without more advanced HF for each of these endpoints are shown in FIGS. 14A and 14B. As an additional sensitivity analysis, the event rate and treatment effect of omecamtiv mecarbil was assessed based on which and how many advanced heart HF criteria were met (FIGS. 15A and 15B). The observed benefits of omecamtiv mecarbil were greatest in patients meeting all 3 advanced HF criteria, which were also the group with the highest overall risk. The combination of a 20% relative risk reduction in the primary endpoint in the context of high baseline risk translated to an absolute risk reduction of 8.3 events/100 patient-years (NNT=12). These results were broadly consistent across a variety of other secondary outcomes from the GALACTIC-HF trial, as shown in Table 12. For the KCCQ, we did not identify a differential effect on the total symptom score (TSS) by advanced HF status (advanced HF inpatient 1.1 increase and outpatient 1.7 decrease in TSS, compared to non-advanced HF (inpatient 3.3 increase, outpatient 0.2 decrease in TSS, p for interaction=0.09).

Safety data for omecamtiv mecarbil vs. placebo by advanced HF category are summarized in Table 13.

TABLE 12

Event Rates by Treatment Assignment and Advanced HF classification

|  | n/N | Rate[1] | n/N | Rate[1] | HR (95% CI); p-value | ARR[1] |
|---|---|---|---|---|---|---|
| More Advanced Heart Failure | | | | | | |
| Primary Endpoint | 510/1106 (46%) | 34.3 | 611/1152 (53%) | 42.6 | 0.80 (0.71, 0.90); p < 0.001 | 8.3 |
| CV Death as 1st Primary Event | 107/1106 (10%) | 7.2 | 142/1152 (12%) | 9.9 | | |
| HF Hosp as 1st Primary Event | 385/1106 (35%) | 25.9 | 441/1152 (38%) | 30.8 | | |
| Urgent Outpatient Visit as 1st Primary Event | 18/1106 (2%) | 1.2 | 28/1152 (2%) | 2.0 | | |
| CV Death | 288/1106 (26%) | 15.5 | 332/1152 (29%) | 17.3 | 0.8 (0.75, 1.03); p = 0.11 | 1.8 |
| Heart Failure Hospitalization | 385/1081 (36%) | 26.2 | 450/1136 (40%) | 31.4 | 0.84 (0.73, 0.96); p = 0.013 | 5.2 |
| All-cause Death | 365/1081 (34%) | 20.1 | 409/1136 (36%) | 21.6 | 0.92 (0.80, 1.06); p = 0.26 | 1.5 |
| Less Advanced Heart Failure | | | | | | |
| Primary Outcome | 1013/3014 (34%) | 21.1 | 996/2960 (34%) | 21.3 | 0.99 (0.91, 1.08); p = 0.84 | 0.2 |
| CV Death as 1st Primary Event | 239/3014 (8%) | 5.0 | 229/2960 (8%) | 4.9 | | |
| HF Hosp as 1st Primary Event | 722/3014 (24%) | 15.0 | 692/2960 (23%) | 14.8 | | |
| Urgent Outpatient Visit as 1st Primary Event | 52/3014 (2%) | 1.1 | 75/2960 (3%) | 1.6 | | |
| CV Death | 520/3014 (17%) | 9.3 | 466/2960 (16%) | 8.5 | 1.10 (0.97, 1.25); p = 0.14 | −0.8 |
| Heart Failure Hospitalization | 746/3014 (25%) | 15.4 | 724/2960 (24%) | 15.3 | 1.01 (0.91, 1.12); p = 0.88 | −0.1 |
| All-cause Death | 692/3014 (23%) | 12.4 | 649/2960 (22%) | 11.9 | 1.05 (0.94, 1.17); p = 037 | 0.6 |

CV = cardiovascular,
HF = heart failure,
HR = hazard ratio
CI = confidence interval,
ARR = absolute risk reduction
[1]per 100 patient years;
ARR = absolute risk reduction

TABLE 13

Safety by Treatment Status and Advanced HF Classification

| Advanced Heart Failure | n = 1079 | n = 1132 | | |
|---|---|---|---|---|
| Any treatment-emergent serious adverse event | 742 (67.3%) | 790 (68.8%) | p = 0.43 | 0.98 (0.92, 1.03) |
| AE: ventricular tachyarrhythmia | 80 (8.0%) | 86 (8.1%) | p = 0.89 | 0.98 (0.73, 1.31) |
| Positively Adjudicated MI | 42 (3.8%) | 29 (2.5%) | p = 0.08 | 1.51 (0.95, 2.40) |
| First Stroke | 18 (1.6%) | 31 (2.7%) | p = 0.08 | 0.60 (0.34, 1.07) |
| Not Advanced HeartFailure | n = 2959 | n = 2920 | | |
| Any treatment-emergent serious adverse event | 1631 (54.2%) | 1645 (55.7%) | p = 0.26 | 0.97 (0.93, 1.02) |
| AE: ventricular tachyarrhythmia | 210 (7.9%) | 218 (8.4%) | p = 0.58 | 0.95 (0.79, 1.14) |
| Positively Adjudicated MI | 80 (2.7%) | 89 (3.0%) | p = 0.41 | 0.88 (0.66, 1.19) |
| First Stroke | 58 (1.9%) | 81 (2.7%) | p = 0.037 | 0.70 (0.50, 0.98) |

SAE = serious adverse event,
AE = adverse event,
MI = myocardial infarction

Patients with more advanced HF were more likely to have treatment emergent serious adverse events than patients without, but these were similar between omecamtiv mecarbil treated patients (67%) and placebo (69%). There were no significant differences in serious adverse events related to ventricular tachyarrhythmias between omecamtiv mecarbil and placebo in the more advanced HF patients (7.9% for omecamtiv vs. 8.1% for placebo). In more advanced HF patients, there were numerically more myocardial infarctions with omecamtiv mecarbil compared to placebo (3.8% vs. 2.5% %, p=0.08) but fewer strokes (1.6% vs. 2.7%, p=0.08). Data on tolerability and changes in biomarkers are shown in Table 4. As in the overall trial, treatment with omecamtiv mecarbil in patients with more advanced HF did not lead to changes in blood pressure, worsening of renal function, or worsening of potassium compared to placebo. Heart rate was modestly lowered with omecamtiv mecarbil compared to placebo (1.9 beats/minute difference in change from 0 to 24 weeks, p<0.001 for omecamtiv mecarbil vs. placebo). In the more advanced HF population, treatment with omecamtiv mecarbil was associated with a significant decrease in NT-proBNP and a small increase in circulating cardiac troponin (Table 14).

TABLE 14

Tolerability by Treatment and Advanced HF status

|  | OM | Placebo | OM | Placebo | Ratio or Difference | p-value |
|---|---|---|---|---|---|---|
| Advanced HF |  |  |  |  |  |  |
| Systolic BP (mm Hg) week 0 to 24 (n = 1849) | 114.0 ± 15.3 | 113.5 ± 14.7 | 116.7 ± 17.3 | 116.0 ± 17.7 | 0.6 (−0.7, 2.0) | p = 0.35 |
| Heart rate (beats/min) week 0 to 24 (n = 1850) | 74.5 ± 12.7 | 74.1 ± 12.3 | 71.2 ± 12.3 | 73.0 ± 12.8 | −1.9 (−2.9, −0.8) | p < 0.001 |
| Potassium (mmol/L) week 0 to 24 (n = 1761) | 4.53 ± 0.57 | 4.56 ± 0.56 | 4.52 ± 0.57 | 4.56 ± 0.58 | −0.03 (−0.08, 0.02) | p = 0.27 |
| Creatinine (mg/dl) week 0 to 24 (n = 1787) | 1.39 ± 0.50 | 1.36 ± 0.48 | 1.37 ± 0.55 | 1.38 ± 0.56 | −0.01 (−0.04, 0.02) | p = 0.53 |
| NT-proBNP (pg/ml) week 0 to 24 [Ratio] (n = 1773) | 2758 [1480, 5838] | 2834 [1416, 5732] | 1837 [856, 4043] | 2030 [918, 4703] | 0.86 (0.78, 0.95) | p = 0.002 |
| Troponin I (ng/L) week 0 to 24 [Median Difference](n = 1613) | 34 [18, 64] | 34 [18, 64] | 41 [18, 74] | 30 [14, 60] | 5 (3, 7) | p < 0.001 |
| Troponin I (ng/L) week 0 to 24 [Ratio] (n = 1613) | 34 [18, 64] | 34 [18, 64] | 41 [18, 74] | 30 [14, 60] | 1.30 (1.21, 1.40) | p < 0.001 |
| Non-Advanced HF |  |  |  |  |  |  |
| Systolic BP (mm Hg) week 0 to 24 (n = 5383) | 117.1 ± 15.4 | 117.9 ± 15.4 | 118.4 ± 16.8 | 119.6 ± 17.9 | −0.7 (−1.5, 0.1) | p = 0.07 |
| Heart rate (beats/min) week 0 to 24 (n = 5383) | 71.7 ± 12.0 | 71.6 ± 11.9 | 69.6 ± 11.3 | 71.0 ± 11.6 | −1.4 (−2.0, −0.9) | p < 0.001 |
| Potassium (mmol/L) week 0 to 24 (n = 5251) | 4.57 ± 0.51 | 4.57 ± 0.51 | 4.56 ± 0.51 | 4.55 ± 0.52 | 0.01 (−0.02, 0.03) | p = 0.58 |
| Creatinine (mg/dl) week 0 to 24 (n = 5278) | 1.27 ± 0.45 | 1.28 ± 0.45 | 1.29 ± 0.49 | 1.28 ± 0.48 | 0.01 (−0.00, 0.03) | p = 0.14 |
| NT-proBNP (pg/ml) week 0 to 24 [Ratio] (n = 5261) | 1753 [864, 3479] | 1795 [893, 3540] | 1274 [531, 2731] | 1391 [613, 2987] | 0.91 (0.86, 0.95) | p < 0.001 |
| Troponin I (ng/L) week 0 to 24 [Median Difference] (n = 4758) | 25 [11, 47] | 25 [11, 47] | 31 [13, 63] | 22 [10, 45] | 4 (3, 5) | p < 0.001 |
| Troponin I (ng/L) week 0 to 24 [Ratio] (n = 4758) | 25 [11, 47] | 25 [11, 47] | 31 [13, 63] | 22 [10, 45] | 1.24 (1.19, 1.29) | p < 0.001 |

BP = blood pressure,
NT-proBNP = amino-terminal-b-type natriuretic peptide

Effect of OM by Baseline NT-ProBNP Level

Natriuretic peptides are fundamental to the understanding of the pathophysiology of heart failure, its diagnosis, assessment of prognosis and treatment. Elevation of N-terminal pro-B-type natriuretic peptide (NT-proBNP) is pathognomonic of heart failure with reduced ejection fraction (HFrEF) and higher blood concentrations of this and other natriuretic peptides are associated with higher rates of non-fatal and fatal outcomes. Conversely, pharmacological therapies that are effective in reducing the risk of hospitalization for worsening heart failure and the risk of death in patients with HFrEF also reduce natriuretic peptides. A newly developed therapy for HFrEF, omecamtiv mecarbil, directly augments cardiac contractility by selectively binding to cardiac myosin, increasing the number of myosin heads (force generators) that bind to the actin filament and initiate the power-stroke at the start of systole. In phase 2 trials in patients with HFrEF, both short-term intravenous treatment and longer-term oral therapy with omecamtiv mecarbil improved cardiac performance and, in the latter, over a 20-week period, reduced left ventricular systolic and diastolic volumes, plasma natriuretic peptide concentrations and heart rate. As a result, the Global Approach to Lowering Adverse Cardiac outcomes Through Improving Contractility in Heart Failure trial (GALACTIC-HF) was conducted to assess whether treatment with omecamtiv mecarbil would improve outcomes in patients with HFrEF, enrolled either as outpatients and in-patients with decompensated heart failure. Over a median of 22 months, omecamtiv mecarbil reduced the risk of risk of the primary composite outcome of a worsening heart failure event or cardiovascular death by 8% (hazard ratio 0.92; 95% confidence interval, 0.86 to 0.99; P=0.03). Before completion of the trial, we prespecified that the effect of randomized treatment would be examined according to baseline NT-proBNP, either less than or equal to median value, or greater than median value (≤median, >median), in relation to randomization setting (outpatient or inpatient), excluding individuals with atrial fibrillation/flutter (AF/F). Here we report the effect of omecamtiv mecarbil according to baseline NT-proBNP level in patients without AF/F and in the overall population. In addition, we describe the effect of omecamtiv mecarbil using NT-proBNP as a continuous as well as a categorical measure and describe the effect of omecamtiv mecarbil on NT-proBNP level.

NT-proBNP and Cardiac Troponin I Measurements

NT-proBNP was measured at baseline and at 2, 6, 24, 48 and 96 weeks after randomization. Plasma NT-proBNP was measured in a central laboratory (Q Squared Solutions) using the Roche Elecsys NT-proBNP two-site electrochemiluminescence immunoassay (analytical range 50-35000 pg/m L).

Statistical Analysis

Although the primary outcome was a composite of heart failure event or cardiovascular death, the trial was designed to provide 90% power to detect a hazard ratio of 0.8 for cardiovascular death, giving a sample size of approximately 8,000 patients. The trial was event-driven, with a target of approximately 1590 cardiovascular deaths. Efficacy analyses were performed according to randomized treatment group assignment (intention-to-treat) on the full analysis set which included all randomized patients except for 24 subjects from a single site excluded due to Good Clinical Practice violations. Baseline characteristics were summarized as frequencies with percentages, means with standard deviation (SD), or medians with interquartile ranges. Differences in baseline characteristics were tested using the Cochrane-Armitage trend test for categorical variables and the analysis of variance test for continuous variables. The difference between treatment groups in NT-proBNP at the time points after randomization in surviving patients was analyzed using an analysis of covariance model, with treatment-group assignment as a fixed-effect factor and baseline NT-proBNP as a covariate. The results of the analyses of covariance are presented as least-squares mean differences with corresponding 95% CIs. Time-to-event data were evaluated with Kaplan-Meier estimates and Cox proportional-hazards models with baseline hazards stratified by randomization setting and region and with treatment group and baseline eGFR as covariates. The safety analyses were performed in patients who underwent randomization and received at least one dose of omecamtiv mecarbil or placebo. All analyses were conducted using STATA version 15.1 (College Station, Tex.) and SAS version 9.4 (SAS Institute, Cary, N.C.). A P-value of 0.05 was considered statistically significant.

Results

A NT-proBNP measurement at baseline was available for 8206 of the 8232 patients randomized. Of these, 5971 patients did not have AF/F on their baseline ECG. The median (Q1, Q3) NT-proBNP level at baseline was 1675 (812-3579) pg/ml among patients not in AF/F and 1998 (993-4079) pg/mL in all patients randomized.

Baseline characteristics according to median baseline NT-proBNP concentration are presented in Table 15 for participants without AF/F and in the overall population.

TABLE 15

Baseline characteristics of patients according to pre-randomization NT-proBNP level (≤median or >median) in the prespecified analysis population (no atrial fibrillation/flutter at baseline) and in all patients randomized.

|  | No AF/F | | | All patients | | |
| --- | --- | --- | --- | --- | --- | --- |
| NT-proBNP | ≤median N = 2987 | >median N = 2984 | P-value | ≤median N = 4105 | >median N = 4101 | P-value |
| Age (years), mean (SD) | 61.6 ± 11.4 | 64.9 ± 11.5 | <0.001 | 62.5 ± 11.3 | 66.5 ± 11.0 | <0.001 |
| Male sex, N (%) | 2334 (78.1) | 2300 (77.1) | 0.33 | 3259 (79.4) | 3203 (78.1) | 0.15 |
| Race, N (%) | | | <0.001 | | | <0.001 |
| Asian | 316 (10.6) | 240 (8.0) | | 402 (9.8) | 308 (7.5) | |
| Black | 234 (7.8) | 249 (8.3) | | 290 (7.1) | 266 (6.5) | |
| White | 2238 (74.9) | 2262 (75.8) | | 3159 (77.0) | 3220 (78.5) | |
| Other | 199 (6.7) | 233 (8.2) | | 254 (6.2) | 307 (7.5) | |
| Geographic region, N (%) | | | <0.001 | | | <0.001 |
| Asia | 300 (10.0) | 222 (7.4) | | 382 (9.3) | 288 (7.0) | |
| Western Europe | 587 (19.7) | 718 (24.1) | | 827 (20.1) | 1086 (26.5) | |
| Eastern Europe | 972 (32.5) | 818 (27.4) | | 1408 (34.3) | 1273 (31.0) | |
| North America | 586 (19.6) | 542 (18.2) | | 757 (18.4) | 611 (14.9) | |
| Latin America | 542 (18.1) | 684 (22.9) | | 731 (17.8) | 843 (20.6) | |
| Randomized as an inpatient, N (%) | 569 (19.0) | 776 (26.0) | <0.001 | 871 (21.2) | 1188 (29.0) | <0.001 |
| Physiological measures | | | | | | |
| Systolic blood pressure (mmHg), mean (SD) | 119.0 ± 14.8 | 115.0 ± 15.9 | <0.001 | 118.5 ± 14.8 | 114.4 ± 15.7 | <0.001 |

TABLE 15-continued

Baseline characteristics of patients according to pre-randomization NT-proBNP level (≤median or >median) in the prespecified analysis population (no atrial fibrillation/flutter at baseline) and in all patients randomized.

| | No AF/F | | | All patients | | |
|---|---|---|---|---|---|---|
| NT-proBNP | ≤median N = 2987 | >median N = 2984 | P-value | ≤median N = 4105 | >median N = 4101 | P-value |
| Heart rate (bpm) | 69.9 ± 10.9 | 72.8 ± 11.9 | <0.001 | 70.8 ± 11.4 | 73.9 ± 12.7 | <0.001 |
| BMI (kg/m$^2$) | 29.6 ± 6.2 | 27.2 ± 5.8 | <0.001 | 29.6 ± 6.3 | 27.3 ± 5.8 | <0.001 |
| eGFR (mL/min/1.73 m$^2$), mean (SD) | 67.4 ± 21.8 | 57.0 ± 22.0 | <0.001 | 66.0 ± 21.4 | 54.9 ± 21.0 | <0.001 |
| eGFR N <60 mL/min/1.73 m$^2$ N (%) | 1163 (38.9) | 1764 (59.1) | <0.001 | 1705 (41.5) | 2599 (63.4) | <0.001 |
| Ischemic etiology, N (%) | 1624 (54.4) | 1708 (57.2) | 0.026 | 2185.0 (53.2) | 2216.0 (54.0) | 0.46 |
| LVEF, mean (SD) | 27.4 ± 6.0 | 25.3 ± 6.4 | <0.001 | 27.4 ± 6.0 | 25.7 ± 6.4 | <0.001 |
| NYHA class, N (%) | | | <0.001 | | | <0.001 |
| II | 1893 (63.4) | 1454 (48.7) | | 2484 (60.5) | 1875 (45.7) | |
| III | 1045 (35.0) | 1418 (47.5) | | 1539 (37.5) | 2060 (50.2) | |
| IV | 49 (1.6) | 112 (3.8) | | 82 (2.0) | 166 (4.0) | |
| KCCQ-TSS, mean (SD) | 71.9 ± 23.3 | 64.4 ± 25.7 | <0.001 | 70.7 ± 23.8 | 62.3 ± 25.7 | <0.001 |
| Atrial fibrillation/flutter*, N (%) | — | — | — | 725 (17.7) | 1510 (36.8) | |
| Medical history, N (%) | | | | | | |
| Hypertension | 2085 (69.8) | 2038 (68.3) | 0.21 | 2908 (70.8) | 2854 (69.6) | 0.22 |
| Type 2 diabetes | 1188 (39.8) | 1288 (43.2) | 0.008 | 1662.0 (40.5) | 1702.0 (41.5) | p = 0.35 |
| Previous MI | 1315 (44.0) | 1361 (45.6) | 0.22 | 1727 (42.1) | 1696 (41.4) | 0.51 |
| Treatment, N (%) | | | | | | |
| ACEI/ARB/ARNI | 2752.0 (92.1) | 2481.0 (83.1) | <0.001 | 3752.0 (91.4) | 3388.0 (82.6) | <0.001 |
| ARNI | 629.0 (21.1) | 536.0 (18.0) | 0.003 | 862.0 (21.0) | 728.0 (17.8) | <0.001 |
| Beta-blocker | 2865.0 (95.9) | 2771.0 (92.9) | <0.001 | 3921.0 (95.5) | 3819.0 (93.1) | <0.001 |
| MRA | 2377.0 (79.6) | 2238.0 (75.0) | <0.001 | 3279.0 (79.9) | 3101.0 (75.6) | <0.001 |
| Diuretic | 2541 (85.1) | 2732 (91.6) | <0.001 | 3554 (86.6) | 3801 (92.7) | <0.001 |
| Digoxin | 319 (10.7) | 372 (12.5) | 0.031 | 610 (14.9) | 771 (18.8) | <0.001 |
| ICD | 893.0 (29.9) | 1222.0 (33.9) | <0.001 | 1012.0 (29.8) | 1380.0 (33.7) | <0.001 |
| CRT-P/CRT-D | 352.0 (11.8) | 460.0 (15.4) | <0.001 | 480.0 (11.7) | 672.0 (16.4) | <0.001 |

*Percentages may not total 100 because of rounding
ACE = angiotensin-converting enzyme;
ARB = angiotensin-receptor blocker;
ARNI = angiotensin receptor-neprilysin inhibitor;
BMI = body mass index;
CRT-P/D = cardiac resynchronization therapy with or without a defibrillator;
GFR = glomerular filtration rate;
ICD = implantable cardioverter-defibrillator;
KCCQ-TSS = Kansas City Cardiomyopathy Questionnaire total symptom score-range from 0 to 100, with higher scores indicating fewer symptoms;
LVEF = left ventricular ejection fraction;
MI = myocardial infarction;
MRA = mineralocorticoid receptor antagonist;
NT-proBNP = N-terminal pro-B-type natriuretic peptide;
NYHA = New York Heart association.

Compared to those with NT-proBNP level less than or equal to the median (≤median), patients with a level greater than median (>median) were older, more often from Western Europe or Latin America, and less frequently from Asia. Participants with a NT-proBNP level greater than median had a lower mean body mass index, eGFR (and larger proportion of patients with eGFR<60 mL/min/1.73 m$^2$) and systolic blood pressure, but higher heart rate and troponin I. They were also more likely to have a lower ejection fraction, and considerably worse NYHA functional class and KCCQ-TSS. These differences were seen both in participants without AF/F and in the overall population. Some differences were only seen in patients without AF/F and not in the overall population. Participants without AF/F, with a NT-proBNP level greater than median, were more likely to have diabetes and an ischemic etiology, than those with a NT-proBNP less than or equal to the median (these differences were not significant in the overall population).

With respect to heart failure treatment, patients with a NT-proBNP level greater than median were less often treated with renin-angiotensin system blockers (including sacubitril-valsartan), mineralocorticoid receptor antagonists and beta-blockers, but had more often prescribed a diuretic and digoxin (even in patients without AF/F) and were more likely to have an implanted cardiac device.

Generally, these differences were also observed whether patients were enrolled as an outpatient or an inpatient, and in patients with AF/F.

Hospitalization and Mortality Outcomes in Relation to Baseline Concentration of NT-proBNP Event rates were higher in patients with a NT-proBNP greater than the median, compared with less than or equal to the median, in participants without AF/F and in the overall population, as shown by comparison of the placebo groups in Table 16. When NT-proBNP was examined as a continuous variable, the rate of the primary endpoint rose steeply with increasing NT-proBNP concentration (FIGS. 16A-16D and 17A-17D). The same was observed whether patients were enrolled as an outpatient or an inpatient, and in patients with AF/F.

Effect of Omecamtiv Mecarbil on Outcomes According to Baseline Concentration of NT-proBNP Table 16 shows the effect of omecamtiv mecarbil on the prespecified morbidity and mortality endpoints, according to baseline NT-proBNP level divided at the median, as prespecified, in patients without AF/F and in the overall trial population. Additional analyses of the effect of omecamtiv mecarbil examining NT-proBNP as a continuous variable are shown in (FIGS. 18A-18D and 19A-19D).

with increasing NT-proBNP became clearer as shown in FIGS. 18A-18D and 19A-19D.

Qualitatively similar findings were seen in participants enrolled in both the outpatient and inpatient setting. A completely different pattern was observed in patients with AF/F at baseline, with a higher event rate in the omecamtiv mecarbil groups, compared with the placebo group, especially in patients with a NT-proBNP less than or equal to the median.

Secondary Outcomes

Examination of the secondary hospitalization and mortality outcomes in patients without AF/F suggested the interaction between baseline NT-proBNP level and the effect of omecamtiv mecarbil was more evident for heart failure

TABLE 16

Outcomes according to baseline NT-proBNP level (less than or equal to the median or greater than the median) in relation to randomized treatment assignment in the prespecified analysis population (no atrial fibrillation/flutter at baseline) and in all patients randomized

| | No AF/F (n = 5971) | | | | | | All patients (n = 8206) | | | | | |
|---|---|---|---|---|---|---|---|---|---|---|---|---|
| | Placebo (n = 3006) | | OM (n = 2965) | | HR | P | Placebo (n = 4099) | | OM (n = 4107) | | HR | P |
| | n (%) | Rate[1] | n (%) | Rate[1] | (95% CI) | value | n (%) | Rate[1] | n (%) | Rate[1] | (95% CI) | value |
| 1° Outcome[2,3] | | | | | | | | | | | | |
| ≤NTproBNP | 352 (23) | 13.42 | 328 (22) | 12.42 | 0.94 (0.80, 1.09) | 0.392 | 518 (25) | 14.84 | 537 (26) | 15.00 | 1.02 (0.90, 1.15) | 0.790 |
| >NTproBNP | 748 (50) | 38.85 | 650 (44) | 31.30 | 0.81 (0.73, 0.90) | 0.000 | 1080 (52) | 41.59 | 981 (48) | 36.52 | 0.88 (0.81, 0.96) | 0.003 |
| Hospitalization[3,4] | | | | | | | | | | | | |
| ≤NTproBNP | 263 (17) | 10.02 | 254 (17) | 9.62 | 0.97 (0.82, 1.15) | 0.728 | 399 (20) | 11.43 | 424 (20) | 11.84 | 1.04 (0.91, 1.19) | 0.565 |
| >NTproBNP | 570 (38) | 29.62 | 483 (32) | 23.26 | 0.79 (0.70, 0.89) | 0.000 | 830 (40) | 31.97 | 750 (37) | 27.93 | 0.88 (0.79, 0.97) | 0.008 |
| CV death[3] | | | | | | | | | | | | |
| ≤NTproBNP | 141 (9) | 4.85 | 135 (9) | 4.64 | 0.96 (0.76, 1.22) | 0.761 | 202 (10) | 5.13 | 227 (11) | 5.63 | 1.11 (0.92, 1.34) | 0.296 |
| >NTproBNP | 405 (27) | 16.32 | 363 (24) | 14.29 | 0.87 (0.75, 1.00) | 0.047 | 591 (29) | 17.18 | 578 (28) | 17.15 | 0.99 (0.88, 1.11) | 0.811 |
| All-cause death | | | | | | | | | | | | |
| ≤NTproBNP | 205 (14) | 7.05 | 196 (13) | 6.74 | 0.96 (0.79, 1.17) | 0.715 | 292 (14) | 7.42 | 327 (16) | 8.11 | 1.10 (0.94, 1.29) | 0.223 |
| >NTproBNP | 530 (35) | 21.35 | 474 (32) | 18.67 | 0.86 (0.76, 0.97) | 0.017 | 766 (37) | 22.27 | 737 (36) | 21.87 | 0.97 (0.88, 1.07) | 0.544 |

[1]per 100 person-years
[2]a composite of time to heart failure hospitalization or cardiovascular death, whichever came first
[3]NTproBNP median values
[4]hospitalization for HF
AF/F = atrial fibrillation/flutter
OM = omecamtiv mecarbil
HF = heart failure
Numbers of patients in subgroups
No AF/F NTproBNP ≤ median: placebo = 1511/OM = 1476. NTproBNP > median: placebo = 1495/OM = 1489
All patients: NTproBNP ≤ median: placebo = 2032/OM = 2073 NTproBNP > median: placebo = 2067/OM = 2034

Primary Composite Outcome

Among patients without AF/F, compared to placebo, omecamtiv mecarbil had more benefit on the primary endpoint in participants with a NT-proBNP greater than the median (HR 0.81, 95% CI 0.73-0.90) than in patients with a NT-proBNP less than or equal to the median (HR 0.94, 0.80-1.09); P for interaction=0.035. A similar interaction was seen in the overall population: HR 0.88, 0.80-0.96 in patients with NT-proBNP>median and 1.01, 0.90-1.15 in participants with a NT-proBNP less than or equal to the median; P for interaction=0.095.

When NT-proBNP was examined as a continuous variable, the increasing beneficial effect of omecamtiv mecarbil hospitalization than for cardiovascular or all-cause death (Table 16 and FIGS. 18A-18D and 19A-19D). While both hospitalization and mortality were reduced by omecamtiv mecarbil in participants without AF/F and a NT-proBNP greater than the median, the mortality benefits were lost when the overall population was analyzed, because of the absence of an effect of omecamtiv mecarbil in patients with AF/F. Even the larger benefit of omecamtiv mecarbil on heart failure hospitalization was attenuated by the addition of patients with AF/F in the overall population.

Table 17 shows the effect of omecamtiv mecarbil on physiologic measures and on plasma biomarkers according to baseline NT-proBNP level divided at the median, in patients without AF/F and in the overall trial population.

TABLE 17

Change from baseline to 24 weeks in physiologic measures and biomarkers according to baseline NT-proBNP level (≤median or >median) in relation to randomized treatment assignment in the prespecified analysis population (no atrial fibrillation/flutter at baseline) and in all patients randomized.

| | No AF/F (n = 5971) | | | | | | All patients (n = 8206) | | | | | |
|---|---|---|---|---|---|---|---|---|---|---|---|---|
| | Placebo (n = 3006) | | OM (n = 2965) | | Δ/ Ratio | P value | Placebo (n = 4099) | | OM (n = 4107) | | Δ/ Ratio | P value |
| | $t_0$ | 24 wks | $t_0$ | 24 wks | | | $t_0$ | 24 wks | $t_0$ | 24 wks | | |
| SBP (mmHg) | | | | | | | | | | | | |
| ≤NT proBNP | 119 (15) | 122 (18) | 119 (15) | 120 (16) | −1.0 (−2.1, 0.1) | 0.06 | 119 (14) | 121 (17) | 118 (15) | 120 (16) | −0.8 (−1.7, 0.2) | 0.11 |
| >NT proBNP | 115 (16) | 117 (19) | 117 (18) | 120 (16) | 0.3 (−0.8, 1.4) | 0.59 | 114 (16) | 116 (18) | 114 (16) | 116 (17) | −0.1 (−1.0, 0.9) | 0.88 |
| HR (bpm) | | | | | | | | | | | | |
| ≤NT proBNP | 70 (11) | 70 (11) | 70 (11) | 69 (11) | −1.5 (−2.2, −0.8) | <0.001 | 71 (12) | 71 (12) | 71 (11) | 70 (11) | −1.5 (−2.2, −0.09) | <0.001 |
| >NT proBNP | 73 (12) | 71 (11) | 73 (12) | 70 (12) | −1.7 (−2.5, −0.9) | <0.001 | 74 (12) | 72 (12) | 74 (13) | 70 (12) | −1.6 (−2.3, −0.8) | <0.001 |
| Creatine (mg/dL) | | | | | | | | | | | | |
| ≤NT proBNP | 1.19 (0.40) | 1.18 (0.40) | 1.16 (0.36) | 1.17 (0.42) | 0.02 (0.00, 0.04) | 0.07 | 1.20 (0.40) | 1.20 (0.39) | 1.19 (0.37) | 1.21 (0.43) | 0.02 (0.00, 0.04) | 0.019 |
| >NT proBNP | 1.37 (0.50) | 1.40 (0.56) | 1.39 (0.52) | 1.37 (0.50) | −0.01 (−0.03, 0.02) | 0.66 | 1.40 (0.49) | 1.43 (0.57) | 1.42 (0.52) | 1.43 (0.56) | −0.01 (−0.03, 0.02) | 0.54 |
| NT-proBNP (pg/mL) | | | | | | | | | | | | |
| ≤NTproBNP | 829 (535, 1174) | 691 (332, 1150) | 791 (506, 1176) | 614 (332, 1150) | 0.95 (0.88, 1.01) | 0.11 | 914 (610, 1444) | 818 (410, 1480) | 992 (592, 1469) | 772 (385, 1472) | 0.95 (0.90, 1.01) | 0.10 |
| >NTproBNP | 3574 (2387, 6312) | 2754 (1424, 5241) | 3586 (2364, 6353) | 2302 (1146, 4689) | 0.83 (0.76, 0.90) | <0.001 | 4065 (2798, 6952) | 3207 (1766, 5774) | 4100 (2732, 6972) | 2809 (1474, 5145) | 0.84 (0.78, 0.89) | <0.001 |
| Troponin I (ng/L) | | | | | | | | | | | | |
| ≤NTproBNP | 19 (10, 37) | 16 (10, 35) | 18 (10, 35) | 16 (10, 35) | 1.25 (1.18, 1.31) | <0.001 | 20 (1039) | 18 (1037) | 19 (1038) | 24 (1050) | 1.28 (1.22, 1.34) | <0.001 |
| >NTproBNP | 33 (18, 61) | 31 (16, 56) | 36 (18, 67) | 40 (20, 78) | 1.23 (1.16, 1.31) | <0.001 | 35 (19, 64) | 34 (17, 62) | 37 (19, 67) | 44 (22, 81) | 1.23 (1.17, 1.29) | <0.001 |

AF/F = atrial fibrillation/flutter
BP = blood pressure
BPM = beats per minute
OM = omecamtiv mecarbil
NT-proBNP = N-terminal pro-B-type natriuretic peptide Changes from baseline (t0) to the 24-week visit are provided. Omecamtiv mecarbil did not have a significant effect on systolic blood pressure in any subgroup but did reduce heart rate, significantly, by 1-2 beats per minute in in all 4 patient subgroups. Omecamtiv mecarbil also increased troponin I, significantly, and by a similar proportional amount, in all 4 patient subgroups. By contrast, omecamtiv mecarbil reduced NT-proBNP only in patients with a baseline value NT-proBNP greater than the median at baseline, as shown in more detail in FIGS. 20A-F.

Safety Outcomes

The occurrence of adverse events according to treatment assignment according to NT-proBNP category is shown Table 18.

TABLE 18

Adverse events according to baseline NT-proBNP level (less than or equal to the median or greater than the median) in relation to randomized treatment assignment in the prespecified analysis population (no atrial fibrillation/flutter at baseline) and in all patients randomized.

| | No AF/F (n = 5971) | | | | All patients (n = 8206) | | | |
|---|---|---|---|---|---|---|---|---|
| | Placebo (n = 3006) | OM (n = 2965) | RR | P value | Placebo (n = 4099) | OM (n = 4107) | RR | P value |
| Ventricular tachyarrhythmia | | | | | | | | |
| ≤median NT-proBNP | 104 (8.1) | 84 (6.7) | 0.82 (0.62, 1.09) | 0.17 | 142 (8.2) | 130 (7.3) | 0.89 (0.71, 1.12) | 0.32 |
| >median NT-proBNP | 112 (8.2) | 115 (8.6) | 1.05 (0.82, 1.35) | 0.69 | 161 (8.4) | 160 (8.7) | 1.03 (0.83, 1.27) | 0.79 |
| Torsade/QT prolongation | | | | | | | | |
| ≤median NT-proBNP | 57 (4.4) | 47 (3.7) | 0.84 (0.58, 1.23) | 0.37 | 86 (4.9) | 78 (4.4) | 0.88 (0.65, 1.19) | 0.41 |
| >median NT-proBNP | 72 (5.2) | 71 (5.3) | 1.01 (0.73, 1.39) | 0.95 | 108 (5.6) | 98 (5.3) | 0.94 (0.72, 1.23) | 0.64 |
| Ventricular tachyarrhythmia leading to treatment | | | | | | | | |
| ≤median NT-proBNP | 44 (2.9) | 29 (2.0) | 0.67 (0.42, 1.07) | 0.09 | 58 (2.9) | 51 (2.5) | 0.86 (0.59, 1.25) | 0.43 |
| >median NT-proBNP | 43 (2.9) | 49 (3.3) | 1.15 (0.77, 1.72) | 0.51 | 68 (3.3) | 68 (3.4) | 1.02 (0.73, 1.42) | 0.91 |
| Major cardiac ischemic events | | | | | | | | |
| ≤median NT-proBNP | 76 (5.0) | 86 (5.8) | 1.16 (0.86, 1.56) | 0.34 | 101 (5.0) | 114 (5.5) | 1.10 (0.85, 1.43) | 0.46 |
| >median NT-proBNP | 77 (5.2) | 83 (5.6) | 1.08 (0.80, 1.47) | 0.60 | 87 (4.2) | 85 (4.2) | 0.99 (0.74, 1.33) | 0.97 |
| Stroke | | | | | | | | |
| ≤median NT-proBNP | 31 (2.1) | 25 (1.7) | 0.83 (0.49, 1.39) | 0.47 | 52 (2.6) | 36 (1.7) | 0.68 (0.44, 1.03) | 0.07 |
| >median NT-proBNP | 40 (2.7) | 29 (2.0) | 0.73 (0.45, 1.17) | 0.19 | 59 (2.9) | 40 (2.0) | 0.69 (0.46, 1.03) | 0.07 |

AF/F = atrial fibrillation/flutter
OM = omecamtiv mecarbil
Torsade = Torsade de pointes ventricular tachycardia
Numbers of patients in subgroups
No AF/F NTproBNP ≤ median: placebo = 1511/OM = 1476.
NTproBNP > median: placebo = 1495/OM = 1489
All patients NTproBNP median: placebo = 2032/OM = 2073 NTproBNP > median: placebo = 2067/OM = 2034
Rate is per 100 person-years Comparison of the placebo groups showed no substantial difference in any adverse event in patients with a baseline NT-proBNP concentration greater than the median compared to less than or equal to the median. Similarly, there was no strong or consistent evidence that any adverse event was more common with omecamtiv mecarbil, compared to placebo, in any of the 4 subgroups of patients.

In GALACTIC-HF, the benefit of omecamtiv mecarbil appeared to be larger in patients with higher baseline NT-proBNP levels, especially in patients without AF/F.

Effect of OM by Baseline Atrial Fibrillation/Flutter (AF/F)

Atrial fibrillation is common in patients with heart failure and contributes to morbidity and mortality. Atrial fibrillation has not modified the treatment effect of renin-angiotensin-aldosterone inhibitors that have proven beneficial in heart failure, but may modify the treatment effect of beta-blockers. Here we report the effect of omecamtiv mecarbil according to baseline status of in patients either without AF/F or with AF/F. Further exploration of digoxin use within the two subpopulations was also assessed.

Results

A determination of AF/F at baseline was available the 8232 patients randomized. Of these, 5987 patients did not have AF/F on their baseline ECG. Baseline characteristics according to median baseline AF/F status are presented in Table 19 for participants without AF/F and with AF/F.

TABLE 19

Baseline characteristics of patients according to pre-randomization atrial fibrillation/flutter status (no atrial fibrillation/flutter at baseline or having atrial fibrillation/flutter at baseline) in all patients randomized.

| Clinical Characteristics | No AF/Flutter at baseline n = 5987 | AF/Flutter at baseline n = 2245 | P-value |
|---|---|---|---|
| Demographics | | | |
| Age-yr | 63.3 ± 11.6 | 67.9 ± 9.9 | p <0.001 |
| Sex, Female | 1340 (22.4%) | 409 (18.2%) | p <0.001 |
| Race | | | p <0.001 |
| Asian | 556 (9.3%) | 154 (6.9%) | |

TABLE 19-continued

Baseline characteristics of patients according to pre-randomization atrial fibrillation/flutter status (no atrial fibrillation/flutter at baseline or having atrial fibrillation/flutter at baseline) in all patients randomized.

| Clinical Characteristics | No AF/Flutter at baseline n = 5987 | AF/Flutter at baseline n = 2245 | P-value |
|---|---|---|---|
| Black | 487 (8.1%) | 75 (3.3%) | |
| Other | 433 (7.2%) | 130 (5.8%) | |
| White | 4511 (75.3%) | 1886 (84.0%) | |
| Geographic Region | | | P <0.001 |
| Asia | 522 (8.7%) | 148 (6.6%) | |
| Eastern Europe/Russia | 1790 (29.9%) | 891 (39.7%) | |
| Latin America | 1226 (20.5%) | 348 (15.5%) | |
| US And Canada | 1138 (19.0%) | 248 (11.0%) | |
| Western Europe/South Africa/Australasia | 1311 (21.9%) | 610 (27.2%) | |
| Randomization Setting: In-patient | 1361 (22.7%) | 723 (32.2%) | p <0.001 |
| Hypertension Hx | 4136 (69.1%) | 1648 (73.4%) | P <0.001 |
| Type 2 diabetes mellitus | 2431 (40.6%) | 878 (39.1%) | P = 0.22 |
| History of stroke | 497 (8.3%) | 257 (11.4%) | P <0.001 |
| Ischemic heart failure etiology | 3341 (55.8%) | 1074 (47.8%) | P <0.001 |
| LVEF-% | 26.4 ± 6.3 | 27.1 ± 6.1 | P <0.001 |
| NYHA Classification | | | P <0.001 |
| Class II | 3353 (56.0%) | 1015 (45.2%) | |
| Class III | 2473 (41.3%) | 1143 (50.9%) | |
| Class IV | 161 (2.7%) | 87 (3.9%) | |
| SBP-mmHg | 117.0 ± 15.5 | 115.1 ± 14.8 | P <0.001 |
| Heart rate-beats/min | 71.3 ± 11.5 | 75.1 ± 13.4 | P <0.001 |
| NT-proBNP-pg/mL | 1675 [812, 3579] | 2873 [1699, 5294] | P <0.001 |
| Cardiac Troponin I-ng/L | 25 [13, 48] | 31 [16, 59] | P <0.001 |
| eGFR-mL/min/1.73 $m^2$ | 60.6 [45.7, 76.1] | 53.4 [40.4, 68.1] | P <0.001 |
| Heart Failure Therapies | | | |
| ACEi, ARB or ARNi | 5246 (87.6%) | 1913 (85.2%) | P = 0.004 |
| BB | 5650 (94.4%) | 2113 (94.1%) | P = 0.66 |
| MRA | 4627 (77.3%) | 1770 (78.8%) | P = 0.13 |
| Digoxin | 693 (11.6%) | 692 (30.8%) | P <0.001 |
| Cardiac Resynchronization Therapy | 815 (13.6%) | 343 (15.3%) | P = 0.05 |
| Implantable Cardioverter Defibrillator | 1913 (32.0%) | 701 (31.2%) | P = 0.53 |

Figure 21A:
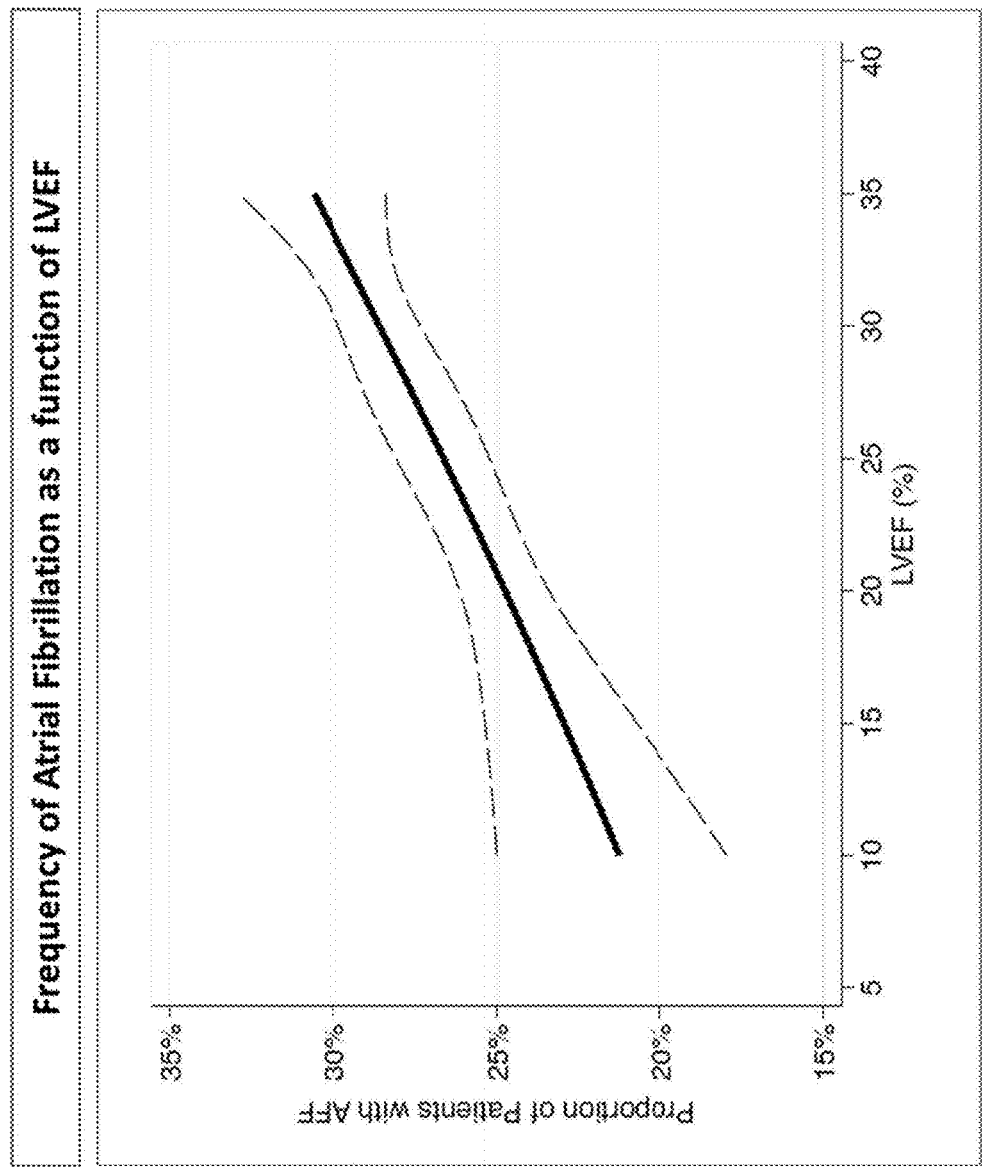
FIG. 21A shows the proportion of patients having AFF as a function of the percentage of LVEF.

FIG. 21A depicts the frequency of AFF in patients having LVEF 35%. AFF was observed to coincide with higher LVEF (but less than 35%).

Figure 21B:
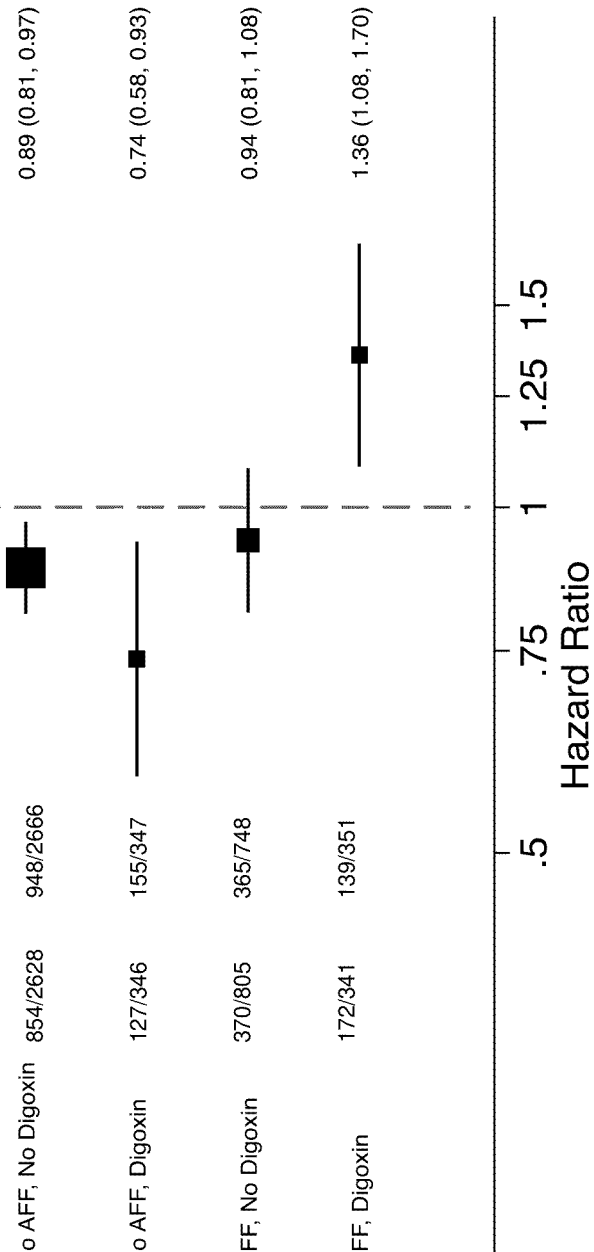
FIG. 21B shows effect of omecamtiv mecarbil in patients with or without AFF who were or were not receiving digoxin.
Figure 21C:
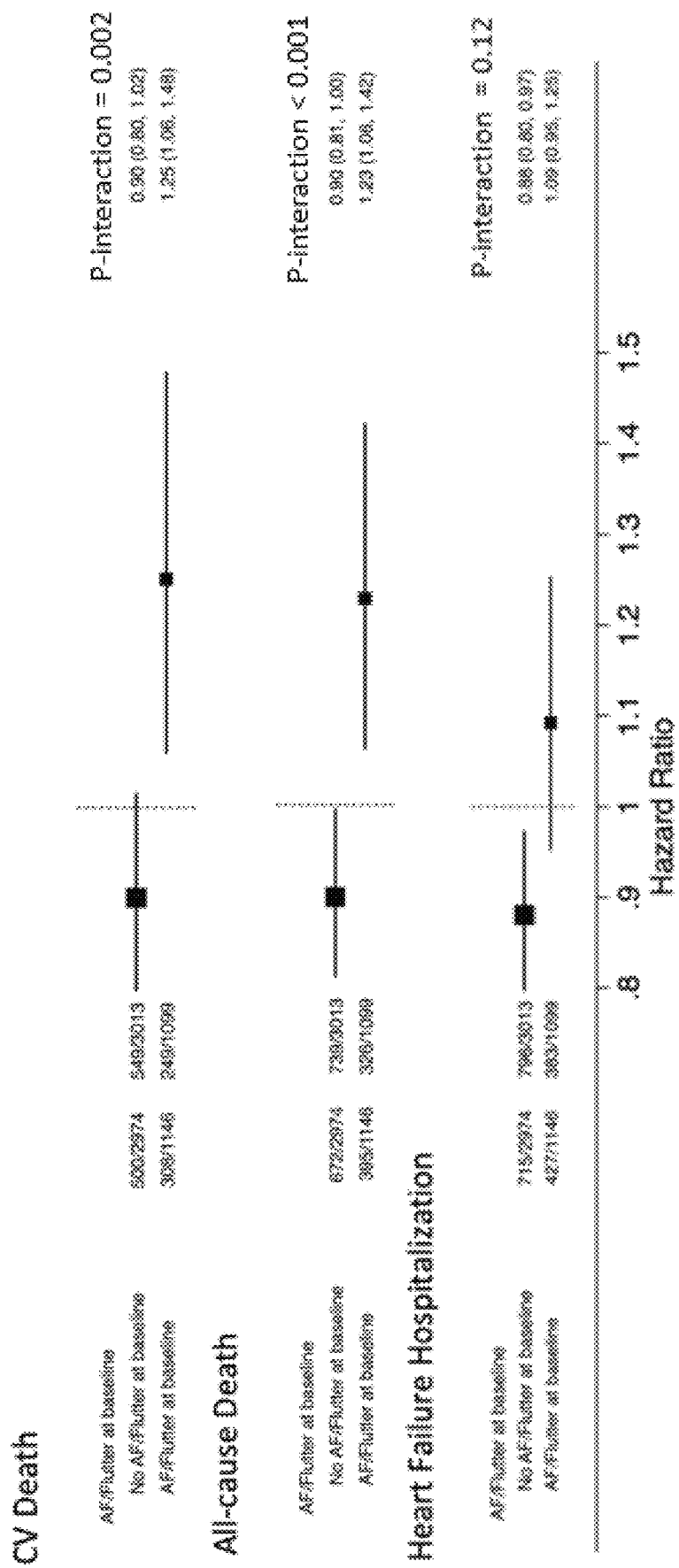
FIG. 21C shows the effect of omecamtiv mecarbil in patients with or without AFF on mortality, for cardiovascular death or all-cause death, and heart failure hospitalization.
Figure 21D:
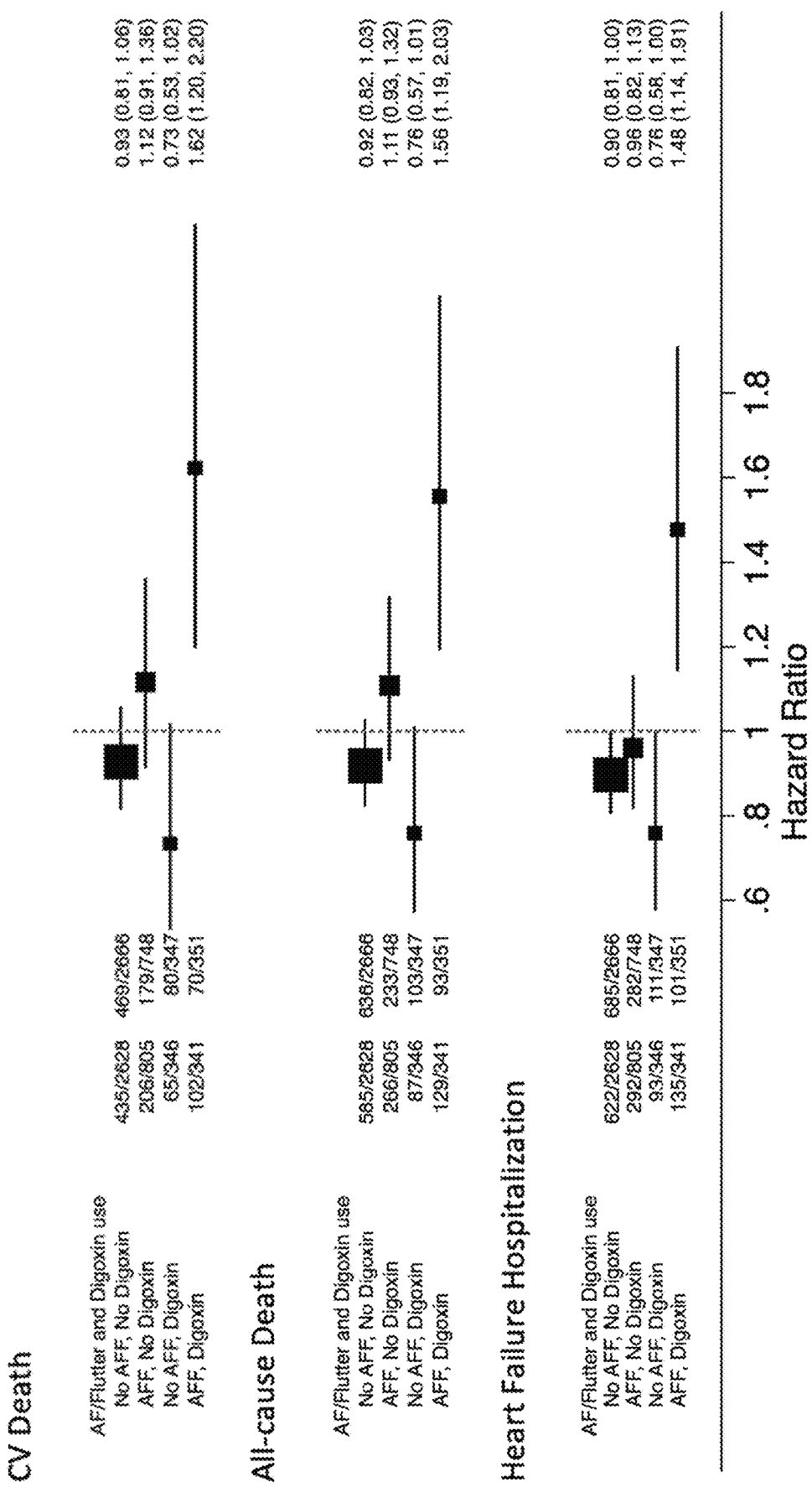
FIG. 21D shows the effect of omecamtiv mecarbil in patients with or without AFF who were or were not receiving digoxin on mortality, for cardiovascular death or all-cause death, and heart failure hospitalization.
Figure 21E:
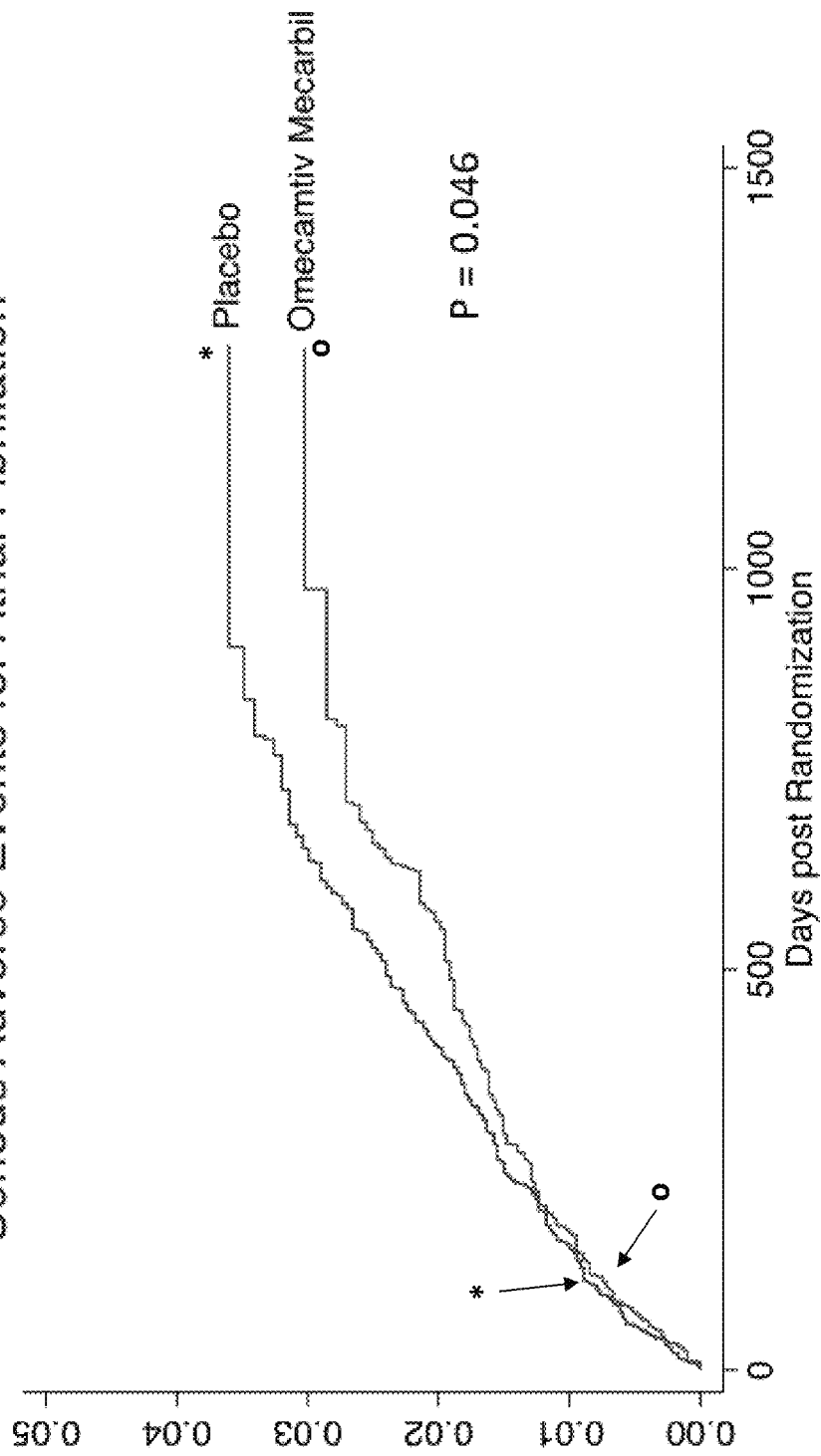
FIG. 21E shows the effect of omecamtiv mecarbil in patients with AFF as compared to placebo on the occurrence of serious adverse events.

The influence of AFF on the effectiveness of OM on the primary and secondary outcome in patients who were or were not receiving digoxin was evaluated. In one of 24 prespecified subgroups, patients with AFF (n=2245, 27%) were older, more likely to be randomized as an inpatient, less likely to have a history of ischemic etiology or myocardial infarction, had a worse NYHA class, worse quality of life, lower eGFR, and higher NT-proBNP at baseline. AFF at baseline was associated with a modestly increased adjusted risk of cardiovascular death or heart failure events (HR 1.17, 95% CI 1.09, 1.27). Using a multivariable covariate-interaction model, the treatment effect of OM appeared to be modified by AFF (interaction p=0.012), with patients without AFF deriving greater benefit (FIG. 21B, top panel). As further shown in FIG. 21B, the presence of AFF was also found to modify the treatment effect of omecamtiv mecarbil as considered for cardiovascular (CV) death (interaction p=0.002), all-cause death (interaction p<0.001), with patients without AFF deriving greater benefit. However, as illustrated in FIG. 21E, treatment with omecamtiv mecarbil led to a significant reduction in serious adverse events for patients having atrial fibrillation/flutter at baseline (interaction p=0.046), with the omecamtiv mecarbil treatment arm having 55 events per 2974 patients and the placebo arm having 78 events per 3013 patients over the course of the study. The treatment effect modification by AFF was significantly more pronounced in digoxin users than in non-users (p=0.004), with strong evidence of effect modification in digoxin users in AFF (p=0.001) and minimal evidence of effect modification in non-users (p=0.52) or digoxin users not in AFF (FIG. 21B, bottom panel). In FIG. 21D, the effect of digoxin use (digoxin or no digoxin) in tandem with omecamtiv mecarbil for patients with AFF and without AFF is shown for cardiovascular death, all-cause death and heart failure hospitalization.

Atrial fibrillation or flutter at baseline modified the treatment effect of omecamtiv mecarbil, even after multivariable adjustment, with greater benefit observed in patients not in AFF. The treatment effect modification by AFF was concentrated in patients using digoxin in AFF with minimal evidence of effect modification in non-users in AFF. Digoxin did not modify the treatment effect of omecamtiv mecarbil in patients not in AFF.

At 6 weeks, omecamtiv mecarbil PK values were similar in those taking and those not taking digoxin (median 286 vs. 280 ng/ml, p=0.78). In patients in whom digoxin doses were known, digoxin doses were similar in both treatment arms (0.12 mg vs. 0.12 mg, p=0.85) and similar in patients with and without AFF at baseline (0.12 mg vs 0.12 mg, p=0.44).

In patients in AFF at baseline taking omecamtiv mecarbil, there was less troponin I increase at 6 weeks in those taking digoxin (+29%, +21% to +38%) vs those not taking digoxin (+45%, +38% to 53%) (p=0.026).

Figure 21F:
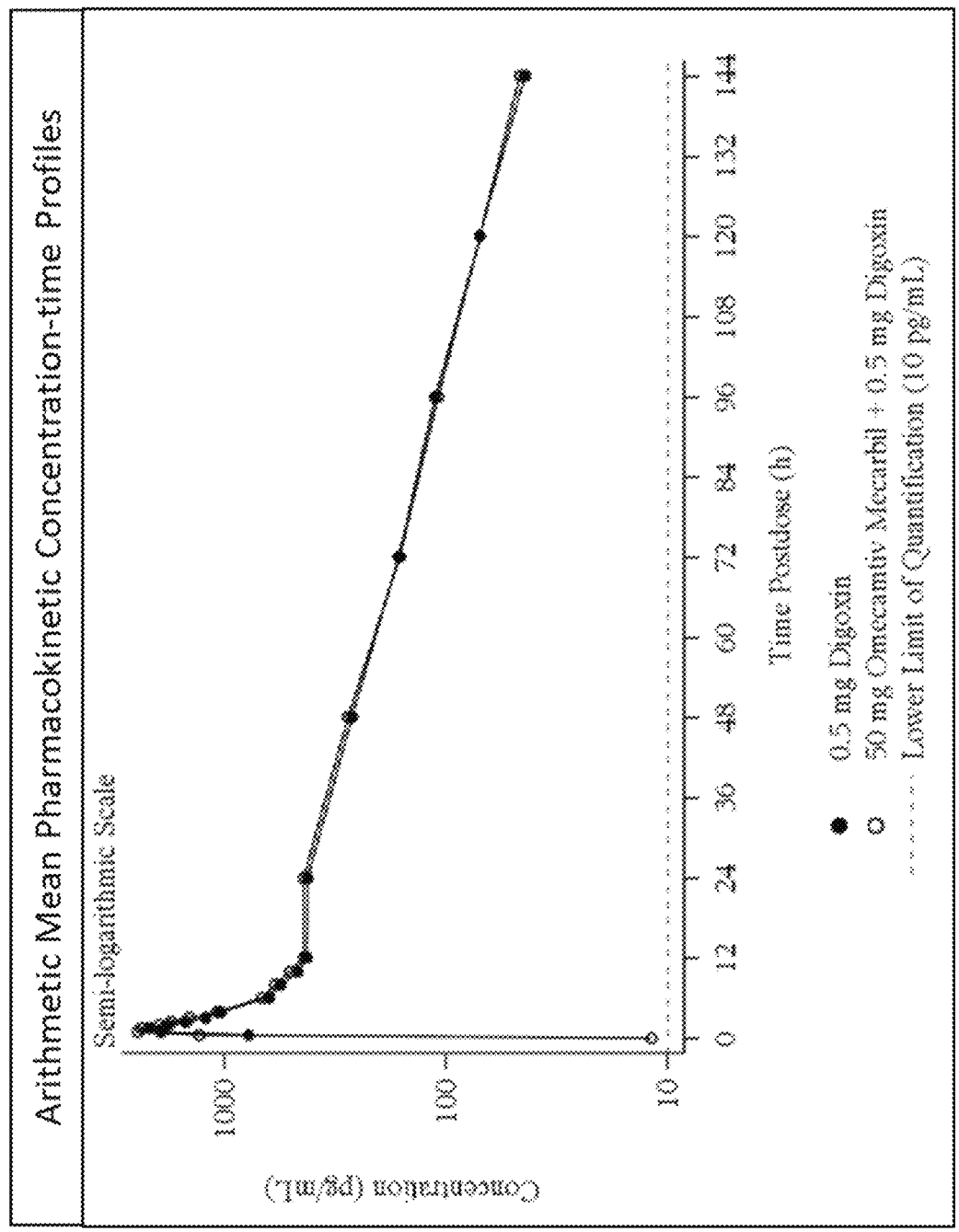
FIG. 21F shows arithmetic mean pharmacokinetic concentration-time profiles for digoxin administration alone and digoxin administration with omecamtiv mecarbil.
Figure 21G:
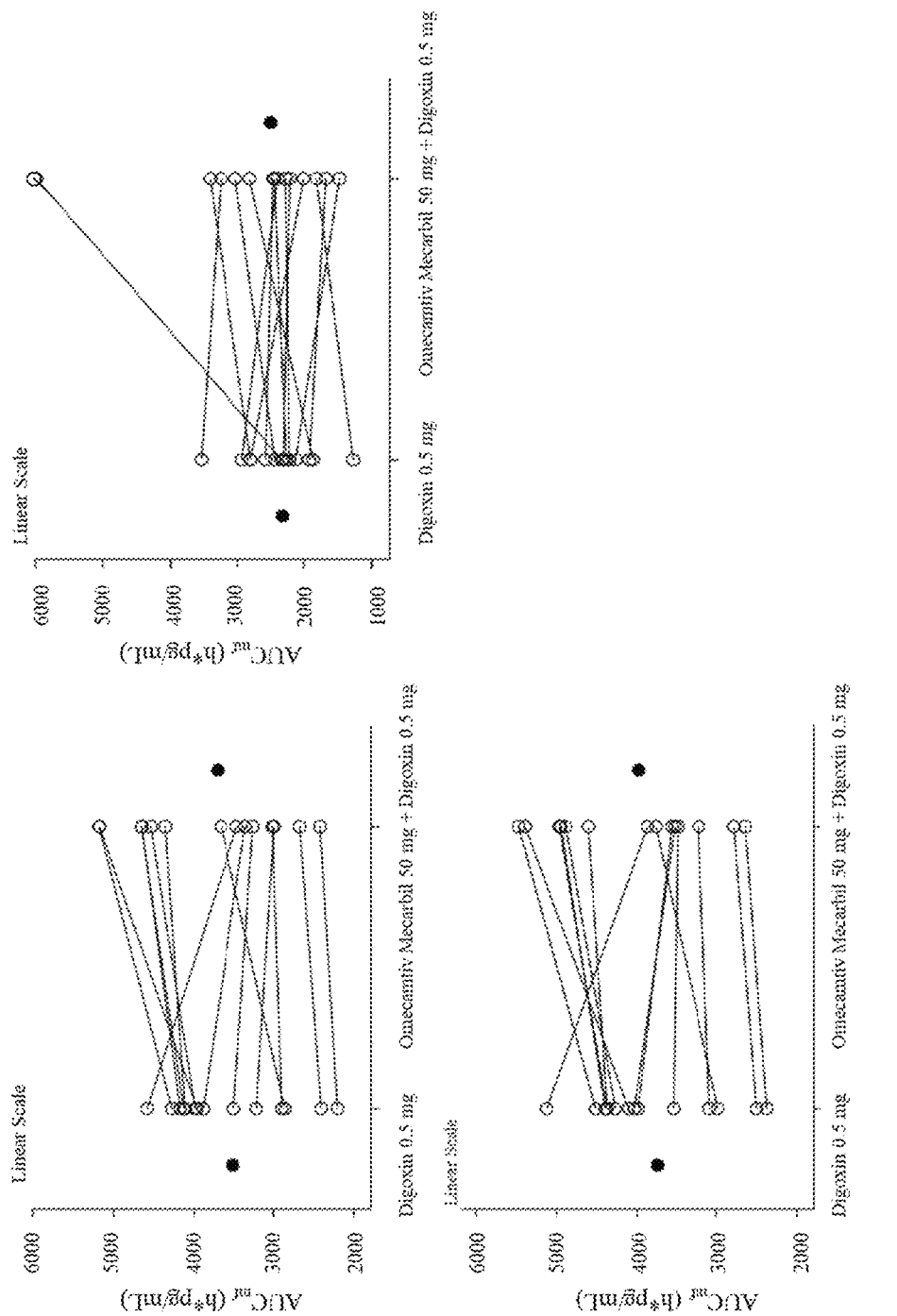
FIG. 21G shows geometric mean pharmacokinetic parameters for digoxin administration alone and digoxin administration with omecamtiv mecarbil.

FIGS. 21F and 21G depict data from a study evaluating any drug-drug interaction between digoxin and omecamtiv mecarbil, showing PK values for digoxin.

Patients in atrial fibrillation/flutter at baseline were less likely to benefit from OM than patients without AFF, although this effect modification appeared to be driven by digoxin use in those patients, and suggests that the when considering OM, the combination of AFF and digoxin is a potential risk factor.

Among patients with EF≤30%, without AFF, and without taking digoxin at baseline, OM led to significant clinical benefits and reductions in resource utilization, as presented in Table 21.

TABLE 21

Outcomes and resources used in the prespecified analysis population (EF ≤30%, no AFF, and no digoxin).

| Resource Use | OM (n = 2674) | Pbo (n = 2695) | | |
|---|---|---|---|---|
| Time to first HFE | 18.9/ 100 pt yrs | 22.7/ 100 pt yrs | HR 0.85, 0.77-0.93, p <0.001 | ARR 3.8/100 pt yrs NNT 26.5 |
| Frequency of HFE (all events) | 31.2/ 100 pt yrs | 38.0/ 100 pt yrs | HR 0.85, CI 0.75-0.96 | ARR 6.7/100 pt yrs NNT 14.9 |
| Cumulative rate of HFEs at 36 months | 81.8/ 100 pts | 102.4/ 100 pts | Rate Ratio 0.799 | increasing treatment effect over time |
| Resource Intensity | /100 pt yrs | /100 pt yrs | | |
| Total days in hospital | 524.1 | 652.2 | Rate Ratio 0.80, CI 0.79-0.82 | |
| IV Diuretics /Inotropes Nasodilators | 35.7 | 42.3 | Rate Ratio 0.84, CI 0.79-0.90 | |
| Mechanical circulatory support during HF hospitalizations | 2.2 | 2.4 | n/a | |
| Mechanical fluid removal during HF hospitalizations | 0.8 | 0.9 | n/a | |

ARR = absolute risk reduction.
CI = 95% confidence interval.
HFE = heart failure event.
NNT = number needed to treat.
OM = omecamtiv mecarbil + standard care.
Pbo = placebo + standard care.

Effect of OM by Baseline Systolic Blood Pressure (SBP)

Systolic blood pressure (SBP) is a major predictor of outcomes in patients with heart failure and reduced ejection fraction (HFrEF). Omecamtiv mecarbil directly improves cardiac function and reduced the primary composite endpoint of an episode of worsening HF (urgent clinic visit, emergency department visit, or hospitalization) or cardiovascular death in the Global Approach to Lowering Adverse Cardiac outcomes Through Improving Contractility in Heart Failure trial (GALACTIC-HF). This trial provided data on the efficacy and tolerability of omecamtiv mecarbil according to baseline SBP values. In contrast to other HFrEF therapies, which may not be tolerated in patients with low baseline blood pressure (e.g., <100 mmHg), the present study was able to enroll patients with SBP at baseline of 85 mmHg or greater.

Results

Figure 23A:
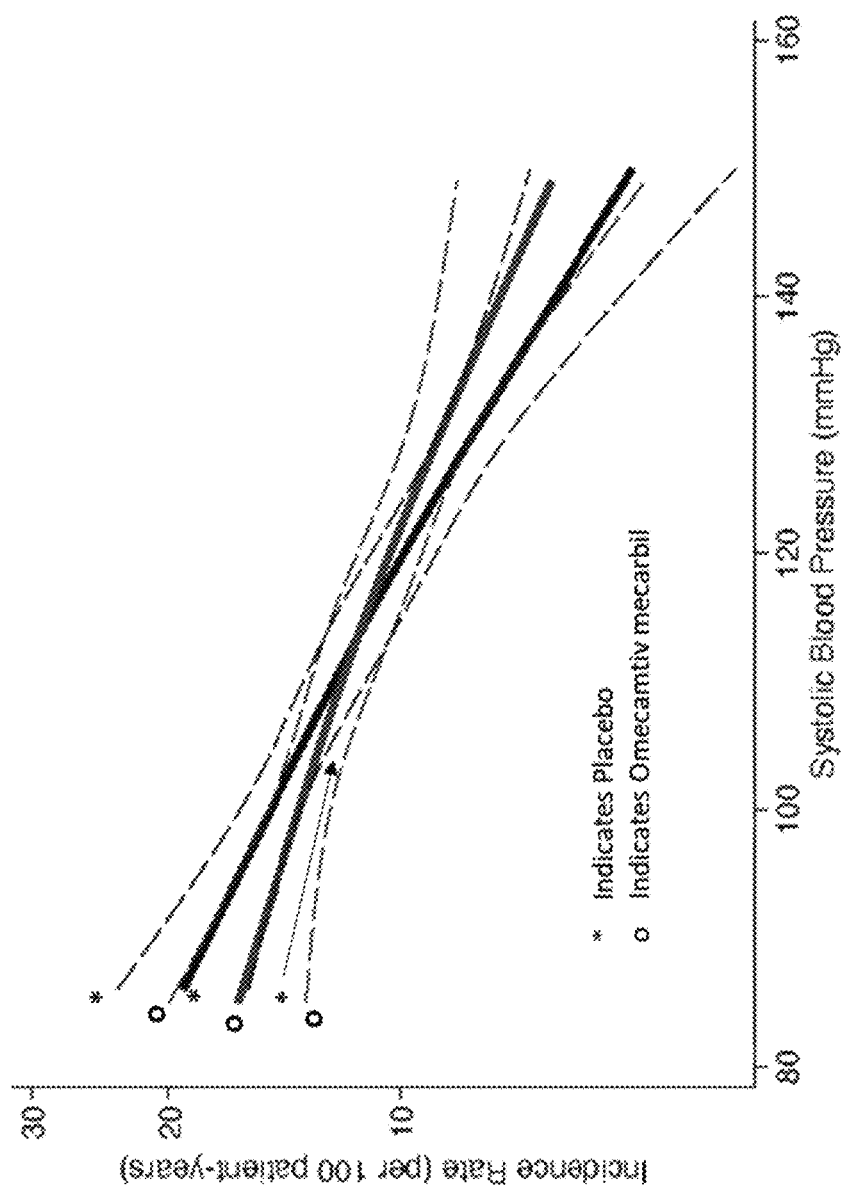
FIG. 23A shows outcomes according to baseline systolic blood pressure (SBP) in all patients randomized (primary composite outcome) (placebo—stars; omecamtiv mecarbil—circles).
Figure 23B:
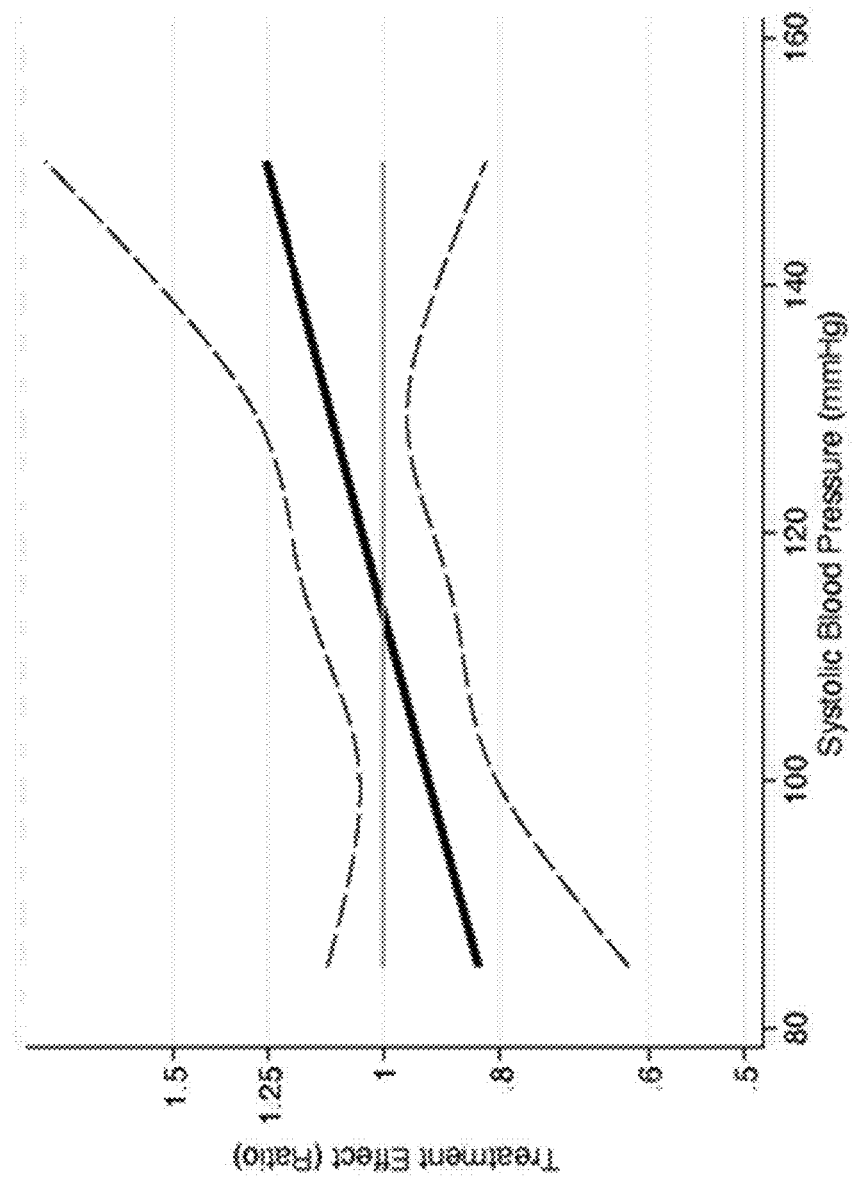
FIG. 23B shows the treatment effect of omecamtiv mecarbil on primary composite outcomes according to baseline systolic blood pressure (SBP).

The 8232 randomized patients were subdivided according to SBP at baseline: <100 mmHg (n=1473), 101-110 mmHg (n=1734), 111-120 mmHg (n=1824), 121-130 mmHg (n=1627), and >130 mmHg (n=1574). Significant differences between these subgroups were found with respect of multiple baseline characteristics. The primary composite endpoint occurred in 715 (48.5%), 682 (39.3%), 679 (37.2%), 556 (34.2%), and 498 (31.6%) patients in each SBP subgroup, respectively. Hazard ratios (HRs) and 95% confidence intervals (CIs) for the treatment effect on the primary outcome were of 0.81, 0.70-0.94; 0.88, 0.76-1.03; 1.03, 0.88-1.19; 0.87, 0.73-1.03; and 1.07, 0.90-1.28 in each SBP subgroup, respectively. When examined as a continuous variable, baseline SBP had a linear inverse relation with the primary event rate and a linear direct relation with the treatment effect (FIGS. 23A and 23B). No significant change in SBP and no difference in adverse events with omecamtiv mecarbil, compared with placebo, occurred during follow-up in each subgroup.

Omecamtiv mecarbil did not change SBP from baseline and was well tolerated independently from SBP at baseline, including in patients having low baseline blood pressure (<100 mmHg) for whom the use of other HFrEF therapies cannot be tolerated or may be associated with the added cost of increased averse events or worsening renal function. Omecamtiv mecarbil tended to have a larger effect on the primary outcome, compared with placebo, in the patients with lower SBP at baseline (≤100 mmHg).

Effect of Food

Administration of OM with a high-fat, high-calorie meal in healthy subjects had no clinically significant effect on its systemic exposure.

Distribution

OM was observed to be moderately bound to plasma proteins (81.5%) and the protein binding was independent of drug concentration up to 4000 ng/mL. After a single 35 mg dose of radiolabeled OM to healthy subjects, the blood to plasma ratio of total radioactivity was approximately 0.4, indicating that radioactivity did not disproportionately partition into blood components. The volume of distribution at steady state was approximately 4.8-6.6 L/kg.

Elimination

Clearance of OM after oral administration was primarily through metabolism in the liver. The total systemic clearance was found to be 11.7 L/hr with mean renal clearance of 1 L/hr, accounting for less than 10% of the systemic clearance. The median half-life of OM was found to be approximately 23-32 hours in patients with heart failure. OM was observed to be extensively metabolized in the liver by multiple metabolic pathways, including CYP3A4 and CYP2D6. Following oral administration of radiolabeled OM to healthy subjects, approximately 49% of the dose was excreted in urine (primarily as metabolites with 8% of parent compound recovered) and 38% in feces (primarily as unchanged drug).

Patients with Hepatic Impairment

The pharmacokinetics of a single dose of OM 25 mg were evaluated in patients with mild (Child-Pugh A) or moderate (Child-Pugh B) hepatic impairment. The pharmacokinetics (Cmax and AUC) of OM in patients with mild or moderate hepatic impairment were similar to those in patients with normal hepatic function.

Drug Interactions—Effects of Other Drugs on the Pharmacokinetics of OM

OM was found to be metabolized in vitro by multiple CYP enzymes including CYP3A4 and CYP2D6 and is a substrate of P-gp and BCRP. OM may be administered with drugs that are inhibitors or inducers of CYP3A4, CYP2D6, P-gp or BCRP. The effect of co-administered drugs on OM plasma exposures is presented in Table 22.

TABLE 22

Change in OM Pharmacokinetics in the Presence of Co-administered Drugs

| Co-administered Drug | Dose of Co-administered Drug | OM Dose | N | % Change and Mean Ratio of OM Pharmacokinetic Parameters (90% CI)[a] | |
|---|---|---|---|---|---|
| | | | | Cmax | AUC |
| P-gp Inhibitor: Amiodarone | 600 mg SD | 50 mg SD | 14 | ↔ 1.08 (0.96-1.22) | ↑ 21% 1.21 (1.08-1.36) |
| Moderate CYP3A Inhibitor: Diltiazem | 240 mg QD × 8 days | 10 mg SD | 8 | ↓21% 0.79 (0.60-1.04) | ↔ 1.08 (0.97-1.22) |
| Strong CYP3A and P-gp Inhibitor: Ketoconazole | 200 mg BID × 8 days | 10 mg SD | 8 | ↔ 1.03 (0.76-1.40) | ↑51% 1.51 (1.20-1.91) |
| CYP2D6 Genotype: PM versus EM[b] | NA | NA | 8, 16[b] | ↓18% 0.82 (0.63-1.07) | ↑30% 1.30 (0.93-1.82) |
| pH Modifying Agent: Omeprazole | 40 mg QD × 6 days | 50 mg SD | 12 | ↔ 1.01 (0.95-1.07) | ↔ 0.95 (0.82-1.09) |

↔ = no change;
↑ = increase;
↓ = decrease;
CI: Confidence Interval;
NA: not applicable;
SD: single dose
[a]Ratios for Cmax and AUC compare co-administration of the drug with OM versus administration of OM alone.
[b]PM (N = 8): poor CYP2D6 metabolizer; EM (N = 16): extensive CYP2D6 metabolizer.
CYP2D6 metabolic genotype had no clinically relevant effect on the pharmacokinetics of OM, indicating that inhibitors of CYP2D6 have no clinically relevant effect on OM exposures.

Drug Interactions—Effects of OM on the Pharmacokinetics of Other Drugs

In vitro, OM was found to be an inhibitor of P-gp, BCRP, MATE1, MATE 2-K, CYP2C8 and an inducer of CYP3A4. Clinical studies and the results of physiologically based pharmacokinetic modeling indicate that OM is a weak inhibitor of CYP2C8 and BCRP, and a weak inducer of CYP3A4. OM may be administered with drugs that are substrates of CYP3A4, CYP2C8, P-gp or BCRP. A summary of results from clinical studies is provided in Table 23.

TABLE 23

Change in Pharmacokinetics Co-administered Drugs in the Presence of OM

| Co-administered Drug | Dose of Co-administered Drug | OM Dose | N | % Change and Mean Ratio of Co-administered Drug Pharmacokinetic Parameters (90% CI)[a] | |
|---|---|---|---|---|---|
| | | | | Cmax | AUC |
| Sensitive CYP3A Substrate: Midazolam | 5 mg SD | 25 mg BID | 14 | ↓10% 0.90 (0.75-1.08) | ↓18% 0.82 (0.71-0.94) |
| Sensitive P-gp | 0.5 mg SD | 50 mg SD | 15 | ↑8% | ↔ |

TABLE 23-continued

Change in Pharmacokinetics Co-administered Drugs in the Presence of OM

| Co-administered Drug | Dose of Co-administered Drug | OM Dose | N | % Change and Mean Ratio of Co-administered Drug Pharmacokinetic Parameters (90% CI)[a] | |
|---|---|---|---|---|---|
| | | | | Cmax | AUC |
| Substrate: Digoxin | | | | 1.08 (0.92-1.26) | 1.06 (0.99-1.14) |
| Sensitive BCRP Substrate: Rosuvastatin | 10 mg SD | 50 mg SD | 14 | ↑45% 1.54 (1.33-1.79) | ↑27% 1.27 (1.14-1.42) |
| Sensitive MATE 1/2K Substrate Metformin | 850 mg SD | 25 mg BID | 14 | ↔ 1.10 (1.01-1.21) | ↔ 0.99 (0.92-1.05) |

↔ = no change;
↑ = increase;
↓ = decrease;
BID = twice daily;
CI: Confidence Interval;
NA: not applicable;
SD: single dose
[a]Ratios for Cmax and AUC compare co-administration of the drug with OM versus administration of OM alone.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate the invention and does not pose a limitation on the scope of the invention unless otherwise claimed. No language in the specification should be construed as indicating any non-claimed element as essential to the practice of the invention.

REFERENCES

Ahmad T, Miller P E, McCullough M, et al. Why has positive inotropy failed in chronic heart failure? Lessons from prior inotrope trials. Eur J Heart Fail 2019; 21:1064-78.

Psotka M A, Gottlieb S S, Francis G S, et al. Cardiac Calcitropes, Myotropes, and Mitotropes. J Am Coll Cardiol 2019; 73:2345-53.

Malik F I, Hartman J J, Elias K A, et al. Cardiac myosin activation: a potential therapeutic approach for systolic heart failure. Science 2011; 331:1439-43.

Psotka M A, Teerlink J R. Direct Myosin Activation by Omecamtiv Mecarbil for Heart Failure with Reduced Ejection Fraction. Handb Exp Pharmacol 2017; 243:465-90.

Planelles-Herrero V J, Hartman J J, Robert-Paganin J, Malik F I, Houdusse A. Mechanistic and structural basis for activation of cardiac myosin force production by omecamtiv mecarbil. Nat Commun 2017; 8:190.

Teerlink J R, Clarke C P, Saikali K G, et al. Dose-dependent augmentation of cardiac systolic function with the selective cardiac myosin activator, omecamtiv mecarbil: a first-in-man study. Lancet 2011; 378:667-75.

Cleland J G, Teerlink J R, Senior R, et al. The effects of the cardiac myosin activator, omecamtiv mecarbil, on cardiac function in systolic heart failure: a double-blind, placebo-controlled, crossover, dose-ranging phase 2 trial. Lancet 2011; 378:676-83.

Teerlink J R, Felker G M, McMurray J J, et al. Acute Treatment With Omecamtiv Mecarbil to Increase Contractility in Acute Heart Failure: The ATOMIC-AHF Study. J Am Coll Cardiol 2016; 67:1444-55.

Teerlink J R, Felker G M, McMurray J J, et al. Chronic Oral Study of Myosin Activation to Increase Contractility in Heart Failure (COSMIC-HF): a phase 2, pharmacokinetic, randomised, placebo-controlled trial. Lancet 2016; 388:2895-903.

Teerlink J R, Diaz R, Felker G M, et al. Omecamtiv Mecarbil in Chronic Heart Failure With Reduced Ejection Fraction: Rationale and Design of GALACTIC-HF. JACC Heart Fail 2020; 8:329-40.

Hicks K A, Mahaffey K W, Mehran R, et al. 2017 Cardiovascular and Stroke Endpoint Definitions for Clinical Trials. J Am Coll Cardiol 2018; 71:1021-34.

Haybittle J L. Repeated assessment of results in clinical trials of cancer treatment. Br J Radiol 1971; 44:793-7.

Peto R, Pike M C, Armitage P, et al. Design and analysis of randomized clinical trials requiring prolonged observation of each patient. I. Introduction and design. Br J Cancer 1976; 34:585-612.

Hardy R J, Thompson S G. A likelihood approach to meta-analysis with random effects. Stat Med 1996; 15:619-29.

Teerlink J R, Diaz R, Felker G M, et al. Omecamtiv Mecarbil in Chronic Heart Failure with Reduced Ejection Fraction, GALACTIC-HF: Baseline Characteristics and Comparison with Contemporary Clinical Trials. Eur J Heart Fail 2020.

Benjamini Y, Hochberg Y. Controlling the False Discovery Rate: A Practical and Powerful Approach to Multiple Testing. J R Statist Soc B 1995; 57:289-300.

Shen Y T, Malik F I, Zhao X, et al. Improvement of cardiac function by a cardiac Myosin activator in conscious dogs with systolic heart failure. Circ Heart Fail 2010; 3:522-7.

Kramer D G, Trikalinos T A, Kent D M, Antonopoulos G V, Konstam M A, Udelson J E. Quantitative evaluation of drug or device effects on ventricular remodeling as predictors of therapeutic effects on mortality in patients with heart failure and reduced ejection fraction: a meta-analytic approach. J Am Coll Cardiol 2010; 56:392-406.

Wessler B S, McCauley M, Morine K, Konstam M A, Udelson J E. Relation between therapy-induced changes in natriuretic peptide levels and long-term therapeutic effects on mortality in patients with heart failure and reduced ejection fraction. Eur J Heart Fail 2019; 21:613-20.

Vaduganathan M, Claggett B, Packer M, et al. Natriuretic Peptides as Biomarkers of Treatment Response in Clinical Trials of Heart Failure. JACC Heart Fail 2018; 6:564-9.

Butler J, Khan M S, Mori C, et al. Minimal clinically important difference in quality of life scores for patients with heart failure and reduced ejection fraction. Eur J Heart Fail 2020; 22:999-1005.

Tahhan A S, Vaduganathan M, Greene S J, et al. Enrollment of Older Patients, Women, and Racial and Ethnic Minorities in Contemporary Heart Failure Clinical Trials: A Systematic Review. JAMA Cardiol 2018; 3:1011-9.

McMurray J J V, Solomon S D, lnzucchi S E, et al. Dapagliflozin in Patients with Heart Failure and Reduced Ejection Fraction. N Engl J Med 2019; 381:1995-2008.

Packer M, Anker S D, Butler J, et al. Cardiovascular and Renal Outcomes with Empagliflozin in Heart Failure. N Engl J Med 2020; 383:1413-24.

Fang J C, Ewald G A, Allen L A, Butler J, Westlake Canary C A, Colvin-Adams M, Dickinson M G, Levy P, Stough W G, Sweitzer N K, Teerlink J R, Whellan D J, Albert N M, Krishnamani R, Rich M W, Walsh M N, Bonnell M R, Carson P E, Chan M C, Dries D L, Hernandez A F, Hershberger R E, Katz S D, Moore S, Rodgers J E, Rogers J G, Vest A R, Givertz M M and Heart Failure Society of America Guidelines C. Advanced (stage D) heart failure: a statement from the Heart Failure Society of America Guidelines Committee. Journal of cardiac failure. 2015; 21:519-34.

Crespo-Leiro M G, Metra M, Lund L H, Milicic D, Costanzo M R, Filippatos G, Gustafsson F, Tsui S, Barge-Caballero E, De Jonge N, Frigerio M, Hamdan R, Hasin T, Hulsmann M, Nalbantgil S, Potena L, Bauersachs J, Gkouziouta A, Ruhparwar A, Ristic A D, Straburzynska-Migaj E, McDonagh T, Seferovic P and Ruschitzka F. Advanced heart failure: a position statement of the Heart Failure Association of the European Society of Cardiology. European journal of heart failure. 2018; 20:1505-1535.

Writing Committee M, Yancy C W, Jessup M, Bozkurt B, Butler J, Casey D E, Jr., Drazner M H, Fonarow G C, Geraci S A, Horwich T, Januzzi J L, Johnson M R, Kasper E K, Levy W C, Masoudi F A, McBride P E, McMurray J J, Mitchell J E, Peterson P N, Riegel B, Sam F, Stevenson L W, Tang W H, Tsai E J, Wilkoff B L and American College of Cardiology Foundation/American Heart Association Task Force on Practice G. 2013 ACCF/AHA guideline for the management of heart failure: a report of the American College of Cardiology Foundation/American Heart Association Task Force on practice guidelines. Circulation. 2013; 128:e240-327.

Metra M, Ponikowski P, Dickstein K, McMurray J J, Gavazzi A, Bergh C H, Fraser A G, Jaarsma T, Pitsis A, Mohacsi P, Bohm M, Anker S, Dargie H, Brutsaert D, Komajda M and Heart Failure Association of the European Society of C. Advanced chronic heart failure: A position statement from the Study Group on Advanced Heart Failure of the Heart Failure Association of the European Society of Cardiology. European journal of heart failure. 2007; 9:684-94.

Allen L A, Stevenson L W, Grady K L, Goldstein N E, Matlock D D, Arnold R M, Cook N R, Felker G M, Francis G S, Hauptman P J, Havranek E P, Krumholz H M, Mancini D, Riegel B, Spertus J A, American Heart A, Council on Quality of C, Outcomes R, Council on Cardiovascular N, Council on Clinical C, Council on Cardiovascular R, Intervention, Council on Cardiovascular S and Anesthesia. Decision making in advanced heart failure: a scientific statement from the American Heart Association. Circulation. 2012; 125:1928-52.

Allen L A, Fonarow G C, Grau-Sepulveda M V, Hernandez A F, Peterson P N, Partovian C, Li S X, Heidenreich P A, Bhatt D L, Peterson E D, Krumholz H M and American Heart Association's Get With The Guidelines Heart Failure I. Hospital variation in intravenous inotrope use for patients hospitalized with heart failure: insights from Get With The Guidelines. Circ Heart Fail. 2014; 7:251-60.

Nizamic T, Murad M H, Allen L A, Mcllvennan C K, Wordingham S E, Matlock D D and Dunlay S M. Ambulatory Inotrope Infusions in Advanced Heart Failure: A Systematic Review and Meta-Analysis. JACC Heart failure. 2018; 6:757-767.

Teerlink J R, Clarke C P, Saikali K G, Lee J H, Chen M M, Escandon R D, Elliott L, Bee R, Habibzadeh M R, Goldman J H, Schiller N B, Malik F I and Wolff A A. Dose-dependent augmentation of cardiac systolic function with the selective cardiac myosin activator, omecamtiv mecarbil: a first-in-man study. Lancet. 2011; 378:667-75.

Cleland J G, Teerlink J R, Senior R, Nifontov E M, Mc Murray J J, Lang C C, Tsyrlin V A, Greenberg B H, Mayet J, Francis D P, Shaburishvili T, Monaghan M, Saltzberg M, Neyses L, Wasserman S M, Lee J H, Saikali K G, Clarke C P, Goldman J H, Wolff A A and Malik F I. The effects of the cardiac myosin activator, omecamtiv mecarbil, on cardiac function in systolic heart failure: a double-blind, placebo-controlled, crossover, dose-ranging phase 2 trial. Lancet. 2011; 378:676-83.

Teerlink J R, Felker G M, McMurray J J, Solomon S D, Adams K F, Jr., Cleland J G, Ezekowitz J A, Goudev A, Macdonald P, Metra M, Mitrovic V, Ponikowski P, Serpytis P, Spinar J, Tomcsanyi J, Vandekerckhove H J, Voors A A, Monsalvo M L, Johnston J, Malik F I, Honarpour N and Investigators C-H. Chronic Oral Study of Myosin Activation to Increase Contractility in Heart Failure (COSMIC-HF): a phase 2, pharmacokinetic, randomised, placebo-controlled trial. Lancet. 2016; 388:2895-2903.

Teerlink J R, Diaz R, Felker G M, McMurray J J V, Metra M, Solomon S D, Adams K F, Anand I, Arias-Mendoza A, Biering-Sorensen T, Bohm M, Bonderman D, Cleland J G F, Corbalan R, Crespo-Leiro M G, Dahlstrom U, Echeverria L E, Fang J C, Filippatos G, Fonseca C, Goncalvesova E, Goudev A R, Howlett J G, Lanfear D E, Li J, Lund M, Macdonald P, Mareev V, Momomura S I, O'Meara E, Parkhomenko A, Ponikowski P, Ramires F J A, Serpytis P, Sliwa K, Spinar J, Suter™, Tomcsanyi J, Vandekerckhove H, Vinereanu D, Voors A A, Yilmaz M B, Zannad F, Sharpsten L, Legg J C, Varin C, Honarpour N, Abbasi S A, Malik F I, Kurtz C E and Investigators G-H. Cardiac Myosin Activation with Omecamtiv Mecarbil in Systolic Heart Failure. N Engl J Med. 2020.

Teerlink J R, Diaz R, Felker G M, McMurray J J V, Metra M, Solomon S D, Adams K F, Anand I, Arias-Mendoza A, Biering-Sorensen T, Bohm M, Bonderman D, Cleland J G F, Corbalan R, Crespo-Leiro M G, Dahlstrom U, Echeverria Correa L E, Fang J C, Filippatos G, Fonseca C, Goncalvesova E, Goudev A R, Howlett J G, Lanfear D E, Lund M, Macdonald P, Mareev V, Momomura S I, O'Meara E, Parkhomenko A, Ponikowski P, Ramires F J A, Serpytis P, Sliwa K, Spinar J, Suter™, Tomcsanyi J, Vandekerckhove H, Vinereanu D, Voors A A, Yilmaz M B, Zannad F, Sharpsten L, Legg J C, Abbasi S A, Varin C, Malik F I, Kurtz C E and Investigators G-H. Omecamtiv mecarbil in chronic heart failure with reduced ejection fraction: GALACTIC-HF baseline characteristics and comparison with contemporary clinical trials. European journal of heart failure. 2020; 22:2160-2171.

Teerlink J R, Diaz R, Felker G M, McMurray J J V, Metra M, Solomon S D, Legg J C, Buchele G, Varin C, Kurtz C E, Malik F I and Honarpour N. Omecamtiv Mecarbil in Chronic Heart Failure With Reduced Ejection Fraction: Rationale and Design of GALACTIC-HF. JACC Heart failure. 2020; 8:329-340.

Unroe K T, Greiner M A, Hernandez A F, Whellan D J, Kaul P, Schulman K A, Peterson E D and Curtis L H. Resource Use in the Last 6 Months of Life Among Medicare Beneficiaries With Heart Failure, 2000-2007. Archives of internal medicine. 2011; 171:196-203.

Stewart G C, Kittleson M M, Patel P C, Cowger J A, Patel C B, Mountis M M, Johnson F L, Guglin M E, Rame J E, Teuteberg J J and Stevenson L W. INTERMACS (Interagency Registry for Mechanically Assisted Circulatory Support) Profiling Identifies Ambulatory Patients at High Risk on Medical Therapy After Hospitalizations for Heart Failure. Circ Heart Fail. 2016; 9.

Lee D S, Tu J V, Juurlink D N, Alter D A, Ko D T, Austin P C, Chong A, Stukel T A, Levy D and Laupacis A. Risk-treatment mismatch in the pharmacotherapy of heart failure. JAMA. 2005; 294:1240-7.

Ammar K A, Jacobsen S J, Mahoney D W, Kors J A, Redfield M M, Burnett J C and Rodeheffer R J. Prevalence and Prognostic Significance of Heart Failure Stages. Circulation. 2007; 115:1563-1570.

Mann D L, Greene S J, Givertz M M, Vader J M, Starling R C, Ambrosy A P, Shah P, McNulty S E, Mahr C, Gupta D, Redfield M M, Lala A, Lewis G D, Mohammed S F, Gilotra N A, Devore A D, Gorodeski E Z, Desvigne-Nickens P, Hernandez A F and Braunwald E. SacubitrilNalsartan in Advanced Heart Failure With Reduced Ejection Fraction. JACC: Heart Failure. 2020; 8:789-799.

Packer M, Bristow M R, Cohn J N, Colucci W S, Fowler M B, Gilbert E M, Shusterman N H and The USCHFSG. The Effect of Carvedilol on Morbidity and Mortality in Patients with Chronic Heart Failure. N Engl J Med. 1996; 334:1349-1355.

Pitt B, Zannad F, Remme W J, Cody R, Castaigne A, Perez A, Palensky J and Wittes J. The effect of spironolactone on morbidity and mortality in patients with severe heart failure. Randomized Aldactone Evaluation Study Investigators. N Engl J Med. 1999; 341:709-17.

Metra M, Eichhorn E, Abraham W T, Linseman J, Bohm M, Corbalan R, DeMets D, De Marco T, Elkayam U, Gerber M, Komajda M, Liu P, Mareev V, Perrone S V, Poole-Wilson P, Roecker E, Stewart J, Swedberg K, Tendera M, Wiens B, Bristow M R and Investigators E. Effects of low-dose oral enoximone administration on mortality, morbidity, and exercise capacity in patients with advanced heart failure: the randomized, double-blind, placebo-controlled, parallel group ESSENTIAL trials. Eur Heart J. 2009; 30:3015-26.

Psotka M A, Gottlieb S S, Francis G S, et al. Cardiac Calcitropes, Myotropes, and Mitotropes. J Am Coll Cardiol 2019; 73:2345-2353.

Malik F I, Hartman J J, Elias K A, et al. Cardiac myosin activation: a potential therapeutic approach for systolic heart failure. Science 2011; 331:1439-43.

Psotka M A, Teerlink J R. Direct Myosin Activation by Omecamtiv Mecarbil for Heart Failure with Reduced Ejection Fraction. Handb Exp Pharmacol 2017; 243:465-490.

Planelles-Herrero V J, Hartman J J, Robert-Paganin J, Malik F I, Houdusse A. Mechanistic and structural basis for activation of cardiac myosin force production by omecamtiv mecarbil. Nat Commun 2017; 8:190.

Teerlink J R, Felker G M, McMurray J J, et al. Chronic Oral Study of Myosin Activation to Increase Contractility in Heart Failure (COSMIC-HF): a phase 2, pharmacokinetic, randomised, placebo-controlled trial. Lancet 2016; 388:2895-2903.

Biering-Sorensen T, Minamisawa M, Claggett B, et al. Cardiac Myosin Activator Omecamtiv Mecarbil Improves Left Ventricular Myocardial Deformation in Chronic Heart Failure: The COSMIC-HF Trial. Circ Heart Fail 2020; 13:e008007.

Teerlink J R, Diaz R, Felker G M, et al. Omecamtiv mecarbil in chronic heart failure with reduced ejection fraction: GALACTIC-HF baseline characteristics and comparison with contemporary clinical trials. Eur J Heart Fail 2020; 22:2160-2171.

Teerlink J R, Diaz R, Felker G M, et al. Cardiac Myosin Activation with Omecamtiv Mecarbil in Systolic Heart Failure. N Engl J Med 2021; 384:105-116.

Teerlink J R, Diaz R, Felker G M, et al. Omecamtiv Mecarbil in Chronic Heart Failure With Reduced Ejection Fraction: Rationale and Design of GALACTIC-HF. JACC Heart Fail 2020; 8:329-340.

Hicks K A, Mahaffey K W, Mehran R, et al. 2017 Cardiovascular and Stroke Endpoint Definitions for Clinical Trials. J Am Coll Cardiol 2018; 71:1021-1034.

Ahmad T, Miller P E, McCullough M, et al. Why has positive inotropy failed in chronic heart failure? Lessons from prior inotrope trials. Eur J Heart Fail 2019; 21:1064-1078.

Teerlink J R, Clarke C P, Saikali K G, et al. Dose-dependent augmentation of cardiac systolic function with the selective cardiac myosin activator, omecamtiv mecarbil: a first-in-man study. Lancet 2011; 378:667-75.

Cleland J G, Teerlink J R, Senior R, et al. The effects of the cardiac myosin activator, omecamtiv mecarbil, on cardiac function in systolic heart failure: a double-blind, placebo-controlled, crossover, dose-ranging phase 2 trial. Lancet 2011; 378:676-83.

Teerlink J R, Felker G M, McMurray J J, et al. Acute Treatment With Omecamtiv Mecarbil to Increase Contractility in Acute Heart Failure: The ATOMIC-AHF Study. J Am Coll Cardiol 2016; 67:1444-55.

Cleland J G F, Bunting K V, Flather M D, et al. Beta-blockers for heart failure with reduced, mid-range, and preserved ejection fraction: an individual patient-level analysis of double-blind randomized trials. Eur Heart J 2018; 39:26-35.

Solomon S D, Claggett B, Desai A S, et al. Influence of Ejection Fraction on Outcomes and Efficacy of SacubitrilNalsartan (LCZ696) in Heart Failure with Reduced Ejection Fraction: The Prospective Comparison of ARNI with ACEI to Determine Impact on Global Mortality and Morbidity in Heart Failure (PARADIGM-HF) Trial. Circ Heart Fail 2016; 9:e002744.

Solomon S D, Vaduganathan M, B L C, et al. SacubitrilNalsartan Across the Spectrum of Ejection Fraction in Heart Failure. Circulation 2020; 141:352-361.

Dewan P, Solomon S D, Jhund P S, et al. Efficacy and safety of sodium-glucose co-transporter 2 inhibition according to left ventricular ejection fraction in DAPA-HF. Eur J Heart Fail 2020; 22:1247-1258.

Center for Drug Evaluation and Research, Food and Drug Administration. Integrated Review, Application Number 2143770rig1s000, NDA 214377 Vericiguat. 2021.

Solomon S D, Anavekar N, Skali H, et al. Influence of ejection fraction on cardiovascular outcomes in a broad spectrum of heart failure patients. Circulation 2005; 112: 3738-44.

Ibrahim N E, Burnett J C Jr, Butler J, Camacho A, Felker G M, Fiuzat M, O'Connor C, Solomon S D, Vaduganathan M, Zile M R, Januzzi J L Jr. Natriuretic Peptides as Inclusion Criteria in Clinical Trials: A JACC: Heart Failure Position Paper. JACC Heart Fail. 2020 May; 8(5):347-358.

Burnett J C Jr. Atrial Natriuretic Peptide, Heart Failure and the Heart as an Endocrine Organ. Clin Chem. 2019 December; 65(12):1602-1603.

Mueller C, McDonald K, de Boer R A, Maisel A, Cleland J G F, Kozhuharov N, Coats A J S, Metra M, Mebazaa A, Ruschitzka F, Lainscak M, Filippatos G, Seferovic P M, Meijers W C, Bayes-Genis A, Mueller T, Richards M, Januzzi J L Jr; Heart Failure Association of the European Society of Cardiology. Heart Failure Association of the European Society of Cardiology practical guidance on the use of natriuretic peptide concentrations. Eur J Heart Fail. 2019 June; 21(6):715-731.

Wessler B S, McCauley M, Morine K, Konstam M A, Udelson J E. Relation between therapy-induced changes in natriuretic peptide levels and long-term therapeutic effects on mortality in patients with heart failure and reduced ejection fraction. Eur J Heart Fail. 2019 May; 21(5):613-620.

Troughton R W, Frampton C M, Brunner-La Rocca H P, Pfisterer M, Eurlings L W, Erntell H, Persson H, O'Connor C M, Moertl D, Karlstrom P, Dahlstrom U, Gaggin H K, Januzzi J L, Berger R, Richards A M, Pinto Y M, Nicholls MG. Effect of B-type natriuretic peptide-guided treatment of chronic heart failure on total mortality and hospitalization: an individual patient meta-analysis. Eur Heart J. 2014 Jun. 14; 35(23):1559-67.

Vaduganathan M, Claggett B, Packer M, McMurray J J V, Rouleau J L, Zile M R, Swedberg K, Solomon S D. Natriuretic Peptides as Biomarkers of Treatment Response in Clinical Trials of Heart Failure. JACC Heart Fail. 2018 July; 6(7):564-569.

Zile M R, Claggett B L, Prescott M F, McMurray J J, Packer M, Rouleau J L, Swedberg K, Desai A S, Gong J, Shi V C, Solomon S D. Prognostic Implications of Changes in N-Terminal Pro-B-Type Natriuretic Peptide in Patients With Heart Failure. J Am Coll Cardiol. 2016 Dec. 6; 68(22):2425-2436.

Malik F I, Hartman J J, Elias K A, Morgan B P, Rodriguez H, Brejc K, Anderson R L, Sueoka S H, Lee K H, Finer J T, Sakowicz R, Baliga R, Cox D R, Garard M, Godinez G, Kawas R, Kraynack E, Lenzi D, Lu P P, Muci A, Niu C, Qian X, Pierce D W, Pokrovskii M, Suehiro I, Sylvester S, Tochimoto T, Valdez C, Wang W, Katori T, Kass D A, Shen Y T, Vatner S F, Morgans D J. Cardiac myosin activation: a potential therapeutic approach for systolic heart failure. Science. 2011 Mar. 18; 331(6023):1439-43.

Cleland J G, Teerlink J R, Senior R, Nifontov E M, Mc Murray J J, Lang C C, Tsyrlin V A, Greenberg B H, Mayet J, Francis D P, Shaburishvili T, Monaghan M, Saltzberg M, Neyses L, Wasserman S M, Lee J H, Saikali K G, Clarke C P, Goldman J H, Wolff A A, Malik F I. The effects of the cardiac myosin activator, omecamtiv mecarbil, on cardiac function in systolic heart failure: a double-blind, placebo-controlled, crossover, dose-ranging phase 2 trial. Lancet. 2011 Aug. 20; 378(9792):676-83.

Teerlink J R, Felker G M, McMurray J J V, Ponikowski P, Metra M, Filippatos G S, Ezekowitz J A, Dickstein K, Cleland J G F, Kim J B, Lei L, Knusel B, Wolff A A, Malik F I, Wasserman S M; ATOMIC-AHF Investigators. Acute Treatment With Omecamtiv Mecarbil to Increase Contractility in Acute Heart Failure: The ATOMIC-AHF Study. J Am Coll Cardiol. 2016 Mar. 29; 67(12):1444-1455.

Teerlink J R, Felker G M, McMurray J J, Solomon S D, Adams K F Jr, Cleland J G, Ezekowitz J A, Goudev A, Macdonald P, Metra M, Mitrovic V, Ponikowski P, Serpytis P, Spinar J, Tomcsanyi J, Vandekerckhove H J, Voors A A, Monsalvo M L, Johnston J, Malik F I, Honarpour N; COSMIC-HF Investigators. Chronic Oral Study of Myosin Activation to Increase Contractility in Heart Failure (COSMIC-HF): a phase 2, pharmacokinetic, randomised, placebo-controlled trial. Lancet. 2016 Dec. 10; 388 (10062):2895-2903.

Teerlink J R, Diaz R, Felker G M, McMurray J J V, Metra M, Solomon S D, Legg J C, Buchele G, Varin C, Kurtz C E, Malik F I, Honarpour N. Omecamtiv Mecarbil in Chronic Heart Failure With Reduced Ejection Fraction: Rationale and Design of GALACTIC-HF. JACC Heart Fail. 2020 April; 8(4):329-340.

Teerlink J R, Diaz R, Felker G M, McMurray J J V, Metra M, Solomon S D, Adams K F, Anand I, Arias-Mendoza A, Biering-Sørensen T, Böhm M, Bonderman D, Cleland J G F, Corbalan R, Crespo-Leiro M G, Dahlstrom U, Echeverria Correa L E, Fang J C, Filippatos G, Fonseca C, Goncalvesova E, Goudev A R, Howlett J G, Lanfear D E, Lund M, Macdonald P, Mareev V, Momomura S I, O'Meara E, Parkhomenko A, Ponikowski P, Ramires F J A, Serpytis P, Sliwa K, Spinar J, Suter™, Tomcsanyi J, Vandekerckhove H, Vinereanu D, Voors A A, Yilmaz M B, Zannad F, Sharpsten L, Legg J C, Abbasi S A, Varin C, Malik F I, Kurtz C E; GALACTIC-HF Investigators. Omecamtiv mecarbil in chronic heart failure with reduced ejection fraction: GALACTIC-HF baseline characteristics and comparison with contemporary clinical trials. Eur J Heart Fail. 2020 November; 22(11):2160-2171.

Teerlink J R, Diaz R, Felker G M, McMurray J J V, Metra M, Solomon S D, Adams K F, Anand I, Arias-Mendoza A, Biering-Sørensen T, Böhm M, Bonderman D, Cleland J G F, Corbalan R, Crespo-Leiro M G, Dahlstrom U, Echeverria L E, Fang J C, Filippatos G, Fonseca C, Goncalvesova E, Goudev A R, Howlett J G, Lanfear D E, Li J, Lund M, Macdonald P, Mareev V, Momomura S I, O'Meara E, Parkhomenko A, Ponikowski P, Ramires F J A, Serpytis P, Sliwa K, Spinar J, Suter™, Tomcsanyi J, Vandekerckhove H, Vinereanu D, Voors A A, Yilmaz M B, Zannad F, Sharpsten L, Legg J C, Varin C, Honarpour N, Abbasi S A, Malik F I, Kurtz C E; GALACTIC-HF Investigators. Cardiac Myosin Activation with Omecamtiv Mecarbil in Systolic Heart Failure. N Engl J Med. 2021 Jan. 14; 384(2):105-116.

Grodin J L, Liebo M J, Butler J, Metra M, Felker G M, Hernandez A F, Voors A A, McMurray J J, Armstrong P W, O'Connor C, Starling R C, Troughton R W, Tang W H W. Prognostic Implications of Changes in Amino-Terminal Pro-B-Type Natriuretic Peptide in Acute Decompensated Heart Failure: Insights From ASCEND-HF. J Card Fail. 2019 September; 25(9):703-711.

Rørth R, Jhund P S, Yilmaz M B, Kristensen S L, Welsh P, Desai A S, Kober L, Prescott M F, Rouleau J L, Solomon S D, Swedberg K, Zile M R, Packer M, McMurray J J V. Comparison of BNP and NT-proBNP in Patients With Heart Failure and Reduced Ejection Fraction. Circ Heart Fail. 2020 February; 13(2):e006541.

Kristensen S L, Mogensen U M, Jhund P S, Rørth R, Anand I S, Carson P E, Desai A S, Pitt B, Pfeffer M A, Solomon S D, Zile M R, Kober L, McMurray J J V. N-Terminal Pro-B-Type Natriuretic Peptide Levels for Risk Prediction in Patients With Heart Failure and Preserved Ejection Fraction According to Atrial Fibrillation Status. Circ Heart Fail. 2019 March; 12(3):e005766.

Kristensen S L, Jhund P S, Mogensen U M, Rørth R, Abraham W T, Desai A, Dickstein K, Rouleau J L, Zile M R, Swedberg K, Packer M, Solomon S D, Kober L, McMurray J J V; PARADIGM-HF and ATMOSPHERE Committees and Investigators. Prognostic Value of N-Terminal Pro-B-Type Natriuretic Peptide Levels in Heart Failure Patients With and Without Atrial Fibrillation. Circ Heart Fail. 2017 October; 10(10):e004409.

Loungani R S, Mentz R J, Agarwal R, DeVore A D, Patel C B, Rogers J G, Russell S D, Felker G M. Biomarkers in Advanced Heart Failure: Implications for Managing Patients With Mechanical Circulatory Support and Cardiac Transplantation. Circ Heart Fail. 2020 July; 13(7): e006840.

Cui D, Liao Y, Li G, Chen Y. Levosimendan Can Improve the Level of B-Type Natriuretic Peptide and the Left Ventricular Ejection Fraction of Patients with Advanced Heart Failure: A Meta-analysis of Randomized Controlled Trials. Am J Cardiovasc Drugs. 2021 January; 21(1):73-81.

Comin-Colet J, Manito N, Segovia-Cubero J, Delgado J, Garcia Pinilla J M, Almenar L, Crespo-Leiro M G, Sionis A, Blasco T, Pascual-Figal D, Gonzalez-Vilchez F, Lambert-Rodriguez J L, Grau M, Bruguera J; LION-HEART Study Investigators. Efficacy and safety of intermittent intravenous outpatient administration of levosimendan in patients with advanced heart failure: the LION-HEART multicentre randomised trial. EurJ Heart Fail. 2018 July; 20(7):1128-1136.

Najjar E, Stålhberg M, Hage C, Ottenblad E, Manouras A, Haugen Löfman I, Lund L H. Haemodynamic effects of levosimendan in advanced but stable chronic heart failure. ESC Heart Fail. 2018 June; 5(3):302-308.

Ezekowitz J A, O'Connor C M, Troughton R W, Alemayehu W G, Westerhout C M, Voors A A, Butler J, Lam C S P, Ponikowski P, Emdin M, Patel M J, Pieske B, Roessig L, Hernandez A F, Armstrong P W. N-Terminal Pro-B-Type Natriuretic Peptide and Clinical Outcomes: Vericiguat Heart Failure With Reduced Ejection Fraction Study. JACC Heart Fail. 2020 November; 8(11):931-939.

Kotecha, D. et al. Efficacy of β blockers in patients with heart failure plus atrial fibrillation: an individual-patient data meta-analysis. The Lancet, Dec. 20, 2014, VOLUME 384, ISSUE 9961, p 2235-2243.

What is claimed:

1. A method of treating heart failure in a patient who has a left ventricular ejection fraction (LVEF) of less than or equal to 28% at baseline, comprising administering to the patient a therapeutically effective amount of omecamtiv mecarbil, or a hydrate, a salt, or a salt of a hydrate thereof.

2. The method of claim 1, wherein the patient does not exhibit atrial fibrillation or atrial flutter.

3. The method of claim 2, wherein the patient has a pretreatment level of NT-proBNP of at least 2,000 pg/mL.

4. The method of claim 1, wherein the patient has a pretreatment level of NT-proBNP of at least 2,000 pg/mL.

5. The method of claim 1, wherein the patient is an inpatient.

6. The method of claim 1, wherein the patient is an outpatient.

7. The method of claim 1, wherein the omecamtiv mecarbil, or the hydrate, salt, or salt of the hydrate thereof is administered orally.

8. The method of claim 7, wherein the omecamtiv mecarbil, or the hydrate, salt, or salt of the hydrate thereof is administered as a tablet.

9. The method of claim 1, comprising administering to the patient a therapeutically effective amount of omecamtiv mecarbil dihydrochloride hydrate.

10. The method of claim 1, wherein the omecamtiv mecarbil, or the hydrate, salt, or salt of the hydrate thereof is administered as a modified release matrix tablet.

11. The method of claim 1, wherein the omecamtiv mecarbil, or the hydrate, salt, or salt of the hydrate thereof is administered in a dosage of 25 mg twice daily, 37.5 mg twice daily, or 50 mg twice daily.

12. The method of claim 1, wherein the patient has undergone cardiac resynchronization therapy (CRT) prior to treatment.

13. The method of claim 1, wherein the patient has an implantable cardioverter defibrillator (ICD) device.

14. The method of claim 1, further comprising administering to the patient a therapeutically effective amount of an angiotensin-converting enzyme inhibitor.

15. The method of claim 1, further comprising administering to the patient a therapeutically effective amount of a mineralocorticoid receptor antagonist.

16. The method of claim 1, wherein the patient is not receiving digoxin.

17. The method of claim 2, wherein the patient is not receiving digoxin.

18. The method of claim 1, wherein the patient has an LVEF of less than 25%.

19. The method of claim 1, wherein the patient has an LVEF of less than 22%.

20. A method of treating heart failure in a patient who has low blood pressure, comprising administering to the patient a therapeutically effective amount of omecamtiv mecarbil, or a hydrate, a salt, or a salt of a hydrate thereof.

21. The method of claim 20, wherein the patient has a systolic blood pressure (SBP) of less than or equal to 100 mmHg.

22. The method of claim 20, wherein the patient has an LVEF of less than 28%.

23. The method of claim 20, wherein the patient has an LVEF of less than 25%.

24. The method of claim 20, wherein the patient has an LVEF of less than 22%.

25. The method of claim 20, wherein the patient has a pretreatment level of NT-proBNP of at least 2,000 pg/mL.

26. The method of claim 20, wherein the omecamtiv mecarbil, or the hydrate, salt, or salt of the hydrate thereof is administered orally.

27. The method of claim 26, wherein the omecamtiv mecarbil, or the hydrate, salt, or salt of the hydrate thereof is administered as a tablet.

28. The method of claim 20, comprising administering to the patient a therapeutically effective amount of omecamtiv mecarbil dihydrochloride hydrate.

29. The method of claim 20, wherein the omecamtiv mecarbil, or the hydrate, salt, or salt of the hydrate thereof is administered as a modified release matrix tablet.

30. The method of claim 20, wherein the omecamtiv mecarbil, or the hydrate, salt, or salt of the hydrate thereof is administered in a dosage of 25 mg twice daily, 37.5 mg twice daily, or 50 mg twice daily.

* * * * *